(12) United States Patent
Sharma et al.

(10) Patent No.: US 8,580,747 B2
(45) Date of Patent: *Nov. 12, 2013

(54) CYCLIC NATRIURETIC PEPTIDE CONSTRUCTS

(75) Inventors: Shubh D. Sharma, Cranbury, NJ (US); Margarita Bastos, Plainsboro, NJ (US); Wei Yang, Edison, NJ (US); Hui-Zhi Cai, East Brunswick, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 789 days.

This patent is subject to a terminal disclaimer.

(21) Appl. No.: 12/622,055

(22) Filed: Nov. 19, 2009

(65) Prior Publication Data

US 2010/0075895 A1    Mar. 25, 2010

Related U.S. Application Data

(63) Continuation of application No. 11/694,260, filed on Mar. 30, 2007, now Pat. No. 7,622,440.

(60) Provisional application No. 60/743,960, filed on Mar. 30, 2006, provisional application No. 60/743,961, filed on Mar. 30, 2006.

(51) Int. Cl.
*A61K 38/10* (2006.01)
*A61K 38/12* (2006.01)

(52) U.S. Cl.
USPC .......... 514/21.5; 530/327; 530/317; 514/21.1

(58) Field of Classification Search
None
See application file for complete search history.

(56) References Cited

U.S. PATENT DOCUMENTS

| | | |
|---|---|---|
| 4,251,438 A | 2/1981 | Moon |
| 4,341,698 A | 7/1982 | Carr et al. |
| 4,496,544 A | 1/1985 | Needleman |
| 4,609,725 A | 9/1986 | Brady et al. |
| 4,656,158 A | 4/1987 | Matsuo et al. |
| 4,673,732 A | 6/1987 | Kiso et al. |
| 4,716,147 A | 12/1987 | Tjoeng et al. |
| 4,757,048 A | 7/1988 | Lewicki et al. |
| 4,764,504 A | 8/1988 | Johnson et al. |
| 4,804,650 A | 2/1989 | Lewicki et al. |
| 4,816,443 A | 3/1989 | Brady et al. |
| 4,824,937 A | 4/1989 | Deghenghi et al. |
| 4,861,755 A | 8/1989 | Breipohl et al. |
| 4,904,763 A | 2/1990 | Matsuo et al. |
| 4,935,492 A | 6/1990 | Lewicki et al. |
| 4,938,763 A | 7/1990 | Dunn et al. |
| 4,952,561 A | 8/1990 | Scolnick et al. |
| 5,047,397 A | 9/1991 | Scarborough et al. |
| 5,057,495 A | 10/1991 | Flynn et al. |
| 5,057,603 A | 10/1991 | Nutt et al. |
| 5,091,366 A | 2/1992 | Nutt et al. |
| 5,095,004 A | 3/1992 | Rakhit et al. |
| 5,106,834 A | 4/1992 | Bovy et al. |
| 5,114,923 A | 5/1992 | Seihamer et al. |
| 5,159,061 A | 10/1992 | Fujino et al. |
| 5,204,328 A | 4/1993 | Nutt et al. |
| 5,212,286 A | 5/1993 | Lewicki et al. |
| 5,352,587 A | 10/1994 | Chang et al. |
| 5,359,030 A | 10/1994 | Ekwuribe et al. |
| 5,376,635 A | 12/1994 | Rakhit et al. |
| 5,418,219 A | 5/1995 | Ueda |
| 5,559,232 A | 9/1996 | Ackermann et al. |
| 5,567,662 A | 10/1996 | Dunmead et al. |
| 5,583,108 A | 12/1996 | Wei et al. |
| 5,665,704 A | 9/1997 | Lowe et al. |
| 5,672,662 A | 9/1997 | Harris et al. |
| 5,681,811 A | 10/1997 | Ekwuribe et al. |
| 5,693,608 A | 12/1997 | Bechgaard et al. |
| 5,846,932 A | 12/1998 | Lowe et al. |
| 5,908,825 A | 6/1999 | Fasano et al. |
| 5,932,462 A | 8/1999 | Harris et al. |
| 5,965,533 A | 10/1999 | Chen et al. |
| 5,977,070 A | 11/1999 | Piazza et al. |

(Continued)

FOREIGN PATENT DOCUMENTS

| | | |
|---|---|---|
| DE | 3022401 | 1/1981 |
| EP | 0223143 | 5/1987 |

(Continued)

OTHER PUBLICATIONS

Rubsam, 2000, Tetrahedron, 56, 8481-8487.*
[Retrieved from]: http://www.answers.com/topic/peptide, 13 pages, retrieved on Nov. 2, 2012.*
Dutta, A.S., et al., Potent Cyclic Monomeric and Dimeric Peptide, etc., Journal of Peptide Science, 2000, vol. 6, 321-341.
de Visser, et al., Solidphase synthesis of polymyxin B1 and analogues via a safety-catch approach, J. Peptide Res., 2003, vol. 61, 298-306.
Masuzawa, et al., The Reaction of C-Substituted Ethylenediamine with the Ester of Alpha-Halo Acid, Apr. 1965, vol. 38, No. 12, 2078-2081.

(Continued)

*Primary Examiner* — Satyanarayana R Gudibande
(74) *Attorney, Agent, or Firm* — Stephen A. Slusher

(57) ABSTRACT

Cyclic constructs with an N-terminus and a C-terminus which bind to a natriuretic peptide receptor and include a plurality of amino acid residues, at least one amino acid surrogate of formula I:

(I)

where R, R', Q, Y, W, Z, J, x and n are as defined in the specification, and optionally at least one prosthetic group, pharmaceutical compositions including such cyclic constructs, and methods of treating congestive heart failure or other conditions, syndromes or diseases for which induction of anti-hypertensive, cardiovascular, renal or endocrine effects are desired.

19 Claims, 2 Drawing Sheets

(56) References Cited

U.S. PATENT DOCUMENTS

| | | | |
|---|---|---|---|
| 6,028,055 A | 2/2000 | Lowe et al. | |
| 6,083,982 A | 7/2000 | Wechter et al. | |
| 6,124,430 A | 9/2000 | Mischak et al. | |
| 6,150,402 A | 11/2000 | Wechter et al. | |
| 6,309,633 B1 | 10/2001 | Ekwuribe et al. | |
| 6,407,211 B1 | 6/2002 | Burnett et al. | |
| 6,432,438 B1 | 8/2002 | Shukla et al. | |
| 6,525,022 B1 | 2/2003 | Lowe et al. | |
| 6,586,396 B1 | 7/2003 | Seilhamer et al. | |
| 6,673,767 B1 | 1/2004 | Brodbeck et al. | |
| 6,737,505 B2 | 5/2004 | Bentley et al. | |
| 6,818,619 B2 | 11/2004 | Burnett et al. | |
| 6,858,580 B2 | 2/2005 | Ekwuribe et al. | |
| 7,622,440 B2 * | 11/2009 | Sharma et al. | 514/1.1 |
| 2004/0002458 A1 | 1/2004 | Seihamer et al. | |
| 2004/0063630 A1 | 4/2004 | Schreiner et al. | |
| 2004/0077537 A1 | 4/2004 | Schreiner et al. | |
| 2004/0235734 A1 | 11/2004 | Bossard et al. | |
| 2005/0113286 A1 | 5/2005 | Schreiner et al. | |
| 2005/0176641 A1 | 8/2005 | Bakis et al. | |
| 2006/0019890 A1 | 1/2006 | Kapoun et al. | |
| 2006/0034903 A1 | 2/2006 | Maa et al. | |

FOREIGN PATENT DOCUMENTS

| | | | |
|---|---|---|---|
| EP | 0291999 | | 11/1988 |
| EP | 0323740 | | 7/1989 |
| EP | 0341603 | | 11/1989 |
| EP | 0350318 | | 1/1990 |
| EP | 0356124 | | 2/1990 |
| EP | 0385476 | | 9/1990 |
| EP | 0542863 | | 11/1997 |
| EP | 0497368 | | 6/2002 |
| FR | 2717484 | | 9/1995 |
| WO | WO 85/04870 | | 11/1985 |
| WO | WO 85/04872 | | 11/1985 |
| WO | WO 88/03537 | | 5/1988 |
| WO | WO 88/06596 | | 9/1988 |
| WO | WO 89/05654 | | 6/1989 |
| WO | WO 89/10935 | | 11/1989 |
| WO | WO 90/01940 | | 3/1990 |
| WO | WO 90/14362 | | 11/1990 |
| WO | WO 92/06998 | | 4/1992 |
| WO | WO 92/21361 | | 12/1992 |
| WO | WO 95/13296 | | 5/1995 |
| WO | WO 99/08510 | | 2/1999 |
| WO | WO 99/12576 | | 3/1999 |
| WO | WO 99/48913 | * | 9/1999 |
| WO | WO 00/18422 | | 4/2000 |
| WO | WO 01/16295 | | 3/2001 |
| WO | WO 02/085925 | | 10/2002 |
| WO | WO-02/085925 | * | 10/2002 |
| WO | WO 03/079979 | | 10/2003 |
| WO | WO 2004/047871 | | 6/2004 |
| WO | WO 2007/115175 | | 10/2007 |
| WO | WO 2007/115182 | | 10/2007 |

OTHER PUBLICATIONS

Shreder, K., et al., Synthesis of a Constrained Enkephalin Analog to Illustrate a Novel, etc., Tetrahedron Letters, 1998, V. 39, 221-224.
Communication from European Patent Office in European Patent Appl. No. 07759821.7, Oct. 2, 2009, including Supple. European Search Report and European Search Opinion.
Tervonen, V., Salmon cardiac natriuretic peptide is a volume-regulating hormone. Am. J. Physiol. Endocrinol. Metab. 283:E353-61 (2002).
Takei, Y., et al., A new natriuretic peptide isolated from cardiac atria of trout, *Oncorhynchus mykiss*. FEBS Letters, 414:377-380 (1997).
Schweitz, H, et al., A new member of the natriuretic peptide family is present in the venom of the green mamba (*Dendroaspis angusticeps*). J. Biol. Chem. 267:13928-13932 (1992).
Lisy, O., et al., Renal actions of synthetic dendroaspis natriuretic peptide, Kidney International, 56:502-508 (1999).
Fry, B.G., et al., Novel natriuretic peptides from the venom of the inland (*Oxyuranus microlepidotus*): isolation, etc. Biochem. Biophys. Res. Comm. 327:1011-1015 (2005).
Schmitt, M., et al., Modulation of the natriuretic peptide system in heart failure: from bench to bedside?, Clinical Science 105:141-160 (2003).
Li, B., et al., Minimization of a polypeptide hormone, Science 270:1657-1660 (1995).
Veronese, F.M., et al., PEGylation, successful approach to drug delivery, Drug Discovery Today 10:1451-1458 (2005).
Synthetic Peptides: A User's Guide, G. A. Grant, editor, W.H. Freeman & Co., New York (1992), including the text and table set forth at pp. 11 through 24.
Hruby, V.J., et al., Emerging Approaches in the Molecular Design of Receptor-Selective Peptide Ligands, etc., Biochem. J. 268:249-262 (1990).
Toniolo, C., Conformationally Restricted Peptides Through Short-Range Cyclizations, Int. J. Peptide Protein Res. 35:287-300 (1990).
Cheng, Y., et al., Relationship Between the Inhibition Constant (K1) and the Concentration of Inhibitor, etc., Biochem. Pharmacol. 22:3099-3108 (1973).
Parikh, J.R., et al., Sulfur Trioxide in the Oxidation of Alcohols by Dimethyl Sulfoxide, J. Am. Chem. Soc. 89:5505-5507 (1967).
Clark, J.S., et al., Synthesis of novel alpha-substituted and alpha,alpha-disubstituted amino acids by rearrangement of ammonium ylides, etc., Org. Lett. 4(5):765-768 (2002).
Guino, M., et al., Wang-aldehyde resin as a recyclable support for the synthesis of alpha,alpha-disubstituted amino acid derivatives. Org Biomol. Chem. 3:3188-3193 (2005).
Kotha S., et al., Synthesis and modification of dibenzylglycine derivatives via the Suzuki-Miyaura cross-coupling reaction, J. Pept. Res. 64:72-85 (2004).
Merrifield R.B., Solid phase synthesis (Nobel lecture). Angew. Chem. 24 (10):799-810 (1985).
Barn D.R., et al., Synthesis of an array of amides by aluminum chloride assisted cleavage of resin-bound esters, Tetrahedron Letters 37(18), 3213-3216 (1996).
DeGrado W. F., et al., Solid-phase synthesis of protected peptides on a polymer bound oxime: Preparation of segments comprising, etc., J. Org. Chem. 47:3258-3261 (1982).
Flaim, S.F., et al., Chronic arteriovenous shunt: evaluation of a model for heart failure in rat, Am. J. Physiol., 236:H698-H704 (1979).
Garcia, R. and Diebold, S., Simple, rapid and effective method of producing aortocaval shunts in the rat, Cardiovasc. Res. 24:430-432 (1990).
Clemens, L.E., et al., Human brain natriuretic peptide reduces blood pressure in normotensive and acute norepinephrine-induced, etc., Am. J. Hypertens. 10:654-661 (1997).
Abassi, Z.A., et al., Renal and systemic effects of urodilatin in rats with high-output heart failure, Am. J. Physiol. 262:F615-F621 (1992).
Sugase, Kenji, et al., Structure-Activity Relationships for Mini Atrial Natriuretic Peptide by Proline-Scanning Mutagenesis and Shortening of Peptide Backbone, Bioorganic & (Continued from above) Medicinal Chemistry Letters 12 (2002) 1245-1247.

* cited by examiner

SEQUENCE LISTING

```
<160> NUMBER OF SEQ ID NOS: 101

<210> SEQ ID NO 1
<211> LENGTH: 15
<212> TYPE: PRT
<213> ORGANISM: Homo sapiens
<220> FEATURE:
<221> NAME/KEY: DOMAIN
<222> LOCATION: (1)..(15)
<223> OTHER INFORMATION: ANP derivative
<220> FEATURE:
<221> NAME/KEY: DISULFID
<222> LOCATION: (2)..(13)
<220> FEATURE:
<221> NAME/KEY: MOD_RES
<222> LOCATION: (15)..(15)
<223> OTHER INFORMATION: AMIDATION

<400> SEQUENCE: 1

Met Cys His Phe Gly Gly Arg Met Asp Arg Ile Ser Cys Tyr Arg
1               5                   10                  15
```

```
<210> SEQ ID NO 2
<211> LENGTH: 15
<212> TYPE: PRT
<213> ORGANISM: Homo sapiens
<220> FEATURE:
<221> NAME/KEY: DOMAIN
<222> LOCATION: (1)..(15)
<223> OTHER INFORMATION: ANP derivative
<220> FEATURE:
<221> NAME/KEY: MISC_FEATURE
<222> LOCATION: (2)..(2)
<223> OTHER INFORMATION: Xaa is any amino acid forming a cyclic peptide
      with the amino acid in position 13
<220> FEATURE:
<221> NAME/KEY: MISC_FEATURE
<222> LOCATION: (13)..(13)
<223> OTHER INFORMATION: Xaa is any amino acid forming a cyclic peptide
      with the amino acid in position 2
<220> FEATURE:
<221> NAME/KEY: MOD_RES
<222> LOCATION: (15)..(15)
<223> OTHER INFORMATION: AMIDATION

<400> SEQUENCE: 2

Met Xaa His Phe Gly Gly Arg Met Asp Arg Ile Ser Xaa Tyr Arg
1               5                   10                  15

<210> SEQ ID NO 3
<211> LENGTH: 14
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (14)..(14)
<223> OTHER INFORMATION: AMIDATION

<400> SEQUENCE: 3

Cys His Phe Gly Gly Arg Xaa Asp Arg Ile Ser Cys Tyr Arg
1               5                   10

<210> SEQ ID NO 4
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (8)..(8)
<223> OTHER INFORMATION: Nle

<400> SEQUENCE: 4

Xaa Cys His Phe Gly Gly Arg Xaa Asp Arg Ile Ser Cys
1               5                   10

<210> SEQ ID NO 5
<211> LENGTH: 11
<212> TYPE: PRT
<213> ORGANISM: Homo sapiens
```

```
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (4)..(4)
<223> OTHER INFORMATION: Nle

<400> SEQUENCE: 5

Gly Gly Arg Xaa Asp Arg Ile Ser Cys Tyr Arg
1               5                   10

<210> SEQ ID NO 6
<211> LENGTH: 10
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (8)..(8)
<223> OTHER INFORMATION: Nle

<400> SEQUENCE: 6

Xaa Cys His Phe Gly Gly Arg Xaa Asp Arg
1               5                   10

<210> SEQ ID NO 7
<211> LENGTH: 4
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate

<400> SEQUENCE: 7

Ser Cys Tyr Arg
1

<210> SEQ ID NO 8
<211> LENGTH: 5
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (1)..(1)
<223> OTHER INFORMATION: Nle

<400> SEQUENCE: 8

Xaa Cys His Phe Gly
1               5

<210> SEQ ID NO 9
<211> LENGTH: 9
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
```

```
<220> FEATURE:
<221> NAME/KEY: MOD_RES
<222> LOCATION: (2)..(2)
<223> OTHER INFORMATION: Nle

<400> SEQUENCE: 9

Arg Xaa Asp Arg Ile Ser Cys Tyr Arg
1               5

<210> SEQ ID NO 10
<211> LENGTH: 6
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (1)..(1)
<223> OTHER INFORMATION: Nle

<400> SEQUENCE: 10

Xaa Cys His Phe Gly Gly
1               5

<210> SEQ ID NO 11
<211> LENGTH: 8
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (1)..(1)
<223> OTHER INFORMATION: Nle

<400> SEQUENCE: 11

Xaa Asp Arg Ile Ser Cys Tyr Arg
1               5

<210> SEQ ID NO 12
<211> LENGTH: 12
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (5)..(5)
<223> OTHER INFORMATION: Nle

<400> SEQUENCE: 12

Phe Gly Gly Arg Xaa Asp Arg Ile Ser Cys Tyr Arg
1               5                   10

<210> SEQ ID NO 13
<211> LENGTH: 14
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (1)..(1)
<223> OTHER INFORMATION: Nle
```

```
<220> FEATURE:
<221> NAME/KEY: MOD_RES
<222> LOCATION: (8)..(8)
<223> OTHER INFORMATION: Nle

<400> SEQUENCE: 13

Xaa Cys His Phe Gly Gly Arg Xaa Asp Arg Ile Ser Cys Tyr
1               5                   10

<210> SEQ ID NO 14
<211> LENGTH: 4
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (1)..(1)
<223> OTHER INFORMATION: Nle

<400> SEQUENCE: 14

Xaa Cys His Phe
1

<210> SEQ ID NO 15
<211> LENGTH: 10
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (3)..(3)
<223> OTHER INFORMATION: Nle

<400> SEQUENCE: 15

Gly Arg Xaa Asp Arg Ile Ser Cys Tyr Arg
1               5                   10

<210> SEQ ID NO 16
<211> LENGTH: 6
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (1)..(1)
<223> OTHER INFORMATION: Nle

<400> SEQUENCE: 16

Xaa Cys His Phe Gly Gly
1               5

<210> SEQ ID NO 17
<211> LENGTH: 8
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (1)..(1)
<223> OTHER INFORMATION: Nle
```

```
<400> SEQUENCE: 17

Xaa Asp Arg Ile Ser Cys Tyr Arg
1               5

<210> SEQ ID NO 18
<211> LENGTH: 5
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate

<400> SEQUENCE: 18

Cys His Phe Gly Gly
1               5

<210> SEQ ID NO 19
<211> LENGTH: 12
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 19

Cys His Phe Gly Gly Arg Xaa Asp Arg Ile Ser Cys
1               5                   10

<210> SEQ ID NO 20
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 20

Cys His Phe Gly Gly Arg Xaa Asp Arg Ile Ser Cys Tyr
1               5                   10

<210> SEQ ID NO 21
<211> LENGTH: 10
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (4)..(4)
<223> OTHER INFORMATION: Nle

<400> SEQUENCE: 21

Gly Gly Arg Xaa Asp Arg Ile Ser Cys Tyr
1               5                   10

<210> SEQ ID NO 22
```

```
<211> LENGTH: 8
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (2)..(2)
<223> OTHER INFORMATION: Nle

<400> SEQUENCE: 22

Arg Xaa Asp Arg Ile Ser Cys Tyr
1               5

<210> SEQ ID NO 23
<211> LENGTH: 7
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (1)..(1)
<223> OTHER INFORMATION: Nle

<400> SEQUENCE: 23

Xaa Asp Arg Ile Ser Cys Tyr
1               5

<210> SEQ ID NO 24
<211> LENGTH: 9
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (3)..(3)
<223> OTHER INFORMATION: Nle

<400> SEQUENCE: 24

Gly Arg Xaa Asp Arg Ile Ser Cys Tyr
1               5

<210> SEQ ID NO 25
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 25

Cys Ala Phe Gly Gly Arg Xaa Asp Arg Ile Ser Cys Tyr
1               5                   10

<210> SEQ ID NO 26
<211> LENGTH: 13
<212> TYPE: PRT
<213> ORGANISM: Homo sapiens
<220> FEATURE:
```

-continued

```
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 26

Cys His Ala Gly Gly Arg Xaa Asp Arg Ile Ser Cys Tyr
1               5                   10

<210> SEQ ID NO 27
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 27

Cys His Phe Ala Gly Arg Xaa Asp Arg Ile Ser Cys Tyr
1               5                   10

<210> SEQ ID NO 28
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 28

Cys His Phe Gly Ala Arg Xaa Asp Arg Ile Ser Cys Tyr
1               5                   10

<210> SEQ ID NO 29
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 29

Cys His Phe Gly Gly Ala Xaa Asp Arg Ile Ser Cys Tyr
1               5                   10

<210> SEQ ID NO 30
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
```

```
<400> SEQUENCE: 30

Cys His Phe Gly Gly Arg Ala Asp Arg Ile Ser Cys Tyr
1               5                   10

<210> SEQ ID NO 31
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 31

Cys His Phe Gly Gly Arg Xaa Ala Arg Ile Ser Cys Tyr
1               5                   10

<210> SEQ ID NO 32
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 32

Cys His Phe Gly Gly Arg Xaa Asp Ala Ile Ser Cys Tyr
1               5                   10

<210> SEQ ID NO 33
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 33

Cys His Phe Gly Gly Arg Xaa Asp Arg Ala Ser Cys Tyr
1               5                   10

<210> SEQ ID NO 34
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 34

Cys His Phe Gly Gly Arg Xaa Asp Arg Ile Ala Cys Tyr
1               5                   10
```

```
<210> SEQ ID NO 35
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 35

Cys His Phe Gly Gly Lys Xaa Asp Arg Ile Ser Cys Tyr
1               5                   10

<210> SEQ ID NO 36
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 36

Cys His Phe Gly Gly Arg Xaa Asp Lys Ile Ser Cys Tyr
1               5                   10

<210> SEQ ID NO 37
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 37

Cys His Phe Gly Gly Arg Xaa Asp Arg Ile Ser Cys Ala
1               5                   10

<210> SEQ ID NO 38
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (6)..(6)
<223> OTHER INFORMATION: Orn
<220> FEATURE:
<221> NAME/KEY: MOD_RES
<222> LOCATION: (7)..(7)
<223> OTHER INFORMATION: Nle

<400> SEQUENCE: 38

Cys His Phe Gly Gly Xaa Xaa Asp Arg Ile Ser Cys Tyr
1               5                   10
```

```
<210> SEQ ID NO 39
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (9)..(9)
<223> OTHER INFORMATION: Orn

<400> SEQUENCE: 39

Cys His Phe Gly Gly Arg Xaa Asp Xaa Ile Ser Cys Tyr
1               5                   10

<210> SEQ ID NO 40
<211> LENGTH: 14
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (8)..(8)
<223> OTHER INFORMATION: Nle

<400> SEQUENCE: 40

Leu Cys His Phe Gly Gly Arg Xaa Asp Arg Ile Ser Cys Tyr
1               5                   10

<210> SEQ ID NO 41
<211> LENGTH: 14
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (8)..(8)
<223> OTHER INFORMATION: Nle

<400> SEQUENCE: 41

Val Cys His Phe Gly Gly Arg Xaa Asp Arg Ile Ser Cys Tyr
1               5                   10

<210> SEQ ID NO 42
<211> LENGTH: 14
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (8)..(8)
<223> OTHER INFORMATION: Nle

<400> SEQUENCE: 42

Ile Cys His Phe Gly Gly Arg Xaa Asp Arg Ile Ser Cys Tyr
1               5                   10
```

```
<210> SEQ ID NO 43
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 43

Cys Ala Phe Gly Gly Arg Xaa Asp Arg Ile Ala Cys Tyr
1               5                   10

<210> SEQ ID NO 44
<211> LENGTH: 11
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (6)..(6)
<223> OTHER INFORMATION: Nle

<400> SEQUENCE: 44

Cys Phe Gly Gly Arg Xaa Asp Arg Ile Cys Tyr
1               5                   10

<210> SEQ ID NO 45
<211> LENGTH: 9
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (8)..(8)
<223> OTHER INFORMATION: Nle

<400> SEQUENCE: 45

Xaa Cys His Phe Gly Gly Arg Xaa Asp
1               5

<210> SEQ ID NO 46
<211> LENGTH: 5
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate

<400> SEQUENCE: 46

Ile Ser Cys Tyr Arg
1               5

<210> SEQ ID NO 47
<211> LENGTH: 10
```

```
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 47

Cys His Phe Gly Gly Arg Xaa Asp Arg Ile
1               5                   10

<210> SEQ ID NO 48
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate

<400> SEQUENCE: 48

Cys His Phe Gly Gly Arg Val Asp Arg Ile Ser Cys Tyr
1               5                   10

<210> SEQ ID NO 49
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate

<400> SEQUENCE: 49

Cys His Phe Gly Gly Arg Ile Asp Arg Ile Ser Cys Tyr
1               5                   10

<210> SEQ ID NO 50
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 50

Cys His Phe Gly Gly Arg Xaa Asp Arg Val Ser Cys Tyr
1               5                   10

<210> SEQ ID NO 51
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 51
```

```
Cys His Phe Gly Gly Arg Xaa Asp Arg Leu Ser Cys Tyr
1               5                   10
```

<210> SEQ ID NO 52
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 52

```
Cys His Leu Gly Gly Arg Xaa Asp Arg Ile Ser Cys Tyr
1               5                   10
```

<210> SEQ ID NO 53
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate

<400> SEQUENCE: 53

```
Cys His Phe Gly Gly Arg Leu Asp Arg Ile Ser Cys Tyr
1               5                   10
```

<210> SEQ ID NO 54
<211> LENGTH: 8
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (2)..(2)
<223> OTHER INFORMATION: Nle

<400> SEQUENCE: 54

```
Gly Xaa Asp Arg Ile Ser Cys Tyr
1               5
```

<210> SEQ ID NO 55
<211> LENGTH: 8
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (8)..(8)
<223> OTHER INFORMATION: Nle

<400> SEQUENCE: 55

```
Xaa Cys His Phe Gly Gly Arg Xaa
1               5
```

```
<210> SEQ ID NO 56
<211> LENGTH: 6
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate

<400> SEQUENCE: 56

Arg Ile Ser Cys Tyr Arg
1               5

<210> SEQ ID NO 57
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (6)..(6)
<223> OTHER INFORMATION: Orn
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (9)..(9)
<223> OTHER INFORMATION: Orn

<400> SEQUENCE: 57

Cys Xaa Phe Gly Gly Xaa Xaa Asp Xaa Ile Ser Cys Tyr
1               5                   10

<210> SEQ ID NO 58
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (6)..(6)
<223> OTHER INFORMATION: Orn
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (9)..(9)
<223> OTHER INFORMATION: Orn
<220> FEATURE:
<221> NAME/KEY: MOD_RES
<222> LOCATION: (11)..(11)
<223> OTHER INFORMATION: Orn

<400> SEQUENCE: 58

Cys Xaa Phe Gly Gly Xaa Xaa Asp Xaa Ile Xaa Cys Tyr
1               5                   10
```

```
<210> SEQ ID NO 59
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (11)..(11)
<223> OTHER INFORMATION: Orn

<400> SEQUENCE: 59

Cys His Phe Gly Gly Arg Xaa Asp Arg Ile Xaa Cys Tyr
1               5                   10

<210> SEQ ID NO 60
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 60

Cys His Phe Gly Gly Lys Xaa Asp Lys Ile Ser Cys Tyr
1               5                   10

<210> SEQ ID NO 61
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 61

Cys Lys Phe Gly Gly Arg Xaa Asp Arg Ile Ser Cys Tyr
1               5                   10

<210> SEQ ID NO 62
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (7)..(7)
<223> OTHER INFORMATION: Nle
<220> FEATURE:
```

```
<221> NAME/KEY: MOD_RES
<222> LOCATION: (11)..(11)
<223> OTHER INFORMATION: Orn

<400> SEQUENCE: 62

Cys Xaa Phe Gly Gly Arg Xaa Asp Arg Ile Xaa Cys Tyr
1               5                   10

<210> SEQ ID NO 63
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 63

Cys Lys Phe Gly Gly Arg Xaa Asp Arg Ile Lys Cys Tyr
1               5                   10

<210> SEQ ID NO 64
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (2)..(2)
<223> OTHER INFORMATION: Orn
<220> FEATURE:
<221> NAME/KEY: MOD_RES
<222> LOCATION: (7)..(7)
<223> OTHER INFORMATION: Nle

<400> SEQUENCE: 64

Cys Xaa Phe Gly Gly Arg Xaa Asp Arg Ile Ser Cys Tyr
1               5                   10

<210> SEQ ID NO 65
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (6)..(6)
<223> OTHER INFORMATION: Orn
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (9)..(9)
<223> OTHER INFORMATION: Orn

<400> SEQUENCE: 65

Cys His Phe Gly Gly Xaa Xaa Asp Xaa Ile Ser Cys Tyr
1               5                   10

<210> SEQ ID NO 66
```

```
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 66

Cys His Phe Gly Gly Arg Xaa Asp Arg Ile Ser Cys Lys
1               5                   10

<210> SEQ ID NO 67
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 67

Cys His Phe Gly Gly Arg Xaa Asp Arg Ile Ser Cys Tyr
1               5                   10

<210> SEQ ID NO 68
<211> LENGTH: 14
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 68

Cys His Phe Gly Gly Arg Xaa Asp Arg Ile Ser Cys Tyr Ala
1               5                   10

<210> SEQ ID NO 69
<211> LENGTH: 14
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 69

Cys His Phe Gly Gly Arg Xaa Asp Arg Ile Ser Cys Tyr Arg
1               5                   10

<210> SEQ ID NO 70
<211> LENGTH: 15
<212> TYPE: PRT
<213> ORGANISM: Homo sapiens
<220> FEATURE:
```

```
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 70

Cys His Phe Gly Gly Arg Xaa Asp Arg Ile Ser Cys Tyr Ala Arg
1               5                   10                  15

<210> SEQ ID NO 71
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 71

Cys His Phe Gly Gly Arg Xaa Asp Arg Ile Ser Cys Phe
1               5                   10

<210> SEQ ID NO 72
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle
<220> FEATURE:
<221> NAME/KEY: MISC_FEATURE
<222> LOCATION: (9)..(10)
<223> OTHER INFORMATION: peptide bond through side chains of Asp and Arg

<400> SEQUENCE: 72

Cys His Phe Gly Gly Arg Xaa Asp Arg Ile Ser Cys Tyr
1               5                   10

<210> SEQ ID NO 73
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (10)..(10)
<223> OTHER INFORMATION: Aib

<400> SEQUENCE: 73

Cys His Phe Gly Gly Arg Xaa Asp Arg Xaa Ser Cys Tyr
1               5                   10

<210> SEQ ID NO 74
```

```
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Aib

<400> SEQUENCE: 74

Cys His Phe Gly Gly Arg Xaa Asp Arg Ile Ser Cys Tyr
1               5                   10

<210> SEQ ID NO 75
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (5)..(5)
<223> OTHER INFORMATION: Aib
<220> FEATURE:
<221> NAME/KEY: MOD_RES
<222> LOCATION: (7)..(7)
<223> OTHER INFORMATION: Nle

<400> SEQUENCE: 75

Cys His Phe Gly Xaa Arg Xaa Asp Arg Ile Ser Cys Tyr
1               5                   10

<210> SEQ ID NO 76
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (4)..(4)
<223> OTHER INFORMATION: Aib
<220> FEATURE:
<221> NAME/KEY: MOD_RES
<222> LOCATION: (7)..(7)
<223> OTHER INFORMATION: Nle

<400> SEQUENCE: 76

Cys His Phe Xaa Gly Arg Xaa Asp Arg Ile Ser Cys Tyr
1               5                   10

<210> SEQ ID NO 77
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 77

Cys His Phe Gly Gly Arg Xaa Lys Arg Ile Ser Cys Tyr
```

<210> SEQ ID NO 78
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (8)..(8)
<223> OTHER INFORMATION: Orn

<400> SEQUENCE: 78

Cys His Phe Gly Gly Arg Xaa Xaa Arg Ile Ser Cys Tyr
1               5                   10

<210> SEQ ID NO 79
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: 2-amino-2-butyl-hexanoic acid

<400> SEQUENCE: 79

Cys His Phe Gly Gly Arg Xaa Asp Arg Ile Ser Cys Tyr
1               5                   10

<210> SEQ ID NO 80
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Aib

<400> SEQUENCE: 80

Cys His Phe Gly Gly Arg Xaa Asp Arg Ile Ser Cys Tyr
1               5                   10

<210> SEQ ID NO 81
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (4)..(4)
<223> OTHER INFORMATION: Aib
<220> FEATURE:
<221> NAME/KEY: MOD_RES
<222> LOCATION: (7)..(7)
<223> OTHER INFORMATION: Nle

```
<400> SEQUENCE: 81

Cys His Phe Xaa Gly Arg Xaa Asp Arg Ile Ser Cys Tyr
1               5                   10

<210> SEQ ID NO 82
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (5)..(5)
<223> OTHER INFORMATION: Aib
<220> FEATURE:
<221> NAME/KEY: MOD_RES
<222> LOCATION: (7)..(7)
<223> OTHER INFORMATION: Nle

<400> SEQUENCE: 82

Cys His Phe Gly Xaa Arg Xaa Asp Arg Ile Ser Cys Tyr
1               5                   10

<210> SEQ ID NO 83
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of pegylated derivative of human ANP
      with non-amino acid surrogate
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(2)
<223> OTHER INFORMATION: conjugated with PET-5K-OSu
<220> FEATURE:
<221> NAME/KEY: MOD_RES
<222> LOCATION: (7)..(7)
<223> OTHER INFORMATION: Nle

<400> SEQUENCE: 83

Cys Xaa Phe Gly Gly Arg Xaa Asp Arg Ile Ser Cys Tyr
1               5                   10

<210> SEQ ID NO 84
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of pegylated derivative of human ANP
      with non-amino acid surrogate
<220> FEATURE:
<221> NAME/KEY: MISC_FEATURE
<222> LOCATION: (6)..(6)
<223> OTHER INFORMATION: conjugated with PEG-5K-OSu
<220> FEATURE:
<221> NAME/KEY: MOD_RES
<222> LOCATION: (7)..(7)
<223> OTHER INFORMATION: Nle

<400> SEQUENCE: 84

Cys His Phe Gly Gly Lys Xaa Asp Arg Ile Ser Cys Tyr
1               5                   10
```

```
<210> SEQ ID NO 85
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of pegylated derivative of human ANP
      with non-amino acid surrogate
<220> FEATURE:
<221> NAME/KEY: MOD_RES
<222> LOCATION: (7)..(7)
<223> OTHER INFORMATION: Nle
<220> FEATURE:
<221> NAME/KEY: MISC_FEATURE
<222> LOCATION: (8)..(8)
<223> OTHER INFORMATION: conjugated with PEG-5K-OSu

<400> SEQUENCE: 85

Cys His Phe Gly Gly Arg Xaa Lys Arg Ile Ser Cys Tyr
1               5                   10

<210> SEQ ID NO 86
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of pegylated derivative of human ANP
      with non-amino acid surrogate
<220> FEATURE:
<221> NAME/KEY: MISC_FEATURE
<222> LOCATION: (2)..(2)
<223> OTHER INFORMATION: conjugated with PEG-5K-OSu
<220> FEATURE:
<221> NAME/KEY: MOD_RES
<222> LOCATION: (7)..(7)
<223> OTHER INFORMATION: Nle

<400> SEQUENCE: 86

Cys Lys Phe Gly Gly Arg Xaa Asp Arg Ile Ser Cys Tyr
1               5                   10

<210> SEQ ID NO 87
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of pegylated derivative of human ANP
      with non-amino acid surrogate
<220> FEATURE:
<221> NAME/KEY: MOD_RES
<222> LOCATION: (6)..(6)
<223> OTHER INFORMATION: Orn
<220> FEATURE:
<221> NAME/KEY: MISC_FEATURE
<222> LOCATION: (6)..(6)
<223> OTHER INFORMATION: conjugated with PEG-5K-OSu
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (9)..(9)
<223> OTHER INFORMATION: Orn
<220> FEATURE:
<221> NAME/KEY: MISC_FEATURE
<222> LOCATION: (9)..(9)
<223> OTHER INFORMATION: conjugated with PEG-5K-OSu

<400> SEQUENCE: 87

Cys His Phe Gly Gly Xaa Xaa Asp Xaa Ile Ser Cys Tyr
1               5                   10
```

```
<210> SEQ ID NO 88
<211> LENGTH: 8
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (7)..(7)
<223> OTHER INFORMATION: Nle

<400> SEQUENCE: 88

Cys His Phe Gly Gly Arg Xaa Asp
1               5

<210> SEQ ID NO 89
<211> LENGTH: 4
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate

<400> SEQUENCE: 89

Ile Ser Cys Tyr
1

<210> SEQ ID NO 90
<211> LENGTH: 14
<212> TYPE: PRT
<213> ORGANISM: Homo sapiens
<220> FEATURE:
<221> NAME/KEY: MISC_FEATURE
<223> OTHER INFORMATION: Portion of derivative of human ANP with non-
      amino acid surrogate
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (8)..(8)
<223> OTHER INFORMATION: Nle

<400> SEQUENCE: 90

Xaa Cys His Phe Gly Gly Arg Xaa Asp Arg Ile Ser Cys Tyr
1               5                   10

<210> SEQ ID NO 91
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of pegylated derivative of human ANP
      with non-amino acid surrogate
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(2)
<223> OTHER INFORMATION: conjugated with PEG-5K-OSu
<220> FEATURE:
<221> NAME/KEY: MOD_RES
<222> LOCATION: (6)..(6)
<223> OTHER INFORMATION: Orn
<220> FEATURE:
<221> NAME/KEY: MISC_FEATURE
```

```
<222> LOCATION: (6)..(6)
<223> OTHER INFORMATION: conjugated with PEG-5K-OSu
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (9)..(9)
<223> OTHER INFORMATION: Orn
<220> FEATURE:
<221> NAME/KEY: MISC_FEATURE
<222> LOCATION: (9)..(9)
<223> OTHER INFORMATION: conjugated with PEG-5K-OSu
<220> FEATURE:
<221> NAME/KEY: MOD_RES
<222> LOCATION: (11)..(11)
<223> OTHER INFORMATION: Orn
<220> FEATURE:
<221> NAME/KEY: MISC_FEATURE
<222> LOCATION: (11)..(11)
<223> OTHER INFORMATION: conjugated with PEG-5K-OSu

<400> SEQUENCE: 91

Cys Xaa Phe Gly Gly Xaa Xaa Asp Xaa Ile Xaa Cys Tyr
1               5                   10

<210> SEQ ID NO 92
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of pegylated derivative of human ANP
      with non-amino acid surrogate
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(2)
<223> OTHER INFORMATION: conjugated with PEG-5K-OSu
<220> FEATURE:
<221> NAME/KEY: MOD_RES
<222> LOCATION: (6)..(6)
<223> OTHER INFORMATION: Orn
<220> FEATURE:
<221> NAME/KEY: MISC_FEATURE
<222> LOCATION: (6)..(6)
<223> OTHER INFORMATION: conjugated with PEG-5K-OSu
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (9)..(9)
<223> OTHER INFORMATION: Orn
<220> FEATURE:
<221> NAME/KEY: MISC_FEATURE
<222> LOCATION: (9)..(9)
<223> OTHER INFORMATION: conjugated with PEG-5K-OSu

<400> SEQUENCE: 92

Cys Xaa Phe Gly Gly Xaa Xaa Asp Xaa Ile Ser Cys Tyr
1               5                   10

<210> SEQ ID NO 93
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of pegylated derivative of human ANP
      with non-amino acid surrogate
```

```
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(2)
<223> OTHER INFORMATION: conjugated with PEG-5K-OSu
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (11)..(11)
<223> OTHER INFORMATION: Orn
<220> FEATURE:
<221> NAME/KEY: MISC_FEATURE
<222> LOCATION: (11)..(11)
<223> OTHER INFORMATION: conjugated with PEG-5K-OSu

<400> SEQUENCE: 93

Cys Xaa Phe Gly Gly Arg Xaa Asp Arg Ile Xaa Cys Tyr
1               5                   10

<210> SEQ ID NO 94
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of pegylated derivative of human ANP
      with non-amino acid surrogate
<220> FEATURE:
<221> NAME/KEY: MISC_FEATURE
<222> LOCATION: (2)..(2)
<223> OTHER INFORMATION: conjugated with PEG-5K-OSu
<220> FEATURE:
<221> NAME/KEY: MOD_RES
<222> LOCATION: (7)..(7)
<223> OTHER INFORMATION: Nle
<220> FEATURE:
<221> NAME/KEY: MISC_FEATURE
<222> LOCATION: (11)..(11)
<223> OTHER INFORMATION: conjugated with PEG-5K-OSu

<400> SEQUENCE: 94

Cys Lys Phe Gly Gly Arg Xaa Asp Arg Ile Lys Cys Tyr
1               5                   10

<210> SEQ ID NO 95
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of pegylated derivative of human ANP
      with non-amino acid surrogate
<220> FEATURE:
<221> NAME/KEY: MISC_FEATURE
<222> LOCATION: (6)..(6)
<223> OTHER INFORMATION: conjugated with PEG-5K-OSu
<220> FEATURE:
<221> NAME/KEY: MOD_RES
<222> LOCATION: (7)..(7)
<223> OTHER INFORMATION: Nle
<220> FEATURE:
<221> NAME/KEY: MISC_FEATURE
<222> LOCATION: (9)..(9)
<223> OTHER INFORMATION: conjugated with PEG-5K-OSu

<400> SEQUENCE: 95

Cys His Phe Gly Gly Lys Xaa Asp Lys Ile Ser Cys Tyr
1               5                   10
```

<210> SEQ ID NO 96
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of pegylated derivative of human ANP
      with non-amino acid surrogate
<220> FEATURE:
<221> NAME/KEY: MOD_RES
<222> LOCATION: (7)..(7)
<223> OTHER INFORMATION: Nle
<220> FEATURE:
<221> NAME/KEY: MISC_FEATURE
<222> LOCATION: (9)..(9)
<223> OTHER INFORMATION: conjugated with PEG-5K-OSu

<400> SEQUENCE: 96

Cys His Phe Gly Gly Arg Xaa Asp Lys Ile Ser Cys Tyr
1               5                   10

<210> SEQ ID NO 97
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of pegylated derivative of human ANP
      with non-amino acid surrogate
<220> FEATURE:
<221> NAME/KEY: MISC_FEATURE
<222> LOCATION: (2)..(2)
<223> OTHER INFORMATION: conjugated with PEG-5K-OSu
<220> FEATURE:
<221> NAME/KEY: MOD_RES
<222> LOCATION: (7)..(7)
<223> OTHER INFORMATION: Nle
<220> FEATURE:
<221> NAME/KEY: MISC_FEATURE
<222> LOCATION: (9)..(9)
<223> OTHER INFORMATION: conjugated with PEG-5K-OSu

<400> SEQUENCE: 97

Cys Lys Phe Gly Gly Arg Xaa Asp Lys Ile Ser Cys Tyr
1               5                   10

<210> SEQ ID NO 98
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of pegylated derivative of human ANP
      with non-amino acid surrogate
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(2)
<223> OTHER INFORMATION: conjugated with PEG-5K-OSu
<220> FEATURE:
<221> NAME/KEY: MOD_RES
<222> LOCATION: (7)..(7)
<223> OTHER INFORMATION: Nle
<220> FEATURE:
<221> NAME/KEY: MOD_RES
<222> LOCATION: (9)..(9)
<223> OTHER INFORMATION: Orn
<220> FEATURE:
<221> NAME/KEY: MISC_FEATURE
<222> LOCATION: (9)..(9)
<223> OTHER INFORMATION: conjugated with PEG-5K-OSu

```
<400> SEQUENCE: 98

Cys Xaa Phe Gly Gly Arg Xaa Asp Xaa Ile Ser Cys Tyr
 1               5                  10

<210> SEQ ID NO 99
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of pegylated derivative of human ANP
      with non-amino acid surrogate
<220> FEATURE:
<221> NAME/KEY: MISC_FEATURE
<222> LOCATION: (2)..(2)
<223> OTHER INFORMATION: conjugated with PEG-5K-OSu
<220> FEATURE:
<221> NAME/KEY: MISC_FEATURE
<222> LOCATION: (6)..(6)
<223> OTHER INFORMATION: conjugated with PEG-5K-OSu
<220> FEATURE:
<221> NAME/KEY: MOD_RES
<222> LOCATION: (7)..(7)
<223> OTHER INFORMATION: Nle

<400> SEQUENCE: 99

Cys Lys Phe Gly Gly Lys Xaa Asp Arg Ile Ser Cys Tyr
 1               5                  10

<210> SEQ ID NO 100
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of pegylated derivative of human ANP
      with non-amino acid surrogate
<220> FEATURE:
<221> NAME/KEY: MOD_RES
<222> LOCATION: (2)..(2)
<223> OTHER INFORMATION: Orn
<220> FEATURE:
<221> NAME/KEY: MISC_FEATURE
<222> LOCATION: (2)..(2)
<223> OTHER INFORMATION: conjugated with PEG-5K-OSu
<220> FEATURE:
<221> NAME/KEY: MOD_RES
<222> LOCATION: (6)..(6)
<223> OTHER INFORMATION: Orn
<220> FEATURE:
<221> NAME/KEY: MISC_FEATURE
<222> LOCATION: (6)..(6)
<223> OTHER INFORMATION: conjugated with PEG-5K-OSu
<220> FEATURE:
<221> NAME/KEY: MOD_RES
<222> LOCATION: (7)..(7)
<223> OTHER INFORMATION: Nle

<400> SEQUENCE: 100

Cys Xaa Phe Gly Gly Xaa Xaa Asp Arg Ile Ser Cys Tyr
 1               5                  10

<210> SEQ ID NO 101
<211> LENGTH: 13
<212> TYPE: PRT
<213> ORGANISM: Homo sapiens
<220> FEATURE:
<221> NAME/KEY: MISC_FEATURE
<223> OTHER INFORMATION: Portion of pegylated derivative of human ANP
      with non-amino acid surrogate
<220> FEATURE:
<221> NAME/KEY: MOD_RES
<222> LOCATION: (7)..(7)
<223> OTHER INFORMATION: Nle
```

<220> FEATURE:
<221> NAME/KEY: MISC_FEATURE
<222> LOCATION: (11)..(11)
<223> OTHER INFORMATION: conjugated with PEG-5K-OSu

<400> SEQUENCE: 101

Cys His Phe Gly Gly Arg Xaa Asp Arg Ile Lys Cys Tyr
1               5                   10

CYCLIC NATRIURETIC PEPTIDE CONSTRUCTS

CROSS-REFERENCE TO RELATED APPLICATIONS

This application is a continuation application to U.S. Ser. No. 11/694,260 entitled "Cyclic Natriuretic Peptide Constructs", filed on Mar. 30, 2007, now U.S. Pat. No. 7,622,440, issued on Nov. 24, 2009.

U.S. Ser. No. 11/694,260 claims priority to and the benefit of the filing of U.S. Provisional Patent Application Ser. No. 60/743,960 entitled "Cyclic Natriuretic Peptide Constructs", filed on Mar. 30, 2006, and of U.S. Provisional Patent Application Ser. No. 60/743,961 entitled "Cyclic Natriuretic Peptide Constructs with Prosthetic Groups", filed on Mar. 30, 2006, and the specification and claims thereof of each are incorporated herein by reference.

A related application entitled "Amino Acid Surrogates for Peptidic Constructs" was filed on Mar. 30, 2007, U.S. patent application Ser. No. 11/694,181, and the specification and claims thereof are incorporated herein by reference.

BACKGROUND OF THE INVENTION

1. Field of the Invention (Technical Field)

The present invention relates to cyclic natriuretic peptide constructs which include a plurality of amino acid residues, one or more ring-constrained amino acid surrogates and optionally one or more prosthetic groups, which constructs bind a natriuretic peptide receptor and may be employed for therapeutic purposes.

2. Background Art

The natriuretic peptide system has been extensively explored since the identification of the human atrial natriuretic peptide (ANP) sequence and gene structure in 1984. ANP is sometimes also called "ANF", or atrial natriuretic factor. ANP is part of the natriuretic peptide system, which in humans involves an ANP gene, which through differences in post-translational processing results in both ANP and urodilatin, a gene which produces BNP, or brain natriuretic peptide, and a gene which produces CNP, or c-type natriuretic peptide. ANP, urodilatin, BNP and CNP are each ring structures, with a 17 amino acid loop formed by a cysteine-cysteine disulfide linkage. The amino acid sequence and structure of human ANP (hANP) is shown in FIG. 1. ANP, urodilatin, BNP and CNP are closely related, differing by some five or six amino acids within the ring, though the N- and C-terminal tails are substantially different.

There are three known natriuretic peptide receptors called natriuretic peptide receptors A, B and C (NPRA, NPRB and NPRC). NPRA and NPRB are linked to guanylyl cyclases, while NPRC is a G-protein linked clearance receptor. ANP, BNP and CNP are the primary endogenous mammalian natriuretic peptides identified to date. However, there are a number of non-mammalian natriuretic peptides that have been identified and may have therapeutic application in mammals. These include salmon natriuretic or cardiac peptide (sCP), ventricular natriuretic peptide (VNP), a cardiac natriuretic peptide identified in eels and a variety of fish, dendroaspis natriuretic peptide (DNP), a natriuretic peptide identified in mamba snake venom, and three natriuretic-like peptides (TNP-a, TNP-b, and TNP-c) isolated from taipan snake venom. See generally Tervonen V, Ruskoaho H, Lecklin T, Ilves M, Vuolteenaho O, Salmon cardiac natriuretic peptide is a volume-regulating hormone. *Am. J. Physiol. Endocrinol. Metab.* 283:E353-61 (2002); Takei Y, Fukuzawa A, Itahara Y, Watanabe T X, Yoshizawa Kumagaye K, Nakajima K, Yasuda A, Smith M P, Duff D W, Olson K R. A new natriuretic peptide isolated from cardiac atria of trout, *Oncorhynchus mykiss. FEBS Lett.* 414:377-80 (1997); Schweitz H, Vigne P, Moinier D, Frelin C, Lazdunski M. A new member of the natriuretic peptide family is present in the venom of the green mamba (*Dendroaspis angusticeps*). *J. Biol. Chem.* 267:13928-32 (1992); Lisy O, Jougasaki M, Heublein D M, Schirger J A, Chen H H, Wennberg P W, Burnett J C. Renal actions of synthetic dendroaspis natriuretic peptide. *Kidney Int.* 56:502-8 (1999); and Fry B G, Wickramaratana J C, Lemme S, Beuve A, Garbers D, Hodgson W C, Alewood P. Novel natriuretic peptides from the venom of the inland (*Oxyuranus microlepidotus*): isolation, chemical and biological characterisation. *Biochem. Biophys. Res. Comm.* 327:1011-1015 (2005).

ANP is endogenously secreted predominately in response to increased atrial pressure, but other factors, including cytokine receptor stimulation, may contribute to endogenous secretion. Once released, ANP is a hormonal regulator of blood pressure, sodium and fluid homeostasis, providing vasorelaxant effects, affecting cardiovascular remodeling, and the like. Thus ANP, including endogenous ANP, is effective in congestive heart failure and other cardiovascular disease, in part by providing a defense against a chronically activated renin-angiotensin-aldosterone system. Circulating ANP is rapidly removed from the circulation by two mechanisms, binding to a natriuretic peptide receptor and enzymatic degradation.

Human ANP is also referred to as wild-type human ANP, hANP, ANP(1-28) and ANP(99-126) (the later referring to the relevant sequence within proANP(1-126), which is normally cleaved at $Arg^{98}$-$Ser^{99}$ in the C-terminal region during secretion). Hereafter human ANP is sometimes referred to as "hANP."

In general, natriuretic peptides and variants thereof are believed to have utility in the treatment of congestive heart failure, renal hypertension, acute kidney failure and related conditions, as well as any condition, disease or syndrome for which a diuretic, natriuretic and/or vasodilatory response would have a therapeutic or preventative effect. One review article describing natriuretic peptides, including ANP, and use of the natriuretic peptide system in heart failure is Schmitt M., Cockcroft J. R., and Frenneaux M. P. Modulation of the natriuretic peptide system in heart failure: from bench to bedside? *Clinical Science* 105:141-160 (2003).

A large number of ANP mimetics and variations have been made, some of which are substantially reduced in size from ANP. On ANP version that is reduced in size yet is biologically active is the 15-mer disulfide cyclic peptide H-Met-cyclo(Cys-His-Phe-Gly-Gly-Arg-Met-Asp-Arg-Ile-Ser-Cys)-Tyr-Arg-$NH_2$ (SEQ ID NO:1) as described in Li B, Tom J Y, Oare D, Yen R, Fairbrother W J, Wells J A, Cunningham B C. Minimization of a polypeptide hormone. *Science* 270: 1657-60 (1995). This 15-mer peptide is commonly referred to as "mini-ANP".

A number of patents and patent applications have been filed on different synthetic mimics of natriuretic peptides, asserted to be superior to wild-type natriuretic peptides based on one or more factors. These include the constructs disclosed in the following U.S. Pat. Nos. 4,496,544; 4,609,725; 4,656, 158; 4,673,732; 4,716,147; 4,757,048; 4,764,504; 4,804,650; 4,816,443; 4,824,937; 4,861,755; 4,904,763; 4,935,492; 4,952,561; 5,047,397; 5,057,495; 5,057,603; 5,091,366; 5,095,004; 5,106,834; 5,114,923; 5,159,061; 5,204,328; 5,212,286; 5,352,587; 5,376,635; 5,418,219; 5,665,704; 5,846,932; 5,583,108; 5,965,533; 6,028,055; 6,083,982; 6,124,430; 6,150,402; 6,407,211; 6,525,022; 6,586,396 and 6,818,619; and in the following U.S. Patent Application Publications: 2004/0002458; 2004/0063630; 2004/0077537; 2005/0113286; 2005/0176641; 2006/0030004. In addition, various non-U.S. patents and patent applications disclose constructs, including: WO 85/04870; WO 85/04872; WO 88/03537; WO 88/06596; WO 89/10935; WO 89/05654; WO 90/01940; WO 90/14362; WO 92/06998; WO 95/13296; WO 99/08510; WO 99/12576; WO 01/016295; WO 2004/047871; WO 2005/072055; EPO 0 291 999; EPO 0 323 740; EPO 0 341 603; EPO 0 350 318; EPO 0 356 124; EPO 0 385 476; EPO 0 497 368; and EPO 0 542 863. Chimeric natriuretic peptides, such as a peptide call "vasonatrin peptide" and described as a chimera of ANP and CNP, are described, as in U.S. Pat. No. 5,583,108, or in U.S. Pat. Nos. 6,407,211 and 6,818,619, disclosing chimeric peptides of dendroaspis. The teachings of each of the foregoing patents and patent applications are incorporated by reference as if set forth in full.

There is one natriuretic peptide product approved by the Food and Drug Administration in the United States, sold under the generic name nestiritide and the tradename Natrecor® (Scios Inc.). This is a human B-type natriuretic peptide manufactured from *E. coli* using recombinant DNA technology. This product is approved only for intravenous infusion for treatment of patients with actutely decompensated congestive heart failure who have dyspnea at rest or with minimal activity. While effective, the pharmacokinetics and half-life of nestiritide are such that the product can only be employed by intravenous infusion, which limits use of the drug to a hospital or skilled medical center setting.

Notwithstanding the large number of compounds that have been developed, virtually none are commercialized or in active clinical development. There is a substantial need for products with improved characteristics, including improved potency, half-life, modes of administration, bioavailability or prolonged duration of effect, which products are effective for one or more therapeutic indications, and which preferably may be administered on an out-patient basis.

BRIEF SUMMARY OF THE INVENTION

In one aspect the invention provides a cyclic construct which binds to a receptor for a natriuretic peptide, including but not limited to a receptor for ANP, BNP, CNP, sCP, DNP, TNP-a, TNP-b or TNP-c, wherein such construct includes a plurality of amino acid residues, at least one amino acid surrogate of the general formula I:

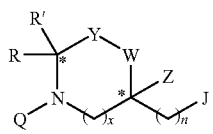

(I)

where R and R' are each independently H or a natural or unnatural amino acid side chain moiety or derivative of an amino acid side chain moiety; x is 1 or 2; Y is $CH_2$ or C=O; W is $CH_2$, NH or NR'''; Z is H or $CH_3$; n is 0, 1 or 2; J is —C(=O)— unless the surrogate is at the C-terminus position of the construct, in which case J is —H, —OH, —C(=O)—OH, —C(=O)—$NH_2$ or a C-terminus capping group; Q is a bond unless the surrogate is at the N-terminus position of the construct, in which case Q is —H or an amine capping group; R''' is an acyl, a $C_1$ to $C_{17}$ linear or branched alkyl chain, a $C_2$ to $C_{19}$ linear or branched alkyl acyl chain, a $C_1$ to $C_{17}$ linear or branched omega amino aliphatic, or a $C_1$ to $C_{17}$ linear or branched omega amino aliphatic acyl; optionally at least one prosthetic group covalently bonded to a reactive group in a side chain of at least one of the amino acid residues, to an amine capping group where the surrogate is at the N-terminus position of the construct, or to a C-terminus capping group where the surrogate is at the C-terminus position of the construct; and the carbon atoms marked with an asterisk can have any stereochemical configuration. The construct is a cyclic construct, cyclized by a bond between side chains of two amino acid residues, between an amino acid residue side chain and an R or R' group of an amino acid surrogate, between R or R' groups of two amino acid surrogates, between a terminal group of the construct and an amino acid residue side chain, or between a terminal group of the construct and an R or R' group of an amino acid surrogate. Preferable the two amino acid residues forming a bond between the side chains thereof are separated by between about eight and ten amino acid residues and optionally zero, one or two amino acid surrogates. The plurality of amino acid residues may include any amino acid residue selected from the group consisting of natural or unnatural α-amino acids, β-amino acids, α,α-disubstituted amino acids and N-substituted amino acids, including all (R) or (S) configurations of any of the foregoing.

The prosthetic group(s) may include polymeric groups comprising repeat units including one or more carbon and hydrogen atoms, and optionally other atoms, including oxygen. Such polymeric groups are preferably water-soluble polymers, and are preferably poly(alkylene oxide), poly(vinyl pyrrolidone), poly(vinyl alcohol), polyoxazoline or poly(acryloylmorpholine). A preferred poly(alkylene oxide) is poly(ethylene glycol) (PEG), optionally derivatized with a linking group.

In one aspect, J is a C-terminus capping group selected from
—$(CH_2)_m$—OH,
—C(=O)—$(CH_2)_m$—N($v_1$)($v_2$),
—C(=O)—O—$(CH_2)_m$—$CH_3$,
—O—$(CH_2)_m$—$CH_3$,
—O—$(CH_2)_m$—N($v_1$)($v_2$),
—O—$(CH_2)_m$—OH,
—C(=O)—NH—$(CH_2)_m$—S($v_1$),
—C(=O)—NH—$(CH_2)_m$—$CH_3$,
—C(=O)—NH—$(CH_2)_m$—N($v_1$)($v_2$),
—C(=O)—N—(($CH_2)_m$—N($v_1$)($v_2$))$_2$,
—C(=O)—NH—CH(—C(=O)—OH)—$(CH_2)_m$—N($v_1$)($v_2$),
—C(=O)—NH—$(CH_2)_m$—NH—C(=O)—CH(N($v_1$)($v_2$))(($CH_2)_m$—N($v_1$)($v_2$)), or
—C(=O)—NH—CH(—C(=O)—N($v_1$)($v_2$))—$(CH_2)_m$—N($v_1$)($v_2$);
including all (R) or (S) configurations of the foregoing, where $v_1$ and $v_2$ are each independently H or a $C_1$ to $C_{17}$ linear or branched alkyl chain and m is in each instance independently 0 to 17.

In another aspect where the amino acid surrogate is at the C-terminus position of the construct, J is a C-terminus capping group consisting of an omega amino aliphatic, terminal aryl or aralkyl group or any single natural or unnatural α-amino acid, β-amino acid, α,α-disubstituted amino acid or N-substituted amino acid, including all (R) or (S) configurations of an α,α-disubstituted amino acid where the substituents are different, optionally in combination with a C-terminus capping group as defined above.

In another aspect, Q is an amine capping group selected from
—$(CH_2)_m$—N($v_3$)($v_4$),
—$(CH_2)_m$—$CH_3$, —$(CH_2)_m$—$O(v_3)$,
—$(CH_2)_m$—$C(=O)$-$(v_3)$,
—$(CH_2)_m$—$C(=O)$—$O$-$(v_3)$,
—$(CH_2)_m$—$S(v_3)$,
—$C(=O)$—$(CH_2)_m$—$CH_3$,
—$C(=O)$—$(CH_2)_m$—$N(v_3)(v_4)$,
—$C(=O)$—$(CH_2)_m$—$C(=O)$-$(v_3)$,
—$C(=O)$—$(CH_2)_m$—$O(v_3)$, or
—$C(=O)$—$(CH_2)_m$—$S(v_3)$;
where $v_3$ and $v_4$ are each independently H, a $C_1$ to $C_{17}$ linear or branched alkyl chain or a $C_2$ to $C_{19}$ linear or branched alkyl acyl chain, on the proviso that if one of $v_3$ or $v_4$ is an alkyl acyl chain, then the other of $v_3$ or $v_4$ is H, and m is 0 to 17.

In a related aspect, an amino acid surrogate of formula I is at the C-terminus position of the construct, and at least one of R and R' is a natural or unnatural amino acid side chain moiety or derivative of an amino acid side chain moiety with a heteroatom group comprising at least one nitrogen atom, and the remaining one of R and R' is H or a natural or unnatural amino acid side chain moiety or derivative of an amino acid side chain moiety.

In a related embodiment, the invention provides a construct which binds to a receptor for a natriuretic peptide, including but not limited to a receptor for ANP, BNP, CNP, sCP, DNP, TNP-a, TNP-b or TNP-c, wherein such construct includes a plurality of amino acid residues and at least one amino acid surrogate located at any position other than the C-terminus position or N-terminus position and covalently bonded by two peptide bonds, and of formula II:

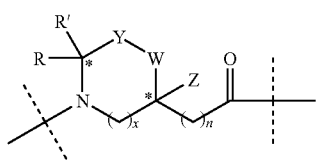

(II)

where R and R' are each independently H or a natural or unnatural amino acid side chain moiety or derivative of an amino acid side chain moiety; x is 1 or 2; Y is $CH_2$ or $C=O$; W is $CH_2$, NH or NR'''; Z is H or $CH_3$; R''' is an acyl, a $C_1$ to $C_{17}$ linear or branched alkyl chain, a $C_2$ to $C_{19}$ linear or branched alkyl acyl chain, a $C_1$ to $C_{17}$ linear or branched omega amino aliphatic, or a $C_1$ to $C_{17}$ linear or branched omega amino aliphatic acyl; n is 0, 1 or 2; the carbon atoms marked with an asterisk can have any stereochemical configuration; and the broken lines indicate the bond forming a peptide bond.

Where the surrogate of formula I is at the C-terminus of the construct, it is covalently bonded thereto by a single peptide bond, such that the surrogate has the formula:

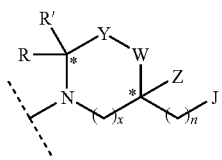

where the broken line indicates the bond forming a peptide bond. Where the surrogate is at the N-terminus of the construct it is preferably of formula I, and is covalently bonded thereto by a single bond peptide bond, such that the surrogate has the formula:

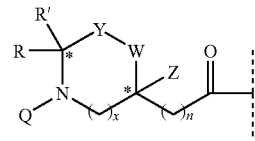

where the broken line indicates the bond forming a peptide bond. However, where the surrogate is at other than at the N-terminus or C-terminus of the construct, it is preferably of formula II and is covalently bonded thereto by two peptide bonds.

In different embodiments of the invention, one amino acid surrogate may be employed in a construct of the invention, two amino acid surrogates may be employed in a construct of the invention, or more than two amino acid surrogates may be employed in a construct of the invention.

In another preferred embodiment, the invention provides a construct wherein one or more peptide bonds between amino acid residues are substituted with a non-peptide bond.

A primary object of the present invention is to provide natriuretic receptor-specific constructs.

Another object of the present invention is to provide natriuretic receptor-specific constructs wherein one or more amino acid residues are substituted by a ring-constrained amino acid surrogate.

Another object of the present invention is to provide a natriuretic receptor-specific construct wherein the construct exhibits, upon administration to a mammal, one or more advantages relative to the corresponding amino acid sequence not comprising an amino acid surrogate, the advantages selected from the group consisting of increased resistance to enzymatic degradation, increased circulation half life, increased bioavailability, increased efficacy, prolonged duration of effect and combinations of the foregoing.

Another object of the present invention is to provide a natriuretic receptor-specific construct wherein the construct has at least 10% of the maximal cGMP stimulating activity as the same concentration of the corresponding amino acid sequence not comprising an amino acid surrogate.

Another object of the present invention is to provide a natriuretic receptor-specific construct wherein the construct has at least 50% of the maximal cGMP stimulating activity as the same concentration of the corresponding amino acid sequence not comprising an amino acid surrogate.

Another object of the present invention is to provide a natriuretic receptor-specific construct wherein the construct has at least 100% of the maximal cGMP stimulating activity as the same concentration of the corresponding amino acid sequence not comprising an amino acid surrogate.

Another object of the present invention is to provide a natriuretic receptor-specific construct wherein the construct has more than 100% of the maximal cGMP stimulating activity as the same concentration of the corresponding amino acid sequence not comprising an amino acid surrogate.

Another object of the present invention is to provide a natriuretic receptor-specific construct wherein the construct has an equilibrium receptor binding affinity, determined by the Ki (nM) value, no greater than two log orders higher than the Ki (nM) value of the corresponding amino acid sequence not comprising an amino acid surrogate.

Another object of the present invention is to provide a natriuretic receptor-specific construct wherein the construct has an equilibrium receptor binding affinity, determined by the Ki (nM) value, no greater than three times higher than the Ki (nM) value of the corresponding amino acid sequence not comprising an amino acid surrogate.

Another object of the present invention is to provide a natriuretic receptor-specific construct wherein the construct has an equilibrium receptor binding affinity, determined by the Ki (nM) value, equal to or less than than the Ki (nM) value of the corresponding amino acid sequence not comprising an amino acid surrogate.

Another object of the present invention is to provide a natriuretic receptor-specific construct wherein the construct has an equilibrium receptor binding affinity, determined by the Ki (nM) value, less than the Ki (nM) value of the corresponding amino acid sequence not comprising an amino acid surrogate.

Another object of the present invention is to provide a natriuretic receptor-specific construct wherein the construct has a receptor binding affinity with respect to a natriuretic peptide receptor greater than the receptor binding affinity of the corresponding amino acid sequence not comprising an amino acid surrogate.

Another object of the present invention is to provide a natriuretic receptor-specific construct wherein the construct has biological efficacy, determined by decrease in blood pressure or increase in urine output over time, at least as efficacious as or more efficacious than than the same dose of the corresponding amino acid sequence not comprising an amino acid surrogate.

Another object of the present invention is to provide a natriuretic receptor-specific construct wherein the construct has biological efficacy, determined by decrease in blood pressure or increase in urine output over time, more efficacious than the same dose of the corresponding amino acid sequence not comprising an amino acid surrogate.

Another object of the present invention is to provide a natriuretic receptor-specific construct wherein the corresponding amino acid sequence not comprising an amino acid surrogate has at least about 60% homology with the sequence of a natriuretic peptide.

Another object of the present invention is to provide a natriuretic receptor-specific construct wherein the corresponding amino acid sequence not comprising an amino acid surrogate has at least about 80% homology with the sequence of a natriuretic peptide.

Another object of the present invention is to provide a natriuretic receptor-specific construct wherein the corresponding amino acid sequence not comprising an amino acid surrogate has at least about 60% homology with the sequence of a peptide that binds to a receptor for ANP, BNP, CNP, sCP, DNP, TNP-a, TNP-b or TNP-c.

Another object of the present invention is to provide a natriuretic receptor-specific construct wherein the corresponding amino acid sequence not comprising an amino acid surrogate has at least about 80% homology with the sequence of a peptide that binds to a receptor for ANP, BNP, CNP, sCP, DNP, TNP-a, TNP-b or TNP-c.

Another object of the present invention is to provide a natriuretic receptor-specific construct wherein the corresponding amino acid sequence not comprising an amino acid surrogate has at least about 60% homology with the sequence H-Met-cyclo(Cys-His-Phe-Gly-Gly-Arg-Met-Asp-Arg-Ile-Ser-Cys)-Tyr-Arg-$NH_2$ (SEQ ID NO:1).

Another object of the present invention is to provide a natriuretic receptor-specific construct wherein the corresponding amino acid sequence not comprising an amino acid surrogate has at least about 80% homology with the sequence H-Met-cyclo(Cys-His-Phe-Gly-Gly-Arg-Met-Asp-Arg-Ile-Ser-Cys)-Tyr-Arg-$NH_2$ (SEQ ID NO:1).

Another object of the present invention is to provide a natriuretic receptor-specific construct wherein the corresponding amino acid sequence not comprising an amino acid surrogate has at least about 60% homology with the sequence H-Met-cyclo(Xaa-His-Phe-Gly-Gly-Arg-Met-Asp-Arg-Ile-Ser-Xaa)-Tyr-Arg-$NH_2$ (SEQ ID NO:2), where Xaa are each independently any amino acid residue together forming a cyclic peptide.

Another object of the present invention is to provide a natriuretic receptor-specific construct wherein the corresponding amino acid sequence not comprising an amino acid surrogate has at least about 80% homology with the sequence H-Met-cyclo(Xaa-His-Phe-Gly-Gly-Arg-Met-Asp-Arg-Ile-Ser-Xaa)-Tyr-Arg-$NH_2$ (SEQ ID NO:2), where Xaa are each independently any amino acid residue together forming a cyclic peptide.

Another object of the present invention is to provide a natriuretic receptor-specific construct including a surrogate as defined herein wherein the corresponding amino acid sequence not comprising an amino acid surrogate is a peptide which binds to a receptor for ANP.

Another object of the present invention is to provide a natriuretic receptor-specific construct including a surrogate as defined herein wherein the corresponding amino acid sequence not comprising an amino acid surrogate is a peptide which binds to a receptor for BNP.

Another object of the present invention is to provide natriuretic receptor-specific constructs with greater bioavailability and half-life than natural or recombinant forms of ANP or BNP.

Another object of the present invention is to provide natriuretic receptor-specific constructs which may be administered to patients with congestive heart failure.

Another object of the present invention is to provide natriuretic receptor-specific constructs which may be administered by at least one route of administration in addition to intravenous administration.

Another object of the present invention is to provide natriuretic receptor-specific constructs which may be administered to patients by subcutaneous or intramuscular injection.

Another object of the present invention is to provide natriuretic receptor-specific constructs with increased resistance to degradation but which have a significantly high binding affinity to its receptor.

Another object of the present invention is to provide natriuretic receptor-specific constructs in a sustained release formulation.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings illustrate one or more embodiments of the present invention and, together with the description, serve to explain principles of the invention. The drawings are only for the purpose of illustrating one or more preferred embodiments of the invention and are not to be construed as limiting the invention. In the drawings.

DETAILED DESCRIPTION OF THE INVENTION

Figure 1:
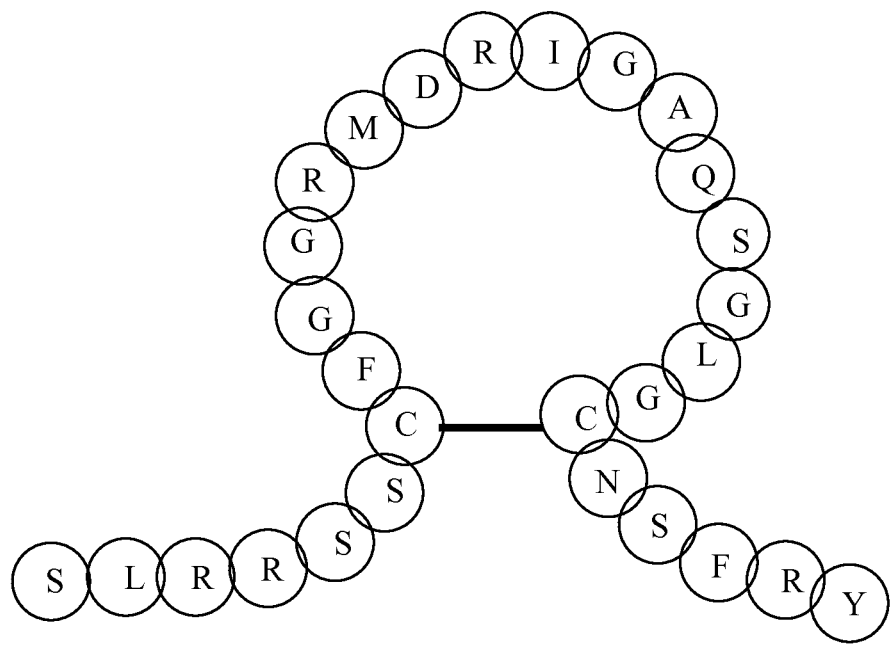
FIG. 1 is the sequence of wild-type endogenous human ANP (hANP)

The invention provides natriuretic receptor-specific constructs made of a plurality of amino acid residues, at least one ring-constrained amino acid surrogate and optionally at least one prosthetic group. The ring-constrained amino acid surrogates employed in the invention are preferably such that they may be made with a conventional amino protected N-terminus, using a protecting group such as Fmoc, and a reactive carboxyl C-terminus, and may thus be employed in conventional peptide synthesis methodologies, it being understood that if the amino acid surrogate is at the C-terminus position of the construct, that other than a carboxyl terminus may be employed on such surrogate. Thus, in a preferred embodiment the invention provides synthetically made constructs, synthesized using peptide synthesis methodologies modified as appropriate, and comprising a plurality of amino acid residues and at least one ring-constrained amino acid surrogate, In a related preferred embodiment, the construct further includes at least one prosthetic group.

Preferred prosthetic groups include polymeric groups comprising repeat units including one or more carbon and hydrogen atoms, and optionally other atoms, including oxygen. Such polymeric groups are preferably water-soluble polymers, and are preferably poly(alkylene oxide), poly(vinyl pyrrolidone), poly(vinyl alcohol), polyoxazoline or poly (acryloylmorpholine). A preferred poly(alkylene oxide) is poly(ethylene glycol) (PEG), optionally derivatized with a linking group.

In one aspect, the invention provides a construct with an amino acid sequence that is a homolog of a known natriuretic peptide, such as ANP or BNP, or is a homolog of any known peptide variant of a natriuretic peptide, wherein the construct includes at least one amino acid surrogate of formula I or II. The corresponding amino acid sequence not comprising an amino acid surrogate may be identical to a known natriuretic peptide or a known peptide variant, or may be homologous thereto, such as a corresponding amino acid sequence that is at least 60% homologous, or more preferably is at least about 80% homologous. As used herein, the phrase "corresponding amino acid sequence not comprising an amino acid surrogate" means an amino acid sequence, including a known amino acid sequence, that binds to a receptor for a natriuretic peptide and that does not include a surrogate. Such known amino acid sequence is identical to the construct if the amino acid sequence is the same but for the substitution by or addition of one or more amino acid surrogates. Similarly, homology is determined by reference to identity of the known amino acid sequence to the construct but for the substitution by or addition of one or more amino acid surrogates.

In another aspect, the invention provides a construct that is modeled on a known peptide which binds to a receptor for a natriuretic peptide, but which includes one or more amino acid surrogates, such surrogates being either substituted for one or more amino acid residues contained in the known peptide, or in addition to the sequence comprising the known peptide. The known peptide may be any natriuretic peptide known in the art, including but not limited to those disclosed in any publication, patent, application or reference cited herein, including but not limited to the natriuretic peptides disclosed in U.S. Pat. Nos. 4,496,544; 4,609,725; 4,656,158; 4,673,732; 4,716,147; 4,757,048; 4,764,504; 4,804,650; 4,816,443; 4,824,937; 4,861,755; 4,904,763; 4,935,492; 4,952,561; 5,047,397; 5,057,495; 5,057,603; 5,091,366; 5,095,004; 5,106,834; 5,114,923; 5,159,061; 5,204,328; 5,212,286; 5,352,587; 5,376,635; 5,418,219; 5,665,704; 5,846,932; 5,583,108; 5,965,533; 6,028,055; 6,083,982; 6,124,430; 6,150,402; 6,407,211; 6,525,022; 6,586,396 or 6,818,619; in U.S. Patent Application Publications 2004/0002458; 2004/0063630; 2004/0077537; 2005/0113286; 2005/0176641; or 2006/0030004; or in various non-U.S. patents and patent applications, including WO 85/04870; WO 85/04872; WO 88/03537; WO 88/06596; WO 89/10935; WO 89/05654; WO 90/01940; WO 90/14362; WO 92/06998; WO 95/13296; WO 99/08510; WO 99/12576; WO 01/016295; WO 2004/047871; WO 2005/072055; EPO 0 291 999; EPO 0 323 740; EPO 0 341 603; EPO 0 350 318; EPO 0 356 124; EPO 0 385 476; EPO 0 497 368; or EPO 0 542 863. In one aspect, the known peptide is a peptide or homolog thereof disclosed in U.S. Pat. Nos. 4,656,158, 4,824,937, 4,935,492, 5,159,061, 5,204,328, 5,376,635, 5,665,704, 5,846,932, 6,028,055, 6,407,211, 6,525,022, 6,586,396, or 6,818,619, U.S. Patent Application Publications 2004/0002458, 2004/0063630, or 2005/0176641, or International Patent Application Publications WO 2004/047871 or WO 2005/072055. The teachings of each of the foregoing patents and patent applications are incorporated by reference as if set forth in full.

In one particularly preferred embodiment, the invention provides a construct, comprising an amino acid sequence which binds to a natriuretic peptide receptor, wherein one or more amino acid residues in such amino acid sequence which binds to a natriuretic peptide receptor is substituted with an amino acid surrogate of formula I. In one aspect, the amino acid sequence which binds to a natriuretic peptide receptor is, prior to substitution, H-Met-cyclo(Cys-His-Phe-Gly-Gly-Arg-Met-Asp-Arg-Ile-Ser-Cys)-Tyr-Arg-NH$_2$ (SEQ ID NO:1).

In yet another aspect the invention provides a construct that binds to a receptor for a natriuretic peptide, including a receptor for ANP or BNP, and includes at least one amino acid surrogate of formula I or II, but which construct is not homologous to any known peptide that binds to a receptor for a natriuretic peptide.

In one embodiment, the invention provides a cyclic construct of formula III:

(III)

where

Aaa¹ is an L- or D-isomer of an α-amino acid or β-amino acid or an α,α-disubstituted amino acid derived from an α-amino acid, including where Aaa¹ is an L- or D-isomer of an α-amino acid or β-amino acid including or derived from Nle, Ala, Leu, Ile, Val, Arg, Phe, Lys, Tyr, Asp, Nva, Met, Met(O), or Met(O₂), or an α,α-disubstituted amino acid derived from Nle, Ala, Leu, Ile, Val, Arg, Phe, Lys, Tyr, Asp, Nva, Met, Met(O), or Met(O₂), including all (R) or (S) configurations of α,α-disubstituted amino acids where the substituents are different, or Aaa¹ is an acyl comprising a $C_2$ to $C_{18}$ linear alkyl, a $C_3$ to $C_{17}$ branched alkyl, a $C_2$ to $C_{18}$ linear alkenyl or alkynyl or a $C_3$ to $C_{18}$ branched alkenyl or alkynyl, or Aaa¹ is an amino acid surrogate of the structure:

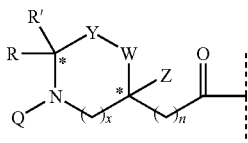

wherein the broken line indicates a peptide bond; R and R' are independently H, a linear or branched $C_1$ to $C_6$ aliphatic chain, —(CH₂)_y—S—CH₃, —(CH₂)_y—S(=O)—CH₃, —(CH₂)_y—S(O₂)—CH₃, a bond and a cyclopropane, cyclobutane, cyclopentane, or cyclohexane ring, or a $C_1$ to $C_3$ aliphatic chain and a cyclopropane, cyclobutane, cyclopentane, or cyclohexane ring; x is 1 or 2; Y is CH₂ or C=O; W is CH₂, NH or NR'''; Z is H or CH₃; Q is —H, —(CH₂)_m—N(v₃)(v₄), —(CH₂)_m—CH₃, —(CH₂)_m—O(v₃), —(CH₂)_m—C(=O)-(v₃), —(CH₂)_m—C(=O)—O-(v₃), —(CH₂)_m—S(v₃), —C(=O)—(CH₂)_m—CH₃, —C(=O)—(CH₂)_m—N(v₃)(v₄), —C(=O)—(CH₂)_m—C(=O)-(v₃), —C(=O)—(CH₂)_m—O(v₃), or —C(=O)—(CH₂)_m—S(v₃); R''' is an acyl, a $C_1$ to $C_{17}$ linear or branched alkyl chain, a $C_2$ to $C_{19}$ linear or branched alkyl acyl chain, a $C_1$ to $C_{17}$ linear or branched omega amino aliphatic, or a $C_1$ to $C_{17}$ linear or branched omega amino aliphatic acyl; n is 0, 1 or 2; m is 0 to 17; y is 1 to 5; v₃ and v₄ are each independently H, a $C_1$ to $C_{17}$ linear or branched alkyl chain or a $C_2$ to $C_{19}$ linear or branched alkyl acyl chain, on the proviso that if one of v₃ or v₄ is an alkyl acyl chain, then the other of v₃ or v₄ is H; and the carbon atoms marked with an asterisk can have any stereochemical configuration;

Aaa² and Aaa¹³ are the same or different, and are each L- or D-isomer amino acid residues forming a cyclic bridge through the side chains of each of Aaa² and Aaa¹³ wherein the linking group of the cyclic bridge is —S—S—, —S—CH₂—S—, —S—CH₂—, —CH₂—S—, —C(=O)—NH—, —NH—C(=O)—, —CH₂—NH—, —NH—CH₂—, —CH₂—S(O)_n— where n is 1 or 2, —S(O)_n—CH₂— where n is 1 or 2, —CH₂—CH₂—, —CH=CH— (E or Z), —C≡C—, —C(=O)—O—, —O—C(=O)—, —C(=O)—CH₂—, —CH₂—C(=O)—, —O—C(=O)—NH—, —NH—C(=O)—O—, or —NH—C(=O)—NH—;

Aaa³ is an L- or D-isomer of an α-amino acid or β-amino acid including or derived from His, Ala, Ser, Thr, Lys, HLys, Orn, Cys, HCys, Dap, or Dab, or an α,α-disubstituted amino acid derived from His, Ala, Ser, Thr, Lys, HLys, Orn, Cys, HCys, Dap, or Dab, including all (R) or (S) configurations of α,α-disubstituted amino acids where the substituents are different, or Aaa³ is an amino acid surrogate of the structure:

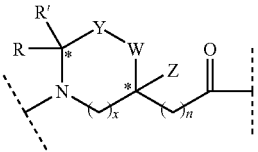

where R and R' are independently H or an amino acid side chain moiety of His, Ala, Ser, Thr, Lys, HLys, Orn, Cys, HCys, Dap, or Dab or a derivative of an amino acid side chain moiety of His, Ala, Ser, Thr, Lys, HLys, Orn, Cys, HCys, Dap, or Dab; x is 1 or 2; Y is CH₂ or C=O; W is CH₂, NH or NR'''; Z is H or CH₃; R''' is an acyl, a $C_1$ to $C_{17}$ linear or branched alkyl chain, a $C_2$ to $C_{19}$ linear or branched alkyl acyl chain, a $C_1$ to $C_{17}$ linear or branched omega amino aliphatic, or a $C_1$ to $C_{17}$ linear or branched omega amino aliphatic acyl; and n is 0, 1 or 2;

Aaa⁴ is an L- or D-isomer of an α-amino acid or β-amino acid including or derived from substituted or unsubstituted Phe, HPhe or Pgl, or Tyr, Leu, Ile, Val, Ala, Nle, Nva or Tle, or an α,α-disubstituted amino acid derived from substituted or unsubstituted Phe, HPhe or Pgl, or Tyr, Leu, Ile, Val, Ala, Nle, Nva or Tle, including all (R) or (S) configurations of α,α-disubstituted amino acids where the substituents are different, or Aaa⁴ is an amino acid surrogate as for Aaa³ where R and R' are independently H or an amino acid side chain moiety of substituted or unsubstituted Phe, HPhe or Pgl, or Tyr, Leu, Ile, Val, Ala, Nle, Nva or Tle or a derivative of an amino acid side chain moiety of substituted or unsubstituted Phe, HPhe or Pgl, or Tyr, Leu, Ile, Val, Ala, Nle, Nva or Tle;

Aaa⁵ is Gly, Sar, an L- or D-isomer of an α-amino acid or β-amino acid including or derived from Ala, or Aib, which is the α,α-disubstituted amino acid derived from Ala, or Aaa⁵ is an amino acid surrogate as for Aaa³ where R and R' are independently H or —CH₃;

Aaa⁶ is Gly, Sar, an L- or D-isomer of an α-amino acid or β-amino acid including or derived from Ala, or Aib, or Aaa⁶ is an amino acid surrogate as for Aaa³ where R and R' are independently H or —CH₃;

Aaa⁷ is an L- or D-isomer of an α-amino acid or β-amino acid including or derived from Arg, His, Ala, Ser, HSer, Thr, Lys, HLys, Orn, Cys, HCys, Cit, Abu, Dap, or Dab, or an α,α-disubstituted amino acid derived from Arg, His, Ala, Ser, HSer, Thr, Lys, HLys, Orn, Cys, HCys, Cit, Abu, Dap, or Dab, including all (R) or (S) configurations of α,α-disubstituted amino acids where the substituents are different, or Aaa⁷ is an amino acid surrogate as for Aaa³ where R and R' are independently H or an amino acid side chain moiety of Arg, His, Ala, Ser, HSer, Thr, Lys, HLys, Orn, Cys, HCys, Abu, Dap, or Dab or a derivative of an amino acid side chain moiety of Arg, His, Ala, Ser, HSer, Thr, Lys, HLys, Orn, Cys, HCys, Abu, Dap, or Dab;

Aaa⁸ is Gly, an L- or D-isomer of an α-amino acid or β-amino acid including or derived from Nle, Ile, Leu, Val, Phe, Ala, Nva, Met(O), Met(O₂), or Tle, or an α,α-disubstituted amino acid derived from Nle, Ile, Leu, Val, Phe, Ala, Nva, Met(O), Met(O₂), or Tle, including all (R) or (S) configurations of α,α-disubstituted amino acids where the substituents are different, or Aaa⁸ is an amino acid surrogate as for Aaa³ where R and R' are independently H or an amino acid side chain moiety of Nle, Ile, Leu, Val, Phe, Ala, Nva, Met(O), Met(O₂), or Tle, or a derivative of an amino acid side chain moiety of Nle, Ile, Leu, Val, Phe, Ala, Nva, Met(O), Met(O₂), or Tle;

Aaa⁹ is an L- or D-isomer of an α-amino acid or β-amino acid including or derived from Asp, Glu, His, Ala, Ser, Thr, Lys, HLys, Cys, HCys, Met(O), Met(O₂), Orn, Dap, or Dab, or an α,α-disubstituted amino acid derived from Asp, Glu, His, Ala, Ser, Thr, Lys, HLys, Cys, HCys, Met(O), Met(O₂), Orn, Dap, or Dab, including all (R) or (S) configurations of α,α-disubstituted amino acids where the substituents are different, or Aaa⁹ is an amino acid surrogate as for Aaa³ where R and R' are independently H or an amino acid side chain moiety of Asp, Glu, His, Ala, Ser, Thr, Lys, HLys, Cys, HCys, Met(O), Met(O₂), Orn, Dap, or Dab or a derivative of an amino acid side chain moiety of Asp, Glu, His, Ala, Ser, Thr, Lys, HLys, Cys, HCys, Met(O), Met(O₂), Orn, Dap, or Dab;

Aaa¹⁰ is an L- or D-isomer of an α-amino acid or β-amino acid including or derived from Arg, His, Ala, Ser, Thr, Lys, HLys, Cys, HCys, Cit, Met(O), Orn, Dap, or Dab, or an α,α-disubstituted amino acid derived from Arg, His, Ala, Ser, Thr, Lys, HLys, Cys, HCys, Cit, Met(O), Orn, Dap, or Dab, including all (R) or (S) configurations of α,α-disubstituted amino acids where the substituents are different, or Aaa¹⁰ is an amino acid surrogate as for Aaa³ where R and R' are independently H or an amino acid side chain moiety of Arg, His, Ala, Ser, Thr, Lys, HLys, Cys, HCys, Met(O), Orn, Dap, or Dab or a derivative of an amino acid side chain moiety of Arg, His, Ala, Ser, Thr, Lys, HLys, Cys, HCys, Met(O), Orn, Dap, or Dab;

Aaa¹¹ is Gly or a D- or L-isomer of an α-amino acid or β-amino acid including or derived from Nle, Ile, Leu, Val, Phe, Ala, Nva, Cys, HCys, Abu or Tle, or an α,α-disubstituted amino acid derived from Nle, Ile, Leu, Val, Phe, Ala, Nva, Cys, HCys, Abu or Tle, including all (R) or (S) configurations of α,α-disubstituted amino acids where the substituents are different, or Aaa¹¹ is an amino acid surrogate as for Aaa³ where R and R' are independently H or an amino acid side chain moiety of Nle, Ile, Leu, Val, Phe, Ala, Nva, Cys, HCys, Abu or Tle or a derivative of an amino acid side chain moiety of Nle, Ile, Leu, Val, Phe, Ala, Nva, Cys, HCys, Abu or Tle;

Aaa¹² is Gly, an L- or D-isomer of an α-amino acid or β-amino acid including or derived from Ser, Nle, Ile, Leu, Val, Phe, Ala, Nva, Arg, Lys, Orn, Cys, HCys, Abu or Tle, or an α,α-disubstituted amino acid derived from Ser, Nle, Ile, Leu, Val, Phe, Ala, Nva, Arg, Lys, Orn, Cys, HCys, Abu or Tle, including all (R) or (S) configurations of α,α-disubstituted amino acids where the substituents are different, or Aaa¹² is an amino acid surrogate as for Aaa³ where R and R' are independently H or an amino acid side chain moiety of Ser, Nle, Ile, Leu, Val, Phe, Ala, Nva, Arg, Lys, Orn, Cys, HCys, Abu or Tle or a derivative of an amino acid side chain moiety of Ser, Nle, Ile, Leu, Val, Phe, Ala, Nva, Arg, Lys, Orn, Cys, HCys, Abu or Tle;

Aaa¹⁴ is an L- or D-isomer of an α-amino acid or β-amino acid including or derived from substituted or unsubstituted Phe, HPhe or Pgl, or Tyr, Leu, Ile, Val, Ala, Lys, Orn, Nle, Nva or Tle, or an α, α-disubstituted amino acid derived from substituted or unsubstituted Phe, HPhe or Pgl, or Tyr, Leu, Ile, Val, Ala, Lys, Orn, Nle, Nva or Tle, including all (R) or (S) configurations of α,α-disubstituted amino acids where the substituents are different, or Aaa¹⁴ is an amino acid surrogate of the structure of formula II as for Aaa³ where R and R' are independently H or an amino acid side chain moiety of substituted or unsubstituted Phe, HPhe or Pgl, or Tyr, Leu, Ile, Val, Ala, Lys, Orn, Nle, Nva or Tle or a derivative of an amino acid side chain moiety of substituted or unsubstituted Phe, HPhe or Pgl, or Tyr, Leu, Ile, Val, Ala, Lys, Orn, Nle, Nva or Tle; and Aaa¹⁵ is a D- or L-isomer of an α-amino acid or β-amino acid including or derived from Ala, Arg, Orn, Lys, Ala, Dap, Dab, HArg, or HLys, or an α,α-disubstituted amino acid derived from Ala, Arg, Orn, Lys, Ala, Dap, Dab, HArg, or HLys, including all (R) or (S) configurations of α,α-disubstituted amino acids where the substituents are different, or Aaa¹⁵ is an amino acid surrogate of the structure:

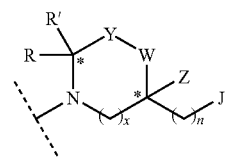

wherein the broken line indicates a peptide bond; at least one of R and R' is —(CH₂)_y—R" and if one, the remaining of R and R' is H, where R" is:
—NH₂,
—NH—C(=NH)—NH₂,
—NH—(CH₂)_y—NH₂,
—NH—C(=O)—NH₂,
—C(=O)—NH₂,
—C(=O)—NH—CH₃,
—C(=O)—NH—(CH₂)_y—NH₂,
—NH—C(=NH)—NH-Me,
—NH—C(=NH)—NH-Et,
—NH—C(=NH)—NH—Pr,
—NH—C(=NH)—NH—Pr-i,
—NH—C(=O)—CH₃,
—NH—C(=O)—CH₂—CH₃,
—NH—C(=O)—CH—(CH₃)₂,
—NH—C(=O)—O—CH₃,
—NH—C(=O)—O—CH₂—CH₃,
—NH—C(=O)—O—C—(CH₃)₃,
—NH—C(=O)—NH—CH₃,
—NH—C(=N—C(=O)—O—C—(CH₃)₃)—NH—C(=O)—O—C—(CH₃)₃,
—N(C(=O)—O—C—(CH₃)₃)—C(=NH)—NH—C(=O)—O—C—(CH₃)₃,

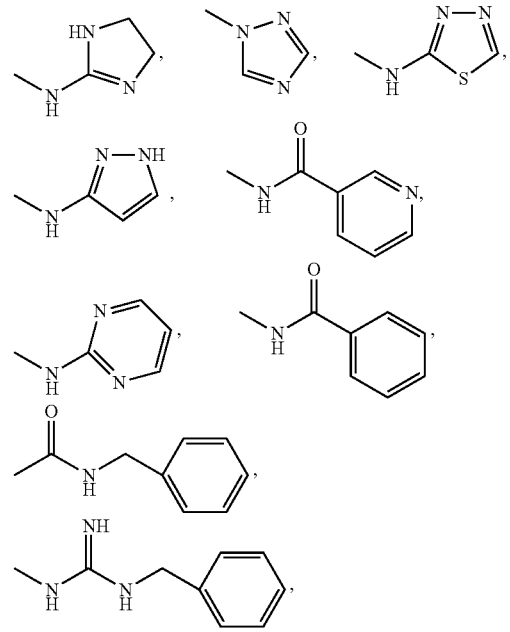

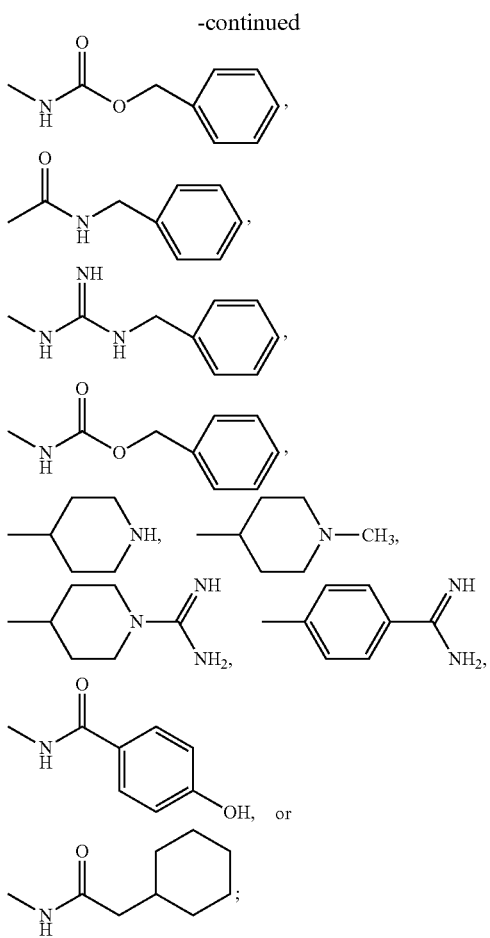

x is 1 or 2; Y is $CH_2$ or C=O; W is $CH_2$, NH or NR'''; Z is H or $CH_3$; J is —H, —$(CH_2)_m$—OH, —C(=O)—$CH_2)_m$—OH, —C(=O)—$(CH_2)_m$—$N(v_1)(v_2)$, —C(=O)—O—$(CH_2)_m$—$CH_3$, —O—$(CH_2)_m$—$CH_3$, —O—$(CH_2)_m$—$N(v_1)(v_2)$, —O—$(CH_2)_m$—OH, —C(=O)—NH—$(CH_2)_m$—$CH_3$, —C(=O)—NH—$(CH_2)_m$—$N(v_1)(v_2)$, —C(=O)—NH—$(CH_2)_m$—$S(v_1)$, —C(=O)—N—$((CH_2)_m$—$N(v_1)(v_2))_2$, —C(=O)—NH—CH(—C(=O)—OH)—$(CH_2)_m$—$N(v_1)(v_2)$, —C(=O)—NH—$(CH_2)_m$—NH—C(=O)—$CH(N(v_1)(v_2))((CH_2)_m$—$N(v_1)(v_2))$, —C(=O)—NH—CH(—C(=O)—$N(v_1)(v_2))$—$(CH_2)_m$—$N(v_1)(v_2)$, an omega amino aliphatic, terminal aryl or aralkyl group, any single natural or unnatural α-amino acid, β-amino acid or α,α-disubstituted amino acid in combination with one of the foregoing groups defining J, or any single natural or unnatural α-amino acid, β-amino acid or α,α-disubstituted amino acid, including all (R) and (S) configurations of any of the foregoing; R''' is an acyl, a $C_1$ to $C_{17}$ linear or branched alkyl chain, a $C_2$ to $C_{19}$ linear or branched alkyl acyl chain, a $C_1$ to $C_{17}$ linear or branched omega amino aliphatic, or a $C_1$ to $C_{17}$ linear or branched omega amino aliphatic acyl; $v_1$ and $v_2$ are each independently H or a $C_1$ to $C_{17}$ linear or branched alkyl chain; n is 0, 1 or 2; m is 0 to 17; y is 1 to 5; and the carbon atoms marked with an asterisk can have any stereochemical configuration;

on the proviso that at least one of $Aaa^1$, $Aaa^3$ through $Aaa^{12}$, $Aaa^{14}$ or $Aaa^{15}$ is an amino acid surrogate.

A related embodiment of formula III provides a construct where one or more of $Aaa^1$, $Aaa^3$ to $Aaa^{12}$, $Aaa^{14}$ or $Aaa^{15}$ is an amino acid surrogate as defined above, and where a prosthetic group, as hereafter defined, is attached to a reactive group of a side chain of an amino acid residue at one or more of $Aaa^1$, $Aaa^3$ to $Aaa^{12}$, $Aaa^{14}$ or $Aaa^{15}$, to a reactive R or R' group of an amino acid surrogate at $Aaa^3$ to $Aaa^{12}$ or $Aaa^{14}$, directly or through a Q group to the terminal amine of an amino acid surrogate at $Aaa^1$, to a reactive terminal carboxyl of an amino acid surrogate at $Aaa^5$, or to a reactive group forming a part of J of an amino acid surrogate at $Aaa^{15}$. The reactive group to which the one or more prosthetic groups are covalently bonded may be a primary amine, a secondary amine, a carboxyl group, a thiol group or a hydroxyl group. In one aspect, the prosthetic group may be covalently bound to a reactive amine in position $Aaa^1$, $Aaa^3$, $Aaa^7$, $Aaa^{10}$, $Aaa^{12}$ or $Aaa^{15}$ or a combination of the foregoing. In another aspect, the prosthetic group may be covalently bound to a reactive carboxyl in position $Aaa^9$ or $Aaa^{15}$ or both. In another aspect, the prosthetic group may be covalently bound to a reactive thiol in position $Aaa^3$, $Aaa^7$, $Aaa^9$, $Aaa^{10}$, $Aaa^{11}$, or $Aaa^{12}$ or a combination of the foregoing.

In a preferred aspect of the construct of formula III, one, two or three of $Aaa^1$ to $Aaa^{15}$ (excluding $Aaa^2$ and $Aaa^{13}$) are an amino acid surrogate of one of the foregoing formulas. In a first particularly preferred aspect, one of $Aaa^1$, $Aaa^5$ and $Aaa^{15}$ is an amino acid surrogate. In a second particularly preferred aspect, two of $Aaa^1$, $Aaa^5$ and $Aaa^{15}$ are amino acid surrogates. In a third particularly preferred aspect, each of $Aaa^1$, $Aaa^5$ and $Aaa^{15}$ are amino acid surrogates. In another particularly preferred aspect, one, two or three of $Aaa^1$, $Aaa^5$ and $Aaa^{15}$ are amino acid surrogates, and the construct is a cyclic construct formed by disulfide bond formation through the side chains of $Aaa^2$ and $Aaa^{13}$. In another particularly preferred aspect, where two or more of $Aaa^1$ to $Aaa^{15}$ are amino acid surrogates the amino acid surrogates are not contiguous, which is to say that each amino acid surrogate is separate from each other amino acid surrogate by at least one amino acid residue being interposed therebetween in the primary sequence.

In yet another preferred embodiment, in the construct of formula III at least one of $Aaa^3$, $Aaa^5$, $Aaa^6$, $Aaa^7$, $Aaa^9$, $Aaa^{10}$, or $Aaa^{12}$ is an L- or D-isomer of Ala, preferably an L-isomer of Ala.

In yet another embodiment, the invention provides a construct of formula III further comprising one or more non-peptide bonds. Non-peptide bonds may be employed to decrease the susceptibility of a construct of the invention to degradation, such as improving the in vivo stability of constructs towards tryptic-like proteases by replacing the native peptide bond before each Lys or Arg residue with a non-peptide bond, such as an isostere of an amide, a substituted amide or a peptidomimetic linkage. In one specific embodiment, native peptide bonds are replaced with peptide bonds having a reversed polarity. In general, any non-peptide bond may be employed, and may be utilized between any two residues. A non-peptide bond includes bonds in which the carbon atom participating in the bond between two residues is reduced from a carbonyl carbon to a methylene carbon, such as a non-peptide bond —$CH_2$—NH— or its isostere —NH—$CH_2$—, or the use of other bonds such as —$CH_2$—S—, —$CH_2$—O—, or —C(=O)—$CH_2$— or an isostere of any of the foregoing, or —$CH_2$—$CH_2$— or —CH=CH—. In general, non-peptide bonds include an imino, ester, hydrazine, semicarbazide, oxime, or azo bond.

The constructs defined above may include one or more prosthetic groups. Prosthetic groups may be employed to modulate the residence time in circulation, to modulate bioavailability, modulate immunogenicity of constructs, or the like. In general, prosthetic groups "modulate" by increasing the residence time, bioavailability or the like, as the case may be, but prosthetic groups may optionally decrease residence time, bioavailability or the like. A "prosthetic group" thus includes any compound conjugated, such as by a covalent bond, to a construct of any formula, for purposes of improving pharmacokinetic or pharmacodynamic properties of the construct. Preferred prosthetic groups include polymeric groups, comprising repeat units which in turn comprise one or more carbon and hydrogen atoms, and optionally other atoms, including oxygen atoms. Such polymeric groups are preferably water-soluble polymers, and are preferably poly (alkylene oxide), poly(vinyl pyrrolidone), poly(vinyl alcohol), polyoxazoline or poly(acryloylmorpholine). A preferred poly(alkylene oxide) is poly(ethylene glycol) (PEG). In addition to PEG, other poly(alkylene glycol) polymers may be employed, such as poly(propylene glycol) and poly (butylene glycol).

In one embodiment, the prosthetic group is one or more PEG polymers covalently bound to a reactive group of the construct. The PEG polymer, or other prosthetic group, may be covalently bound to a reactive group on the side chain of one or more amino acid residues, or may be covalently bound to a reactive group on an amino acid surrogate. Such reactive groups of an amino acid surrogate may include a group covalently bound, directly or through one or more intermediates, to Q or J, or may include a reactive group forming a part of R or R'.

If PEG is employed as the prosthetic group, the PEG polymer may have a molecular weight of from about 200 MW to about 50000 MW. The PEG polymer may be linear, and if linear, may be monofunctional, with a reactive group at one end and a non-reactive group at the other end, homobifunctional, with the same reactive group at each end, or heterobifunctional, with a different reactive group at each end. Alternatively, the PEG polymer may be branched, having generally a "Y"-shaped configuration, multi-armed, such as with two, three, four or eight arms, or other configurations known in the art. The PEG polymer preferably has at least one derivatized reactive group for linking to one or more defined groups on the construct of any of formula III through XIII, preferably by means of a covalent bond. The derivativized reactive group may link to, for example, an amine, hydroxyl, thiol, or carboxyl group on a construct, including on a terminal group of an amino acid residue, on a side chain of an amino acid residue, on a Q group of a surrogate, on a J group of a surrogate, or on an R or R' group of a surrogate.

The PEG polymer preferably has, at one end, an end-cap group, such as a hydroxyl, alkoxy, substituted alkoxy, alekenoxy, substituted alkenoxy, alkynoxy, substituted alkynoxy, aryloxy or substituted aryloxy. The PEG polymer further preferably has, at least one other end, a derivatized reactive group. In one embodiment, the PEG polymer is a linear or branched polyether with a terminal hydroxyl group, such as a monomethoxy PEG, which is derivatized with a linking group, such as an amine, maleimide or carboxylic acid. The available reactive groups of the construct dictate the derivatized linking group employed on the PEG polymer. Thus, in one embodiment, the N-terminal amine of the construct is employed, using a carboxylic acid derivatized PEG. In another embodiment, the C-terminal amine of the construct is employed, again using a carboxylic acid derivatized PEG. In yet another embodiment, if a Lys residue or homolog thereof is present in the construct, either the α or ε amino group thereof may be employed, again using a carboxylic acid derivatized PEG. Maleimide derivatized PEG may be employed with either a reactive thiol or hydroxyl group on the construct. Similarly, amine derivatized PEG may be employed with a reactive carboxyl group on any terminal group or side chain of an amino acid residue, on a Q group of a surrogate, on a J group of a surrogate, or on an R or R' group of a surrogate.

Thus, in one aspect, PEG is activiated with one or more electrophilic groups and may be employed for coupling to amino groups of the construct, including coupling to an E amino group of a side chain or an N-terminal or C-terminal amine. Representative electrophilic reactive groups include succinimidyl α-methylbutanoate and other α-methylbutyric acid esters, as disclosed in U.S. Pat. Nos. 5,672,662 and 6,737,505, and may be be used with proteins, as disclosed in U.S. Patent Application Publication 2004/0235734. Alternatively, succinimidyl propionate may be employed as a reactive group, as disclosed in U.S. Pat. No. 5,567,662, or N-hydroxysuccinimide may be employed with a branched PEG, as disclosed in U.S. Pat. No. 5,932,462. The teachings of each of the foregoing patents and patent applications are incorporated by reference as if set forth in full.

In another aspect, PEG polymers are provided with one or more reactive aldehyde groups, and employed for coupling to a terminal primary amine, such as an N-terminal or C-terminal amine. In another aspect, PEG polymers are provided with one or more thiol-reactive groups, such as a maleimide, orthopyridyldisulfide, or thiol group, and are employed for coupling to a reactive thiol in the construct of any of formula III through XIII, such as a reactive thiol in a cysteine side chain or a reactive thiol in a Q group of a construct.

In one aspect, any of the methods, conjugates or schemes as disclosed in International Patent Publication No. WO 2004/047871, or any reference cited therein, may be employed with the constructs of this invention. The teaching of the foregoing patent applications is incorporated by reference as if set forth in full.

In general, some form of chemical modification may be employed to make an active PEG derivative with a reactive group. The reactive group may be an active carbonate, an active ester, an aldehyde, or tresylate. In part, the reactive group of the PEG determines the amino acid terminal group or side chain moiety to which the PEG derivative is bound. In general, site specific PEGylation is preferred, in part because the resulting construct is homogeneous, minimizing loss of biological activity and reducing immunogenicity.

In one embodiment, the PEG has a molecular weight of from about 200 MW to about 50,000 MW, more preferably from about 2,000 MW to about 20,000 MW. In another embodiment, monomethoxy PEG, such as of the formula $CH_3-O(CH_2-CH_2-O)_n-CH_2-CH_2-OH$ or $CH_3-O(CH_2-CH_2-O)_n-H$, where n is any integer from 2 to about 1200, is employed, preferably derivatized with an amine, maleimide or carboxylic acid linking group.

In another embodiment, the prosthetic group, such as PEG, is conjugated to a construct by means of an enzymatically labile linker as described in Veronese F M and Pasut G. Pegylation, successful approach to drug delivery. *Drug Discovery Today* 10:1451-1458 (2005), and the methods disclosed therein are incorporated here by reference.

In another embodiment, the prosthetic group employed is a polymer with both a lipophilic moiety and a hydrophilic polymer moiety, as disclosed in U.S. Pat. Nos. 5,359,030 and 5,681,811. In a related embodiment, the prosthetic group employed is an oligomer conjugate with a hydrophilic component, such as a PEG polymer, and a lipophilic component, such as a branched fatty acid or alkyl chain, linked by a hydrolyzable bond, such as an ester bond, as disclosed in U.S. Pat. No. 6,309,633. In another related embodiment, the prosthetic group employed is an oligomer that includes poly(propylene glycol), and preferably at least two poly(propylene glycol) subunits, as disclosed in U.S. Pat. No. 6,858,580. The teachings of each of the foregoing patents and patent applications are incorporated by reference as if set forth in full.

In yet another embodiment, the teachings of U.S. Published Patent Application 2004/0203081 are incorporated here by reference, including specifically teachings relating to prosthetic groups, referred to in such application as "modifying moieties," attached to various natriuretic compounds, and specifically oligomeric structures having a variety of lengths and configurations. In a related embodiment, the teachings of International Patent Publication WO 2004/047871 are incorporated by reference, including teachings related to "modifying moieties" attached by means of "modifying moiety conjugation sites" to natriuretic molecules binding to NPRA, it being understood that similar methods could be employed with natriuretic molecules binding to other natriuretic receptors.

Certain terms as used throughout the specification and claims are defined as follows.

The "construct" and "amino acid residue sequences" of this invention can be a) naturally-occurring, b) produced by chemical synthesis, c) produced by recombinant DNA technology, d) produced by biochemical or enzymatic fragmentation of larger molecules, e) produced by methods resulting from a combination of methods a through d listed above, or f) produced by any other means for producing peptides or amino acid sequences.

By employing chemical synthesis, a preferred means of production, it is possible to introduce various amino acids which do not naturally occur into the construct, modify the N- or C-terminus, and the like, thereby providing for improved stability and formulation, resistance to protease degradation, and the like, and to introduce one or more amino acid surrogates into the construct.

The term "peptide" as used throughout the specification and claims is intended to include any structure comprised of two or more amino acids, including chemical modifications and derivatives of amino acids. The amino acids forming all or a part of a peptide may be naturally occurring amino acids, stereoisomers and modifications of such amino acids, non-protein amino acids, post-translationally modified amino acids, enzymatically modified amino acids, and the like. The term "peptide" also includes dimers or multimers of peptides. A "manufactured" peptide includes a peptide produced by chemical synthesis, recombinant DNA technology, biochemical or enzymatic fragmentation of larger molecules, combinations of the foregoing or, in general, made by any other method.

The term "amino acid side chain moiety" used in this invention, including as used in the specification and claims, includes any side chain of any amino acid, as the term "amino acid" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition. A "derivative of an amino acid side chain moiety" as hereafter defined is included within the definition of an amino acid side chain moiety.

The "derivative of an amino acid side chain moiety" is a modification to or variation in any amino acid side chain moiety, including a modification to or variation in either a naturally occurring or unnatural amino acid side chain moiety, wherein the modification or variation includes: (a) adding one or more saturated or unsaturated carbon atoms to an existing alkyl, aryl, or aralkyl chain; (b) substituting a carbon in the side chain with another atom, preferably oxygen or nitrogen; (c) adding a terminal group to a carbon atom of the side chain, including methyl (—$CH_3$), methoxy (—$OCH_3$), nitro (—$NO_2$), hydroxyl (—OH), or cyano (—C≡N); (d) for side chain moieties including a hydroxy, thiol or amino groups, adding a suitable hydroxy, thiol or amino protecting group; or (e) for side chain moieties including a ring structure, adding one or ring substituents, including hydroxyl, halogen, alkyl, or aryl groups attached directly or through an ether linkage. For amino groups, suitable amino protecting groups include, but are not limited to, Z, Fmoc, Boc, Pbf, Pmc and the like.

The "amino acids" used in embodiments of the present invention, and the term as used in the specification and claims, include the known naturally occurring protein amino acids, which are referred to by both their common three letter abbreviation and single letter abbreviation. See generally *Synthetic Peptides: A User's Guide*, G. A. Grant, editor, W.H. Freeman & Co., New York (1992), the teachings of which are incorporated herein by reference, including the text and table set forth at pages 11 through 24. An "amino acid" includes conventional α-amino acids and further includes β-amino acids, α,α-disubstituted amino acids and N-substituted amino acids wherein at least one side chain is an amino acid side chain moiety as defined herein. An "amino acid" further includes N-alkyl α-amino acids, wherein the N-terminus amino group has a $C_1$ to $C_6$ linear or branched alkyl substituent. It may thus be seen that the term "amino acid" includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V. J., Al-obeidi F., Kazmierski W., *Biochem. J.* 268:249-262 (1990); and Toniolo C., *Int. J. Peptide Protein Res.* 35:287-300 (1990); the teachings of all of which are incorporated herein by reference. In addition, the following abbreviations, including amino acids and protecting and modifying groups thereof, have the meanings given:

Abu—gamma-amino butyric acid
12-Ado—12-amino dodecanoic acid
Aib—alpha-aminoisobutyric acid
6-Ahx—6-amino hexanoic acid
Amc—4-(aminomethyl)-cyclohexane carboxylic acid
8-Aoc—8-amino octanoic acid
Bip—biphenylalanine
Boc—t-butoxycarbonyl
Bzl—benzyl
Bz—benzoyl
Cit—citrulline
Dab—diaminobutyric acid
Dap—diaminopropionic acid
Dip—3,3-diphenylalanine
Disc—1,3-dihydro-2-H-isoindolecarboxylic acid
Et—ethyl
Fmoc—fluorenylmethoxycarbonyl
Hept—heptanoyl($CH_3$—$(CH_2)_5$—C(=O)—)
Hex—hexanoyl($CH_3$—$(CH_2)_4$—C(=O)—)
HArg—homoarginine HCys—homocysteine
HLys—homolysine
HPhe—homophenylalanine
HSer—homoserine
Me—methyl
Met(O)—methionine sulfoxide
Met(O$_2$)—methionine sulfone
Nva—norvaline
Pgl—phenylglycine
Pr—propyl
Pr-i—isopropyl
Sar—sarcosine
Tle—tert-butylalanine
Z—benzyloxycarbonyl In the listing of constructs according to the present invention, conventional amino acid residues have their conventional meaning as given in Chapter 2400 of the *Manual of Patent Examining Procedure*, 8$^{th}$ Ed. Thus, "Nle" is norleucine; "Asp" is aspartic acid; "His" is histidine; "Arg" is arginine; "Trp" is tryptophan; "Lys" is lysine; "Gly" is glycine; "Pro" is proline; "Tyr" is tyrosine, "Ser" is serine and so on. All residues are in the L-isomer configuration unless the D-isomer is specified, as in "D-Ala" for D-alanine.

A single amino acid, including stereoisomers and modifications of naturally occurring protein amino acids, non-protein amino acids, post-translationally modified amino acids, enzymatically synthesized amino acids, derivatized amino acids, an α,α-disubstituted amino acid derived from any of the foregoing (i.e., an α,α-disubstituted amino acid wherein at least one side chain is the same as that of the residue from which it is derived), a β-amino acid derived from any of the foregoing (i.e., a β-amino acid which other than for the presence of a β-carbon is otherwise the same as the residue from which it is derived) and the like, including all of the foregoing, is sometimes referred to herein as a "residue."

An "α,α-disubstituted amino acid" includes any α-amino acid having a further substituent in the α-position, which substituent may be the same as or different from the side chain moiety of the α-amino acid. Suitable substituents, in addition to the side chain moiety of the α-amino acid, include $C_1$ to $C_6$ linear or branched alkyl. Aib is an example of an α,α-disubstituted amino acid. While α,α-disubstituted amino acids can be referred to using conventional L- and D-isomeric references, it is to be understood that such references are for convenience, and that where the substituents at the α-position are different, such amino acid can interchangeably be referred to as an α,α-disubstituted amino acid derived from the L- or D-isomer, as appropriate, of a residue with the designated amino acid side chain moiety. Thus (S)-2-Amino-2-methylhexanoic acid can be referred to as either an α,α-disubstituted amino acid derived from L-Nle or as an α,α-disubstituted amino acid derived from D-Ala. Whenever an α,α-disubstituted amino acid is provided, it is to be understood as including all (R) and (S) configurations thereof.

An "N-substituted amino acid" includes any amino acid wherein an amino acid side chain moiety is covalently bonded to the backbone amino group, optionally where there are no substituents other than H in the α-carbon position. Sarcosine is an example of an N-substituted amino acid. By way of example, sarcosine can be referred to as an N-substituted amino acid derivative of Ala, in that the amino acid side chain moiety of sarcosine and Ala is the same, methyl.

The term "amino acid surrogate" includes a molecule disclosed herein which is a mimic of a residue, including but not limited to piperazine core molecules, keto-piperazine core molecules and diazepine core molecules. Unless otherwise specified, an amino acid surrogate is understood to include both a carboxyl group and amino group, and a group corresponding to an amino acid side chain, or in the case of an amino acid surrogate of glycine, no side chain other than hydrogen. Thus an amino acid surrogate includes a molecule of the general formula of formula I or II given above. An amino acid surrogate further includes molecules of any of the following structures, it being understood that for convenience such structures are given as the isolated surrogate, not including any protecting group and not bound by one or two peptide bonds to one or two amino acid residues forming a part of a construct of the invention:

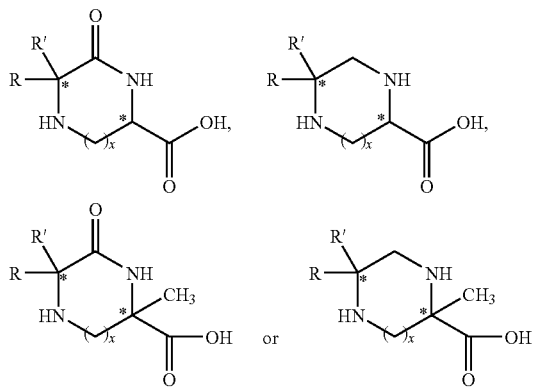

where R, R', x and the asterisks are as defined for the surrogate of formula I. An amino acid surrogate further includes molecules of any of the following structures, again it being understood that for convenience such structures are given as the isolated surrogate, not including any protecting group and not bound by one or two peptide bonds to one or two amino acid residues forming a part of a construct of the invention:

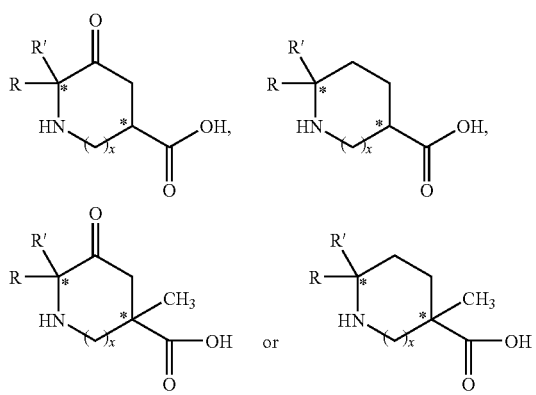

where R, R', x and the asterisks are as defined for the surrogate of formula I. For purposes of synthesis, either the carboxyl group or the amino group of any amino acid surrogate is preferably protected by a protecting group, such that it is not reactive while the protecting group is present, and similarly any reactive group forming a part of R or R' may similarly be protected by a protecting group. It will be appreciated that the surrogates of the present invention have more than one asymmetric center, and therefore are capable of existing in more than one stereoisomeric form. Some of the compounds may also exist as geometric isomers and rotamers. Furthermore, some compounds of the invention may also have conformational axial chirality resulting in atropisomers. The invention extends to each of these forms individually and to mixtures thereof, including racemates. In one aspect, surrogate isomers may be separated conventionally by chromatographic methods or by use of a resolving agent. In another aspect, individual surrogate isomers, or enantiomerically pure surrogates, are prepared by synthetic schemes, such as those disclosed herein or variants of such schemes, employing asymmetric synthesis using chiral intermediates, reagents or catalysts.

The term "C-terminus capping group" includes any terminal group attached through the terminal ring carbon atom or, if provided, terminal carboxyl group, of the C-terminus of a construct. The terminal ring carbon atom or, if provided, terminal carboxyl group, may form a part of a residue, or may form a part of an amino acid surrogate. In a preferred aspect, the C-terminus capping group forms a part of an amino acid surrogate which is at the C-terminus position of the construct. The C-terminus capping group includes, but is not limited to, —$(CH_2)_n$—OH, —$(CH_2)_n$—C(=O)—OH, —$(CH_2)_m$—OH, —$(CH_2)_n$—C(=O)—N($v_1$)($v_2$), —$(CH_2)_n$—C(=O)—$(CH_2)_m$—N($v_1$)($v_2$), —$(CH_2)_n$—O—$(CH_2)_m$—$CH_3$, —$(CH_2)_n$—C(=O)—NH—$(CH_2)_m$—$CH_3$, —$(CH_2)_n$—C(=O)—NH—$(CH_2)_m$—N($v_1$)($v_2$), —$(CH_2)_n$—C(=O)—N—(($CH_2)_m$—N($v_1$)($v_2$))$_2$, —$(CH_2)_n$—C(=O)—NH—CH(—C(=O)—OH)—$(CH_2)_m$—N($v_1$)($v_2$), —C(=O)—NH—$(CH_2)_m$—NH—C(=O)—CH(N($v_1$)($v_2$))(($CH_2)_m$—N($v_1$)($v_2$)), or —$(CH_2)_n$—C(=O)—NH—CH(—C(=O)—$NH_2$)—$(CH_2)_m$—N($v_1$)($v_2$), including all (R) or (S) configurations of the foregoing, where $v_1$ and $v_2$ are each independently H, a $C_1$ to $C_{17}$ linear or branched alkyl chain, m is 0 to 17 and n is 0 to 2; or any omega amino aliphatic, terminal aryl or aralkyl, including groups such as methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7'-amino heptanoyl, 6-Ahx, Amc or 8-Aoc, or any single natural or unnatural α-amino acid, β-amino acid or α,α-disubstituted amino acid, including all (R) or (S) configurations of the foregoing, optionally in combination with any of the foregoing non-amino acid capping groups. In the foregoing, it is to be understood that, for example, —C(=O)—NH—$(CH_2)_m$—NH—C(=O)—CH(N($v_1$)($v_2$))(($CH_2)_m$—N($v_1$)($v_2$)) is:

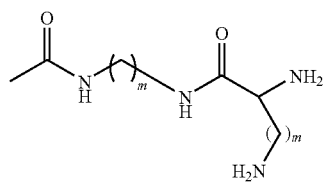

The term "N-terminus capping group" includes any terminal group attached through the terminal amine of the N-terminus of a construct. The terminal amine may form a part of a residue, or may form a part of an amino acid surrogate. In a preferred aspect, the N-terminus capping group forms a part of an amino acid surrogate which is at the N-terminus position of the construct. The N-terminus capping group includes, but is not limited to, any omega amino aliphatic, acyl group or terminal aryl or aralkyl including groups such as methyl, dimethyl, ethyl, propyl, isopropyl, butyl, isobutyl, pentyl, hexyl, allyl, cyclopropane methyl, hexanoyl, heptanoyl, acetyl, propionoyl, butanoyl, phenylacetyl, cyclohexylacetyl, naphthylacetyl, cinnamoyl, phenyl, benzyl, benzoyl, 12-Ado, 7-amino heptanoyl, 6-Ahx, Amc or 8-Aoc, or alternatively an N-terminus capping group is —$(CH_2)_m$—NH($v_3$), —$(CH_2)_m$—$CH_3$, —C(=O)—$(CH_2)_m$—$CH_3$, —C(=O)—$(CH_2)_m$—NH($v_3$), —C(=O)—$(CH_2)_m$—C(=O)—OH, —C(=O)—$(CH_2)_m$—C(=O)-($v_4$), —$(CH_2)_m$—C(=O)—OH, —$(CH_2)_m$—C(=O)-($v_4$), C(=O)—$(CH_2)_m$—O($v_3$), —$(CH_2)_m$—O($v_3$), C(=O)—$(CH_2)_m$—S($v_3$), or —$(CH_2)_m$—S($v_3$), where $v_3$ is H or a $C_1$ to $C_{17}$ linear or branched alkyl chain, and $v_4$ is a $C_1$ to $C_{17}$ linear or branched alkyl chain and m is 0 to 17.

A phenyl ring is "substituted" when the phenyl ring includes one or more substituents independently comprising hydroxyl, halogen, alkyl, or aryl groups attached directly or through an ether linkage. Where the phenyl ring is so substituted, the amino acid residue may be referred to as substituted, as in substituted Phe, substituted HPhe or substituted Pgl.

The term "alkene" includes unsaturated hydrocarbons that contain one or more double carbon-carbon bonds. Examples of alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of alkyl radicals include methyl, ethyl, propyl, isopropyl, butyl, sec-butyl, tertiary butyl, pentyl, isopentyl, hexyl, isohexyl, and the like.

The term "alkynyl" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monocyclic or bicyclic aromatic hydrocarbon radical of 6 to 12 ring atoms, and optionally substituted independently with one or more substituents selected from alkyl, haloalkyl, cycloalkyl, alkoxy, alkylthio, halo, nitro, acyl, cyano, amino, monosubstituted amino, disubstituted amino, hydroxy, carboxy, or alkoxy-carbonyl. Examples of aryl groups include phenyl, biphenyl, naphthyl, 1-naphthyl, and 2-naphthyl, derivatives thereof, and the like.

The term "aralkyl" includes a radical —$R^aR^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group R—C(=O)—, where R is an organic group. An example is the acetyl group $CH_3$—C(=O)—, referred to herein as "Ac".

A peptide or aliphatic moiety is "acylated" when an aryl, alkyl or substituted alkyl group as defined above is bonded through one or more carbonyl {—(C=O)—} groups. A peptide is most usually acylated at the N-terminus.

An "omega amino aliphatic" includes an aliphatic moiety with a terminal amino group. Examples of omega amino aliphatics include 7'-amino-heptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—C(=O)—NH$_2$), such as for example methylamide, ethylamide, propylamide, and the like.

An "imide" includes compounds containing an imido group (—C(=O)—NH—C(=O)—).

An "amine" includes compounds that contain an amino group (—NH$_2$).

A "nitrile" includes compounds that are carboxylic acid derivatives and contain a (—CN) group bound to an organic group.

The term "halogen" is intended to include the halogen atoms fluorine, chlorine, bromine and iodine, and groups including one or more halogen atoms, such as —CF$_3$ and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a construct of the present invention and a pharmaceutically acceptable carrier.

The term "EC$_{50}$" is intended to include the molar concentration of an agonist which produced 50% of the maximum possible response for that agonist. By way of example, a construct which, at a concentration of 72 nM, produces 50% of the maximum possible response for that construct as determined in a cGMP assay, has an EC$_{50}$ of 72 nM. Unless otherwise specified, the molar concentration associated with an EC$_{50}$ determination is in nanomoles (nM).

The term "Ki (nM)" is intended to include the equilibrium receptor binding affinity representing the molar concentration of a competing compound that binds to half the binding sites of a receptor at equilibrium in the absence of a competitor. In general, the Ki is inversely correlated to the affinity of the compound for the receptor, such that if the Ki is low, the affinity is high. Ki may be determined using the equation of Cheng and Prusoff (Cheng Y., Prusoff W. H., *Biochem. Pharmacol.* 22: 3099-3108, 1973):

$$Ki = \frac{EC_{50}}{1 + \frac{[ligand]}{K_d}}$$

where "ligand" is the concentration of ligand, which may be a radioligand, and K$_d$ is an inverse measure of receptor affinity which produces 50% receptor occupancy. Unless otherwise specified, the molar concentration associated with a Ki determination is nM.

The chemical naming protocol and structure diagrams used herein employ and rely on the chemical naming features as utilized by the ChemDraw program (available from Cambridgesoft Corp., Cambridge, Mass.). In particular, certain compound names were derived from the structures using the Autonom program as utilized by Chemdraw Ultra or ISIS base (MDL Corp.). In general, structure diagrams do not depict hydrogen atoms associated with carbon atoms other than in terminal groups and other special circumstances.

Certain structure diagrams and drawings herein, such as those included in Tables 1 and 2, depict constructs composed of amino acid surrogates and amino acid residues, with the surrogates identified by structure diagrams and the amino acid residues identified by a three letter abbreviation. Unless otherwise specified, it is understood that the bond between the surrogate and residue, or between the residue and surrogate, or between a surrogate and residues on both the N-terminus and C-terminus side thereof, is a conventional peptide bond, —C(=O)—NH— or, in the case where the peptide bond is to the ring nitrogen on the N-terminus of the surrogate, —C(=O)—N—. In general, in the depiction of such bonds the atoms of the amino acid surrogate are depicted (e.g., —C(=O)— or —N), but atoms of the amino acid residue are not depicted.

Formulation and Utility

The constructs disclosed herein can be used for both medical applications and animal husbandry or veterinary applications. Typically, the construct, or a pharmaceutical composition including the construct, is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

The constructs disclosed herein may be used for the treatment of any condition, syndrome or disease for which induction of anti-hypertensive, cardiovascular, renal, and/or endocrine effects are desired. This includes specifically any condition, syndrome or disease for which a native natriuretic peptide may be employed. Thus the constructs disclosed herein may be employed to cause desired natriuresis, diuresis and/or vasodilation in a patient.

In one aspect, the constructs disclosed herein are used in the treatment of early stage, such as class 1, congestive heart failure. In another aspect, the constructs disclosed herein are used in the treatment of chronic or decompensated congestive heart failure. In another aspect, the constructs disclosed herein are used in the treatment of acute congestive heart failure, including acutely decompensated congestive heart failure of patients with dyspnea at rest or with minimal activity.

Salt Form of Constructs.

The constructs of this invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include salts of aluminum, ammonium, calcium, copper, ferric, ferrous, lithium, magnesium, manganic, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the construct of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the constructs of this invention are prepared in a suitable solvent from the construct and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the constructs of embodiments of this invention include an acidic moiety, suitable pharmaceutically acceptable salts may include alkali metal salts, such as sodium or potassium salts, or alkaline earth metal salts, such as calcium or magnesium salts.

In addition, Applicants have advantageously discovered that certain salt forms of the peptide constructs of the invention, including pamoate, octanoate, decanoate, oleate, stearate, sodium tannate and palmitate salt forms, have an increased circulation half-life, in some cases doubled, versus the corresponding acetate salt form. These salt forms are particularly well-suited for administration by subcutaneous injection or intramuscular injection, especially for chronic treatment, due to the reduced frequency of dosing that may be achieved as a result of the longer half-lives. While not being limited by theory, it is believed the increased half-life is related to a decrease in solubility in comparison to the acetate salt form. The increased half-life salt forms of the peptide constructs of the invention may be manufactured by any method including, for example, ion exchange, mixing a solution of an acetate salt form of a construct with disodium pamoate to form a pamoate suspension, or use of the desired salt during the final purification step(s) in the manufacture of the constructs.

Pharmaceutical Compositions.

Another embodiment of the present invention provides a pharmaceutical composition that includes a construct of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The constructs of the several embodiments of the present invention may be formulated or compounded into pharmaceutical compositions that include at least one construct of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, manniton, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a construct of this invention over a period of time. For example, gelatin, sodium carboxymethylcellulose and/or other cellulosic excipients may be included to provide time-release or slower-release formulations, especially for administration by subcutaneous and intramuscular injection.

In general, the actual quantity of constructs administered to a patient will vary between fairly wide ranges depending on the mode of administration, the formulation used, and the response desired.

In practical use, the constructs can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, dermal, transdermal, pulmonary, deep lung, inhalation, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, a composition including a construct of this invention may be coated by standard aqueous or nonaqueous techniques. The amount of active construct in such therapeutically useful compositions is such that an effective dosage will be obtained. In another advantageous dosage unit form, sublingual pharmaceutical compositions may be employed, such as sheets, wafers, tablets or the like. The active construct can also be administered intranasally as, for example, by liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Constructs may also be administered parenterally. Solutions or suspensions of these active peptides may be prepared in water suitably mixed with a surfactant such as hydroxypropylcellulose. Dispersions may also be prepared in glycerol, liquid polyethylene glycols and mixtures thereof in oils. These preparations may optionally contain a preservative to prevent the growth of microorganisms. Lyophilized single unit formulations may also be utilized, which are reconstituted, such as with saline, immediately prior to administration, and thus do not require a preservative.

The pharmaceutical forms suitable for injectable use include, for example, sterile aqueous solutions or dispersions and sterile powders, such as lyophilized formulations, for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

Constructs as disclosed herein may be therapeutically applied by means of nasal administration. By "nasal administration" is meant any form of intranasal administration of any of the constructs of this invention. The constructs may be in an aqueous solution, such as a solution including saline, citrate or other common excipients or preservatives. The constructs may also be in a dry or powder formulation.

In an alternative embodiment, constructs may be administered directly into the lung. Intrapulmonary administration may be performed by means of a metered dose inhaler, a device allowing self-administration of a metered bolus of a construct of this invention when actuated by a patient during inspiration. Both dry powder inhalation and nebulized aerosols may be employed.

According to another embodiment of the present invention, constructs of this invention may be formulated with any of a variety of agents that increase effective nasal absorption of drugs, including peptide drugs. These agents should increase nasal absorption without unacceptable damage to the mucosal membrane. U.S. Pat. Nos. 5,693,608, 5,977,070 and 5,908,825, among others, teach a number of pharmaceutical compositions that may be employed, including absorption enhancers, and the teachings of each of the foregoing, and all references and patents cited therein, are incorporated by reference.

If in an aqueous solution, certain constructs of the present invention may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed. In addition to buffering agents, a suitable preservative may be employed, to prevent or limit bacteria and other microbial growth. One such preservative that may be employed is 0.05% benzalkonium chloride.

It is also possible and contemplated that the construct may be in a dried and particulate form. In a preferred embodiment, the particles are between about 0.5 and 6.0 µm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, the constructs may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 µm.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

The constructs of this invention may be therapeutically administered by means of an injection, typically a deep intramuscular injection, such as in the gluteal or deltoid muscle, of a time release injectable formulation. In one embodiment, a construct of this invention is formulated with a PEG, such as poly(ethylene glycol) 3350, and optionally one or more additional excipients and preservatives, including but not limited to excipients such as salts, polysorbate 80, sodium hydroxide or hydrochloric acid to adjust pH, and the like. In another embodiment, a construct of this invention is formulated with a poly(ortho ester), which may be an auto-catalyzed poly(ortho ester) with any of a variable percentage of lactic acid in the polymeric backbone, and optionally one or more additional excipients. In one embodiment poly (D,L-lactide-co-glycolide) polymer (PLGA polymer) is employed, preferably a PLGA polymer with a hydrophilic end group, such as PLGA RG502H from Boehringer Ingelheim, Inc. (Ingelheim, Germany). Such formulations may be made, for example, by combining a construct of this invention in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers, which are preferably also adhesive polymers, may be employed in a time release injectable formulation. The teachings of U.S. Pat. Nos. 4,938,763, 6,432,438, and 6,673,767, and the biodegradable polymers and methods of formulation disclosed therein, are incorporated here by reference. The formulation may be such that an injection is required on a weekly, monthly or other periodic basis, depending on the concentration and amount of construct, the biodegradation rate of the polymer, and other factors known to those of skill in the art.

Routes of Administration.

If it is administered by injection, the injection may be intravenous, subcutaneous, intramuscular, intraperitoneal or other means known in the art. The constructs of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the constructs of this invention are introduced across an epidermal layer of cells may be employed. Administration means may thus include administration through mucous membranes, buccal administration, oral administration, dermal administration, inhalation administration, pulmonary administration, nasal administration, urethral administration, vaginal administration, and the like.

In one aspect, a construct of this invention is administered by means of a time-release injectable formulation, such as a construct of this invention in a formulation with a PEG, poly(ortho ester) or PLGA polymer. In another aspect, a construct of this invention is administered by means of an automated delivery device providing subcutaneous delivery, either continuous or intermittent. Any of the foregoing methods and formulations are particularly applicable for treatment of chronic conditions or syndromes, including chronic congestive heart failure and particularly chronic decompensated congestive heart failure.

In one aspect, any construct of this invention may be administered by subcutaneous administration, including all the methods disclosed in U.S. Pat. No. 6,586,396. In another aspect, a patient, particularly a patient who is relatively compensated or is a patient with congestive heart failure in an outpatient setting, may be administered a construct of this invention by methods and in doses as disclosed in U.S. Patent Application Publication 2004/0077537 and International Patent Application Publication WO 2003/079979. In another aspect, a patient may be administered a construct of this invention by means of the methods as disclosed in U.S. Patent Application Publication 2005/0113286. In yet another aspect, a patient who has undergone myocardial injury may be treated for cardiac remodeling by means of the methods as disclosed in U.S. Patent Application Publication 2006/0019890.

A construct of this invention may also be administered by transdermal administration, including by means of the delivery system, including the apparatus, and the methods as disclosed in U.S. Patent Application Publication 2006/0034903. Similarly, the hydrogel formulations and solid state formulations disclosed therein may be adapted for use with the constructs of this invention.

Therapeutically Effective Amount.

In general, the actual quantity of a construct of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus, a therapeutically effective amount includes an amount of a construct or pharmaceutical composition of this invention that is sufficient to induce a desired effect, including specifically an anti-hypertensive, cardiovascular, renal and/or endocrine effect. In one aspect a therapeutically effective amount is an amount that results in desired natriuresis, diuresis and/or vasodilation.

In general, the constructs of this invention are highly active. For example, a construct can be administered at about 0.001, 0.01, 0.05, 0.1, 0.5, 1, 5, 10 or 100 µg/kg body weight, depending on the specific construct selected, the desired therapeutic response, the route of administration, the formulation and other factors known to those of skill in the art.

Combination Therapy

It is also possible and contemplated that constructs according to several embodiments of the present invention are used in combination with other drugs or agents, particularly in the treatment of congestive heart failure.

According to another aspect of the present invention, a method for treating congestive heart failure is provided. The method includes administering to the patient having congestive heart failure a therapeutically effective amount of a construct as disclosed herein in combination with a therapeutically effective amount of another compound that is useful in the treatment of congestive heart failure, or alternative that is useful in extending the bioavailability of a construct of this invention in a patient. In one aspect, a patient may be administered a construct of this invention in combination with a diuretic, such as by means of the methods and diuretics disclosed in U.S. Patent Application Publication 2004/0063630. Diuretics which may be employed in combination include thiazide-, loop- and potassium-sparing diuretics, including without limitation diuretics such as hydrochlorothiazide (Hydrodiuril®), chlorthalindone, furosemide (Lasix®), spironolactone (Aldactone®) and triamterine.

In another aspect of the present invention, a method for treating congestive heart failure is provided by administering a therapeutically effective amount of a construct as disclosed herein in combination with a therapeutically effective amount of an anti-hypertensive agent other than a diuretic. Such anti-hypertensive agents include generally calcium channel blockers (including dihydropyridines and non-dihydropyridines), sympatholytic agents, non-specific adrenergic blocking agents, α-adrenergic antagonists (including nonselective and selective α1-blocking agents), β-blockers (including non-selective as well as selective blockers and those with intrinsic sympathomimetic activity), vasodilators (for treatment of resistant and emergent hypertension), angiotensin converting enzyme inhibitors and angiotensin II antagonists. Anti-hypertensive agents that may be employed in combination include mixed α and β antagonists such as labetolol (Normodyne®); vasodilators such as hyralazine (Apresoline®), minoxidil (Loniten®), nitroprusside (Nipride®), or diazoxide (Hyperstat IV®); calcium blockers such as nifedipine (Adalat®), diltiazem (Cardizem®), or verapamil (Calan®); sympatholytics such as clonidine (Catapres®), methyldopa (Aldomet®), reserpine (Serpasil®), or guanethidine (Ismelin®); ACE inhibitors such as captopril (Capoten®), enalapril (Vasotec®) or lisinopril (Prinivil®); α-adrenergic antagonists such as phentolamine (Regitine®) or prazosin (Minipress®); angiotensin II antagonists such as losartan (Cozaar®); or β-adrenergic antagonists such as propranolol (Inderal®), nadolol (Corgard®), metoprolol (Lopressor®) or pindolol.

Other Indications

While a primary use of the constructs of the present invention is in the treatment and amelioration of symptoms of congesive heart failure, acute kidney failure and renal hypertension, the constructs of the present invention may be employed in any treatment scheme or modality for which natriuretic, diuretic and/or vasodilator compounds provide a therapeutic benefit. Thus, in one aspect, the constructs of the present invention may be employed as additives to peritoneal dialysis solutions, as disclosed in U.S. Pat. No. 5,965,533. In another aspect, the constructs of the present invention may be employed in opthomologic applications, as disclosed in International Patent Publication WO 00/18422.

Synthetic Methods of Amino Acid Surrogates

The following examples of methods of synthesis of amino acid surrogates of the invention are intended to be exemplary, and it is to be understood that variations thereon may be undertaken by one of skill in the art, and such variations are intended to be included herein.

Synthesis of Ketopiperazine Scaffolds Mimicking Amino Acids without Functionalized R Side Chain (Methods A and B)

The constructs were prepared by a variety of methods as described in Methods A and B.

Method A:

The dipeptides (3) were formed by the mixed anhydride method, using Boc-serine (OBn)-OH (1), and an α-amino ester (2). The dipeptides were obtained in high yields, and usually no purification was required. Reduction of both the methyl ester and the amide group was done using diborane-tetrahydrofuran, with the secondary amines protected to give the di-Boc protected amino alcohol intermediates (4). Oxidation of the alcohols with pyridinium dichromate (PDC) with concomitant cyclization gave the piperazine-2-ones (5) in one step. Benzyl ether removal by hydrogenation, followed by protecting group exchange gave the Fmoc protected piperazine-2-ones (6). Finally, the primary alcohol was oxidized to the acid by any of a number of different methods (PDC, Jones oxidation, ruthenium chloride-sodium periodate, 2,2,6,6-tetramethyl-1-piperidinyloxy, free radical (TEMPO) oxidation) to give the final products (7).

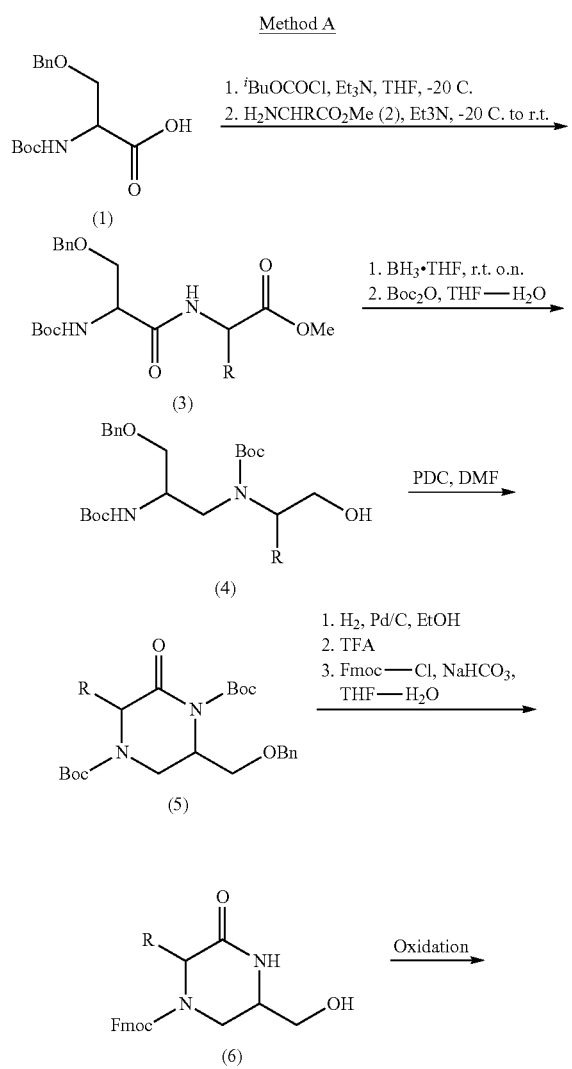

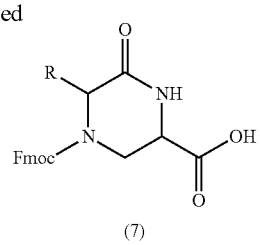

Synthesis of 2-(3-benzyloxy-2-tert-butoxycarbonylamino-propionylamino)-2-substituted acetic acid methyl ester (3): To a solution of 10 mmol of Boc serine benzyl ether (1) in 30 mL of dry tetrahydrofuran, kept at −20° C. under nitrogen, was added 22 mmol of triethylamine, followed by the slow addition of 11.4 mmol of isobutylchloroformate. A white solid precipitated out. The slurry was stirred for 15 minutes, and then 11.1 mmol of α-amino ester (2) was added in one portion. The slurry was stirred at −20° C. for 30 minutes, and then allowed to warm up to room temperature, stirred for 2 hours, and then concentrated to dryness. The mixture was then partitioned between 50 mL of ethyl acetate/30 mL of 1N hydrochloric acid solution. The layers were separated, and the organic layer washed with 1×20 mL of 1N hydrochloric acid, and 1×20 mL of saturated sodium bicarbonate solution, dried over magnesium sulfate and concentrated. Compounds (3) were usually obtained in yields above 90%, and no purification was required.

| R | Analytical Data for Compounds (3) |
|---|---|
| Ph (benzyl) | $^1$H NMR δ (CDCl$_3$): 1.43 (s, 9H, $^t$Bu), 3.0-3.18 (two sets of dd, 2H, CH$_2$—Ph), 3.50-3.57 (t, 1H, CH$_2$O), 3.68 (s, 3H, CH$_3$O), 3.87-3.96 (br. d, 1H, CH$_2$O), 4.23-4.33 (br. m, 1H, CHN), 4.45-4.57 (dd, 2H, CH$_2$O), 4.80-4.88 (m, 1H, CHN), 5.30-5.37 (m, 1H, NH), 7.0-7.38 (a series of m, 10H, Ph), yield = 96%, $t_R$ = 6.88 min, (M$^+$ + 1) = 456.99 |
| isobutyl | $^1$H NMR δ (CDCl$_3$): 0.81-0.96 (a series of m, 6H, CH$_3$), 1.00-1.16 (m, 1H, CH$_2$), 1.30-1.45 (m, 1H, CH$_2$), 1.45 (s, 9H, $^t$Bu), 1.80-1.96 (m, 1H, CH), 3.54-3.64 (dd, 1H, CH$_2$O), 3.70 (s, 3H, CH$_3$O), 3.82-3.96 (dd, 1H, CH$_2$O), 4.28-4.40 (m, 1H, CHN), 4.51-4.61 (m, and s, 3H, CH$_2$O, and CHN), 5.51-5.61 (br. d, 1H, NH), 7.12-7.37 (br. m, 5H, Ph), yield = quant., $t_R$ = 6.93 min, (M$^+$ + 1) = 423.25 |
| H | $^1$H NMR δ (CDCl$_3$): 1.45 (s, 9H, $^t$Bu), 3.73 (s, 3H, CH$_3$O), 3.84-3.90 (m, 2H, CH$_2$N), 4.01-4.17 (m, 2H, CH$_2$O), 4.32-4.38 (br. m, 1H, CHN), 4.54-4.58 (d, 2H, CH$_2$O), 5.46-5.57 (d, 1H, NH), 7.05-7.12 (br. m, 1H, Ph), 7.24-7.40 (m, 4H, Ph), yield = quant., $t_R$ = 5.51 min, (M$^+$ + 1) = 367.07 |

Synthesis of Di-Boc-2-substituted-(2-amino-3-benzyloxy-propyl-amino)-ethanol (4): To a solution of 35 mmol of (3) in 50 mL of dry tetrahydrofuran, kept at room temperature under nitrogen, was added 200 mL of 1N diborane solution in tetrahydrofuran. The solution was stirred at room temperature overnight, and then slowly poured over an ice-cold solution of 200 mL of 1N hydrochloric acid solution. The biphasic solution was then neutralized with solid sodium hydroxide. 140 mL of a saturated solution of sodium bicarbonate was added, followed by 70 mmol of di-tert-butyl-dicarbonate, and the mixture stirred for 2 days at room temperature, diluted with 200 mL of ethyl acetate and the layers separated. The organic layer was dried over magnesium sulfate, and concentrated. The products (4) were purified by silica gel column chromatography.

| R | Analytical Data for Compounds (4) |
|---|---|
|  Ph | ¹H NMR δ (CDCl₃): 1.42 (s, 9H, ᵗBu), 1.48 (s, 9H, ᵗBu), 2.48-3.02 (a series of m, 2H, CH₂—Ph), 3.1-3.48 (br. m, 1H, CH₂O), 3.25-3.48 (br. m, 2H, CH₂N), 3.50-3.75 (m, 2H, CH₂O), 3.80-3.97 (m, 2H, CH₂O, and CHN), 4.25 (br. m, 1H, CHN), 4.45 (s 2H, CH₂O), 4.9 (br. s, 1H, OH), 5.3 (br. s, 1H, NH), 7.1-7.4 (m, 10H, Ph), yield = 76%, $t_R$ = 8.04 min, (M⁺ + 1) = 515.25 |
| 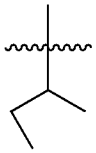 [SMILES: *C(C)CC] | ¹H NMR δ (CDCl₃): 0.84-0.96 (m, CH, CH₂, CH₃), 1.42 (s, 9H, ᵗBu), 1.45 (s, 9H, ᵗBu), 1.42-1.44 (m, 1H, CH), 2.88-3.11 (br. m, 2H, CH₂N), 3.42-3.57 (m, 2H, CH₂O), 3.62-4.10 (two m, 4H, CH₂O, and CHN), 4.51 (s, 2H, CH₂O), 7.27-7.38 (m, 5H, Ph), yield = 80%, $t_R$ = 8.19 min, (M⁺+ 1) = 481.26 |
| 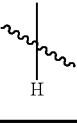 H | ¹H NMR δ (CDCl₃): 1.35-1.43 (m, 18H, ᵗBu), 3.20-3.32 (m, 1H, CH₂N), 3.55-3.84 (a series of m, 8H, CH₂N, CH₂O), 3.90-4.05 (m, 1H, CHN), 4.45 (s, 2H, CH₂O), 4.9-5.02 (m, 1H, NH), 7.2-7.35 (m, 5H, Ph), yield = 56%, $t_R$ = 6.40 min, (M⁺ + 1) = 425.21 |

Synthesis of 1,4-di-Boc-6-benzyloxymethyl-3-substituted-piperazin-2-one (5): A solution of 70 mmol of (4), and 400 mmol of pyridinium dichromate in 300 mL of dry dimethylformamide was stirred at 48° C. under nitrogen for 6 hours, cooled to room temperature, poured into 1500 mL of water, and extracted with 4×500 mL of ethyl ether. The ethereal layers were combined, dried over magnesium sulfate, and concentrated. The products (5) were purified by silica gel column chromatography.

| R | Analytical Data for Compounds (5) |
|---|---|
|  Ph | ¹H NMR δ (CDCl₃): 1.4 (s, 9H, ᵗBu), 1.5 (s, 9H, ᵗBu), 3.05-3.58 (a series of m, CH₂—Ph, and CH₂N), 4.1-4.32 (a series of m, 2H, CH₂N), 4.47 (s, 2H, CH₂O), 4.78-4.86 (br. m, 1H, CHN), 7.12-7.42 (m, 10H, Ph), yield = 42%, $t_R$ = 8.65 min, (M⁺ + 1) = 511.05. |
| 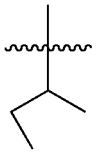 [SMILES: *C(C)CC] | ¹H NMR δ (CDCl₃): 0.82-1.56 (four s, and four m, 27H, ᵗBu, CH, CH₂, and CH₃), 3.20-3.52 (a series of m, 2H, CH₂N), 3.60-3.88 (a series of m, 2H, CH₂O), 4.20-4.60 (a series of m, one s, 4H, CH₂O, CHN), 7.21-7.37 (m, 5H, Ph), yield = 24%, $t_R$ = 9.23 min, (M⁺ + 1) = 477.32. |

Synthesis of 4-Fmoc-6-hydroxymethyl-3-substituted-piperazin-2-one (6): A suspension of 19 mmol of (5) and 2 g of 10% palladium on carbon in 200 mL of ethanol was hydrogenated at room temperature and atmospheric pressure overnight. The suspension was filtered through celite, and concentrated. The residue was redissolved in 40 mL of 50% trifluoroacetic acid in dichloromethane. The solution was stirred at room temperature for 2 hours, and then concentrated. The residue was redissolved in 60 mL of tetrahydrofuran/40 mL of water, and neutralized with solid sodium bicarbonate, followed by the addition of 40 mmol of solid sodium bicarbonate, and 20 mmol of Fmoc chloride. The mixture was then stirred at room temperature for 2 hours, diluted with 300 mL of ethyl acetate, and the layers separated. The organic layer was dried over magnesium sulfate, concentrated, and purified by silica gel column chromatography.

| R | Analytical Data for Compound (6) |
|---|---|
|  Ph | ¹H NMR δ (CDCl₃): 2.15-2.32 (br. m, 1H, CH₂—Ph), 2.70-2.81 (br. m, 1H, CH₂—Ph), 3.0-3.32 (br. m, 3H, CHN, and CH₂N), 3.47-3.65 (br. m, 3H, CH₂O, and CHN), 3.95-4.22 (two m, 2H, CH, and CHN), 4.32-4.48 (br. m, 2H, CH₂O), 4.84-4.92 (br. m, 1H, NH), 6.73-6.83 (br. m, 1H, Ph), 6.92-7.01 (br. m, 1H, Ph), 7.08-7.82 (a series of m, 11H, Ph, and fulvene), yield = 65%, $t_R$ = 5.78 min, (M⁺ + 1) = 443.07. |
| 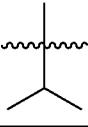 | ¹H NMR δ (CDCl₃): 0.6-1.15 (br. peaks, 7H, CH₂, and CH₃), 1.20-1.42 (br. m, 1H, CH₂), 1.72-2.02 (two br. peaks, 1H, CH), 2.74-2.86 (t, 1/2H, CHN), 2.74-3.74 (a series of br. peaks, 5H, CH₂O, CH₂N, and CHN), 4.16-4.22 (br. m, 1H, CH), 4.52-4.74 (br. m, 2H, CH₂O), 7.24-7.82 (a series of m, 8H, fulvene), yield = 34%, $t_R$ = 5.72 min, (M⁺ + 1) = 408.95 |
| | ¹H NMR δ (CDCl₃): 0.73-1.00 (m, 7H, CH₃), 2.2-2.3 (br. m, 0.5H, CH), 2.74-4.62 (a series of br. peaks, 12H, CH₂N, CH₂O and CHN), 3.68 (s, 3H, CH₃O), 7.26-7.77 (m, 9H, fulvene), yield = 45% (3 steps), $t_R$ = 5.34 min, (M⁺ + 1) = 394.93 |

Synthesis of 4-Fmoc-5-substituted-6-oxo-piperazine-2-carboxylic acid (7): Compounds (7) were prepared by several methods.

(a) To a biphasic solution of 10 mmol of (6) in 180 mL of acetonitrile, 180 mL of carbon tetrachloride, and 240 mL of water, cooled to 0° C., was added 112 mmol of solid sodium periodate, followed by 340 mg of ruthenium chloride. The reaction was allowed to warm up to room temperature, stirred for 2 hours, and then filtered through celite. The layers were separated, and the aqueous layer re-extracted with 2×75 mL of ethyl acetate. The organic layers were combined, dried over magnesium sulfate, and concentrated.

(b) A solution of 12 mmol of (6), and 59 mmol of PDC in 60 mL of dry dimethylformamide was stirred at 48° C. under nitrogen for ~5 hours, cooled to room temperature, and poured over 600 mL of water, and extracted with 3×200 mL of dichloromethane. The organic layers were combined, dried over magnesium sulfate, and concentrated.

(c) To a solution of 17 mmol of (6) in 350 mL of acetone kept at room temperature was added 25 mL of Jones reagent (prepared from 8.0 g of chromic acid, 17.4 mL of water, and 6.9 mL of concentrated sulfuric acid). The mixture was stirred for 1 hour, 150 mL of isopropanol was added, and the mixture filtered through celite. The celite was washed with ethyl acetate. The organic layers were combined and concentrated. The residue was dissolved in 250 mL of ethyl acetate and washed with 2×50 mL of water, dried over magnesium sulfate, and concentrated.

(d) To a solution of 81 mmol alcohol (6) in 810 mL of acetonitrile kept at room temperature, was added phosphate buffer solution (prepared with 7.2 g of sodium phosphate monobasic, and 14.3 g of sodium phosphate dibasic in 295 mL of water), followed by the addition of 3.3 g (20.7 mmol) of TEMPO, and 18.6 g (164.4 mmol) of sodium chlorite, and the biphasic solution placed in an oil bath kept at 43° C., and then a solution of 43.3 mL (25.9 mmol) of sodium hypochlorite solution (prepared by mixing 19.3 mL of 10-13% sodium hypochlorite solution, and 24 mL of water) was added slowly. The reaction was stirred at 43° C. for 4 hours. The solution was cooled to room temperature, and a solution of 200 mL of 10% sodium hydrogen sulfite solution was added, stirred for 10 minutes, diluted with 500 mL of ethyl acetate, and the layers separated. The organic layer was washed with 1×100 mL of brine, 1×160 mL of 1N hydrochloric acid solution, dried over sodium sulfate, and concentrated.

The products (7) were purified by silica gel column chromatography.

| R | Analytical Data for Compounds (7) |
|---|---|
| Ph | $^1$H NMR δ (CDCl$_3$): 2.36-2.45 (dd, 1H, CH$_2$—Ph), 2.62-2.76 (m, 1/2H, CH$_2$—Ph), 2.82-2.98 (m, 1/2H, CH$_2$—Ph), 3.13-3.25 (m, 1H, CH$_2$N), 3.98-4.64 (a series of m, 6H, CHN, CH$_2$O, CH$_2$, and CH), 4.87 (br. m, 1/2H, NH), 6.85 (br. s, 1H, Ph), 7.0-7.40 (a series of m, 12H, Ph and fulvene), 9.18-9.40 (br. d, 1H, CO$_2$H), $t_R$ = 5.91 min, (M$^+$ + 1) = 457.37. |
|  | $^1$H NMR δ (CDCl$_3$): 0.64-1.02 (overlapping t, 6H, CH$_3$), 1.02-1.68 (three br. m, 2H, CH$_2$), 1.96-2.16 (br. m, 1H, CH), 2.88-3.18 (m, 1H, CH$_2$N), 3.85-4.12 (three m, 2H, CH$_2$N, and CHN), 4.18-4.35 (m, 1H, CH), 4.55-4.72 (m, 2H, CH$_2$), 4.75-4.86 (br. m, 1H, NH), 7.28-7.82 (a series of m, 8H, fulvene), 9.1-9.26 (two br. s, 1H, CO$_2$H), $t_R$ = 5.86 min, (M$^+$ + 1) = 423.20. |
|  | $^1$H NMR δ (CDCl$_3$): 0.62-1.03 (m, 7H, CH$_3$), 1.90-2.05 (br. m, 1H, CH), 2.87-4.60 (a series of br. peaks, 8H, CH$_2$N, CH$_2$O and CHN and CH), 7.29-7.80 (m, 9H, fulvene), yield = 61%, $t_R$ = 5.52 min, (M$^+$ + 1) = 409.11 |

Method B:

Intermediates Di-Boc-2-substituted-(2-amino-3-benzyloxy-propyl-amino)-ethanols (4), prepared as described in method A, were oxidized to the acid using TEMPO/isocyanuric acid reagent, and then esterified with iodomethane to give fully protected reduced dipeptide analogs (8). Deprotection of the Boc groups, and the benzyl ether, gave 3-substituted 5-hydroxymethyl-piperazin-2-ones, which were protected as the Fmoc derivatives to give (6), which were oxidized to the final product as described in method A.

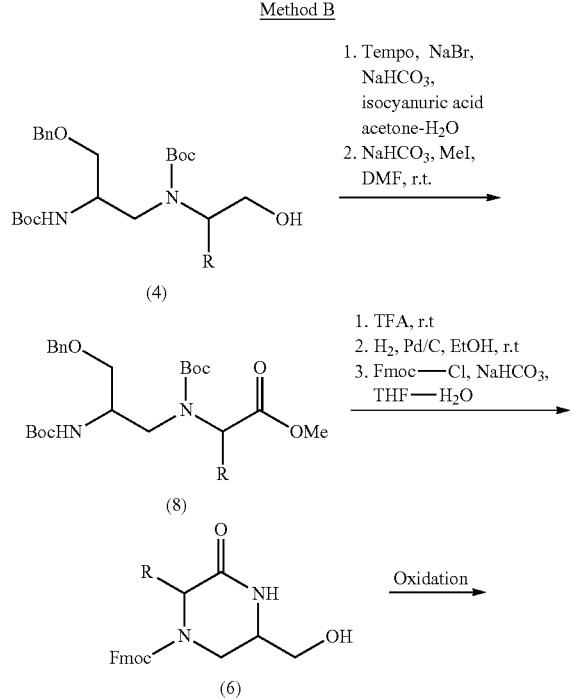

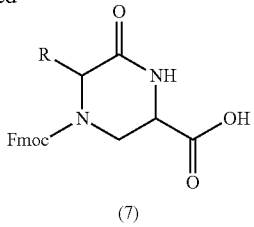

Synthesis of Di-Boc-(2-amino-3-benzyloxy-propylamino)-2-substituted acetic acid methyl ester (8): To a suspension of 76 mmol of (4) in 680 mL of acetone, and 210 mL of a saturated sodium bicarbonate solution, kept at 0° C., was added 21 mmol of solid sodium bromide, and 2.9 mmol of TEMPO, followed by the slow addition of 156 mmol of trichloroisocyanuric acid. The reaction was stirred for 30 minutes at 0° C., and then at room temperature overnight, acidified with a solution of 1N hydrochloric acid, and extracted with 2×300 mL of ethyl acetate. The organic layer was washed with 3×50 mL of 1N hydrochloric acid, dried over magnesium sulfate, and concentrated. The residue was redissolved in 40 mL of dry dimethylformamide and 95 mmol of solid sodium bicarbonate, and 112 mmol of iodomethane was added, and the mixture stirred at room temperature under nitrogen until HPLC showed the reaction was complete; the solution was then diluted with 200 mL of ethyl ether, and washed with 2×100 mL of water, dried over magnesium sulfate, and concentrated. The products (8) were purified by silica gel column chromatography.

| R | Analytical Data for Compounds (8) |
|---|---|
| Ph | $^1$H NMR δ (CDCl$_3$): 1.41 (s, 9H, $^t$Bu), 1.46 (s, 9H, $^t$Bu), 2.44-2.58 (d, 1/2H, CH$_2$—Ph), 2.66-2.88 (d, 1/2H, CH$_2$—Ph), 3.16-3.46 (three sets of m, 5H, CH$_2$-Ph, CH$_2$N, and CH$_2$O), 3.72 (s, 3H, CH$_3$O), 3.75-4.05 (two m, 1H, CHN), 4.42 (s, 2H, CH$_2$O), 4.95-5.10 (d, 1/2H, NH), 5.30-5.38 (d, 1/2H, NH), 7.10-7.38 (m, 10H, Ph), yield = 62%, $t_R$ = 7.75 min, (M$^+$ + 1) = 529.03. |
| H | $^1$H NMR δ (CDCl$_3$): 1.41 (s, 9H, $^t$Bu), 1.42 (s, 9H, $^t$Bu), 3.30-3.60 (br. m, 4H, CH$_2$N, CH$_2$O), 3.70 (s, 3H, CH$_3$O), 3.75-3.95 (m, 2H, CH$_2$N), 4.51 (s, 2H, CH$_2$O), 5.0-5.08 (br. s, 1H, NH), 7.25-7.37 (m, 5H, Ph), yield = 47% $t_R$ = 7.28 min, (M$^+$ + 1) = 453.17. |

Synthesis of 4-Fmoc-6-hydroxymethyl-3-substituted-piperazin-2-one (6): A solution of 36 mmol of (8) in 40 mL of 50% trifluoroacetic acid in dichloromethane was stirred at room temperature for 2 hours, and then poured in 200 mL of saturated sodium bicarbonate solution. The layers were separated, and the organic layer concentrated. The residue was redissolved in 100 mL of ethyl acetate, and washed with 2×50 mL of water, dried over magnesium sulfate, and concentrated. The residue was dissolved in 100 mL of ethanol, and 5 g of 10% palladium on carbon and 35 mL of a 1N hydrochloric acid solution was added, and the mixture hydrogenated at room temperature and atmospheric pressure until HPLC showed the reaction was complete; the solution was then filtered through celite and concentrated. The residue was redissolved in 80 mL of ethyl acetate, 70 mmol of sodium bicarbonate in 30 mL of water was added, and the mixture stirred at room temperature overnight. The ethyl acetate was removed and 100 mL of tetrahydrofuran was added, followed by 178 mmol of solid sodium bicarbonate and 43 mmol of Fmoc chloride, and the mixture was stirred until HPLC showed it was complete, diluted with 300 mL of ethyl acetate, and the layers separated. The organic layer was washed with 2×50 mL of water, dried over magnesium sulfate, and concentrated. The products (6) were purified by silica gel column chromatography.

Synthesis of 4-Fmoc-5-substituted-6-oxo-piperazine-2-carboxylic acid (7): Compounds (7) were prepared as described in method A.

General Common Synthetic Scheme for the Preparation of Ketopiperazine Scaffolds Applicable to Compounds with or without Functionalized R Sidechains (Methods C, E, F)

Method C:

(2-Fmoc-amino-3-R'—O-propylamino)-2-substituted acetic acid methyl esters (10) were prepared by reductive amination of Fmoc O-protected serinal (9) with α-amino esters (2), using either sodium cyanoborohydride or sodium triacetoxyborohydride as the reducing agent. The Fmoc O-protected serinal (9) required for the reductive amination was prepared according to method D, either by reduction of the ester (12) by di-isobutylaluminun hydride, by oxidation of Fmoc O-protected serinol (13) with Dess-Martin periodinane, or by reduction of the Fmoc O-protected serine Weinreb amide (14) with lithium aluminum hydride. The preferred method for the preparation of Fmoc O-protected serinals (9) was the reduction of the Weinreb amide analog. (2-Fmoc-amino-3-R'—O-propylamino)-2-substituted acetic acid methyl esters (10) were then N and O deprotected, cyclized, and Fmoc protected to give 3-substituted 6-hydroxymethyl-piperazin-2-ones (6), which were then oxidized to the final product as described in method A.

The protecting group (R') on the hydroxyl group of Fmoc-O-protected serinal (9) used in the synthesis depends on the nature of the side chain R of the amino ester. When R contained no functional groups, the side chain of Fmoc serine was protected as the $^t$Bu ether. When R contained functional groups, the side chain of Fmoc serine was protected as the trityl ether.

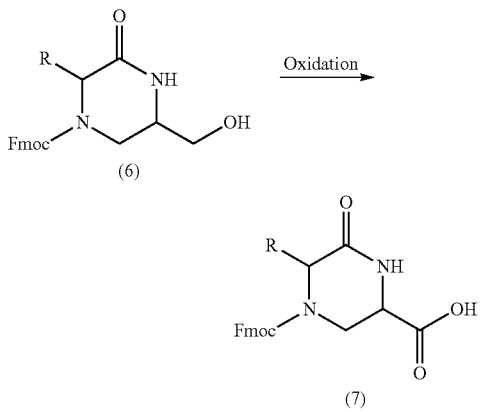

Method D

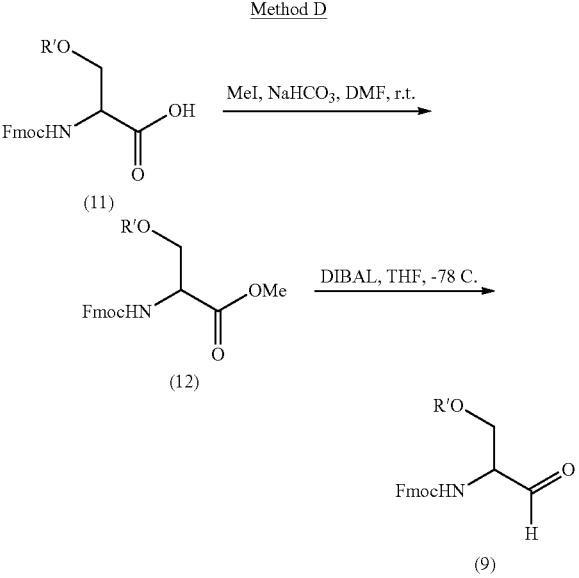

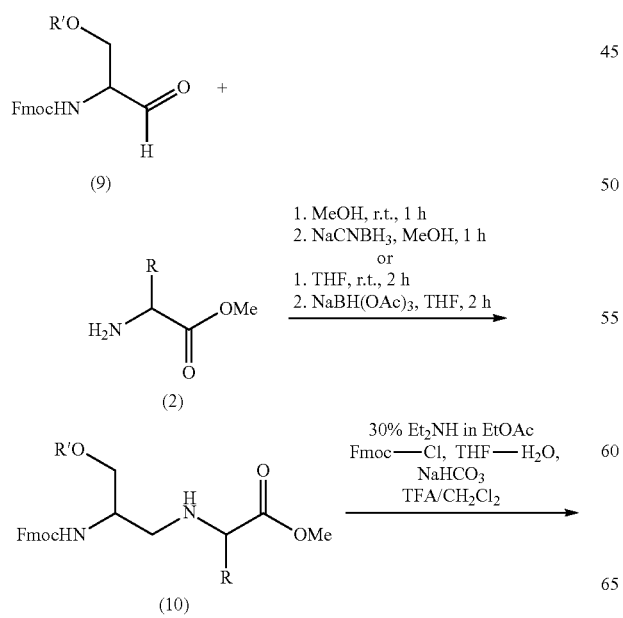

Method C

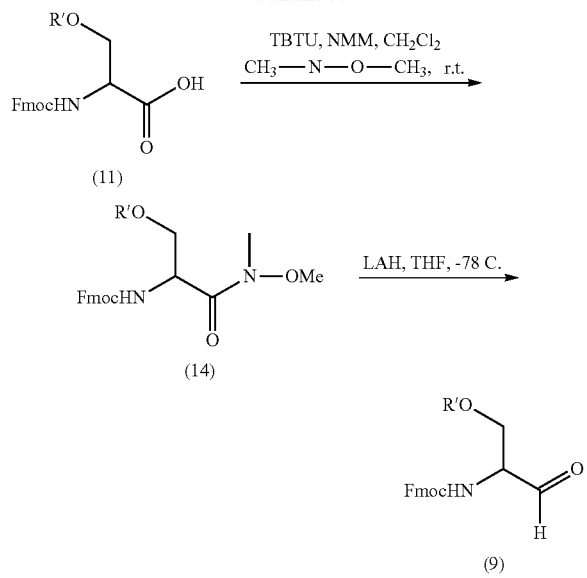

Method D:

Synthesis of various Fmoc-O-protected serinals (9). Synthesis of Fmoc-O—R' serine methyl ester (12): A slight suspension of 80 mmol of Fmoc O—R' serine (11), 10.0 g (120 mmol) of solid sodium bicarbonate, and 10.0 mL (160 mmol) of iodomethane in 80 mL of dry dimethylformamide, kept under nitrogen, was stirred at room temperature overnight. The reaction mixture was then poured over 500 mL of water, and the solid filtered. The solid was redissolved in 800 mL of ethyl acetate, and washed with 1×200 mL of water, dried over magnesium sulfate, and concentrated. No purification was required.

| R' | Analytical Data for Compounds (12) |
|---|---|
| $^t$Bu | $^1$H NMR δ (CDCl$_3$): 1.14 (s, 9H, $^t$Bu), 3.57-3.70 (m, 1H, CH$_2$—O), 3.75 (s, 3H, O—CH$_3$), 3.79-3.83 (m, 1H, CH$_2$—O), 4.01-4.50 (a series of multiples, 4H), 5.64-5.68 (d, 1H, NH), 7.28-7.78 (8H, fulvene), yield = 93% $t_R$ = 7.8 min. |
| Trt | $^1$H NMR δ (CDCl$_3$): 3.42-3.48 (m, 1H, CH$_2$—O), 3.59-3.66 (m, 1H, CH$_2$—O), 3.81 (s, 3H, CH$_3$—O), 4.10-4.18 (m, 1H, CH), 4.36-4.42 (m, 2H, CH$_2$—O), 4.50-4.57 (m, 1H, CH—N), 5.73-5.78 (d, 1H, NH), 7.22-7.82 (8H, fulvene), yield = quant., $t_R$ = 9.04 min. |

Synthesis of Fmoc-O—R' serinol (13): To a solution of 10.0 mmol of Fmoc O—R' serine (11) in 50 mL of dry tetrahydrofuran, kept at −20° C. under nitrogen, was added 1.77 mL (12.7 mmol) of triethyl amine, followed by the slow addition of 1.57 mL (12.0 mmol) of isobutylchloroformate. The mixture was stirred for 30 minutes, and then poured slowly over an ice-cold solution of 3.77 g (99.6 mmol) of sodium borohydride in 10 mL of water, keeping the temperature below 5° C. The reaction was stirred at 0° C. for 15 minutes, and then quenched with 1N hydrochloric acid solution. The reaction mixture was diluted with 100 mL of ethyl acetate, and the layers separated. The organic layer was washed with 2×25 mL of 1N hydrochloric acid solution, 2×25 mL of water, dried over magnesium sulfate and concentrated. The compounds were purified by silica gel column chromatography.

| R' | Analytical Data for Compounds (13) |
|---|---|
| $^t$Bu | $^1$H NMR δ (CDCl$_3$): 1.14 (s, 9H, $^t$Bu), 2.90-2.95 (d, 1/2H, CH$_2$—O), 3.63 (d, 2H, CH$_2$—O), 3.65-3.93 (m, 3H, CH$_2$—O), 4.20-4.35 (t, 1H, CH), 4.35-4.45 (d, 2H, CH$_2$), 5.50-5.57 (d, 1H, NH), 7.26-7.8 (8H, fulvene), yield = 85%, $t_R$ = 6.42 min. |
| Trt | $^1$H NMR δ (CDCl$_3$): 3.24-3.32 (br. d, 1H, CH$_2$—O), 3.30-3.45 (br. m, 1H, CH$_2$—O), 3.60-3.987 (br. m, 3H, CH$_2$—O, and CH—N), 4.13-4.22 (br. m, 1H, CH), 4.32-4.40 (br. d, 2H, CH$_2$), 5.24-5.32 (br. d, 1H, NH), 7.16-7.76 (23H, fulvene, and Trt), yield = 92%, $t_R$ = 8.39 min. |

Synthesis of Fmoc-O—R' serine Weinreb amide (14): A suspension of 20.2 mmol of Fmoc O—R' serine (11), 6.98 g (21.6 mmol) of 2-(1H-benzotriazol-1-yl)-1,1,3,3-tetramethyluronium tetrafluoroborate (TBTU), and 2.5 mL (22.7 mmol) of N-methyl-morpholine in 80 mL of dry dichloromethane was stirred at room temperature under nitrogen for 20 minutes, and then 3.02 g (31 mmol) of N,O-di-methyl-hydroxylamine hydrochloride and 3.3 mL (30 mmol) of N-methyl-morpholine were added, and the suspension stirred at room temperature overnight. The solution formed was then concentrated to dryness, repartitioned between 200 mL of ethyl acetate and 100 mL of water, washed with 2×40 mL of 1N hydrochloric acid solution and then 2×40 mL of saturated sodium bicarbonate solution, dried over magnesium sulfate, and concentrated. No purification was required.

| R' | Analytical Data for Compounds (14) |
|---|---|
| $^t$Bu | $^1$H NMR δ (CDCl$_3$): 1.45 (s, 9H, $^t$Bu), 3.30 (s, 3H, CH$_3$—N), 3.55-3.7 (m, 2H, CH$_2$—O), 3.76 (s, 3H, CH$_3$—O), 4.19-4.26 (m, 1H, CH), 4.30-4.38 (m, 2H, CH$_2$—O), 4.82-4.91 (broad m, 1H, CHN), 5.68-5.75 (d, 1H, NH), 7.2-7.8 (8H, fulvene), yield = quant., $t_R$ = 6.59 min. |
| Trt | $^1$H NMR δ (CDCl$_3$): 3.24 (s, 3H, CH$_3$N), 3.34-3.46 (m 2H, CH$_2$O), 3.62 (s, 3H, CH$_3$O), 4.15-4.37 (two m, CH$_2$, CH), 4.86-4.98 (m 1H, CHN), 5.80-5.86 (d, 1H, NH), 7.18-7.8 (a series of m, 23H, Trt and fulvene), yield = quant., $t_R$ = 8.0 min. |

Synthesis of Fmoc-O—R' serinal (9) from ester (12): To a solution of 3.5 mmol of (12) in 5 mL of tetrahydrofuran, kept at −78° C. under nitrogen, was added slowly 10 mL of 1N diisobutyl aluminum hydride (DIBAL) solution, stirred for 15 minutes, and quenched by the slow addition of a saturated solution of sodium and potassium tartrate. The reaction was allowed to warm up to room temperature, diluted with 50 mL of ethyl acetate, and 50 mL of a saturated solution of sodium and potassium tartrate was added. The layers were separated, and the aqueous layer re-extracted with 1×50 mL of ethyl acetate. The organic layers were combined, dried over magnesium sulfate, and concentrated. Compounds (9) were used without further purification in the next step.

| R' | Analytical Data for Compounds (9) |
|---|---|
| $^t$Bu | $^1$H NMR δ (CDCl$_3$): 1.16 (s, 9H, $^t$Bu), 3.59-3.66 (dd, 1H, CH$_2$O), 3.90-3.98 (dd, 1H, CH$_2$O), 4.20-4.27 (t, 1H, CH), 4.32-4.45 (two m, 3H, CHN, and CH$_2$O), 5.64-5.74 (br. d, 1H, NH), 7.28-7.35 (m, 2H, fulvene), 7.36-7.44 (m, 2H, fulvene), 7.58-7.65 (d, 2H, fulvene), 7.73-7.78 (d, 2H, fulvene), 9.62 (s, 1H, CHO). |
| Trt | $^1$H NMR δ (CDCl$_3$): 3.53-3.61 (dd, 1H, CH$_2$O), 3.66-3.75 (dd, 1H, CH$_2$O), 4.33-4.47 (two m, 4H, CHN, CH, and CH$_2$), 5.66-5.75 (d, 1H, NH), 7.20-7.81 (a series of m, 23H, Trt, and fulvene), 9.6 (s, 1H, CHO). |

Synthesis of Fmoc-O—R' serinal (9) from alcohol (13): To a solution of 80 mmol of Fmoc-O—R' serinol (13) in 200 mL of dry dichloromethane, kept at room temperature under nitrogen, was added 88 mmol of Dess-Martin periodinane, and the reaction was stirred for 2.5 hours and quenched by addition of 400 mL of 10% aqueous sodium thiosulfate solution. The layers were separated, and the organic layer concentrated, diluted with 300 mL of ethyl ether, and washed three times with a saturated aqueous bicarbonate solution containing 10% sodium thiosulfate, dried over magnesium sulfate, and concentrated.

Synthesis of Fmoc-O—R' serinal (9) from Weinreb amide (14): To a solution of 8.8 g (20.2 mmol) of crude Fmoc-O—R' serine Weinreb amide intermediate (14) in 60 mL of dry tetrahydrofuran, cooled to −78° C. under nitrogen, was added 30 mL of 1N lithium aluminum hydride solution in tetrahydrofuran. The solution was stirred for 15 minutes and then quenched by the slow addition of 30 mL of a 1.4N solution of potassium hydrogen sulfate. After warming up to room temperature, the solid was filtered and the filtrate concentrated to dryness. The residue was repartitioned between 50 mL of ethyl acetate and 25 mL of 1N hydrochloric acid solution. The layers separated, and the organic layer was dried over magnesium sulfate, filtered, and concentrated.

Synthesis of (2-Fmoc-amino-3-R'—O-propylamino)-2-substituted acetic acid methyl ester (10): compounds (10) were prepared by reductive amination using sodium cyanoborohydride or sodium triacetoxyborohydride as the reducing agent.

Sodium cyanoborohydride method: To a solution of 8.5 mmol of (2) hydrochloride salt in 20 mL of methanol, kept at room temperature under nitrogen, was added 2.3 mmol of solid potassium hydroxide, and the mixture stirred for 25 minutes. A solution of Fmoc-O—R' serinal (9) in 10 mL of methanol was added to the above suspension, and the reaction mixture was stirred for 1 hour. A solution of 8.5 mL of 1N sodium cyanoborohydride in tetrahydrofuran was added slowly, and the reaction stirred for another 1 hour, filtered, and concentrated. The residue was partitioned between ethyl acetate and water, and the organic layer washed with 1×20 mL of saturated sodium bicarbonate, dried over sodium sulfate, and concentrated.

Sodium triacetoxyborohydride method: A suspension of 21 mmol of (2) hydrochloride salt, and 2.9 mL (21 mmol) of triethyl amine in 50 mL of dry tetrahydrofuran, was stirred at room temperature for 45 min, and then a solution of ~20 mmol crude Fmoc-(O—R')-serinal (9) in 30 mL of tetrahydrofuran was added, followed by 1.7 g of 4A powdered molecular sieves, and the suspension was stirred for an additional 2 h. 6.4 g (30 mmol) of solid sodium triacetoxyborohydride was added, and the suspension stirred at room temperature overnight. The suspension was diluted with methanol, the molecular sieves filtered, and the filtrate concentrated. The residue was partitioned between 100 mL of ethyl acetate and 50 mL of water. The organic layer was dried over sodium sulfate, filtered, and concentrated.

Compounds (10) were purified by silica gel column chromatography.

| R' | R | Analytical Data for Compounds (10) |
|---|---|---|
| tBu | (—CH(CH₃)—, propyl group) | $^1$H NMR δ (CDCl$_3$): 1.17 (s, 9H, $^t$Bu), 1.26-1.32 (d, 3H, CH$_3$), 2.68-2.80 (br. m, 2H, CH$_2$N), 3.32-3.56 (two br. m, 2H, CH$_2$O), 3.72 (s, 3H, CH$_3$O), 3.66-3.82 (m, 1H, CHN), 4.18-4.28 (t, 1H, CH), 4.30-4.46 (d, 2H, CH$_2$), 5.34-5.44 (br. d, 1H, NH), 7.25-7.44 (two m, 4H, fulvene), 7.59-7.64 (d, 2H, fulvene), 7.74-7.79 (d, 2H, fulvene), yield = 57%, $t_R$ = 4.93 min, (M$^+$ + 1) = 455.67. |
| tBu | (isobutyl branched group) | $^1$H NMR δ (CDCl$_3$): 0.88-0.98 (br. t, 6H CH$_3$), 1.21 (s 9H, $^t$Bu), 1.26-1.34 (m, 2H, CH$_2$), 1.44-1.54 (m, 1H, CH), 2.58-2.86 (two m, 1H, CH$_2$N), 3.25-3.35 (m, 1H, CH$_2$N), 3.37-3.58 (two m, 2H, CH$_2$O), 3.72-3.80 (br. m, 1H, CHN), 4.14-4.31 (m, 1H, CH), 4.32-4.45 (br. d, 2H, CH$_2$O), 5.34-5.44 (br. d, 1H, NH), 7.30-7.84 (a series of m, 8H, fulvene), yield = 50%, $t_R$ = 5.66 min, (M$^+$ + 1) = 511.67. |
| tBu | (methyl, H substituent) | $^1$H NMR δ (CDCl$_3$): 1.17 (s, 9H, $^t$Bu), 2.68-2.78 (m, 1H, CH$_2$N), 2.82-2.92 (m, 1H, CH$_2$N), 3.35-3.55 (m, 4H, CH$_2$N, and CH$_2$O), 3.73 (s, 3H, CH$_3$O), 3.75-3.85 (m, 1H, CHN), 4.20-4.28 (m, 1H, CH), 4.32-4.48 (m, 2H, CH$_2$), 5.40-5.50 (d, 1H, NH), 7.28-7.8 (a series of m, 8H, fulvene), yield = 44%, $t_R$ = 5.02 min, (M$^+$ + 1) = 441.50. |
| tBu | (n-butyl-like chain) | $^1$H NMR δ (CDCl$_3$): 0.84-0.92 (br. t, 3H, CH$_3$), 1.17 (s, 9H, $^t$Bu), 1.28-1.35 (m, 4H, CH$_2$), 1.48-1.84 (two m, 2H, CH$_2$), 2.62-2.82 (m, 2H, CH$_2$N), 3.20-3.33 (m, 1H, CHN), 3.35-3.54 (two m, 2H, CH$_2$O), 3.72 (s, 3H, CH$_3$O), 3.64-3.80 (m, 1H, CHN), 4.20-4.28 (t, 1H, CH), 4.32-4.42 (m, 2H, CH$_2$O), 5.34-5.44 (br. d, 1H, NH), 7.25-7.79 (a series of m, 8H, fulvene), yield = 65%, $t_R$ = 5.85 min, (M$^+$ + 1) = 441.27. |
| Trt | (chain terminating in C(=O)NHTrt) | $^1$H NMR δ (CDCl$_3$): 2.36-2.63 (br. m, 2H, CH$_2$CO), 2.65-2.90 (br. m, 2H, CH$_2$N), 3.05-3.20 (br. m, 2H, CH$_2$O), 3.50-3.64 (br. m, 1H, CHN), 3.68 & 3.69 (two s, 3H, CH$_3$O), 3.82-3.94 (br. m, 1H, CHN), 4.12-4.21 (br. m, 1H, CH), 4.24-4.43 (br. m, 2H, CH$_2$O), 4.90-4.98 (br. d, 1H, NH), 7.15-7.80 (a series of m, 23H, fulvene and Trt), yield = 39%, $t_R$ = 8.13 min, (M$^+$ + 1) = 926.99. |
| Trt | (longer chain terminating in C(=O)NHTrt) | $^1$H NMR δ (CDCl$_3$): 1.68-1.82 (m, 1H, CH$_2$), 1.85-1.99 (m, 1H, CH$_2$), 2.12-2.37 (m, 2H, CH$_2$CO), 2.58-2.96 (a series of four m, 2H, CH$_2$N), 3.08-3.28 (br. m, 2H, CH$_2$O), 3.66 & 3.67 (two s, 3H, CH$_3$O), 3.76-3.89 (br. m, 1H, CHN), 4.15-4.24 (br. m, 1H, CH), 4.28-4.41 (br. d, 2H, CH$_2$O), 5.10-5.22 (br. d, 1/2H, NH), 5.28-5.35 (br. d, 1/2H, NH), 7.15-7.80 (a series of m, 23H, fulvene, and Trt), yield = 43%, $t_R$ = 8.10 min, (M$^+$ + 1) = 940.97. |
| Trt | (chain with guanidino-HN=C(NH)NHPbf) | $^1$H NMR δ (CDCl$_3$): 1.43 (s, 6H, CH$_3$), 1.46-1.56 (m, 4H, CH$_2$), 2.06 (s, 3H, CH$_3$), 2.50 (s, 3H, CH$_3$), 2.57 (s, 3H, CH$_3$), 2.75-2.80 (m, 1H, CH$_2$N), 2.91 (s, 2H, CH$_2$), 3.12-3.32 (three br. m, 4H, CH$_2$N), 3.68 (s, 3H, CH$_3$O), 4.13-4.21 (t, 1H, CH), 4.28-4.38 (d, 2H, CH$_2$), 5.12-5.23 (br. d, 1H, NH), 5.80-6.12 (two br. m, 2H, NH), 7.18-7.80 (a series of m, 23H, fulvene, and Trt), yield = 68%, $t_R$ = 7.52 min, (M$^+$ + 1) = 997.91. |
| Trt | (imidazole-containing side chain, N-Trt) | $^1$H NMR δ (CDCl$_3$): 2.75-2.98 (two m, 2H, CH$_2$N), 3.06-3.18 (m, 1H, CH$_2$N), 3.22-3.33 (m, 1H, CH$_2$N), 3.57 & 3.60 (two s, 3H, CH$_3$O), 3.80-3.92 (m, 1H, CHN), 4.00-4.08 (m, 1H, CH), 4.18-4.30 (br. d, 2H, CH$_2$), 7.00-7.80 (a series of m, 25H, fulvene, Trt, and Imidazole), yield = 57%, $t_R$ = 7.59 min, (M$^+$ + 1) = 949.79. |

| R' | R | Analytical Data for Compounds (10) |
|---|---|---|
| Trt | CH₂-(4-OtBu-phenyl) | ¹H NMR δ (CDCl₃): 1.26 & 1.27 (two s, 9H, ᵗBu), 2.50-2.61 (dd, 1H, CH₂-Ph), 2.76-2.86 (m, 2H, CH₂—Ph, and CH₂N), 2.92-3.20 (m, 1H, CH₂N), 2.92-3.20 (m, 2H, CH₂O), 3.32-3.46 (m, 1H, CH₂O), 3.59 (s, 3H, CH₂O), 3.79-3.88 (m, 1H, CHN), 4.18-4.28 (m, 1H, CH), 4.30-4.37 (br. d, 2H, CH₂O), 5.18-5.26 (br. d, 1H, NH), 6.80-6.88 (d, 2H, Ph), 6.96-7.02 (d, 2H, Ph), 7.18-7.80 (a series of m, 23H, fulvene, and Trt), yield = 23%. |
| Trt | CH₂-CH₂-OtBu | ¹H NMR δ (CDCl₃): 1.11 (s, 9H, ᵗBu), 2.54-2.74 (two m, 2H, CH₂N), 3.02-3.58 (six m, 6H, CH₂O, CH₂N, and CHN), 3.70 (s, 3H, CH₃O), 3.83-3.93 (m, 1H, CHN), 4.15-4.29 (m, 1H, CH), 4.34-4.37 (d, 2H, CH₂), 5.46-5.53 (br. d, 1H, NH), 7.18-7.79 (a series of m, 23H, fulvene and Trt), yield = 45%, (M⁺ + 1) = 713.42. |
| ᵗTrt | C(CH₃)₃ | ¹H NMR δ (CDCl₃): 0.80-0.92 (m, 7H, CH₃), 1.75-1.90 (br. m, 1H, CH), 2.6-4.36 (a series of m, 9H, CH₂O, CH₂N, CHN), 3.68 (s, 3H, CH₃O), 5.5 (d, 0.5H, CH), 7.23-7.77 (m, 24H, fulvene and Trt), yield = 72% (3 steps), $t_R$ = 6.86 min, (M⁺ + 1) = 669.10. |

Synthesis of 4-Fmoc-6-hydroxymethyl-3-substituted-piperazin-2-one (6): For the preparation of compounds (6) three steps were required: (a) Fmoc deprotection with concomitant cyclization, (b) Fmoc protection, and (c) hydroxyl group deprotection.

Fmoc group removal and cyclization: A solution of 10 mmol of cyclic compound in 30 mL of 30% diethyl amine in ethyl acetate solution was stirred at room temperature overnight, and then concentrated to dryness.

(a) Fmoc protection: To a biphasic solution of 10 mmol of compound in 20 mL of tetrahydrofuran and 10 mL of water, was added 2.52 g (30 mmol) of solid sodium bicarbonate, followed by 3.36 g (13 mmol) of Fmoc-Cl. The mixture was stirred for 3 hours, diluted with ethyl acetate, the layers separated, and the organic layer washed with water, dried over magnesium sulfate, and concentrated.

(b) Hydroxyl group deprotection: For compounds containing a ᵗBu ether protecting group: The compounds were deprotected with a solution of 90% trifluoroacetic acid in dichloromethane for 1-2 hours, and then concentrated to dryness. The residue was dissolved in ethyl acetate and washed with a saturated solution of sodium bicarbonate, dried over magnesium sulfate, and then concentrated. For compounds containing a Trt ether protecting group: the compounds were deprotected by adding a solution of 1-10% trifluoroacetic acid in dichloromethane containing 2-10% tri-isopropyl silane. The reaction was instantaneous. The solution was then neutralized by pouring it into a saturated solution of sodium bicarbonate. The layers were separated, dried over sodium sulfate, and concentrated.

Compounds (6) were purified by silica gel column chromatography.

| R | Analytical Data for Compounds (6) |
|---|---|
| CH₃ | ¹H NMR δ (CDCl₃): 1.17-1.35 (b. m, 3H, CH₃), 2.64-2.82 (t, 1H, CH₂N), 3.2-3.8 (two br. m, 3H, CH₂O, CH₂N), 4.18-4.44 (br. t, 1H, CH), 4.64-4.90 (br. d, 2H, CH₂O), 6.70-6.86 (br. s, 1H, NH), 7.22-7.82 (a series of m, 8H, fulvene), yield = 72%, $t_R$ = 4.64 min, (M⁺ + 1) = 367.32. |
| iso-butyl | ¹H NMR δ (CDCl₃): 0.64-1.02 (m, 6H, CH₃), 1.45-1.63 (m, 3H, CH₂, and CH), 2.65-2.84 (m, 1H, CH₂N), 2.89-3.76 (a series of br. m, 5H, CH₂O, and CHN), 4.17-4.28 (br. m, 1H, CH), 4.48-4.82 (three br. m, CH₂O, NH, and OH), 6.95-7.85 (a series of br. m, 8H, fulvene), yield = 51%, $t_R$ = 5.43 min, (M⁺ + 1) = 409.08. |
| H | ¹H NMR δ (CDCl₃): 3.17-3.78 (a series of br. m, 5H, CH₂O, CH₂N, and CHN), 421-4.27 (t, 1H, CH), 4.42-4.68 (br. peak, 2H, CH₂O), 6.62 (br. s, 1H, NH), 7.28-7.81 (a series of m, 8H, fulvene), yield = 67%, $t_R$ = 4.50 min, (M⁺ + 1) = 353.45. |
| n-butyl | ¹H NMR δ (CDCl₃): 0.72-0.90 (br. peak, 3H, CH₃), 1.0-1.40 (br. peak, 4H, CH₂), 1.48-1.90 (three br. peaks, 2H, CH₂), 2.68-2.80 (t, 1H, CH₂N), 3.10-3.70 (four br. peaks, 4H, CH₂O, CHN, and CH₂N), 4.15-4.25 (br. peak, 1H, CH), 4.54-4.62 (br. d, 2H, CH₂O), 7.25-7.80 (a series of m, 8H, fulvene), yield = 72%, $t_R$ = 5.77 min, (M⁺ + 1) = 408.95. |
| CH₂-CH₂-C(=O)-NHTrt | ¹H NMR δ (CDCl₃): 2.50-3.38 (four overlapping br. m, 7H, CH₂—CO, CH₂N, CH₂O, and CHN), 3.42-3.64 (m, 1/2 H, CHN), 3.70-3.88 (m, 1/2 H, CHN), 4.16-4.23 (br. d, 1H, CH), 4.48-4.68 (br. m, 2H, CH₂O), 4.94-5.05 (br. d, 1H, NH), 6.95-7.80 (a series of m, 23H, fulvene and Trt), yield = 83%, $t_R$ = 7.04 min, (M⁺ + 1) = 652.61. |
| CH₂-C(=O)-NHTrt | ¹H NMR δ (CDCl₃): 1.67-1.78 (br. m, 1H, CH₂), 1.81-2.0 (br. m, 1H, CH₂), 2.10-2.43 (br. m, 2H, CH₂—CO), 2.58-2.81 (br. m, 2H, CH₂N), 3.02-3.66 (a series of br. m, 4H, CH₂O, and CHN), 4.17-4.23 (br. m, 1H, CH), 4.40-4.80 (br. m, 2H, CH₂O), 7.15-7.80 (a series of m, 23H, fulvene, and Trt), yield = 80%, $t_R$ = 7.04 min, (M⁺ + 1) = 666.66. |
| (CH₂)₃-NH-C(=NH)-NHPbf | ¹H NMR δ (CDCl₃): 1.43 (s, 6H, CH₃), 1.50-1.60 (br. m, 4H, CH₂), 2.10 (s, 3H, CH₃), 2.48 (s, 3H, CH₃), 2.55 (s, 3H, CH₃), 2.92 (s, 2H, CH₂), 3.08-3.47 (two m, 3H, CH₂O, and CH₂N), 3.57-3.97 (a series of m, 3H, CH₂O, and CHN), 4.15-4.25 (br. m, 1H, CH), 4.44-4.74 (br. m, 2H, CH₂), 7.20-7.80 (a series of br. m, 8H, fulvene), yield = 91%, $t_R$ = 6.05 min, (M⁺ + 1) = 704.71. |
| CH₂-(N-Trt-imidazol-4-yl) | ¹H NMR δ (CDCl₃): 2.14-2.56 (two m, 2H, CH₂-Im), 2.90-3.90 (a series of m, 4H, CH₂N, and CH₂O), 4.0-4.74 (a series of m, 4H, CHN, CH, CH₂), 7.0-7.80 (a series of multiples, 25H, fulvene, Im, and Trt), yield = 64%, $t_R$ = 5.27 min, (M⁺ + 1) = 675.08. |

Analytical Data for Compounds (6)

| R | Analytical Data for Compounds (6) |
|---|---|
| 4-(OtBu)benzyl | $^1$H NMR δ (CDCl$_3$): 1.29 (s, 9 H, $^t$Bu) 2.47-2.74 (a series of m, 2 H, CH$_2$Ph), 2.90-3.04 (m, 1 H, CH$_2$Ph), 3.06-3.45 (three m, 6 H, CH$_2$O, and CH$_2$N), 3.89-4.29 (three m, 2 H, CH, and CHN), 4.32-4.42 (m, 1 H, CHN), 4.56-4.66 (m, 2 H, CH$_2$), 6.81-7.80 (a series of m, 12 H, fulvene, and Ph), yield = 71%, (M$^+$ + 1) = 515.81. |
| CH$_2$OtBu | $^1$H NMR δ (CDCl$_3$): 1.00 & 1.10 (two s, 9 H, $^t$Bu), 3.0-3.74 (four br. m, 7 H, CH$_2$O, CH$_2$N, and CHN), 3.86-4.26 (a series of m, 2 H, CHN, and CH), 4.42-4.68 (br. d, 2 H, CH$_2$), 7.26-7.80 (a series of br. m, 8 H, fulvene), yield = 55%, (M$^+$ + 1) = 439.08. |

Synthesis of 4-Fmoc-5-substituted-6-oxo-piperazine-2-carboxylic acid (7): Compounds (7) were prepared as described in method A. Compounds (7) were purified by silica gel column chromatography.

Analytical Data for Compounds (7)

| R | Analytical Data for Compounds (7) |
|---|---|
| CH$_3$ | $^1$H NMR δ (CDCl$_3$): 1.08-1.20 (br. peak, 1.5 H, CH$_3$), 1.30-1.38 (br. peak, 1.5 H, CH$_3$), 2.86-3.07 (br. m, 1 H, CH$_2$N), 3.83-3.97 (br. m, 1 H, CH$_2$N), 4.18-4.37 (a series of br. peaks, 2 H, CH and CHN), 4.40-4.74 (two br. peaks, 3 H, CH$_2$O, and CHN), 7.28-7.82 (a series of m, 8 H, fulvene), 8.92-9.10 (br. s, 1 H, CO$_2$H), yield = 51%, t$_R$ = 4.80 min, (M$^+$ + 1) = 381.57. |
| isobutyl | $^1$H NMR δ (CDCl$_3$): 0.40-1.60 (a series of br. peaks, 9 H, CH, CH$_2$, and CH$_3$), 2.81-3.09 (br. peak, 1 H, CH$_2$N), 3.68-3.80 (br. peak, 2 H, CHN), 3.96-4.32 (br. peaks, 2 H, CH, and CNH), 4.48-4.68 (br. peak, CH$_2$O), 7.26-7.84 (a series of m, 8 H, fulvene), yield = 50%, t$_R$ = 5.57 min, (M$^+$+ 1), = 423.15. |
| H | $^1$H NMR δ (CDCl$_3$): 3.77-3.99 (m, 1 H, CHN), 3.90-4.35 (a series of m, 5 H, CH$_2$N, CH), 4.44-4.57 (d, 2 H, CH$_2$), 7.3-7.82 (a series of m, 8 H, fulvene), yield = 48%, t$_R$ = 4.58 min, (M$^+$ + 1) = 367.30. |
| n-butyl | $^1$H NMR δ (CDCl$_3$): 0.69-1.90 (a series of br. peaks, CH$_2$, and CH$_3$), 2.85-3.05 (br. peak, 2 H, CH$_2$N), 3.65-3.95 (two br. peaks, 1 H, CHN), 4.00-4.40 (two br. peaks, CH$_2$N, and CH), 4.41-4.74 (br. peak, 3 H, CH$_2$O, and CHN), 7.20-7.80 (a series of br. m, 8 H, fulvene), yield = 70%, t$_R$ = 5.93 min, (M$^+$ + 1) = 423.42. |
| CH$_2$CH$_2$CONHTrt | $^1$H NMR δ (CDCl$_3$): 2.51-3.06 (a series of m, 2 H, CH$_2$—CO), 3.85-4.86 (a series of m, 7 H, CH$_2$N, CHN, CH, and CH$_2$O), 7.0-7.78 (a series of br. m, 23 H, fulvene and Trt), yield = 30%, t$_R$ = 7.04 min, (M$^+$ + 1) = 666.79. |
| CH$_2$CONHTrt | $^1$H NMR δ (CDCl$_3$): 1.74-2.46 (a series of br. m, 4 H, CH$_2$—CO, and CH$_2$), 3.78-4.06 (two m, 2 H, CH$_2$N), 4.16-4.68 (a series of br. m, 5 H, CHN, CH, and CH$_2$O), 7.14-7.82 (a series of br. m, 23 H, fulvene, and Trt), yield = 47%, t$_R$ = 7.11 min, (M$^+$ + 1) = 680.33. |
| (CH$_2$)$_3$NHC(=NH)NHPbf | $^1$H NMR δ (CDCl$_3$): 1.08-1.60 (a series of br. peaks, 8 H, CH$_2$, and CH$_3$), 2.12 (s, 3 H, CH$_3$), 2.48 (s, 3 H, CH$_3$), 2.57 (s, 3 H, CH$_3$), 2.92 (s, 2 H, CH$_3$), 3.10-3.25 (br. m, 2 H, CH$_2$N), 3.82-4.28 (a series of br. m, 4 H, CH$_2$N, CHN, CH), 4.40-4.70 (br. m, 3 H, CHN, and CH$_2$O), 7.20-7.80 (a series of br. m, 8 H, fulvene), yield = 42%, t$_R$ = 6.15 min, (M$^+$ + 1) = 718.69. |
| 4-(OtBu)benzyl | $^1$H NMR δ (CDCl$_3$): 1.28 & 1.34 (two s, 9 H, $^t$Bu), 2.42-3.64 (a series of br. m, 5 H, CH$_2$N, CHN, and CH$_2$Ph), 4.0-4.76 (a series of br. m, 4 H, CHN, CH, and CH$_2$O), 6.60-6.96 (br. m, 4 H, Ph), 7.20-7.80 (a series of br. m, 8 H, fulvene), yield = 67%, (M$^+$ + 1) = 529.17. |
| CH$_2$OtBu | $^1$H NMR δ (CDCl$_3$): 0.96- & 1.10 (two s, 9 H, $^t$Bu), 3.04-3.18 (br. m, 0.5 H, CH$_2$), 3.30-3.94 (four br. m, 3.5 H, CH$_2$N, and CH$_2$O), 3.98-4.32 (br. m, 2 H, CH, and CHN), 4.33-4.74 (two br. m, 3 H, CHN, CH$_2$O), 7.28-7.80 (a series of m, 8 H, fulvene), yield = 60%, (M$^+$ + 1) = 453.37. |

Method E:

(2-Fmoc-amino-3-hydroxy-propyl-Cbz-amino)-2-substituted acetic acid methyl ester (15) were prepared by reductive amination of Fmoc serinal (OR') (9) with an α amino ester (2), using either sodium cyanoborohydride or sodium triacetoxyborohydride as the reducing agent. The secondary amine was protected with benzylchloroformate, and then the hydroxyl group deprotected with trifluoroacetic acid solution. Compounds (15) were then Fmoc deprotected. The amino ester intermediates cyclized immediately to form 4-Cbz-3-substituted 6-hydroxymethyl-piperazin-2-ones (16). Fmoc 3-substituted 6-hydroxymethyl-piperazin-2-ones (6) were prepared by protecting group exchange, and then oxidized to the desired products (7) as described in method A.

Method E

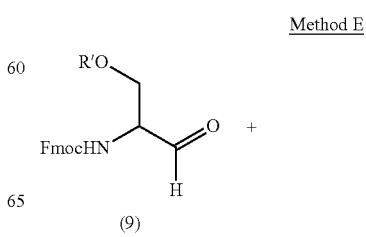

(9)

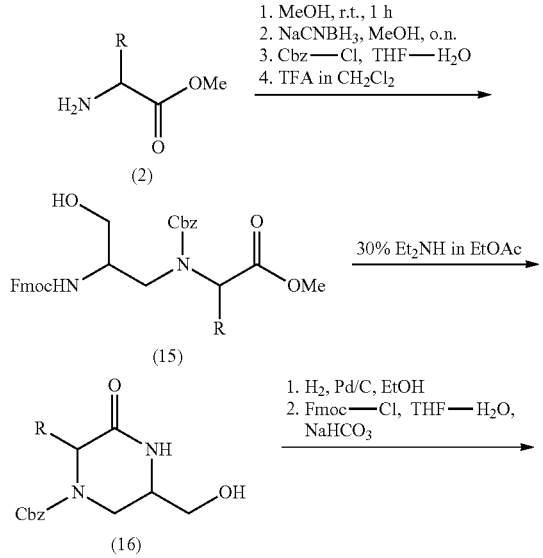

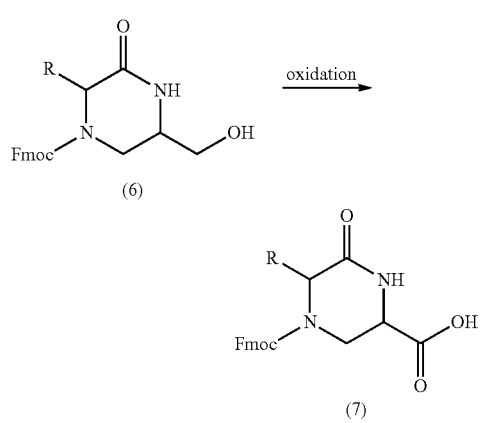

Synthesis of (2-Fmoc-amino-3-hydroxy-propyl-Cbz-amino)-2-substituted acetic acid methyl ester (15): A suspension of 67 mmol of amino ester hydrochloride (2), and 20.9 mmol of solid potassium hydroxide in 80 mL of methanol was stirred at room temperature for 25 minutes, and then added to a suspension of (9) in 250 mL of methanol. The reaction mixture was stirred for 1.5 hours, followed by the slow addition of 70 mL of 1N sodium cyanoborohydride solution in tetrahydrofuran. The reaction was stirred overnight, and then concentrated. The residue was partitioned between 300 mL of tetrahydrofuran and 50 mL of 1N hydrochloric acid solution. The layers were separated, and the organic layer neutralized with a solution of 239 mmol of sodium bicarbonate in 50 mL of water, and then 66 mmol of benzyl chloroformate was added slowly, and the reaction was stirred for 3 hours, diluted with 200 mL of ethyl acetate, and the layers separated. The organic layer was dried over magnesium sulfate, and concentrated. The residue was dissolved in a solution of trifluoroacetic acid in dichloromethane, and stirred at room temperature for 2 hours. The solution was poured over 200 mL of saturated sodium bicarbonate solution. The layers separated, and the organic layer was dried over magnesium sulfate, and concentrated. Compounds (15) were purified by silica gel column chromatography.

| R | Analytical Data for Compounds (15) |
|---|---|
| ![O'Bu structure] | $^1$H NMR δ (CDCl$_3$): 1.38-1.45 (d, 9 H, $^t$Bu), 2.68-2.78 (m, 1/2 H, CH$_2$—CO), 3.0-3.20 (m, and s together, 3.5 H, CH$_2$—CO, CH$_2$—O, and CH$_3$—O), 3.52-3.60 (m, 1 H, CH$_3$—O), 3.96-4.40 (a series of multiples, 4 H), 4.96-5.10 (m, 2 H, CH$_2$—O), 5.77-5.83 (m, 1/2 H, NH), 7.14-7.79, (a series of m, 23 H, Trt and fulvene), yield = 70%, t$_R$ = 9.82 min. |

Synthesis of 4-Cbz-6-hydroxymethyl-3-substituted-piperazin-2-ones (16): A solution of 24 mmol of (15) in 100 mL of 30% diethyl amine in ethyl acetate was stirred at room temperature overnight, and then concentrated to dryness. The compounds were purified by silica gel column chromatography.

| R | Analytical Data for Compounds (16) |
|---|---|
| ![O'Bu structure] | $^1$H NMR δ (CDCl$_3$): 1.36 (d, 9 H, $^t$Bu), 2.60-2.90 (m, 2 H, CH$_2$—CO), 2.94-3.20 (br. m, 2 H, CH$_2$N, 3.38-3.50 (br. m, 2 H, CH$_2$—O), 3.86-4.20 (m, 1 H, CH—N), 4.74-4.84 (br, 1 H, OH), 5.10-5.15 (s, 2 H, CH$_2$—O), 7.26-7.36 (s, 5 H, Ph), 7.87-7.95 (s, 1 H, NH), yield = 70%, t$_R$ = 4.66 min, (M$^+$ + 1) = 379.41. |

Synthesis of 4-Fmoc-6-hydroxymethyl-3-substituted-piperazin-2-ones (6): A suspension of 15 mmol of (16), and 1.8 g of 10% palladium on carbon in 50 mL of ethanol was hydrogenated at room temperature and atmospheric pressure until HPLC showed that the reaction was complete. The mixture was then filtered through celite, concentrated, and the residue was dissolved in 35 mL of tetrahydrofuran, and 10 mL of water, and then 62 mmol of solid sodium bicarbonate was added, followed by 16 mmol of Fmoc-Cl, and the mixture was stirred for 3 hours, diluted with 100 mL of ethyl acetate and 10 mL of water. The layers were separated, and the organic layer dried over magnesium sulfate, and concentrated. Compounds (6) were purified by silica gel column chromatography.

| R | Analytical Data for Compounds (6) |
|---|---|
| ![O'Bu structure] | $^1$H NMR δ (CDCl$_3$): 1.41 (s, 9 H, $^t$Bu), 2.20-2.40 (m, 1/2 H, CH$_2$—CO, 2.64-2.96 (m, 1.5 H, CH$_2$—CO), 2.98-3.16 (m, 1 H, CH$_2$O), 3.2-3.8 (a series of br. m, 4 H, CH$_2$O, and CH$_2$N), 4.20-4.38 (two m, CHN, and CH), 4.5-4.67 (br. m, 2 H, CH$_2$O), 4.70-4.83 (br. m, 1/2 H, NH), 7.27-7.84 (a series of m, 8 H, fulvene), yield = 77%, t$_R$ = 5.78 min, (M$^+$ + 1) = 467.82. |

Synthesis of 4-Fmoc-5-substituted-6-oxo-piperazine-2-carboxylic acid (7): Compounds (7) were prepared as described in method A, and purified by silica gel column chromatography.

| R | Analytical Data for Compounds (7) |
|---|---|
|  | $^1$H NMR δ (CDCl$_3$): 1.4 (s, 9 H, $^t$Bu), 2.20-2.33 (br. d, 1 H, CH$_2$—CO), 2.55-2.67 (br. d, 1 H, CH$_2$—CO), 3.25-3.52 (br. m, 2 H, CH$_2$N), 3.82-3.94, and 4.07-4.18 (br. peaks, 1 H, CHN), 4.20-4.42 (m, 2 H, CHN, CH), 4.50-4.72 (m, 2 H, CH$_2$—O), 7.30-7.82 (8 H, fulvene), 9.20-9.35 (br. s, 1 H, CO$_2$H), yield = 63%, $t_R$ = 6.60 min, (M$^+$ + 1) = 481.17. |

Method F:

(2-Cbz-amino-3-benzyloxy-propylamino)-2-substituted acetic acid methyl esters (20) were prepared by reductive amination of Cbz serinal (OBn) (19) with an α-amino ester (2), using either sodium cyanoborohydride or sodium triacetoxyborohydride as the reducing agent. The Cbz O-Benzyl serinal (19) required for the reductive amination was obtained by oxidation of Cbz serinol (OBn) (18) with Dess-Martin periodinane. Hydrogenation of (20) followed by cyclization gave 3-substituted 6-hydroxymethyl-piperazin-2-ones which was then Fmoc protected to 4-Fmoc-3-substituted 6-hydroxymethyl-piperazin-2-ones (6). The final products (7) were obtained as described in method A.

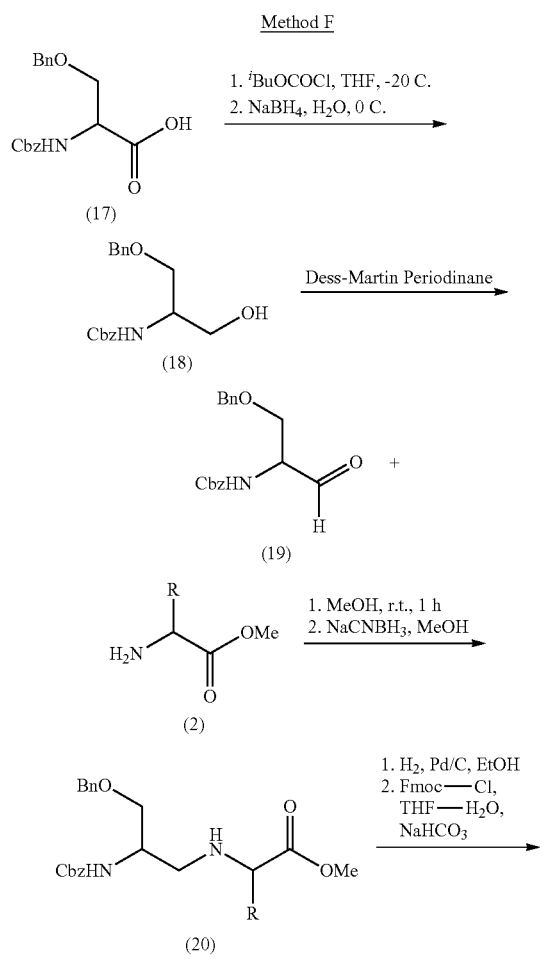

Method F

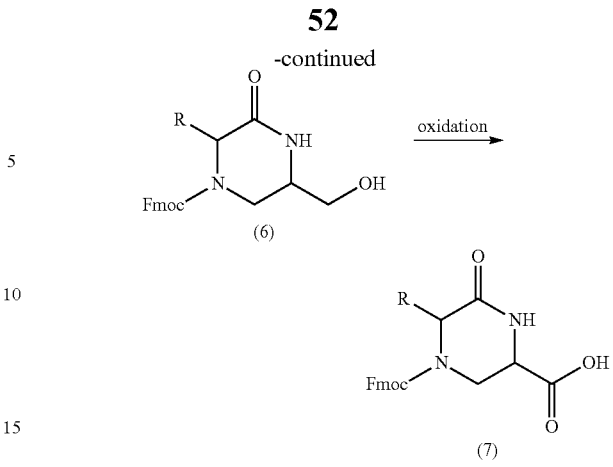

Synthesis of Cbz-serinol (OBn) (18): Compound (18) was prepared as described for compound (13). Compound (18) was obtained in 79% yield after silica gel column chromatography purification. $^1$H NMR δ (CDCl$_3$) 3.57-3.74 (two m, 3H, CHN, and CH$_2$O), 3.76-3.96 (two m, 2H, CH$_2$O), 4.50 (s, 2H, CH$_2$O), 5.10 (s, 2H, CH$_2$O), 5.40-5.50 (br. d, 1H, NH), 7.22-7.38 (m, 10H, Ph); HPLC $t_R$=5.33 min, (M++Na$^+$)=337.64.

Synthesis of Cbz serinal (OBn) (19): Compound (19) was prepared as described for compound (9). To a solution of 80 mmol of Cbz-O-Bn serinol (18) in 200 mL of dry dichloromethane, kept at room temperature under nitrogen, was added 88 mmol of Dess-Martin periodinane, and the reaction stirred for 2.5 hours, and then quenched by addition of 400 mL of 10% aqueous sodium thiosulfate solution. The layers were separated, and the organic layer concentrated, diluted with 300 mL of ethyl ether, and washed three times with a saturated aqueous bicarbonate solution containing 10% sodium thiosulfate, dried over magnesium sulfate, and concentrated. Compound (19) was obtained in 99% crude yield, and used without further purification. $^1$H NMR δ (CDCl$_3$) 3.69-3.78 (dd, 1H, CH$_2$O), 3.99-4.06 (dd, 1H, CH$_2$O), 4.37-4.46 (m, 1H, CHN), 4.47-4.52 (d, 2H, CH$_2$O), 5.14 (s, 2H, CH$_2$O), 5.65-5.75 (br. d, 1H, NH), 7.14-7.48 (a series of m, 9H, Ph), 7.98-8.08 (dd, 1H, Ph), 9.63 (s, 1H, CHO).

Synthesis of (2-Cbz-amino-3-benzyloxy-propylamino)-2-substituted acetic acid methyl esters (20): Compounds (20) were prepared as described for compound (10), but using Cbz serinal (19) as the aldehyde. Compounds (20) were purified by silica gel column chromatography.

| R | Analytical Data for Compounds (20) |
|---|---|
| 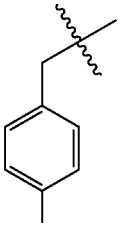 | $^1$H NMR δ (CDCl$_3$): 1.30 (s, 9 H, $^t$Bu), 2.50-2.96 (m, 3 H, CH$_2$Ph, and CH$_2$N), 3.28-3.54 (m, 3 H, CH$_2$N, and CH$_2$O), 3.59 and 3.61 (two s, 3 H, CH$_3$O), 3.68-3.86 (m, 1 H, CHN), 4.41-4.45 (d, 2 H, CH$_2$O), 5.08 (s, 2 H, CH$_2$O), 5.25-5.37 (br. t, 1 H, NH), 6.84-6.88 (d, 2 H, Ph), 6.98-7.04 (d, 2 H, Ph), 7.24-7.37 (m, 10 H, Ph), yield = 50%, (M$^+$ + 1) = 549.35. |

Synthesis of 4-Fmoc-6-hydroxymethyl-3-substituted-piperazin-2-ones (6): A suspension of 38 mmol of (20) in 160 mL of ethanol, 38 mL of 1N hydrochloric acid, and 20 g of 10% palladium on carbon was hydrogenated at room temperature and atmospheric pressure until HPLC showed that the reaction was complete. The mixture was then filtered through celite, and concentrated to dryness. The residue was diluted with 75 mL of tetrahydrofuran and neutralized with a saturated sodium bicarbonate solution. 106 mmol of solid sodium bicarbonate, and 53 mmol of Fmoc chloride were added, and the reaction stirred at room temperature until HPLC showed the reaction was complete, diluted with 300 mL of ethyl acetate and 300 mL of brine. The layers were separated, and the organic layer washed twice with brine, dried over magnesium sulfate, and concentrated. The products (6) were purified by silica gel column chromatography.

Synthesis of 4-Fmoc-5-substituted-6-oxo-piperazine-2-carboxylic acid (7): Compounds (7) were prepared as described in method A.

Synthesis of 2,2-Disubstituted Ketopiperazine Scaffolds Mimicking Amino Acids without Functionalized Side Chains (Method G)

The syntheses of 4-Fmoc-5-substituted-6-oxo-piperazine-2-methyl-2-carboxylic acid scaffolds mimicking amino acids without functionalized side chains was carried out using method G. 2-Boc-amino-3-methoxycarbonyl-1-substituted-methylamino-2-methyl-propionic acid tert-butyl esters (23) were prepared by reductive amination of 2-Boc-amino-2-methyl-3-oxo-propionic acid methyl ester (22) with an α-amino ester (2), using either sodium cyanoborohydride or sodium triacetoxyborohydride as the reducing agent. Compound (22) required for the reductive amination was obtained by oxidation of α-methyl-Boc serine tert-butyl ester (21) with Dess-Martin periodinane. The Boc group of (23) was removed with 2N hydrogen chloride in dioxane, and the amino esters cyclized to unprotected 5-substituted-6-oxo-piperazine-2-methyl-2-carboxylic acid tert-butyl esters (24), which were protected with Fmoc chloride to give 4-Fmoc-5-substituted-6-oxo-piperazine-2-methyl-2-carboxylic acid tert-butyl esters, which were deprotected with trifluoroacetic acid to give the final products (25).

Method G

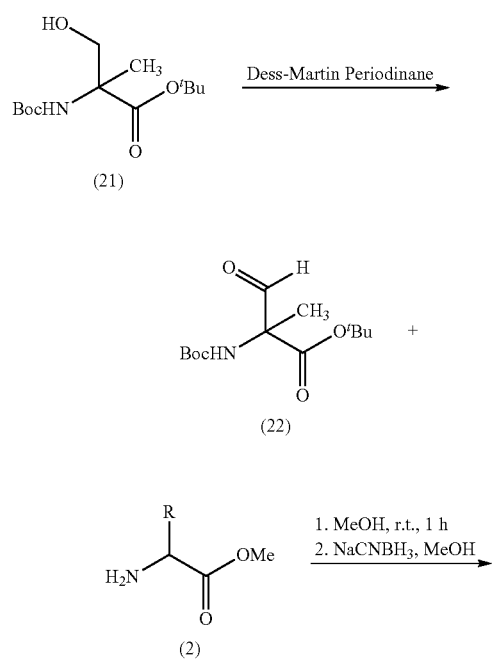

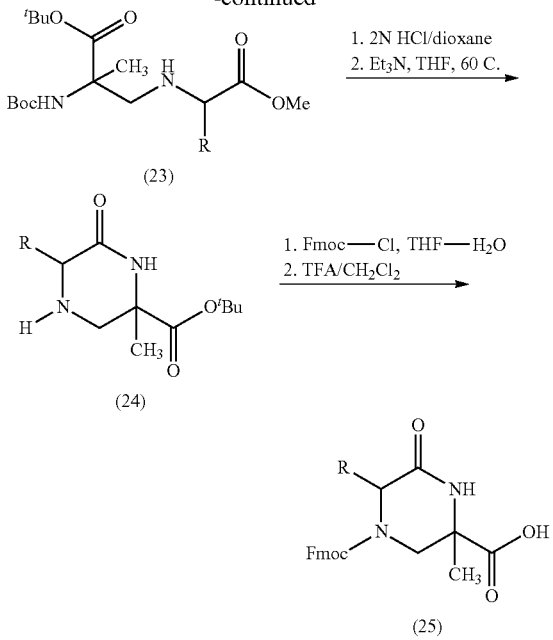

Synthesis of 2-Boc-amino-2-methyl-3-oxo-propionic acid tert-butyl ester (22): Oxidation of Boc α-Methyl serine tert-butyl ester (21) was done using Dess-Martin periodinane as describe before gave the desired product (22) in 96% crude yield. The compound was used without further purification in the next step. $^1$H NMR δ (CDCl$_3$): 1.44 (s, 18H, $^t$Bu), 1.46 (s, 3H, CH$_3$), 5.63-5.70 (br. s, 1H, NH), 9.5 (s, 1H, CHO)

Synthesis of 2-Boc-amino-3-methoxycarbonyl-1-substituted-methylamino-2-methyl-propionic acid tert-butyl ester (23): Compounds (23) were prepared using a procedure similar to the one described for compound (10), but using compound (22) as the aldehyde. Compounds (23) were purified by silica gel column chromatography.

| R | Analytical Data for Compounds (23) |
|---|---|
| ⸺CH$_2$Ph (benzyl) | $^1$H NMR δ (CDCl$_3$): 1.40-1.46 (two s, 21 H, CH$_3$ and $^t$Bu), 2.60-2.72 (br. m, 1 H, CH$_2$Ph), 2.82-3.00 (m, 3 H, CH$_2$Ph, and CH$_2$N), 3.32-3.43 (t, 1 H, CHN), 3.65 (s, 3 H, CH$_3$), 5.62 (br. s, 1 H, NH), 7.13-7.32 (m, 5 H, Ph), yield = 69%, (M$^+$ + 1) = 436.98. |

Synthesis of 2-methyl-6-oxo-5-substituted-piperazine-2-carboxylic acid (25): A solution of 4 mmol of (23) in 8 mL of 2N hydrogen chloride in dioxane was stirred at room temperature for 5 hours, and then concentrated to dryness. The residue was suspended in 20 mL of tetrahydrofuran, neutralized with 10 mmol of triethylamine, and stirred at 60° C. for 2 days. It was then concentrated to dryness, resuspended in 20 mL of tetrahydrofuran and 10 mL of water, solid sodium bicarbonate was added to adjust the pH to basic, followed by 5.6 mmol of solid Fmoc chloride, and the reaction mixture stirred overnight at room temperature, the pH adjusted to 1 with 1N hydrochloric acid solution, diluted with 100 mL of ethyl acetate, and the layers separated. The organic layer was washed with 2×100 mL of brine, dried over magnesium sulfate and concentrated. The residue was dissolved in 10 mL of 50% trifluoroacetic acid in dichloromethane, and the solution stirred at room temperature for 3 hours. The solvent was concentrated, and the products (25) purified by silica gel column chromatography.

| R | Analytical Data for Compounds (25) |
|---|---|
| benzyl group | $^1$H NMR δ (CDCl$_3$): 1.12 (s, 3 H, CH$_3$), 2.50-2.62 (m, 0.5 H, CH$_2$Ph), 2.96-3.38 (three m, 1.5 H, CH$_2$Ph), 3.86-4.52 (a series of m, 6 H, CHN, CH, and CH$_2$O), 6.80-7.80 (a series of m, 13 H, fulvene and Ph), yield = 22%, (M$^+$+ 1) = 471.47 |

Synthesis of 2,2-disubstituted Ketopiperazine Scaffolds Mimicking Amino Acids with Functionalized Side Chains (Method H)

The syntheses of 4-Fmoc-5-substituted-6-oxo-piperazine-2-methyl-2-carboxylic acid scaffolds mimicking amino acids with functionalized side chains are performed using method H. 2-Alloc-amino-3-methoxycarbonyl-1-substituted-methylamino-2-methyl-propionic acid methyl ester (30) is prepared by reductive amination of 2-Alloc-amino-2-methyl-3-oxo-propionic acid methyl ester (28) with an α-amino allyl ester (29), using either sodium cyanoborohydride or sodium triacetoxyborohydride as the reducing agent, followed by protection of the secondary amine with benzylchloroformate. Compound (28) required for the reductive amination is obtained by oxidation of (27) with Dess-Martin periodinane. The allyl ester and the alloc groups of analogs (30) are removed using tetrakistriphenyl phosphine palladium (0) and the amino acid cyclized by reaction with a peptide coupling reagent to give 5-substituted-6-oxo-piperazine-2-methyl-2-carboxylic acid methyl esters (31). 4-Fmoc-5-substituted-6-oxo-piperazine-2-methyl-2-carboxylic acids (25) are obtained by saponification of the methyl ester, followed by protecting group exchange.

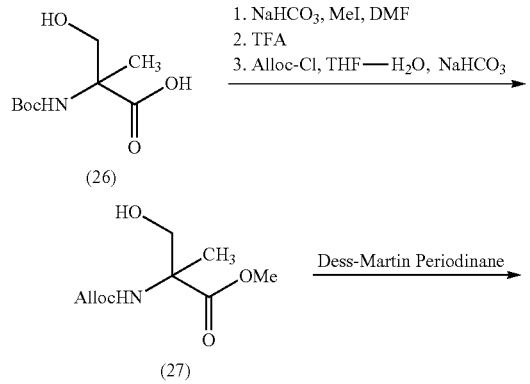

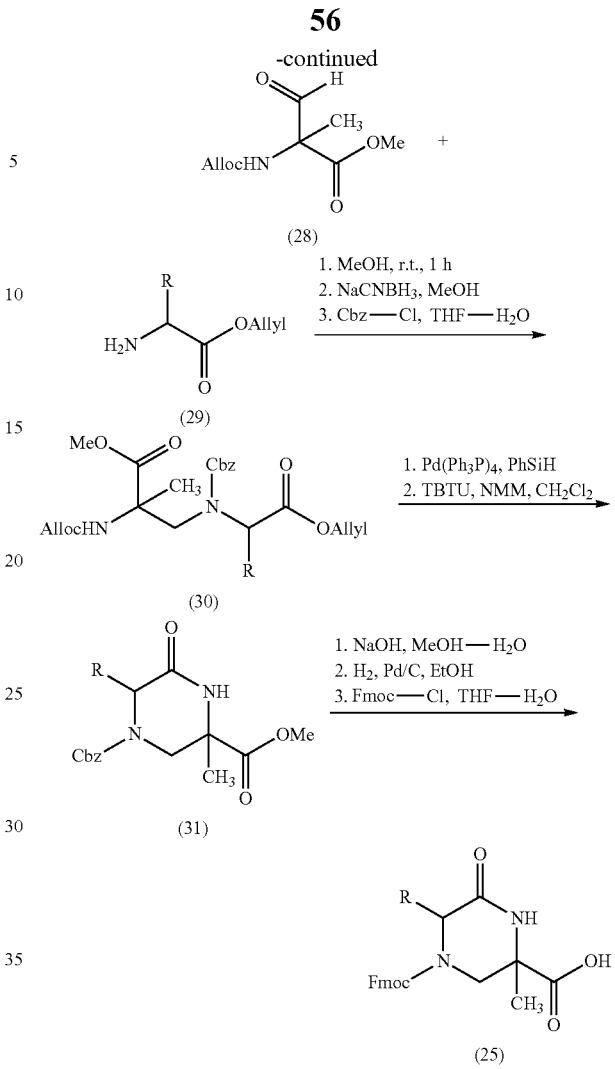

Synthesis of Alloc α-methyl serine methyl ester (27): A solution of 8 mmol of Boc α-methyl serine (26), 1.0 g (12 mmol) of solid sodium bicarbonate, and 1.0 mL (16 mmol) of iodomethane in 8 mL of dry dimethylformamide, kept under nitrogen is stirred overnight. The reaction mixture is then poured over 50 mL of water, and extracted with 50 mL of diethyl ether, and washed with 1×20 mL of water, dried over magnesium sulfate, and concentrated. The residue is dissolved in 20 mL of 90% trifluoroacetic acid in dichloromethane, and the solution is stirred at room temperature for 3 hours, and then concentrated to dryness. The residue is dissolved in 35 mL of tetrahydrofuran, and 10 ml of water, followed by addition of 30 mmol of solid sodium bicarbonate, and the slow addition of 12 mmol of allyl chloroformate. The mixture is stirred at room temperature for 2 hours, diluted with 50 mL of ethyl acetate, and the layers separated. The organic layer is then washed with 1×10 mL of saturated sodium bicarbonate, and 1×10 ml of 1N hydrochloric acid, and 1×10 mL of water, dry over magnesium sulfate, and concentrated. Compound (27) is purified by silica gel column chromatography.

Synthesis of 2-Alloc-amino-2-methyl-3-oxo-propionic acid methyl ester (28): Oxidation of Alloc α-methyl serine methyl ester (27) is done using Dess-Martin periodinane as described above to yield the desired product (28).

Synthesis of 2-Alloc-amino-3-methoxycarbonyl-1-substituted-methyl-Cbz-amino-2-methyl-propionic acid allyl ester (30): Compounds (30) are prepared using a procedure similar to the one described for compounds (15), but using compound (28) as the aldehyde.

Synthesis of 4-Cbz-2-methyl-6-oxo-5-substituted-piperazine-2-carboxylic acid methyl ester (31): To solution of 10 mmol of compound (30) in 30 mL of dichloromethane, kept at room temperature under nitrogen, is added 2 equivalents of phenylsilane and 0.3 equivalents of tetrakistriphenylphosphine palladium (0), and the solution stirred for 2 hours, and then 11 mmol of TBTU, and 14 mmol of N-methyl-morpholine are added, and the solution stirred at room temperature for 2 hours, and then concentrated to dryness.

Synthesis of 4-Fmoc-2-methyl-6-oxo-5-substituted-piperazine-2-carboxylic acid (25): To a solution of 10 mmol of compound (31) in 25 mL of methanol, kept at room temperature under nitrogen, is added slowly 11 mmol of 1N sodium hydroxide solution, and the reaction is stirred at room temperature overnight, neutralized with 21 mL of 1N hydrochloric acid solution, 1 g of 10% palladium on carbon is added, and the suspension hydrogenated at room temperature and atmospheric pressure for 3 hours. The suspension is filtered through celite and concentrated. The residue is redissolved in 25 mL of tetrahydrofuran, and 10 mL of water, followed by the addition of 30 mmol of solid sodium bicarbonate, and 10 mmol of Fmoc chloride, and the reaction is stirred at room temperature under nitrogen for 2 hours. The reaction is then diluted with 50 mL of ethyl acetate, and acidified with 1N hydrochloric acid solution. The layers are then separated, and the organic layer is washed with 1×20 mL of water, dried over magnesium sulfate, and concentrated. Compounds (25) are purified by silica gel column chromatography.

Synthesis of (5-substituted-6-oxo-piperazin-2-yl)-acetic acid Scaffolds (Methods I, J, K)

The syntheses of (5-substituted-6-oxo-piperazin-2-yl)-acetic acid scaffolds were carried out by several methods.

Method I:
(tert-butyl 3-protected-amino-4-(methoxycarbonyl-substituted-methylamino)-butyrates (35) were prepared by reductive amination of tert-butyl 3-protected-amino-4-oxo-butyrate (34) with α-amino esters (2), using either sodium cyanoborohydride or sodium triacetoxyborohydride as the reducing agent. The tert-butyl 3-protected-amino-4-oxo-butyrate (34) required for the reductive amination was prepared by lithium aluminum hydride (LAH) reduction of the Weinreb amide derivatives (33). Tert-butyl (3-protected-amino-4-(methoxycarbonyl-substituted-methylamino)-butyrate analogs (35) were then deprotected, cyclized, and Fmoc protected to give tert-butyl (5-substituted-6-oxo-piperazin-2-yl)-acetates (36), which were then deprotected to give the final products (37).

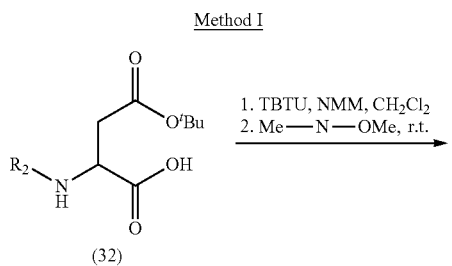

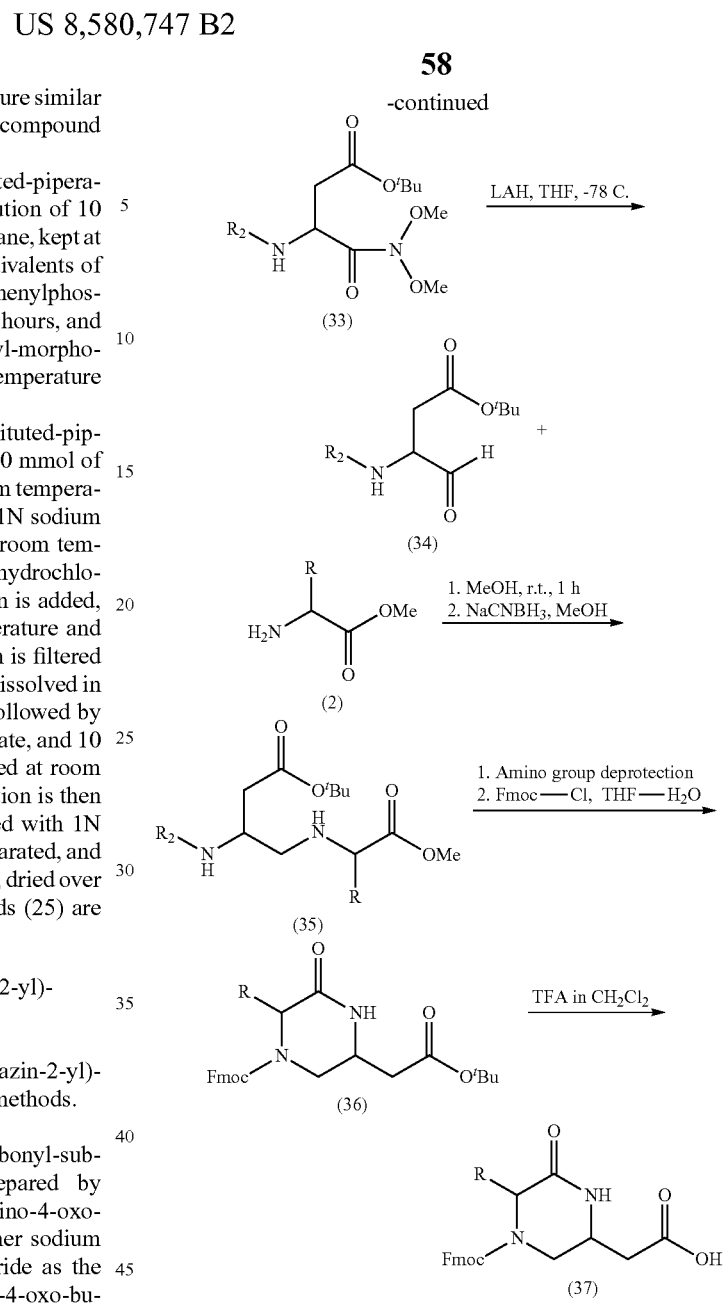

Synthesis of amino protected Asp-(O$^t$Bu) Weinreb amide (33): Compounds (33) were prepared using a procedure similar to the one described for compound (14).

| R$_2$ | Analytical Data for Compounds (33) |
|---|---|
| Cbz | $^1$H NMR δ (CDCl$_3$): 1.40 (s, 9H, $^t$Bu), 2.47-2.59 (dd, 1H, CH$_2$CO), 3.20 (s, 3H, CH$_2$N), 3.77 (s, 3H, CH$_3$O), 4.96-5.05 (br. m, 1H, CHN), 5.05-5.12 (br. d, 2H, CH$_2$O), 5.58-5.66 (br. d, 1H, NH), 7.30-7.36 (br. m, 5H, Ph), yield = 90% |
| Fmoc | $^1$H NMR δ (CDCl$_3$): 1.45 (s, 9H, $^t$Bu), 2.55-2.64 (dd, 1H, CH$_2$CO), 2.69-2.80 (dd, 1H, CH$_2$O), 3.60 (s, 3H, CH$_3$N), 3.79 (s, 3H, CH$_3$O), 4.18-4.26 (t, 1H, CH), 4.32-4.40 (d, 2H, CH$_2$O), 4.98-5.19 (m, 1H, CHN), 5.70-5.76 (br. d, 1H, NH), 7.35-7.80 (a series of m, 8H, fulvene), yield = quant. |

Synthesis of tert-butyl 3-amino protected-amino-4-oxo-butyrate (34): Compounds (34) were prepared using a procedure similar to the one described for compound (9).

| R₂ | Analytical Data for Compounds (34) |
|---|---|
| Cbz | ¹H NMR δ (CDCl₃): 1.40 (s, 9H, ᵗBu), 2.69-2.81 (dd, 1H, CH₂CO), 2.89-3.01 (dd, 1H, CH₂CO), 4.33-4.42 (m 1H, CHN), 5.12 (s, 2H, CH₂O), 5.83-5.88 (br. d, 1H, NH), 7.31-7.39 (br. m, 5H, Ph), 9.64 (s, 1H, CHO) |
| Fmoc | ¹H NMR δ (CDCl₃): 1.45 (s, 9H, ᵗBu), 2.58-3.02 (a series of m, 2H, CH₂CO), 4.20-4.28 (t, 1H, CH), 4.35-4.49 (m, 3H, CH₂O, and CHN), 5.85-5.92 (br. d, 1H, NH), 7.27-7.80 (a series of m, 8H, fulvene), 9.65 (s, 1H, CHO) |

Synthesis of tert-butyl 3-Protected-amino-4-(methoxycarbonyl-substituted-methylamino)-butyrate (35): Compounds (35) were prepared using a procedure similar to the one described for compounds (10), but using compounds (34) as the aldehyde.

| R₂ | R | Analytical Data for Compounds (35) |
|---|---|---|
| Cbz | 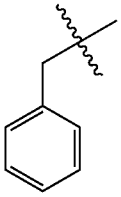 | ¹H NMR δ (CDCl₃): 1.40 (s, 9 H, ᵗBu), 2.27-3.02 (a series of m, 6 H, CH₂CO, CH₂Ph, and CH₂N), 3.43-3.52 (t, 1 H, CHN), 3.65 (s, 3 H, CH₃O), 3.84-3.98 (m, 1 H, CHN), 5.08 (s, 2 H, CH₂O), 5.33-5.44 (br. d, 1 H, NH), 7.11-7.42 (a series of m, 10 H, Ph), yield = 60%, $t_R$ = 4.79 min, (M⁺ + 1) = 471.20. |
| Cbz | 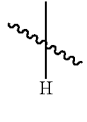 | ¹H NMR δ (CDCl₃): 1.55 (s, 9 H, ᵗBu), 2.42-2.68 (br. m, 2 H, CH₂N), 2.74-2.92 (two dd, 2 H, CH₂CO), 3.46-3.50 (d, 2 H, CH₂N), 3.78 (s, 3 H, CH₃O), 4.02-4.14 (m, 1 H, CHN), 5.15 (s, 2 H, CH₂O), 7.40-7.45 (m, 5 H, Ph), $t_R$ = 3.82, (M⁺ + 1) = 381.28 |
| Cbz | 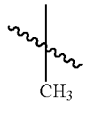 | ¹H NMR δ (CDCl₃): 1.25-1.30 (d, 3 H, CH₃), 1.44 (s, 9 H, ᵗBu), 2.38-2.65 (a series of m, 2 H, CH₂CO), 2.66-2.85 (m, 2 H, CH₂N), 3.60-3.70 (m, 1 H, CHN), 3.7 (s, 3 H, CH₃O), 3.9-4.1 (m, 1 H, CHN), 5.1 (s, 2 H, CH₂O), 5.4-5.6 (br. t, 1 H, NH), 7.28-7.4 (m, 5 H, Ph), $t_R$ = 3.81 min, (M⁺ + 1) = 395.25. |
| Cbz | 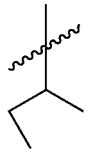 [SMILES: *C(C)CC] | ¹H NMR δ (CDCl₃): 0.84-0.91 (m, 6 H, CH₃), 1.08-1.30 (m, 1 H, CH), 1.45 (s, 9 H, ᵗBu), 1.45-1.70 (m, 2 H, CH₂), 2.39-2.60 (m, 3 H, CH₂CO, CH₂N), 2.74-2.86 (dd, 1 H, CH₂N), 2.98-3.16 (dd, 1 H, CHN), 3.7 (s, 3 H, CH₃O), 3.92-4.08 (br. m, 1 H, CHN), 5.1 (s, 2 H, CH₂O), 7.26-7.45 (m, 5 H, Ph), $t_R$ = 4.56 min, (M⁺ + 1) = 437.31. |

Synthesis of tert-butyl (4-Fmoc-5-substituted-6-oxo-piperazin-2-yl)-acetate (36): For compounds containing Fmoc amino protecting group, a solution of 10 mmol of compound (35) in 30 mL of 30% diethyl amine in ethyl acetate solution was stirred at room temperature overnight, and then concentrated to dryness. For compounds containing Cbz amino protecting group, a solution of 10 mmol of compound (35) in 30 mL of ethanol was hydrogenated at room temperature and atmospheric pressure for 2 hours, filtered through celite, and concentrated to dryness. For Fmoc protection, the residue was dissolved in 20 mL of tetrahydrofuran, and 10 mL of water, and 2.52 g (30 mmol) of solid sodium bicarbonate was added, followed by the addition of 3.3 g (13 mmol) of Fmoc-Cl. The mixture was stirred for 3 hours and diluted with ethyl acetate. The layers separated, and the organic layer was washed with water, dried over magnesium sulfate, and concentrated. Compounds (36) were purified by silica gel column chromatography.

| R | Analytical Data for Compounds (36) |
|---|---|
| 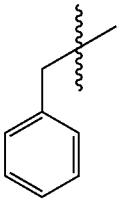 | ¹H NMR δ (CDCl₃): 1.44 (s, 9 H, ᵗBu), 1.71-2.10 (m, 2 H, CH₂CO), 2.10-2.30 (br. d, 1 H, CHN), 2.62-2.82 (br. d, 1 H, CH₂Ph), 2.90-3.74 (a series of br. m, 3 H, CH₂N, CHN), 3.80-4.07 (br. d, 1 H, CHN), 4.10-4.50 (br. m, 3 H, CH₂O, and CH), 6.74-7.80 (a series of m, 23 H, fulvene, and Ph), yield = 75%, $t_R$ = 7.15 min, (M⁺ + 1) = 527.20. |
|  | ¹H NMR δ (CDCl₃): 0.77-1.94 (a series of m, and two s, 18 H, ᵗBu, CH₂, and CH₃), 2.07-2.76 (three m, 3 H, CH₂CO, and CHN), 2.86-3.80 (four m, 2 H, CH₂N), 4.16-4.27 (m, 1 H, CH), 4.30-4.43 (m, 1 H, CHN), 4.50-4.70 (br. m, 2 H, CH₂O), 7.26-7.79 (a series of m, 8 H, fulvene), yield = 40% for three steps, $t_R$ = 7.31 min, (M⁺ + 1) = 493.47. |
|  | ¹H NMR δ (CDCl₃): 1.45 (s, 9 H, ᵗBu), 1.9-2.5 (m 2 H, CH₂CO), 3.02-4.7 (a series of m, 8 H, CH, CH₂, CH₂N), 7.25-7.78 (three m, 8 H, fulvene), $t_R$ = 6.42 min, (M⁺ + 1) = 431.31. |
| 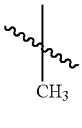 | ¹H NMR δ (CDCl₃): 1.20-1.35 (br. m, 3 H, CH₃), 1.45 (s, 9 H, ᵗBu), 2.1-2.80 (three m, 3 H, CH₂CO, CH₂N), 3.1-4.1 (four m, 3 H, CH₂N, CHN), 4.18-4.26 (br. t, 1 H, CH), 4.28-4.46 (br. m, 1 H, CHN), 4.50-4.68 (br. m, 2 H, CH₂), 7.28-7.8 (three m, 8 H, fulvene), $t_R$ = 6.29 min, (M⁺ + 1) = 451.24. |
| 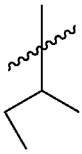 [SMILES: *C(C)CC] | ¹H NMR δ (CDCl₃): 1.20-1.60 (br. m, and s, 15 H, CH₃, ᵗBu), 2.21-2.80 (3 br. m, 2 H, CH₂CO), 3.0-3.9 (four br. m, 2 H, CH₂N), 4.18-4.26 (br. m, 2 H, CH, CHN), 4.38-4.86 (br. m, 3 H, CH₂, CHN), 7.26-7.86 (a series of m, 8 H, fulvene), $t_R$ = 6.90 min, (M⁺ + 1) = 493.31. |

Synthesis of (4-Fmoc-5-substituted-6-oxo-piperazin-2-yl)-acetate (37): Compounds (36) were deprotected with 90% trifluoroacetic acid solution in dichloromethane for 3 hours, and then concentrated to dryness. Final products (37) were purified by silica gel column chromatography.

| R | Analytical Data for Compounds (37) |
|---|---|
| 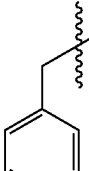 | ¹H NMR δ (CDCl₃): 1.82-2.13 (br. t, 1 H, CHN), 2.32-2.53 (br. d, 1 H, CH₂CO). 2.63-2.81 (br. d, 1 H, CH₂CO), 2.90-3.29 (two br. m, CH₂Ph), 3.38-3.59 (br. m, 1 H, CH₂N), 3.66-3.85 (br. m, 1 H, CH₂N), 3.95-4.24 (two overlapping br. peaks, 2 H, CHN, CH), 4.30-4.93 (br. d, 2 H, CH₂O), 6.84-7.82 (a series of m, 13 H, fulvene, and Ph), 8.08-8.25 (br. d, 1 H, CO₂H), yield = quant., $t_R$ = 5.57 min, (M⁺ + 1) = 471.07. |
|  | ¹H NMR δ (CDCl₃): 0.72-1.92 (five br. m, 9 H, CH₂, and CH₃) , 2.14-2.70 (two br m, 3 H, CH₂CO, and CHN), 3.26-3.62 (two br. m, 1 H, CH₂N), 3.70-3.90 (br. m, 1 H, CH₂N), 4.03-4.30 (two m, 2 H, CHN, and CH), 4.42-4.82 (br. m, 2 H, CH₂O), 7.28-7.82 (a series of m, 8 H, fulvene), 7.97 (s, 1 H, CO₂H), yield = 90%, $t_R$ = 5.61 min, (M⁺ + 1) = 437.76. |

| R | Analytical Data for Compounds (37) |
|---|---|
| H | ¹H NMR δ (CDCl₃): 2.10-2.66 (m, 2 H, CH₂CO), 3.2-3.92 (four m, 3 H, CH₂N, CHN), 3.97-4.06 (m, 1 H, CH), 4.2-4.3 (m, 2 H, CH₂), 4.48-4.62 (m, 2 H, CH₂N), 7.24-7.81 (a series of m, 8 H, fulvene), $t_R$ = 4.74 min, (M⁺ + 1) = 381.13. |
| CH₃ | ¹H NMR δ (CDCl₃): 1.15-1.37 (br. m, 3 H, CH₃), 2.22-2.78 (three br. m, 2 H, CH₂CO), 3.0-4.10 (five br. m, 3 H, CH₂N, CHN), 4.15-4.40 (m, 1 H, CH), 4.45-4.7 (br. m, 3 H, CH₂, CHN), 7.26-8.10 (a series of m, 8 H, fulvene), $t_R$ = 4.66 min, (M⁺ + 1) = 395.32. |
| (isobutyl) | ¹H NMR δ (CDCl₃): 0.6-1.2 (m, 6 H, CH₃), 1.22-2.8 (four m, 4 H, CH₂CO, CH₂), 3.1-4.0 (five m, 3 H, CH₂N, CHN), 4.18-4.32 (m, 1 H, CH), 4.41-4.84 (m, 3 H, CH₂, CHN), 7.26-8.2 (a series of m, 8 H, fulvene), $t_R$ = 5.46 min, (M⁺ + 1) = 437.37. |

Method J:

Diphenylmethyl 3-Fmoc-amino-4-(methoxycarbonyl-substituted-methylamino)-butyrates (41) were prepared by reductive amination of diphenylmethyl 3-Fmoc-amino-4-oxo-butyrate (40) with α-amino esters (2), using either sodium cyanoborohydride or sodium triacetoxyborohydride as the reducing agent. The diphenylmethyl 3-Fmoc-amino-4-oxo-butyrate (40) required for the reductive amination was prepared by lithium aluminum hydride reduction of the Weinreb amide derivative (39), which was formed from commercially available Fmoc-aspartic acid α-allyl ester derivative (38) by protection of the β-ester under Mitsunobu conditions. The allyl ester was removed using palladium (0) catalyst, followed by Weinreb amide formation using TBTU as the coupling agent. Diphenylmethyl 3-Fmoc-amino-4-(methoxycarbonyl-substituted-methylamino)-butyrate (41) was then Fmoc deprotected, cyclized, diphenylmethyl ester removed by hydrogenation, followed by Fmoc protection to give the final product (4-Fmoc-5-substituted-6-oxo-piperazin-2-yl)-acetic acid (37).

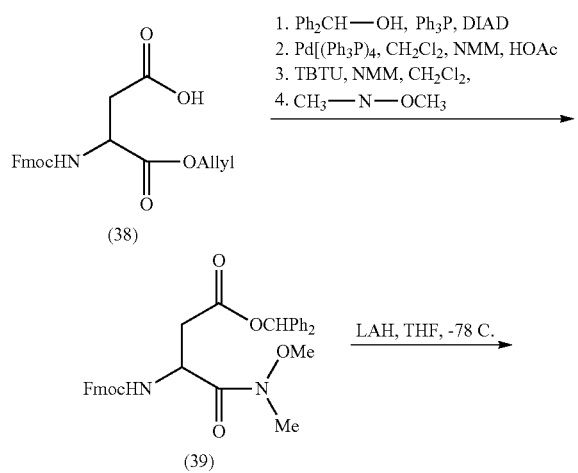

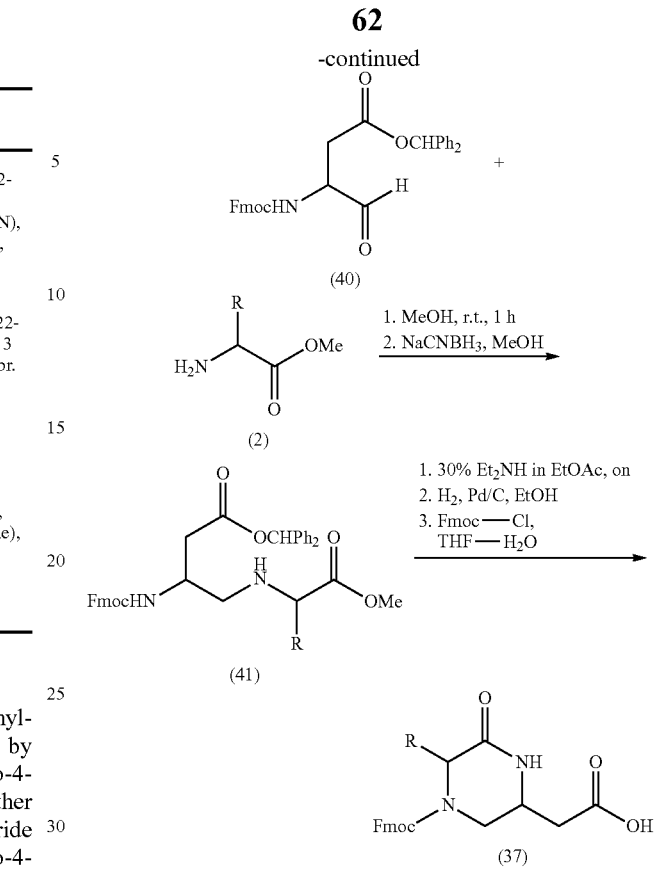

Synthesis of Fmoc-Asp-(OCHPh₂) Weinreb amide (39): To a solution of 5.1 g (13.0 mmol) of Fmoc-aspartic acid α-allyl ester (38) in 30 mL of dry tetrahydrofuran, containing 3.4 g (13 mmol) of triphenylphosphine, and 2.41 g (13.1 mmol) of diphenylmethanol, kept at 0° C. under nitrogen, was added slowly 2.6 mL (13.4 mmol) of diisopropyl azodicarboxylate. The ice bath was removed, and the reaction stirred at room temperature overnight, concentrated to dryness, and then purified by silica gel column chromatography. ¹H NMR δ (CDCl₃) 2.96-3.06 (dd, 1H, CH₂CO), 3.15-3.26 (dd, 1H, CH₂CO), 4.18-4.76 (a series of m, 3H, CH, CH₂), 5.14-5.32 (m, 1H, CHN), 5.76-5.86 (m, 1H, CHO), 7.20-7.80 (a series of m, 18H, fulvene, and Ph); HPLC $t_R$=7.68 min, (M⁺+Na⁺)= 583.90.

The product (9.8 mmol) was then dissolved in 40 mL of a dichloromethane:acetic acid:N-methyl morpholine solution at 37:2:1, containing 1.5 g (1.3 mmol) of tetrakis triphenylphosphine palladium (0), and the solution stirred at room temperature overnight, concentrated to dryness, and partitioned between 100 mL of ethyl acetate and 30 mL of water. The layers were separated, and the organic layer washed with 1×50 mL of water, dried over sodium sulfate, and concentrated. The residue was suspended in 20 mL of dry dichloromethane, and 1.65 mL (15 mmol) of N-methyl morpholine, and 4.07 g (12.7 mmol) of TBTU were added, and the suspension stirred at room temperature for 20 minutes, followed by the addition of 1.65 mL (15 mmol) of N-methyl morpholine, and 1.52 g (15.6 mmol) of N,O-dimethyl hydroxylamine hydrochloride salt. The suspension was stirred at room temperature for 2 hours, concentrated, partitioned between 100 mL of ethyl acetate and 50 mL of water. The organic layer was washed with 1×30 mL of water, 1×30 mL of saturated sodium bicarbonate solution, and 1×30 mL of 1N hydrochloric acid solution, dried over sodium sulfate, and concentrated. The product was purified by silica gel column chromatography. ¹H NMR δ (CDCl₃) 2.76-2.88 (dd, 1H, CH₂CO), 2.89-3.00 (dd, 1H, CH₂CO), 3.16 (s, 3H, CH₃N), 3.70 (s, 3H, CH₃O), 4.14-4.22 (dd, 1H, CH), 4.28-4.40 (t, 2H, CH₂), 5.07-5.16 (dd, 1H, CHN), 5.69-5.76 (d, 1H, CHO), 7.24-7.8 (a series of m, 18H, fulvene, and Ph); HPLC $t_R$=7.08, (M++Na⁺)= 587.03.

Synthesis of Diphenylmethyl 3-Fmoc-amino-4-oxo-butyrate (40): Compound (40) is prepared using a procedure similar to the one described for compound (9).

Synthesis of Diphenylmethyl 3-Fmoc-amino-4-(methoxycarbonyl-substituted-methylamino)-butyrate (41): Compounds (41) were prepared using a procedure similar to the one described for compound (10), but using compound (40) as the aldehyde.

| R | Analytical Data for Compounds (41) |
|---|---|
| ![structure with HN, NH, NHPbf] | ¹H NMR δ (CDCl₃) 1.2-1.7 (m, 4 H, CH₂), 1.42 (s, 3 H, CH₃Ph), 1.60 (s, 6 H, CH₃—Ph), 2.07 (s, 2 H, CH₂), 2.52 (s, 3 H, CH₃—Ph), 2.58 (s, 3 H, CH₃—Ph), 2.08-2.80 (a, series of m, 2 H, CH₂CO), 3.0-3.2 (m, 2 H, CH₂N), 3.64 (s, 3 H, CH₃O), 3.96-4.10 (m, 1 H, CHN), 4.20-4.28 (m, 1 H, CH), 4.28-4.40 (br. m, 2 H, CH₂), 5.82- 6.18 (m, 1 H, CHO), 7.24-7.80 (a series of m, 18 H, fulvene, and Ph), HPLC $t_R$ = 6.53, (M⁺ + 1) = 930.56. |

Synthesis of (4-Fmoc-5-substituted-6-oxo-piperazin-2-yl)-acetic acid (37): A solution of 10 mmol of compound (41) in 30 mL of 30% diethylamine in ethyl acetate was stirred at room temperature for 3 hours. The solution was then concentrated to dryness, redissolved in 2×30 mL of ethyl acetate, and reconcentrated. The residue dissolved in 50 mL of ethanol, and 20 mL of 1N hydrochloric acid solution, and hydrogenated at room temperature and atmospheric pressure overnight, filtered through celite, and concentrated to dryness. The residue was dissolved in 20 mL of tetrahydrofuran, and 10 mL of water, and 2.52 g (30 mmol) of solid sodium bicarbonate was added, followed by the addition of 3.3 g (13 mmol) of Fmoc-Cl. The mixture was stirred for 3 hours, diluted with 100 mL of ethyl acetate, the layers separated, and the organic layer washed with 2×50 mL of water, dried over magnesium sulfate, and concentrated. The product was purified by silica gel column chromatography.

| R | Analytical Data for Compounds (37) |
|---|---|
| ![structure with HN, NH, NHPbf] | ¹H NMR δ (CDCl₃) 1.2-1.6 (m, and s, 7 H, CH₂, CH₃Ph), 2.10 (s, 2 H, CH₂), 2.46 (s, 3 H, CH₃—Ph), 2.56 (s, 3 H, CH₃—Ph), 2.46-2.63 (br. m, 2 H, CH₂CO), 3.0-3.95 (3 b. m, 5 H, CH₂N, CHN), 4.10-4.30 (br. m, 1 H, CH), 4.40-4.80 (br. m, 3 H, CHN, CH₂), 7.22-7.80 (a series of m, 8 H, fulvene), HPLC $t_R$ = 5.73, (M⁺ + 1) 732.24. |

Method K:

The syntheses of (5-substituted-6-oxo-piperazin-2-yl)-acetic acid scaffolds are done starting from commercially available Fmoc-Aspartic acid α tert-butyl ester (42). Fmoc-aspartic acid α tert-butyl ester is reduced to Fmoc-Homoserine α tert-butyl ester with sodium borohydride via the mixed anhydride, followed by protection of the alcohol with benzyl bromide to give Fmoc-Homoserine benzyl ether α tert-butyl ester (43). The tert-butyl ester is then removed with trifluoroacetic acid, and the acid is reduced to the alcohol with sodium borohydride via the mixed anhydride to give 2-Fmoc-amino-4-benzyloxy-1-butanol (44). Alcohol (44) is then converted to 2-Fmoc-amino-4-benzyloxybutanal (45) using Dess-Martin periodinane as described previously. Reductive amination of 2-Fmoc-amino-4-benzyloxybutanal (45) and α-amino ester (2) gives the (2-Fmoc-amino-4-benzyloxy-butylamino)-2-substituted acetic acid methyl ester (46). Fmoc deprotection with diethyl amine gives the free primary amine which cyclizes to 6-benzyloxyethyl-3-substituted-piperazin-2-one spontaneously. The benzyl ether is removed by hydrogenation, and the secondary amine is protected as its Fmoc derivative to give 4-Fmoc-6-hydroxymethyl-3-substituted-piperazin-2-ones (47). Finally, the primary alcohol is oxidized to the acid to give the final products (48) as described in method A.

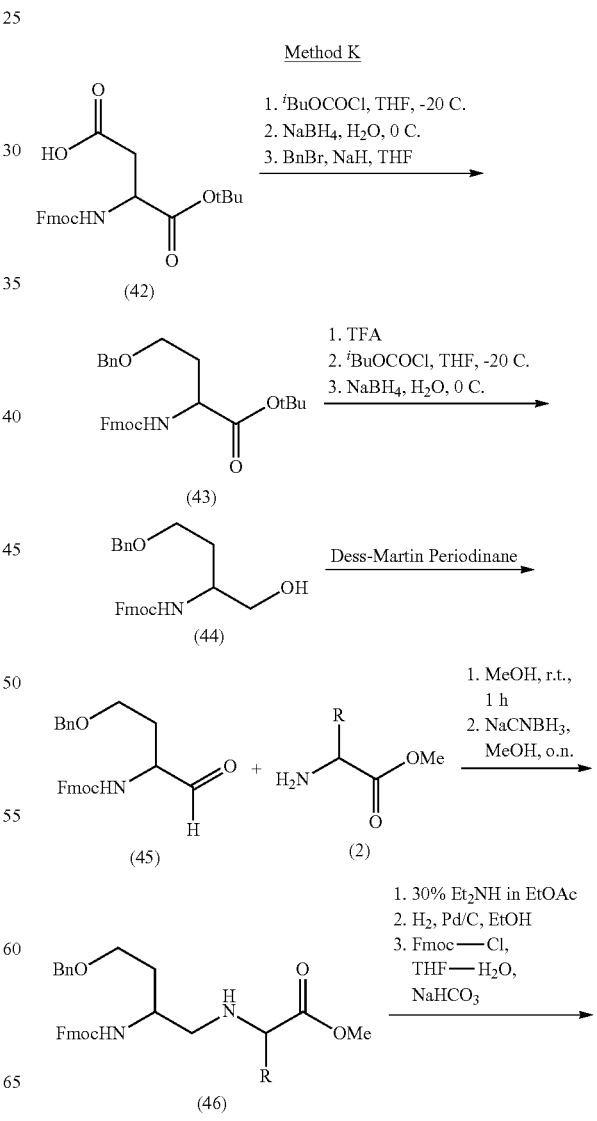

Method K

Synthesis of 2-Substituted 3-Oxo-[1,4]-diazepane-5-carboxylic acid Scaffolds (Methods L, M, N)

The synthesis of 2-substituted 3-oxo-[1,4]-diazepane-5-carboxylic acid scaffolds is done using several methods.

Method L:

tert-butyl 2-Cbz-amino-4-(benzyloxycarbonyl-substituted-methyl-Boc amino)-butyrates (52) are prepared by reductive amination of tert-butyl Cbz-2-amino-4-oxo-butyrate (50) with amino ester (51), using either sodium cyanoborohydride or sodium triacetoxyborohydride as the reducing agent, followed by Boc protection of the secondary amine. The tert-butyl Cbz-2-amino-4-oxo-butyrate (50) required for the reductive amination is prepared by lithium aluminum hydride reduction of the Weinreb amide derivative (49). The diazepane ring is formed by protecting group removal, followed by cyclization with a peptide forming reagent to give (53). Finally, 4-Fmoc-2-substituted 3-oxo-[1,4]-diazepane-5-carboxylic acids (54) are formed by protecting group exchange.

Synthesis of Fmoc-Homoserine (OBn) α tert-butyl ester (43): To a solution of 10.0 mmol of Fmoc Asp-O'Bu (42) in 50 mL of dry tetrahydrofuran, kept at −20° C. under nitrogen, is added 1.77 mL (12.7 mmol) of triethyl amine, followed by the slow addition of 1.57 mL (12.0 mmol) of isobutylchloroformate. The mixture is stirred for 30 minutes, and then poured slowly over an ice-cold solution of 3.77 g (99.6 m mol) of sodium borohydride in 10 mL of water, keeping the temperature below 5° C. The reaction is stirred at 0° C. for 15 minutes, and then quenched with 1N hydrochloric acid solution. The reaction mixture is diluted with 100 mL of ethyl acetate, and the layers separated. The organic layer was washed with 2×25 mL of 1N hydrochloric acid solution, 2×25 mL of water, dried over magnesium sulfate and concentrated, and purified by silica gel column chromatography. Purified compound is then dissolved in 30 mL of tetrahydrofuran, and 12 mmol of 60% sodium hydride dispersion in mineral oil is added, followed by 0.2 mmol of tetrabutylammonium iodide and 12 mmol of benzyl bromide, and the mixture is stirred overnight, quenched with 50 mL of saturated aqueous sodium bicarbonate, and extracted with 100 mL of ethyl acetate. The compound is then purified by silica gel column chromatography.

Synthesis of 2-Fmoc-amino-4-benzyloxy-1-butanol (44): Deprotection of the tert-butyl ester using 90% trifluoroacetic acid is done as described for compound (37) in method I, followed by reduction of the acid to the alcohol with sodium borohydride via the mixed anhydride intermediate as described for compound (13).

Synthesis of 2-Fmoc-amino-4-benzyloxy-butanal (45): 2-Fmoc-amino-4-benzyloxy-1-butanol (44) is oxidized to the aldehyde using Dess-Martin periodinane as described for the synthesis of (9).

Synthesis of (2-Fmoc-amino-4-benzyloxy-butylamino)-2-substituted acetic acid methyl ester (46): reductive amination of 2-Fmoc-amino-4-benzyloxy-butanal (45) with an α-amino ester (2) using either sodium cyanoborohydride or sodium triacetoxyborohydride as the reducing agent is done as described for the synthesis of (10).

Synthesis of 4-Fmoc-6-hydroxymethyl-3-substituted-piperazin-2-ones (47): Fmoc deprotection of (2-Fmoc-amino-4-benzyloxy-butylamino)-2-substituted acetic acid methyl ester (46) with concomitant cyclization, followed by de-benzylation and Fmoc reprotection is done as described for compound (37) in method J.

Synthesis of 4-Fmoc-5-substituted-6-oxo-piperazin-2-yl-acetic acid (37): Oxidation of 4-Fmoc-6-hydroxymethyl-3-substituted-piperazin-2-ones (47) to the acid is done as described in method A. The choice of the oxidizing agent used is based on the nature of the group in the 5-position.

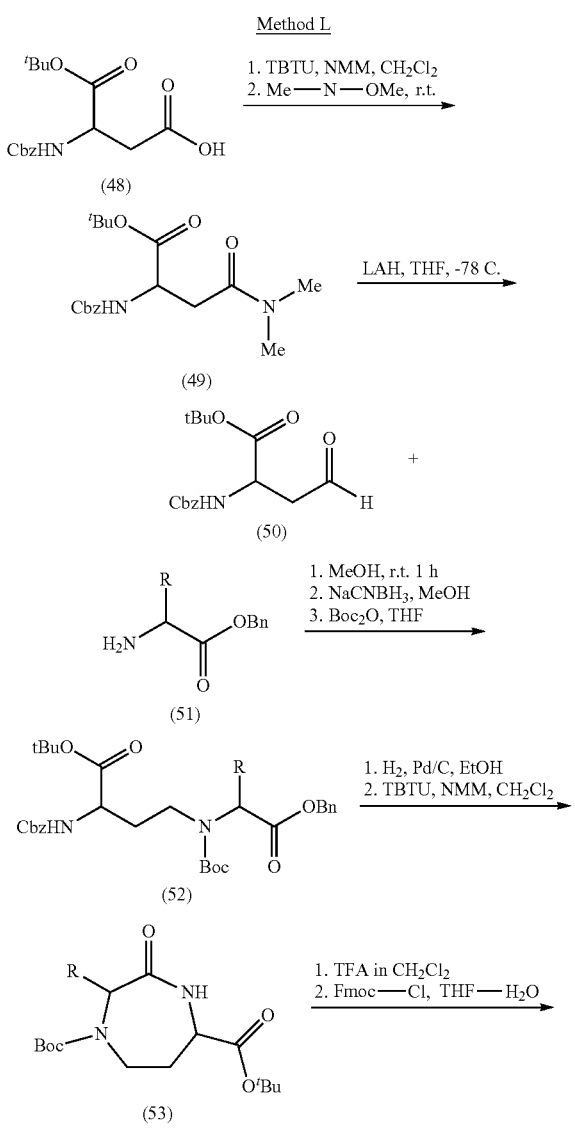

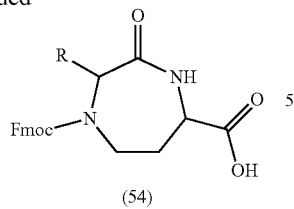

Synthesis of Cbz-Asp-(Weinreb amide)-O'Bu (49): Compound (49) is prepared using a procedure similar to the one described for compound (14).

Synthesis of tert-butyl 3-Cbz-amino-4-oxo-butyrate (50): Compound (50) is prepared using a procedure similar to the one described for compound (9).

Synthesis of tert-butyl 2-Cbz-amino-4-(benzyloxycarbonyl-substituted-methyamino)-butyrate (52): The reductive amination is done with procedure similar to the one described for compound (10). The secondary amine is protected by reaction of the crude mixture with 2 equivalents of Boc dicarbonate in tetrahydrofuran.

Synthesis of tert-butyl 1-Boc 2-substituted-3-oxo-[1,4]-diazepane-5-carboxylate (53): A solution of 10 mmol of compound (52) in 30 mL of ethanol is hydrogenated at room temperature and atmospheric pressure for 2 hours, filter through celite, and concentrated to dryness. The residue is dissolved in 100 mL of dichloromethane and 1.2 equivalents of TBTU, and 2.6 equivalents of N-methyl-morpholine are added. The solution is stirred at room temperature overnight, and then concentrated. The residue is partitioned between 50 mL of ethyl acetate and 25 mL of 1N hydrochloric acid solution, washed with 1×20 mL of a saturated sodium bicarbonate solution, dried over magnesium sulfate, and concentrated.

Synthesis of 1-Fmoc 2-substituted-3-oxo-[1,4]-diazepane-5-carboxylic acid (54): A solution of 10 mmol of compound (53) in 10 mL of 90% trifluoroacetic acid in dichloromethane is stirred at room temperature for 2 hours, and then the solution is concentrated to dryness. The residue is dissolved in 20 mL of tetrahydrofuran and 10 mL of water, and 2.52 g (30 mmol) of solid sodium bicarbonate is added, followed by the addition of 3.36 g (13 mmol) of Fmoc-Cl. The mixture is stirred for 3 hours, and then diluted with ethyl acetate. The layers are separated, and the organic layer washed with 2×50 mL of water, dried over magnesium sulfate, and concentrated.

Method M:

the reduced dipeptide analogs (60) are prepared by reductive amination of diphenylmethyl Alloc-2-amino-4-oxo-butyrate (59) with amino ester (29), using either sodium cyanoborohydride or sodium triacetoxyborohydride as the reducing agent, followed by Cbz protection of the secondary amine. Diphenylmethyl Alloc-2-amino-4-oxo-butyrate (59) required for the reductive amination is prepared by lithium aluminum hydride reduction of the Weinreb amide derivative (58), which is prepared by protecting group exchange of Weinreb amide derivative (57). The diazepane ring is then formed by allyl and alloc group removal, followed by ring closure in the presence of a peptide forming reagent. 2-substituted 3-oxo-[1,4]-diazepane-5-carboxylic acid scaffolds (54) are formed by protecting group exchange.

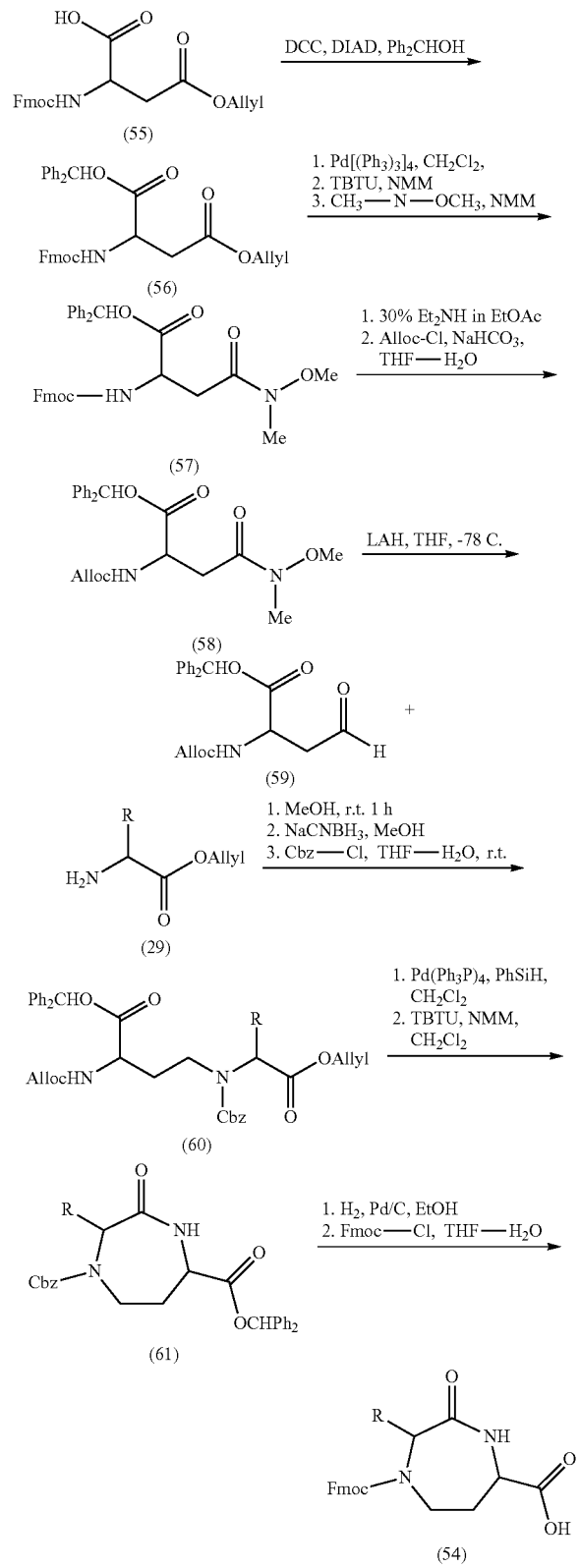

Synthesis of Fmoc-Asp-(Weinreb amide)-OCHPh$_2$ (57): Compound (57) is prepared using a procedure similar to the one described for compound (39).

Synthesis of Alloc-Asp-(Weinreb amide)-OCHPh₂ (58): A solution of 10 mmol of compound (56) in 20 mL of 30% diethylamine in ethyl acetate is stirred for 2 hours, and concentrated to dryness. The residue is dissolved in 20 mL of tetrahydrofuran and 10 mL of water, and 2.52 g (30 mmol) of solid sodium bicarbonate is added, followed by the addition of 13 mmol of Alloc-Cl. The mixture is stirred for 3 hours, and then diluted with ethyl acetate. The layers are separated, and the organic layer washed with water, dried over magnesium sulfate, and concentrated. Compound (58) is purified by silica gel column chromatography.

Synthesis of diphenylmethyl 3-Alloc-amino-4-oxo-butyrate (59): Compound (59) is prepared using a procedure similar to the one described for compound (9).

Synthesis of diphenyl methyl 2-Alloc-amino-4-(allyloxy-carbonyl-substituted-methyamino)-butyrate (60): compound 60 is prepared by reductive amination using a procedure similar to the one described for compounds (15), but using compound (59) as the aldehyde. The product is purified by silica gel column chromatography.

Synthesis of diphenylmethyl 1-Cbz 2-substituted-3-oxo-[1,4]-diazepane-5-carboxylate (61): To a solution of 10 mmol of compound (60) in 30 mL of dichloromethane, kept at room temperature under nitrogen, is added 2 equivalents of phenylsilane and 0.3 equivalents of tetrakistriphenylphosphine palladium (0), and the solution stirred for 2 hours, and then 1.2 equivalents of TBTU and 1.3 equivalents of N-methyl-morpholine are added. The solution is stirred at room temperature overnight and concentrated. The residue is partitioned between 50 mL of ethyl acetate and 25 mL of 1N hydrochloric acid solution, washed with 1×20 mL of a saturated sodium bicarbonate solution, dried over magnesium sulfate, and concentrated.

Synthesis of 1-Fmoc 2-substituted-3-oxo-[1,4]-diazepane-5-carboxylic acid (54): A solution of 10 mmol of compound (61) in 30 mL of ethanol is hydrogenated at room temperature for 2 hours, filtered through celite, and then the solution is concentrated to dryness. The residue is dissolved in 20 mL of tetrahydrofuran, and 10 mL of water, and 2.52 g (30 mmol) of solid sodium bicarbonate is added, followed by the addition of 3.36 g (13 mmol) of Fmoc-Cl. The mixture is stirred for 3 hours, and then diluted with ethyl acetate. The layers are separated, and the organic layer washed with water, dried over magnesium sulfate, and concentrated.

Method N:

Fmoc-Aspartic acid β tert-butyl ester is reduced to Fmoc-Aspartanol β tert-butyl ester (63) with sodium borohydride via the mixed anhydride, followed by protection of the alcohol with allyl bromide to give Fmoc-Aspartanol allyl ether β tert-butyl ester (64). The tert-butyl ester is then removed with trifluoroacetic acid, and the acid reduced to the alcohol with sodium borohydride via the mixed anhydride to give 3-Fmoc-amino-4-allyloxy-1-butanol (65). Alcohol (65) is then converted to 3-Fmoc-amino-4-allyloxybutanal (66) using Dess-Martin periodinane as described previously. Reductive amination of 3-Fmoc-amino-4-allyloxybutanal (66) and α amino ester (51), followed by alloc protection on the secondary amine, gives the (3-Fmoc-amino-4-allyloxy-butyl-alloc-amino)-2-substituted acetic acid benzyl esters (67). Alloc 7-allyloxymethyl-3-substituted-[1,4]-diazepan-2-ones (68) are formed by saponification of the benzyl ester, followed by Fmoc deprotection with diethyl amine to give the free primary amine which is cyclized using a peptide forming reagent such as TBTU. The final products (54) are formed by protecting group exchange: the allyl ether and the alloc are removed by palladium (0), and the secondary amine is protected as its Fmoc derivative to give 4-Fmoc-7-benzyloxymethyl-3-substituted-[1,4]-diazepan-2-ones, followed by primary alcohol oxidation to the acid to give the final products (54). The choice of the oxidizing agent used is based on the nature of the group in the 2-position.

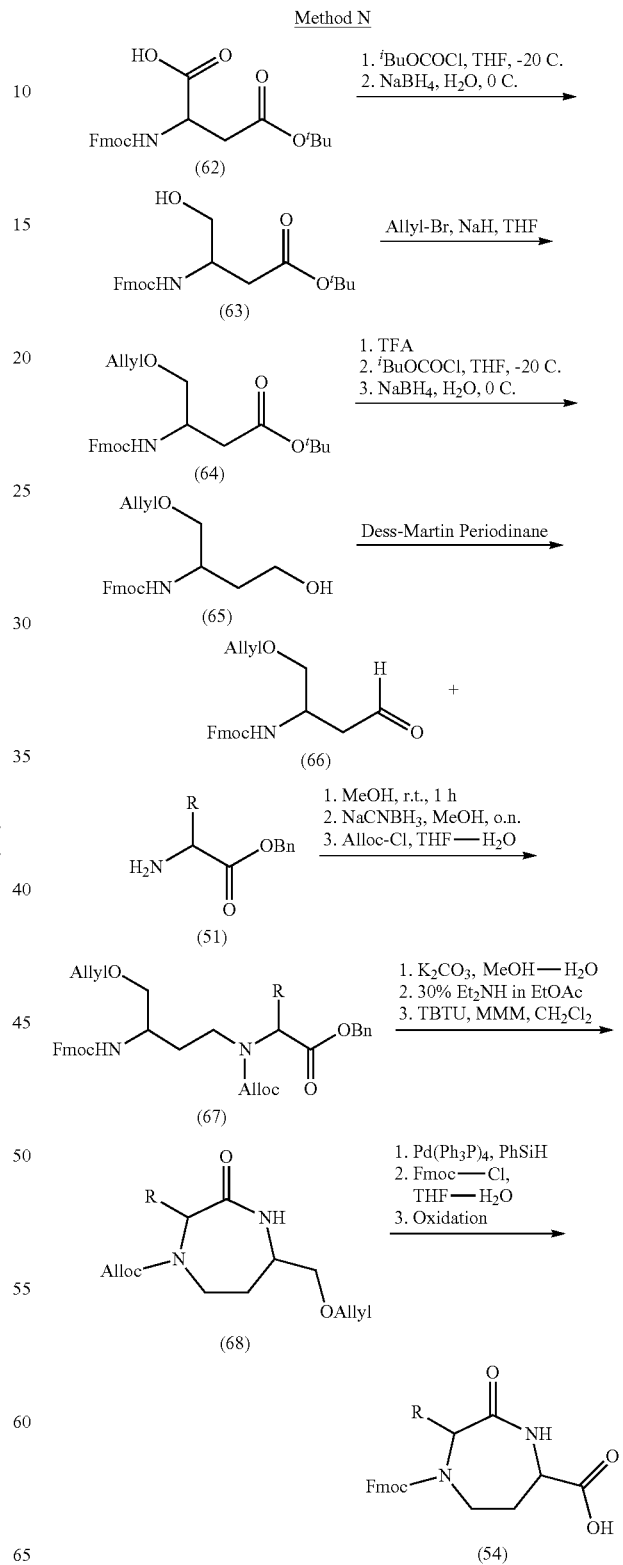

Method N

Synthesis of Fmoc-Aspartanol β tert-butyl ester (63): Compound (63) is prepared as described for the synthesis of compound (13), using Fmoc-Aspartic acid β tert-butyl ester (62) as the starting material.

Synthesis of 3-Fmoc-amino-4-allyloxy-butyric acid tert-butyl ester (64): To a solution of 10 mmol of (63) in 30 mL of tetrahydrofuran, kept at room temperature under nitrogen, is added 12 mmol of 60% sodium hydride dispersion in mineral oil, 2 mmol of tetrabutylammonium iodide, and 13 mmol allyl bromide, and the mixture is stirred overnight, quenched with 10 mL of saturated aqueous sodium bicarbonate, and extracted with 50 mL of ethyl acetate.

Synthesis of 3-Fmoc-amino-4-allyloxy-1-butanol (65): Compound (65) is prepared as described for the synthesis of compound (44).

Synthesis of 3-Fmoc-amino-4-allyloxy-butanal (66): 3-Fmoc-amino-4-allyloxy-1-butanol (65) is oxidized to the aldehyde using Dess-Martin periodinane as described for the synthesis of (9).

Synthesis of (3-Fmoc-amino-4-allyloxy-butyl-alloc-amino)-2-substituted acetic acid methyl ester (67): reductive amination of 3-Fmoc-amino-4-benzyloxy-butanal (66) with an α-amino ester (51) using either sodium cyanoborohydride or sodium triacetoxyborohydride as the reducing agent as described for compound (10), followed by protection of the secondary amine as the alloc derivative, is done as described for compound (15), but using allyl chloroformate instead of benzyl chloroformate.

Synthesis of 4-Alloc-7-allyloxymethyl-3-substituted-[1,4]-diazepan-2-ones (68): A solution of 10 mmol of (3-Fmoc-amino-4-allyloxy-butyl-alloc-amino)-2-substituted acetic acid methyl ester (67), 20 mmol of potassium carbonate in 20 mL of methanol, and 10 mL of water is stirred at room temperature for 3 hours, neutralized with 21 mL of a 1N hydrochloric acid solution, and then concentrated to dryness. The residue is dissolved in 20 mL of 30% diethyl amine in ethyl acetate and stirred at 3 hours, and then concentrated to dryness. The residue is dissolved in 100 mL of dichloromethane, and 12 mmol of TBTU and 24 mmol of N-methylmorpholine are added, and the solution stirred at room temperature overnight, and then concentrated to dryness. The residue is partitioned between 30 mL of ethyl acetate and 30 mL of 1N hydrochloric acid solution, and then the layers separated. The organic layer is washed with 30 mL of a saturated sodium bicarbonate solution, dried over magnesium sulfate, and purified by silica gel column chromatography.

Synthesis of 4-Fmoc-2-substituted-3-oxo-[1,4]-diazepane-5-carboxylic acid (54): To solution of 10 mmol of compound (68) in 30 mL of dichloromethane, kept at room temperature under nitrogen, is added 2 equivalents of phenylsilane and 0.3 equivalents of tetrakistriphenylphosphine palladium (0), and the solution then stirred for 2 hours, and concentrated to dryness. The secondary amine is dissolved in 20 mL of tetrahydrofuran, and 10 mL of water, followed by the addition of 2.52 g (30 mmol) of solid sodium bicarbonate, and 1.2 equivalents of Fmoc-Cl and the biphasic solution is stirred at room temperature for 2 hours, diluted with 30 mL of ethyl acetate, and the layers separated. Oxidation of 4-Fmoc-7-hydroxymethyl-3-substituted-[1,4]-diazepan-2-ones to the final product (54) is done as described in method A. The choice of the oxidizing agent used is based on the nature of the group in the 2-position, as in Method A for the conversion of (6) to (7).

Synthesis of
6-substituted-5-oxo-piperazine-2-carboxylic acid
Scaffolds (Method O)

The syntheses of 6-substituted-5-oxo-piperazine-2-carboxylic acid scaffolds containing non-functionalized side chains in the 6-position are done as outlined in Method O, starting from commercially available 3-Fmoc-amino-1,2-propan-diol 1-chloro-trityl resin (69) which is oxidized to the ketone (70) using Dess-Martin periodinane. Reductive amination of ketone (70) with an α amino ester (2) gives resin bound (1-aminomethyl-2-chloro-trityloxy-ethylamino)-2-substituted acetic acid methyl ester (71), which is cyclized to 5-chlorotrityloxymethyl-3-substituted-piperazin-2-one (72) after deprotection of the amine. Reprotection of the secondary amine, followed by cleavage from the resin, gives Fmoc-5-hydroxymethyl-3-substituted-piperazin-2-one (73) which is oxidized to 6-substituted-5-oxo-piperazine-2-carboxylic acid (74) using either of the procedures described in method A.

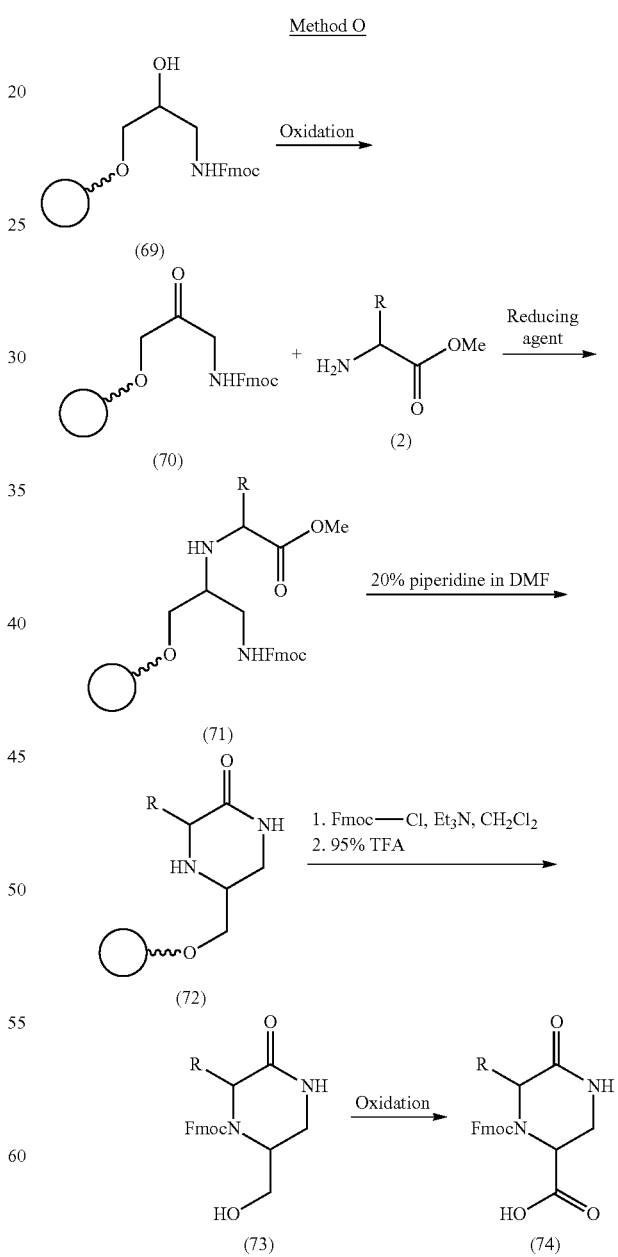

Synthesis of 1-amino-3-chlortrityloxy-propan-2-one (70): the oxidation of resin bound alcohol (69) is done by sulfur trioxide oxidation, NMO/TPAP (N-methylmorpholine-N-oxide/tetrapropyl ammonium perrthenate) oxidation, or PDC oxidation. For sulfur trioxide oxidation, a procedure similar to the one described in Parikh, J. R. and Doering, W. V., *J. Am. Chem. Soc.* 89:5505-5507 (1967) is used. For NMO/TPAP oxidation, to 0.3 mmol of resin-bound alcohol is added a solution of 3 mmol of N-methylmorpholine N-oxide in 10 mL of dry dimethylformamide, and then 0.06 mmol of tetrapropylammonium perruthenate (TPAP) is added to the resin suspension. The reaction is shaken for 80 minutes. The solvent is drained, the resin washed with tetrahydrofuran and dichloromethane, and then dried under vacuum. For PDC oxidation, a suspension of resin bound alcohol in 0.2 M pyridinium dichromate in dimethylformamide is shaken at 37° C. for 4 hours, the solvent is drained, and the resin washed with dimethylformamide, tetrahydrofuran, and dichloromethane.

Synthesis of (1-aminomethyl-2-chloro-trityloxy-ethylamino)-2-substituted acetic acid methyl ester (71): the reductive amination of resin bound ketone (70) with amino ester is done by one of two different methods. In one method, a solution of 2.6 mmol of α amino ester (2) in 20 mL of 1% acetic acid in dimethylformamide is added 2.6 mmol of sodium triacetoxyborohydride, followed by the immediate addition of 0.5 mmol of ketone-derivatized resin (70), and the mixture is shaken for 60 minutes, rinsed with methanol, 10% di-isopropyl ethyl amine, dimethylformamide, and methanol. In a second method, a suspension of 0.05 mmol of ketone-derivatized resin (70) and 2.0 M α amino ester hydrochloride (2) in methanol, containing 0.05 M sodium cyanoborohydride is shaken at room temperature for 5 hours, drained, and washed.

Synthesis of 5-chlorotrityloxymethyl-3-substituted-piperazin-2-one (72): A suspension of 0.05 mmol of resin in 10 mL of 20% piperidine in dimethylformamide is shaken at room temperature for 2 hours.

Synthesis of Fmoc-5-hydroxymethyl-3-substituted-piperazin-2-one (73): A suspension of 0.05 mmol of (72) in 10 mL of dichloromethane, containing 0.25 mmol of Fmoc-Cl and 0.25 mmol of triethyl amine is stirred at room temperature for 6 hours, drained, and washed with dichloromethane. The resin is resuspended in 10 mL of 95% trifluoroacetic acid in dichloromethane, and the suspension shaken for 2 hours, and filtered, and the filtrate is concentrated.

Synthesis of Fmoc-6-substituted-5-oxo-piperazine-2-carboxylic acid (74): Oxidation of (73) to the desired product is done by any of the procedures described for method A.

Synthesis of α,α-Disubstituted Amino Acids
(Methods P and Q)

In certain of the constructs of the invention, it is possible and contemplated to employ a disubstituted amino acid residue, such as an α,α-disubstituted amino acid where the substituents are either the same or different. In one aspect, an α,α-disubstituted amino acid is employed in either the Aaa[1] or Aaa[8] position, wherein at least one of the side chains of the α,α-disubstituted amino acid is a side chain of Nle, Ala, Leu, Ile, Val, Nva, Met(O) or Met($O_2$). The following synthetic Methods P and Q describe making α,α-di-n-butylglycine (2-Amino-2-butyl-hexanoic acid), wherein each of the side chains are —$(CH_2)_3$—$CH_3$, and thus each is the same as the side chain of Nle. However, it is to be understood that similar methods and schemes may be employed in the making of other α,α-disubstituted amino acids, where the substituents are either the same or different. Additionally, any method of making an α,α-disubstituted amino acid may be employed in the practice of this invention, and the practice of this invention is not limited to the methods of the following synthetic schemes. Thus any method known in the art for the synthesis of α,α-disubstituted amino acids may be employed in the practice of this invention. The following teach alternative methods for the making of α,α-disubstituted amino acids: Clark J. S. and Middleton M. D.: Synthesis of novel alpha-substituted and alpha,alpha-disubstituted amino acids by rearrangement of ammonium ylides generated from metal carbenoids. Org. Lett. 4(5):765-8 (2002); Guino M., Hii K. K.: Wang-aldehyde resin as a recyclable support for the synthesis of alpha,alpha-disubstituted amino acid derivatives. Org. Biomol. Chem. 3(17):3188-93 (2005); and Kotha S., Behera M.: Synthesis and modification of dibenzylglycine derivatives via the Suzuki-Miyaura cross-coupling reaction. J. Pept. Res. 64(2):72-85 (2004).

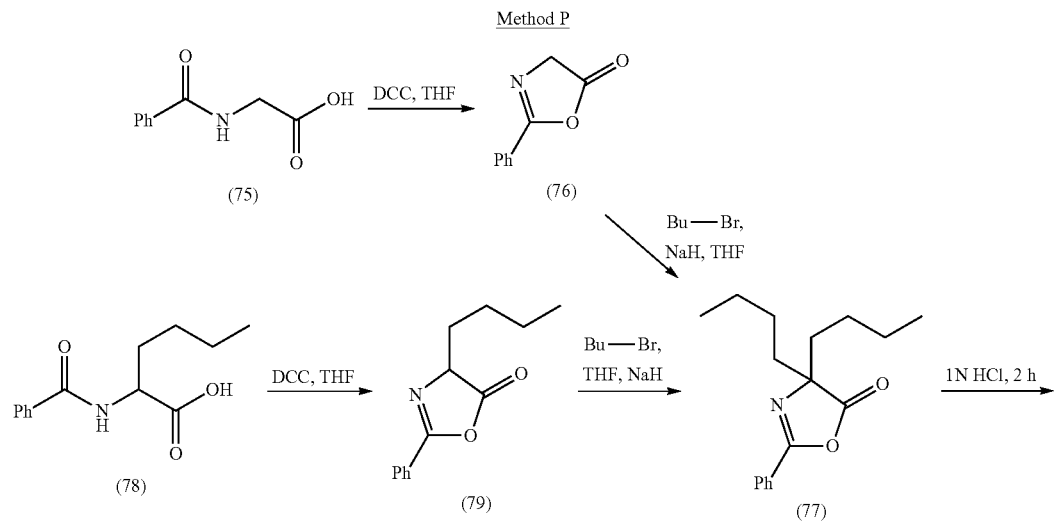

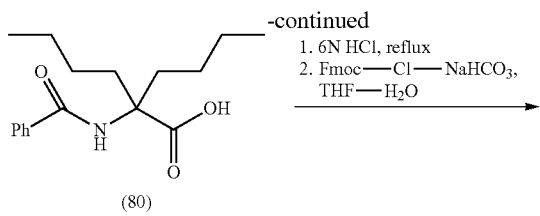

Synthesis of Benzoyl di-n-butylglycine (80): To a solution of 10 mmol benzoyl glycine (75) in 20 mL of dichloromethane, kept at 0° C. under nitrogen, is added slowly 12 mmol of N,N'-dicyclohexylcarbodiimide (DCC), and the s filtered off, and the filtrate concentrated. The residue is Similar methods may be employed by starting with any appropriate amino acid derivative (similar to compound 78), and by using an appropriate alkyl butyl, aryl butyl, or aralkyl butyl reagent the scheme will yield a variety of disubstituted (R, R') amino acid surrogates where R and R' are different.

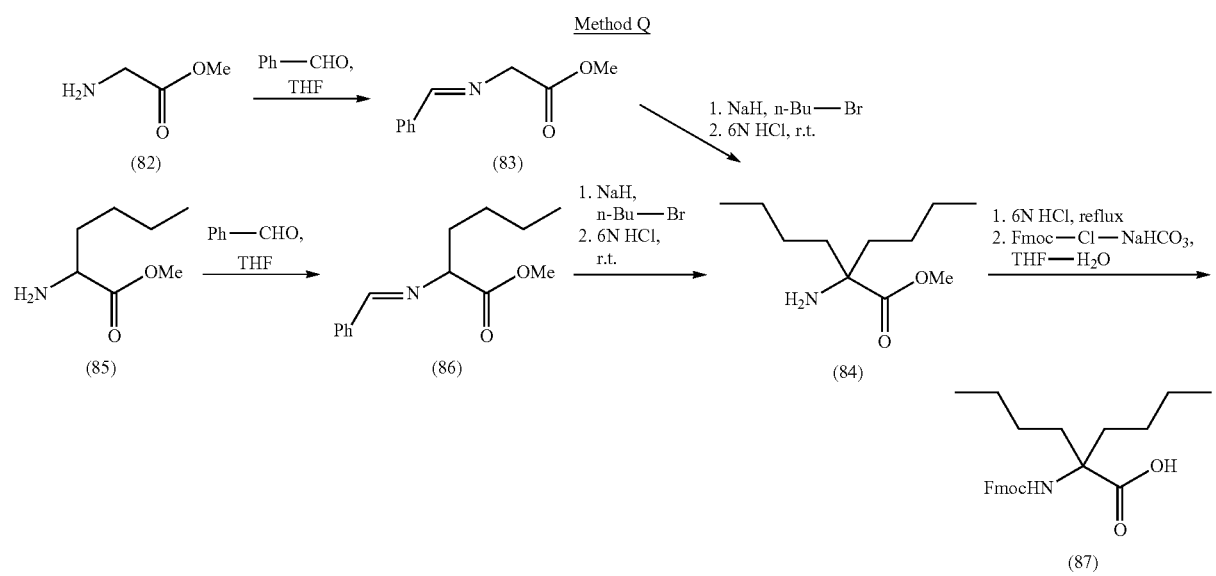

reaction stirred for 2 hours to yield compound (76). The solid idissolved in 15 mL of tetrahydrofuran, cooled to 0° C., and then 24 mmol of sodium hydride is added, followed by 30 mmol of n-butyl bromide. The suspension is stirred at 0° C. for 2 hours and then allowed to warm to room temperature, and the solution concentrated to dryness to yield compound (77). Alternatively, compound (77) can also be prepared from benzoyl norleucine (78) in a similar manner except that 12 mmol of sodium hydride and 15 mmol of n-butyl bromide are used. Compound (77) is dissolved in methanol, 50 mL of 1N hydrochloric acid solution is added, and the solution stirred for 2 hours, and concentrated. Compound (80) is purified by silica gel column chromatography.

Synthesis of Fmoc di-n-butylglycine (81): 10 mmol of compound (80) is dissolved in 30 mL of dioxane, and 10 mL of 6N hydrochloric acid solution is added, and the solution is refluxed overnight. The reaction is cooled to room temperature, concentrated to dryness, redissolved in 30 mL of tetrahydrofuran, and 10 mL of water and 30 mmol of sodium bicarbonate is added, followed by 15 mmol of Fmoc-Cl. The biphasic solution is stirred for 1 hour, and the tetrahydrofuran removed under vacuum. The aqueous solution is extracted with 1×50 mL of diethyl ether, acidified with 1N hydrochloric acid solution, and extracted with 2×50 mL of ethyl acetate. The ethyl acetate layers are combined, dry over sodium sulfate, and concentrated. Compound (81) is purified by silica gel column chromatography.

Synthesis of Fmoc—α,α di-n-butyl glycine (87): To a suspension of 20 mmol of glycine methyl ester hydrochloride (82), and 2 g of powdered molecular sieves in 40 mL of dry tetrahydrofuran, kept at room temperature, is added 24 mmol of potassium hydroxide, followed by 22 mmol of benzaldehyde. The suspension is stirred for 2 hours, filtered, and the filtrate concentrated. The residue is redissolved in 40 mL of dry toluene, and then added to a suspension of 60 mmol of sodium hydride in toluene, followed by the addition of 60 mmol of n-butyl bromide. The suspension is stirred for 12 hours, followed by addition of 30 mL of a solution of 6N hydrochloric acid, stirred at room temperature for 2 hours, and then the layers separated. The hydrochloride salt of (84) thus obtained is used in situ for preparation of (87). To isolate (84) as the hydrochloride salt the aqueous layer is concentrated to dryness and the product crystallized from dry methanol-ether.

Alternatively, compound (84) can be prepared from norleucine methyl ester hydrochloride using a similar synthetic procedure except that 30 mmol of sodium hydride and 30 mmol of n-butyl bromide are used for conversion of (86) to (84).

The aqueous mixture of the hydrochloride form of compound (84) as obtained above is heated to reflux for 1 hour and then cooled to room temperature. It is neutralized with solid sodium hydroxide and then diluted with 30 mL of tetrahydrofuran. Sodium bicarbonate (30 mmol) is added followed by 15 mmol of Fmoc-Cl. The biphasic solution is stirred for 1 hour, and the tetrahydrofuran removed under vacuum. The aqueous solution is extracted with 1×50 mL of diethyl ether, acidified with 1N hydrochloric acid solution, and extracted with 2×50 mL of ethyl acetate. The ethyl acetate layers are combined, dried over sodium sulfate, and concentrated. Compound (87) is purified by silica gel column chromatography.

Similar methods may be employed by starting with any appropriate amino acid derivative (similar to compound 85), and by using an appropriate alkyl butyl, aryl butyl, or aralkyl butyl reagent the scheme will yield a variety of disubstituted (R, R') amino acid surrogates where R and R' are different.

Synthesis of Disubstituted (R, R') Scaffolds (Method R)

The invention further provides for constructs in which amino acid surrogates are employed with two R groups, R and R'. The following method describes synthesis of Fmoc protected (R)-5,5-dibutyl-6-oxo-piperazine-2-carboxylic acid, where R and R' are each groups corresponding to a norleucine side chain moiety. It may be seen that the method below may be modified, based in part on the foregoing methods, to produce similar disubstituted (R, R') amino acid surrogates. Similar methods may be employed such that starting with any appropriate amino acid derivative (a compound similar to compound (84)) the scheme can yield a variety of disubstituted (R, R') amino acid surrogates where R and R' are different.

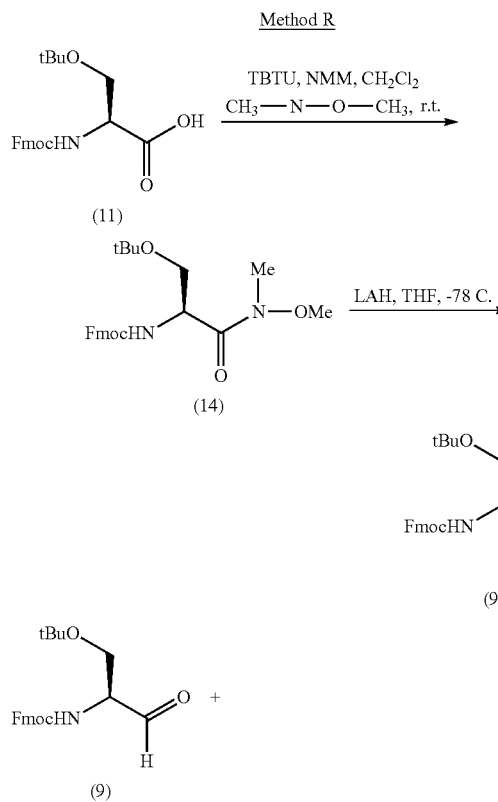

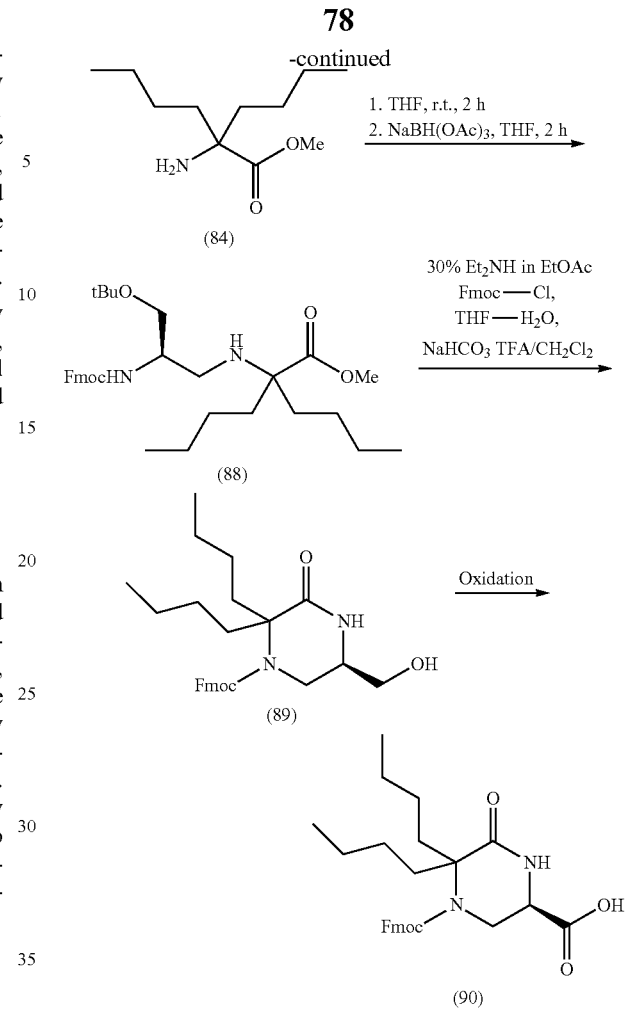

Synthesis of (2-Fmoc-amino-3-tert-butoxy-propylamino)-2,2,di-n-butyl acetic acid methyl ester (88): A suspension of 21 mmol of (84, scheme Q), and 2.9 mL (21 mmol) of triethyl amine in 50 mL of dry tetrahydrofuran, is stirred at room temperature for 45 minutes, and then a solution of ~20 mmol crude Fmoc-(O-t-butyl)-serinal (9, scheme D) in 30 mL of tetrahydrofuran is added, followed by 1.7 g of 4 Å powdered molecular sieves, and the suspension is stirred for an additional 2 hours. 6.4 g (30 mmol) of solid sodium triacetoxyborohydride is added, and the suspension stirred at room temperature overnight. The suspension is diluted with methanol, the molecular sieves filtered, and the filtrate concentrated. The residue is partitioned between 100 mL of ethyl acetate and 50 mL of water. The organic layer is dried over sodium sulfate, filtered, and concentrated. Compound (88) is purified by silica gel column chromatography.

Synthesis of 4-Fmoc-6-hydroxymethyl-3,3-di-n-butyl-piperazin-2-one (89): A solution of 10 mmol of compound (88) in 30 mL of 30% diethyl amine in ethyl acetate is stirred at room temperature overnight, and then concentrated to dryness. The residue is dissolved in 20 mL of tetrahydrofuran and 10 mL of water, 2.52 g (30 mmol) of solid sodium bicarbonate is added, followed by 3.36 g (13 mmol) of Fmoc-Cl. The mixture is stirred for 3 hours, diluted with 50 mL of ethyl acetate, the layers separated, and the organic layer washed with 30 mL of water, dried over magnesium sulfate, and concentrated. The crude mixture is dissolved in a solution of 10 mL of 90% trifluoroacetic acid in dichloromethane, stirred for 2 hours, and then concentrated to dryness. The residue is dissolved in ethyl acetate and washed with 50 mL of a saturated solution of sodium bicarbonate, dried over magnesium sulfate, and concentrated. Compound (89) is purified by silica gel column chromatography.

Synthesis of 4-Fmoc-5,5-di-n-butyl-6-oxo-piperazine-2-carboxylic acid (90): To a solution of 8 mmol alcohol (89) in 81 mL of acetonitrile kept at room temperature, is added phosphate buffer solution (prepared with 0.72 g of sodium phosphate monobasic and 1.43 g of sodium phosphate dibasic in 29.5 mL of water), followed by the addition of 0.33 g (2.1 mmol) of TEMPO, and 1.86 g (16.5 mmol) of sodium chlorite, and the biphasic solution is placed in an oil bath kept at 43° C. A solution of 4.3 mL (2.6 mmol) of sodium hypochlorite solution (prepared by mixing 1.9 mL of 10-13% sodium hypochlorite solution, and 2.4 mL of water) is added slowly. The reaction is stirred at 43° C. for 4 hours, cooled to room temperature, 20 mL of 10% sodium hydrogen sulfite added, stirred for 10 minutes, diluted with 50 mL of ethyl acetate, and the layers separated. The organic layer is washed with 1×10 mL of brine, 1×10 mL of 1N hydrochloric acid solution, dried over sodium sulfate, and concentrated. Compound (90) is purified by silica gel column chromatography.

Synthesis of Constructs of the Invention

The constructs as disclosed in the several embodiments of this invention may be readily synthesized by any known conventional procedure for the formation of a peptide linkage between amino acids. Such conventional procedures include, for example, any solution phase procedure permitting a condensation between the free alpha amino group of an amino acid residue having its carboxyl group or other reactive groups protected and the free primary carboxyl group of another amino acid residue having its amino group or other reactive groups protected. In a preferred conventional procedure, the constructs of this invention may be synthesized by solid-phase synthesis and purified according to methods known in the art. The amino acid surrogates of the present invention may be incorporated into constructs of this invention by methods substantially similar to or identical to those employed with residues. Any of a number of well-known procedures utilizing a variety of resins and reagents may be used to prepare the constructs of this invention.

The process for synthesizing the constructs may be carried out by a procedure whereby each amino acid or amino acid surrogate in the desired sequence is added one at a time in succession to another amino acid residue or amino acid surrogate or by a procedure whereby peptide fragments with the desired amino acid sequence, which may include one or more amino acid surrogates, are first synthesized conventionally and then condensed to provide the desired construct. The resulting construct is cyclized to yield a cyclic construct of the invention.

Solid phase peptide synthesis methods are well known and practiced in the art. In such methods the synthesis of constructs of the invention can be carried out by sequentially incorporating the desired amino acid residues or amino acid surrogates one at a time into the growing peptide chain according to the general principles of solid phase methods. These methods are disclosed in numerous references, including Merrifield R. B., Solid phase synthesis (Nobel lecture). *Angew. Chem.* 24:799-810 (1985) and Barany et al., *The Peptides, Analysis, Synthesis and Biology*, Vol. 2, Gross E. and Meienhofer J., Eds. Academic Press, 1-284 (1980).

In chemical syntheses of constructs, reactive side chain groups of the various amino acid residues or amino acid surrogates are protected with suitable protecting groups, which prevent a chemical reaction from occurring at that site until the protecting group is removed. Also common is the protection of the alpha amino group of an amino acid residue or amino acid surrogate while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods.

Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz); aliphatic urethane-type protecting groups, such as t-butyloxycarbonyl (Boc), diisopropylmethoxycarbonyl, isopropoxycarbonyl, and allyloxycarbonyl. Fmoc is preferred for alpha amino protection.

Guanidino groups may be protected by a suitable protecting group, such as nitro, p-toluenesulfonyl (Tos), Z, pentamethylchromanesulfonyl (Pmc), adamantyloxycarbonyl, pentamethyldihydrobenzofuran-5-sulfonyl (Pbf), Fmoc and Boc. Pbf is one preferred protecting group for Arg. Other preferred protecting groups include Z, Fmoc, and Boc. It is to be understood that particularly guanidino protecting groups may be cleaved and removed during the synthetic process, or may alternatively not be cleaved or removed, in which event the side chain with the protecting group forms a derivative of an amino acid side chain moiety as defined herein. Particularly where the protecting group is labile, and may be removed by some mechanism in vivo upon administration to a patient, the construct becomes a "prodrug", which is to say a construct that is a drug precursor which, following administration to a patient, is converted to the desired drug form in vivo via some chemical or physiological process (e.g., a prodrug on being brought to physiological pH or through enzyme action is converted to the desired drug form).

The constructs of the invention described herein can be prepared using solid phase synthesis, either manually or by means of an automated peptide synthesizer, using programming modules as provided by the manufacturer and following the protocols set forth by the manufacturer, or by modifications of the manufacturers's protocols to improve the yield of difficult couplings.

Solid phase synthesis is commenced from the C-terminal end of the construct by coupling a protected α-amino acid, α-amino acid surrogate or α-amino alcohol mimetic to a suitable resin. Such starting material is prepared by attaching an α-amino-protected amino acid or α-amino-protected amino acid surrogate by an ester linkage to a p-benzyloxybenzyl alcohol (Wang) resin or a 2-chlorotrityl chloride resin, by an amide bond between an Fmoc-Linker, such as p-[(R,S)-α-[1-(9H-fluor-en-9-yl)-methoxyformamido]-2,4-dimethyloxybenzyl]-phenoxyacetic acid (Rink linker) to a benzhydrylamine (BHA) resin, or by other means well known in the art, such as by attaching an α-amino-protected alcohol mimetic to 3,4-dihydro-2H-pyran-2yl-methanol linker attached to chloromethyl polystyrene resin. Fmoc-Linker-BHA resin supports are commercially available and generally used when feasible. The resins are carried through repetitive cycles as necessary to add amino acids sequentially. The alpha amino Fmoc protecting groups are removed under basic conditions. Piperidine, piperazine, diethylamine, or morpholine (20-40% v/v) in N,N-dimethylformamide (DMF) may be used for this purpose.

Following removal of the alpha amino protecting group, the subsequent protected amino acids or amino acid surrogates are coupled stepwise in the desired order to obtain an intermediate, protected peptide-resin. The activating reagents used for coupling of the amino acids in the solid phase synthesis of the peptides are well known in the art. After the construct is synthesized, if desired, the orthogonally protected side chain protecting groups may be removed using methods well known in the art for further derivatization of the construct.

Reactive groups in a construct can be selectively modified, either during solid phase synthesis or after removal from the resin. For example, constructs can be modified to obtain N-terminus modifications, such as acetylation, while on resin, or may be removed from the resin by use of a cleaving reagent and then modified. Methods for N-terminus modification, such as acetylation, or C-terminus modification, such as amidation or introduction of an N-acetyl group, are known in the art. Similarly, methods for modifying side chains of amino acids are well known to those skilled in the art of peptide synthesis. The choice of modifications made to reactive groups present on the construct will be determined, in part, by the characteristics that are desired in the construct.

The construct are, in one embodiment, cyclized prior to cleavage from the resin. For cyclization through reactive side chain moieties, the desired side chains are deprotected, and the construct suspended in a suitable solvent and a cyclic coupling agent added. Suitable solvents include, for example DMF, dichloromethane (DCM) or 1-methyl-2-pyrrolidone (NMP). Suitable cyclic coupling reagents include, for example, 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU), benzotriazole-1-yl-oxy-tris(dimethylamino)phosphonium-hexafluorophosphate (BOP), benzotriazole-1-yl-oxy-tris(pyrrolidino)phosphoniumhexafluorophosphate (PyBOP), 2-(7-aza-1H-benzotriazol-1-yl)-1,1,3,3-tetramethyluronium tetrafluoroborate (TATU), 2-(2-oxo-1(2H)-pyridyl)-1,1,3,3-tetramethyluronium tetrafluoroborate (TPTU) or N,N'-dicyclohexylcarbodiimide/1-hydroxybenzotriazole (DCCl/HOBt). Coupling is conventionally initiated by use of a suitable base, such as N,N-diisopropylethylamine (DIPEA), sym-collidine or N-methylmorpholine (NMM).

Following cleavage of constructs from the solid phase following synthesis, the construct can be purified by any number of methods, such as reverse phase high performance liquid chromatography (RP-HPLC), using a suitable column, such as a $C_{18}$ column. Other methods of separation or purification, such as methods based on the size or charge of the construct, can also be employed. Once purified, the construct can be characterized by any number of methods, such as high performance liquid chromatograph (HPLC), amino acid analysis, mass spectrometry, and the like.

Constructs of the present invention with a substituted amide derivative C-terminus, typically an N-alkyl group, are prepared by solid phase synthesis commenced from the C-terminal end of the construct by coupling a protected alpha amino acid or amino acid surrogate to a suitable resin. Such methods for preparing substituted amide derivatives on solid phase have been described in the art. See, for example, Barn D. R., Morphy J. R., Rees D. C. Synthesis of an array of amides by aluminum chloride assisted cleavage of resin-bound esters. *Tetrahedron Lett.* 37, 3213-3216 (1996); DeGrado W. F. Kaiser E. T. Solid-phase synthesis of protected peptides on a polymer bound oxime: Preparation of segments comprising the sequences of a cytotoxic 26-peptide analogue. *J. Org. Chem.* 47:3258-3261 (1982). Such starting material can be prepared by attaching an alpha amino-protected amino acid or amino acid surrogate by an ester linkage to a p-benzyloxybenzyl alcohol (Wang) resin by well known means. The peptide chain is grown with the desired sequence of amino acids or amino acid surrogates, the product cyclized and resin-treated with a solution of appropriate amine and aluminum chloride (such as methyl amine, dimethyl amine, ethylamine, and so on) in dichloromethane. The resulting amide derivative construct is released in solution from the resin. The resin is filtered and the amide derivative construct recovered by concentration of solvent followed by precipitation with ether. The crude construct is dried and remaining amino acid side chain protective groups cleaved using trifluoroacetic acid (TFA) in the presence of water and triisopropylsilane (TIS). The final product is precipitated by adding cold ether and collected by filtration. Final purification is by RP-HPLC using a $C_{18}$ column.

In one preferred method, the constructs of Example 1 were synthesized by the following methods. Each of the constructs had one or two amino acid surrogates based on a keto-piperazine structure. The amino acid surrogates were synthesized as described above. The constructs were synthesized using Fmoc chemistry. A manual synthetic approach was used for couplings immediately before and after incorporation of the keto-piperazine amino acid surrogate.

The following protocol was employed to attach an amino acid surrogate to resin, such as where the amino acid surrogate was in a terminal position. Rink amide resin (loading at 0.3 mmol/g, Advanced ChemTech) was allowed to swell in DMF for 30 minutes. Fmoc deprotection of the resin was accomplished using 20% piperidine/DMF for 20 minutes. Coupling of the resin with the selected Fmoc-protected keto-piperazine amino acid surrogate (2 eq) was accomplished by overnight incubation in DMF with PyBop (2 eq) and DIEA (4 eq). If following Kaiser testing a positive result was obtained, the coupling reaction was conducting a second time. Acetylation was carried out using $Ac_2O$ (10 eq) and pyridine (20 eq) in DMF.

The following protocol was employed to attach a keto-piperazine amino acid surrogate to peptide-resin. Coupling was carried out by mixing Fmoc-protected keto piperzine amino acid surrogate (2 eq), TBTU (2 eq) and DIEA (4 eq) in DMF and allowing to incubate overnight, again with a repeat of the coupling reaction if a positive Kaiser test obtained. Acetylation was carried out using $Ac_2O$ (10 eq) and pyridine (20 eq) in DMF.

The following protocol was employed to couple an Fmoc-protected amino acid to a keto-piperazine amino acid surrogate on solid phase. In most instances at least two coupling cycles were needed, and frequently three cycles were employed. In a typical cycle Fmoc-protected amino acid (4 eq) was mixed with HOAt (4 eq) and DIC (4 eq) in DMF. The resulting mixture was then mixed overnight in a SPE tube with a keto-piperazine amino acid surrogate attached directly or through intermediates to resin.

Couplings between amino acids that were not directly adjacent to a keto-piperazine amino acid surrogate in the sequence were conducted using standard protocols for solid phase peptide synthesis. The following protecting groups were employed: Boc for Lys and Orn, t-Butyl for Tyr and Ser, Trityl for Cys and His, O-t-Butyl for Asp and Pbf for Arg.

Constructs were cleaved from resin employing a mixture of TFA/thioanisole/phenol/$H_2O$/DTT/TIS (87.5/2.5/2.5/5/2.5/11) (5 mL) for 3 hours. The resulting material was filtered and precipitated from cold ether under freezing conditions for one hour. Precipitated cysteinyl peptide was washed with cold ether at least three times before being use in an oxidation step.

For cyclization to form disulfide bonds via air oxidation, crude cysteinyl construct was dissolved in a mixture of acetonitrile and water. The pH of the reaction mixture was adjusted to 7-8 using 5% NH₄OH. The resulted solution was stirred slowly with 150 mg granular activated carbon for 2 days. Completion of cyclization was confirmed by LC-MS analysis before proceeding to the next process step. After cyclization, solid carbon was filtered from solution. The filtrate was lyophilized or dried in a speed-vac to obtain crude cyclic construct.

Certain constructs of the invention, where the surrogate is bound to resin or other peptide solid support and is at the C-terminal position, may be synthesized by means of the following scheme. The following scheme is exemplified by synthesis of construct 1-132, but it is to be understood that substantially similar methods may be employed for any construct wherein the surrogate is bound to resin or other peptide solid support.

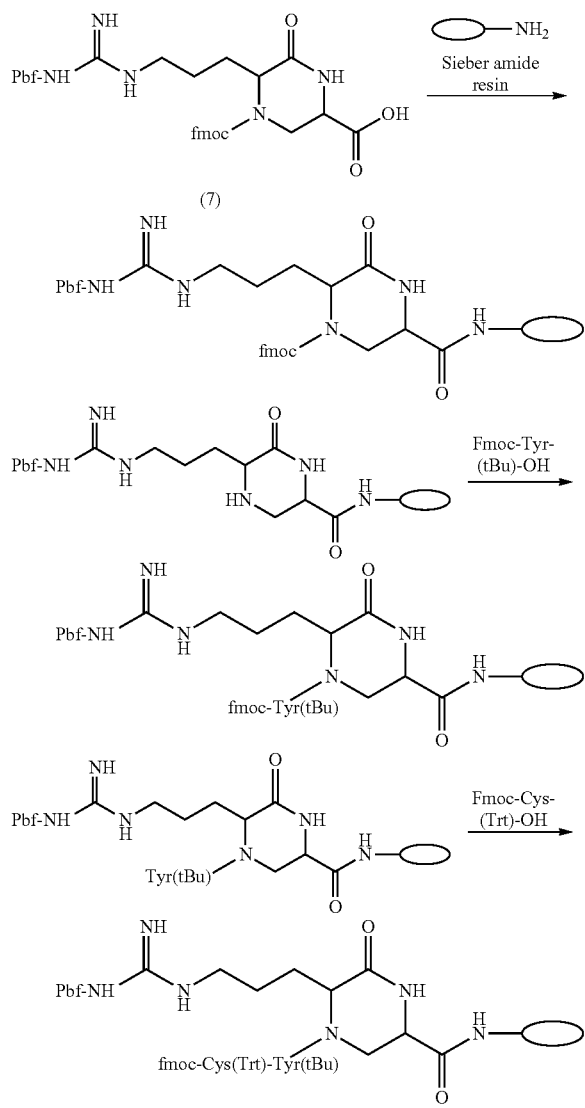

Surrogate (7) is prepared by the scheme of method A above, or any alternative method. Fmoc protected Sieber amide resin was treated by swelling 23.8 g (0.63 mmol/g substitution, 15 mmol) of the resin in 200 mL of a 1:1 mixture of dimethylformamide and dichloromethane for 45 minutes, followed by filtering and washing with 2×125 mL of dimethylformamide. The washed resin was then deprotected with 2×125 mL of 20% piperidine in dimethylformamide for 15 minutes, filtered, and washed with 4×125 mL of dimethylformamide.

A solution of 21.5 g (MW=717, 30 mmol) of Fmoc-protected surrogate (7) in 160 mL of dimethylformamide was added to the deprotected Sieber amide resin as prepared above, followed by 15.6 g (MW=520.3, 30 mmol) of solid PyBop, and 10.4 mL (MW=129.25, d=0.742, 60 mmol) of diisopropylethylamine, followed by another 40 mL of dimethylformamide. The mixture was agitated overnight with nitrogen bubbling. The resin was filtered, and washed with 4×130 mL of dimethylformamide, capped with 150 mL of capping solution consisting of a 3:2:1 solution of dimethylformamide:acetic anhydride:pyridine for 30 minutes, filtered, and washed with 4×130 mL of dimethylformamide to provide surrogate (7) complexed to resin.

The resulting Fmoc-protected surrogate (7) complexed to resin was deprotected with 2×130 mL of 20% piperidine in dimethylformamide for 15 minutes, filtered, and washed with 4×130 mL of dimethylformamide to yield surrogate (7) complexed to resin. A solution of 27.6 g of Fmoc-Tyr-(tBu)-OH (60 mmol, 4 eq.) in dimethylformamide (200 mL) was added to surrogate (7) complexed to resin, followed by a solution of 24.8 g of HCTU (60 mmol, 4 eq.), and 20.8 mL (120 mmol, 8 eq.) of diisopropylethylamine in DMF to a final volume of 200 mL and coupled overnight with nitrogen bubbling. The resulting Fmoc-Tyr-(tBu)-surrogate (7)-resin was isolated by filtration and washed with 2×130 mL of dimethylformamide. In order to ensure complete coupling, the product was again treated with a solution of 27.6 g of Fmoc-Tyr-(tBu)-OH (MW=459.6, 60 mmol, 4 eq.) in dimethylformamide to a final volume of 200 mL followed by a solution of 24.8 g of HCTU (60 mmol, 4 eq.), and diisopropylethylamine (20.8 mL, 120 mmol, 8 eq.) in DMF to a final volume of 200 mL and coupled overnight with nitrogen bubbling. The resin was filtered, and washed with 2×130 mL of dimethylformamide. HPLC and LC/MS showed that coupling between surrogate (7)-resin and Fmoc-Tyr-(tBu)-OH was complete.

The resulting Fmoc-Tyr-(tBu)-surrogate (7)-resin was then capped with 150 mL of capping solution as above for 30 minutes. The resin was then filtered, washed with 4×130 mL of dimethylformamide, 4×130 mL of dichloromethane, 2×130 mL of MeOH, 2×130 mL of diethyl ether, and dried under vacuum to give 36.7 g.

Thereafter each succeeding amino acid may be coupled. Before the coupling of the first amino acid, resulting Fmoc-Tyr-(tBu)-surrogate (7)-resin was swollen for 45 minutes with 200 mL of a 1:1 solution of dimethylformamide:dichloromethane. Each amino acid (Fmoc-AA-OH) was coupled by repeating the following cycle. The terminal amino acid residue was deprotected with 2×125 mL of 20% piperidine in dimethylformamide for 15 minutes, filtered and washed with 4×125 mL of dimethylformamide. The beads were checked by ninhydrin test. A solution of Fmoc-AA-OH (60 mmol, 4 eq.) in dimethylformamide to a final volume of 200 mL was added to resin, followed by a solution of HBTU (60 mmol, 4 eq.), and (120 mmol, 8 eq.) of N-methylmorpholine in DMF to a final volume of 200 mL [concentration of Fmoc-AA-OH=150 mM solution] and coupled for 30 minutes with nitrogen bubbling (coupling reaction checked by ninhydrin test). When the ninhydrin test was negative, the resin was filtered, and washed with 4×130 mL of dimethylformamide.

After all amino acids had been coupled, the resin was washed with 4×130 mL of dichloromethane, 4×130 mL of methanol, 4×130 mL of diethyl ether, and dried under vacuum to give product. The weight increase was quantitative.

100 mL of cleavage reagent consisting of a 81.5:5:5:5:2.5:1 solution of trifluoroacetic acid:phenol:thioanisole:water:DDT:triisopropyl silane was added to 32 g (~6.4 mmol) of the following linear construct:

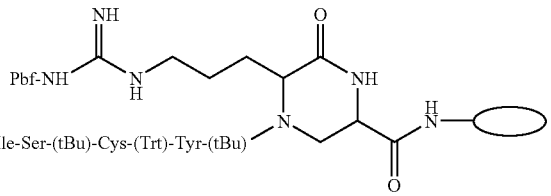

Hept-Cys-(Trt)-His-(Trt)-Phe-D-Ala-Gly-Arg-(Pbf)-D-Nle-Asp-(tBu)-Arg-(Pbf)-Ile-Ser-(tBu)-Cys-(Trt)-Tyr-(tBu)

The suspension was allowed to stand at room temperature for 5 minutes and then filtered. Another 100 mL of cleavage reagent was added to the resin, allowed to stand for 5 minutes, and filtered. This process was repeated.

The resulting resin was then washed with 2×40 mL of trifluoroacetic acid. The filtrates were combined and stirred for 2.5 hours at room temperature, and then concentrated under reduced pressure to ~100 mL volume. Cold diethyl ether (1.5 L, pre-cooled to −20° C.) was added to the filtrate, and then placed in the freezer (−20° C.) for 1 hour, filtered through a sintered glass funnel, and the solids washed with 3×200 mL of cold diethyl ether, and then dried under vacuum for 1 hour with the solids triturated every 15 minutes to make sure solvent was removed efficiently. The following construct was obtained (15.4 g) (103% overall crude yield):

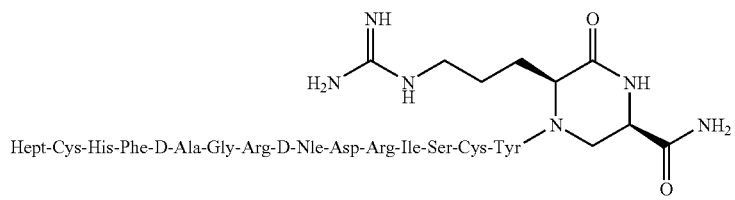

Hept-Cys-His-Phe-D-Ala-Gly-Arg-D-Nle-Asp-Arg-Ile-Ser-Cys-Tyr

The above construct (15.4 g, 6.4 mmol) was dissolved in 16 L of 30% acetonitrile in water. The pH was adjusted to 8.4 using a solution of 5% ammonium hydroxide. Pulverized activated carbon (15.4 g) was added, and the suspension stirred overnight. The carbon was removed by filtration through celite. The celite was washed 3×100 mL 50% acetonitrile in water. The filtrates were combined, diluted with water to a final concentration of 10% acetonitrile, and loaded in the column for purification. Purification of the trifluoroacetate salt of the resulting construct was performed under the following conditions:

Column: Luna $C_{18}$, 10μ, 50×33 mm
Flow: 70 mL/minute
Solvent A: water containing 0.1% trifluoroacetic acid
Solvent B: acetonitrile containing 0.1% trifluoroacetic acid Gradient: 5% solvent B for 5 minutes
26% B to 52% B in 30 minutes The pure fractions were combined and lyophilized to give the purified trifluoroacetate salt of the construct. Dowex SBR, LCNG-OH resin (450 g) was suspended in 2 L of water, and gently stirred for 15 minutes, allowed to stand for 15 minutes, and then decanted. The procedure was repeated, and then 0.5 L of water added, and the slurry transferred into a 6×60 cm column. The water was drained, washed with 4 L of water, and ions exchanged with 6.5 L of 20% acetic acid solution. The resin was allowed to stand at room temperature overnight, and then washed with water until the pH of the filtrate was ~4 (8 L of water used). The trifluoroacetate salt of the above construct (11.1 g), as prepared above, was dissolved in 80 mL of water, and loaded to the ion exchange resin, and eluted with water. Fractions containing 79-1 were combined, and 20% acetic acid solution was added to adjust the final concentration to 5% acetic acid, and then lyophilized. The following construct 1-132 (10.4 g) was obtained:

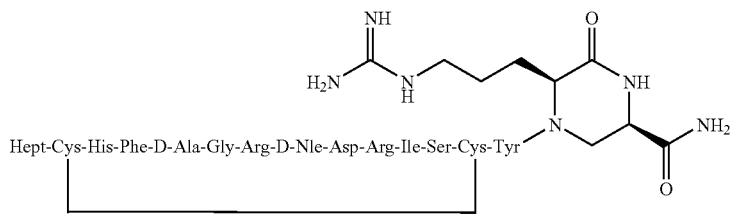

Hept-Cys-His-Phe-D-Ala-Gly-Arg-D-Nle-Asp-Arg-Ile-Ser-Cys-Tyr

Similar methods may be employed with any construct where the surrogate is bound to resin or other peptide solid support and is at the C-terminal position.-

Optional PEGylation of the peptide constructs of the invention may be performed in any manner, such as those described below.

PEGylation of reactive amine groups, such as lysine or ornithine side chains, an omega amino aliphatic in position Aaa[1], or an amine group in J of an amino acid surrogate at Aaa[15] was accomplished by dissolving 0.005 mmol purified construct in 2 mL of dimethylsulfoxide, followed by the addition of 55.5 mg (0.011 mmol, 2 eq) of PEG-5K-OSu (5,000 Da MW methoxy-PEG with a succinimidyl propionate reactive group), with 17.7 µL (0.13 mmol, 20 eq.) of triethyl amine then added, and the slightly cloudy solution stirred at room temperature for 3 hours. Excess PEG-5K-OSu was quenched by the addition of 7 µL (0.111 mmol, 10 eq.) of ethanol amine, and the reaction stirred overnight.

PEGylation of reactive carboxyl groups, such as Asp or Glu side chains or a terminal carboxyl at Aaa[15] on either a residue or surrogate, is accomplished by coupling PEG-NH$_2$ (PEG-amine), to the construct containing a carboxylate group in the side chain of Asp or Glu or at the C-terminus. The peptide construct (0.005 mmol) is dissolved in DMSO (2 mL), followed by the addition of 55.5 mg (0.011 mmol, 2 eq) of PEG-NH$_2$ and HOBt (0.01 mmol). The coupling is started by the addition of 0.0055 mmole of coupling reagent N-ethyl-N'-(3-dimethylaminopropyl)-carbodiimide (EDAC). The slightly cloudy solution stirred at room temperature overnight. The PEGylated peptide construct is then purified by HPLC.

PEGylation of reactive thiol groups, such as Cys or Hcys side chains or a thiol group in Q of an amino acid surrogate at Aaa[1], is accomplished by treating the peptide construct in DMSO with PEG-methyl-maleimide reagent (SunBio, Orinda, Calif.) overnight. The PEGylated peptide construct is then purified by HPLC.

Following PEGylation, the resulting crude mixture was then purified by HPLC, yielding a PEG derivatized construct including one or more amino acid surrogates.

In Vitro and In Vivo Test Systems

Selected constructs were tested in assays to determine binding and functional status. The following assays were employed.

Cell Culture.

A cDNA clone that encodes for human natriuratic peptide receptor A (NPRA) was purchased from Bio S&T Inc. (Montreal, Quebec). The cDNA clone was inserted into the mammalian expression vector pcDNA3.1 (Invitrogen) and transfected into HEK-293 cells. Stable clones were selected by culture of cells in the presence of G418 sulfate. Expression of NPRA was examined by binding of [$^{125}$I]-atrial natriuretic peptide ([$^{125}$I]-ANP) to membrane homogenates prepared from clonal cell lines. HEK-hNPRA cells were maintained in culture at 37° C. in 5% CO$_2$ in Dulbecco's Modified Eagle's Medium (DMEM) supplemented with 10% FBS, G418 sulfate (300 µg/mL) sodium glutamate (0.29 mg/mL), penicillin (100 units/mL) and streptromycin (100 ug/mL).

Competitive Binding Assay.

A competitive inhibition binding assay was performed using crude membrane homogenates prepared from HEK-hNPRA cells. To prepare membrane homogenates, cells were rinsed with phosphate-buffered saline and incubated for 15 minutes at 4° C. in hypotonic lysis buffer (10 mM Tris, pH 7.4+5 mM EDTA). Cells were transferred from plates to polypropylene tubes and homogenized. Homogenates were centrifuged at 25,000×g for 20 minutes. Pellets were resuspended in buffer consisting of 50 mM Tris (pH 7.4) and 1 mM EDTA, homogenized and centrifuged at 25,000×g for 20 minutes. Pellets were resuspended in buffer consisting of 100 mM Tris (pH 7.4) and 10 mM MgCl$_2$ and stored at −80° C. until needed. On the day of an assay, homogenates were thawed and homogenized. Binding of [$^{125}$I]-ANP was carried out in buffer containing 25 mM Hepes (pH 7.4), 100 mM NaCl, 2 mM CaCl$_2$, 5 mM MgCl$_2$, 0.1% BSA and 1 mM 1,10-phenanthroline. Homogenates (1-10 µg protein/well) were incubated with [$^{125}$I]-ANP (25-30 pM) and increasing concentrations of competing ligands in Millipore filter plates for 120 minutes at 4° C. Assays were stopped by addition of cold wash buffer (phosphate-buffered saline) followed by filtration using a vacuum manifold. Bound radioactivity was determined using a gamma counter. Non-specific binding was defined by binding of [$I^{125}$]-hANP to non-transfected HEK293 membranes. Data were analyzed using GraphPad Prism® curve-fitting software.

General Method for Determination of $EC_{50}$.

Functional evaluation of constructs was performed by measuring the accumulation of intracellular cGMP in HEK-293 cells that express recombinant hNPR-A. HEK-NPRA cells were harvested by washing and centrifugation in Cell Dissociation Buffer (Gibco, Life Technologies). Pelleted cells were resuspended in Hank's Balanced Salt Solution (HBSS) containing 10 mM Hepes (pH 7.4), 5 mM MgCl$_2$, 200 mM L-glutamine, 1 mM 1,10-phenanthroline and BSA (0.5 mg/mL). Following centrifugation, cells were resuspended in the above buffer supplemented with 0.5 mM 3-isobutyl-1-methylxanthine (IBMX). Cells (~2×10$^5$/well) were added to each well of a 96-well plate and incubated for 15 minutes at 37° C. Following the pre-incubation period, cells were incubated for an additional 15 minutes in the presence of increasing concentrations of constructs. The reaction was terminated by lysis of the cells with temperature shock. The reaction plate was incubated in a dry ice/ethanol bath for 15 minutes followed by incubation at 90° C. for 10 minutes. Accumulation of cGMP was measured using the cGMP Flashplate RIA (Perkin-Elmer). Data analysis and $EC_{50}$ values were determined by using nonlinear regression analysis with GraphPad Prism® software.

Determination of Mass and Nuclear Magnetic Resonance Analysis.

The mass values of PEG-conjugated constructs were analyzed by MALDI-TOF mass spectrometry (positive ion mode) using alpha-cyano-4-hydroxycinnamic acid (CHCA) as matrix. Methanol was used for sample preparation in construct to matrix ratios of 1:10, 1:20 and 1:30. Alternatively other matrices such as, sinapinic acid (SA) and 2,5-dihydroxybenzoic acid (DHB), and solvents such acetonitrile—0.1% aqueous TFA can be used for sample preparation. Other determinations of mass values were made using a Waters MicroMass ZQ device utilizing a positive mode. For constructs that were not PEGylated, mass determinations were compared with calculated values and expressed in the form of mass weight plus two divided by two ((M+2)/2), unless otherwise specified.

Proton NMR data was obtained using a Bruker 300 MHz spectrometer. The spectra were obtained after dissolving constructs in a deuteriated solvent such as chloroform, DMSO, or methanol as appropriate.

HPLC measurements were made using a Waters Alliance HT with a YMC Pack Pro C$_{18}$ column (4.6×50 mm, 3µ) eluted at 1 mL/minute in a step-wise procedure. Solvent A (water containing 0.1% trifluoroacetic acid v/v) and solvent B (acetonitrile containing 0.1% trifluoroacetic acid v/v) were used as mobile phases. For analysis of keto piperazine intermediates, the column was equilibrated with 10% B and then B was increased to 90% over a period of 8 minutes. For analysis of peptides, the column was equilibrated with 2% B and then B was increased to 90% over a period of 8 minutes.

Animal Models—Blood Pressure Transducer Implantation.

Rats are induced to a surgical plane of anesthesia with isoflurane and maintained on a heating pad. The abdomen is shaved and scrubbed with 70% alcohol and betadine solution. Using aseptic technique, a midline abdominal incision is made in order to expose the descending aorta and vena cava. The contents of the abdomen are retracted gently using wet sterile gauze and retractors. Based on the manufacturer's instructions (described in Data Sciences International's *Multiplus TL Series Device Surgical Manual* 2000: pp. 3.1-3.10), the abdominal aorta is carefully dissected from the surrounding fat and connective tissue and the catheter of the blood pressure transducer is inserted. The catheter of the transducer is secured into place using surgical glue and the body of the transducer stabilized by suturing to the abdominal wall (4-0 silk suture). Care is taken to ensure that hemostasis is maintained during the procedure and that blood flow is not compromised (e.g. aorta will not be occluded for more than 3 minutes at a time). Transducer placement is verified using the telemetry radio signal. After transducer placement, the gauze sponges are removed and the abdominal cavity is flushed with sterile saline. The abdominal incision is then sutured closed with nonabsorbable sutures (4-0 silk suture) in a simple interrupted pattern. The skin is closed using absorbable suture (4-0 vicryl). Finally the animal is removed from the isoflurane and placed in a warm environment while being monitored until it is fully awake.

Surgical Induction of Congestive Heart Failure (Volume Overload).

In this procedure, the descending aorta and vena cava are exposed in the same manner as it is in the implantation procedure for the telemetry device. Once access to the vessels between the renal and iliac bifurcation is obtained, a puncture is made with a 1.8 mm needle (outside diameter) to the descending aorta. The needle is advanced into the inferior vena cava and withdrawn. The ventral puncture site in the descending aorta is sealed with tissue adhesive. The persistence of a shunt between the aorta and vena cava is confirmed visually by the swelling of the vena cava and the mixing of the venous and arterial blood. In the event that a pressure transducer is also implanted, the two procedures are done concurrently. The general methods described in Flaim, S. F., W. J. Minteer, S. H. Nellis, and D. P. Clark: Chronic arteriovenous shunt: evaluation of a model for heart failure in rat. *Am. J. Physiol.* 236:H698-H704 (1979) and Garcia, R. and S. Diebold: Simple, rapid and effective method of producing aortocaval shunts in the rat. *Cardiovasc. Res.* 24:430-432 (1990), are incorporated here by reference.

Blood Pressure Monitoring.

Telemetry signals from the blood pressure transducers (model TA11PA-C40, Data Sciences International, St Paul, Minn.) are collected and analyzed using Dataquest A.R.T. Gold software version 3.0 (Data Sciences International). Rats were observed at approximately the same time each day. Each rat, in its home cage, is placed on a receiver in the observation room and allowed to adjust to the change in location for 30 minutes. Baseline recordings are taken for 30 minutes just prior to dosing and treatment recordings are taken for 135 minutes immediately following IV dosing and 210 minutes following SC dosing. The data are compared to the results after saline dosing in a way similar to methods previously published in Clemens, L. E., R. G. Almirez, K. A. Baudouin, E. B. Grossbard, and A. A. Protter: Human brain natriuretic peptide reduces blood pressure in normotensive and acute norepinephrine-induced hypertensive rabbits. *Am. J. Hypertens.* 10:654-661 (1997), incorporated here by reference.

Diuresis and Natriuresis.

Rats are induced to a surgical plane of anesthesia with sodium pentobarbital and maintained on a heating pad. The abdomen is shaved and scrubbed with 70% alcohol and betadine solution. Using aseptic technique, a midline abdominal incision is made in order to expose the urinary bladder. A purse-string suture is introduced to ventral surface of the bladder and a small incision is made within the suture area. The flared end of a catheter in inserted into the open in and the purse-string suture tightened around it to secure it in place. Urine is collected into preweighed microcentrifuge tubes at various time intervals before and after dosing in a way similar to methods published in Abassi, Z. A., J. R. Powell, E. Golomb, and H. R. Keiser: Renal and systemic effects of urodilatin in rats with high-output heart failure. *Am. J. Physiol.* 262:F615-F621 (1992), incorporated here by reference. Urine volume is measured by weight.

Example 1

The following constructs were synthesized, using amino acid surrogates of one or more of the foregoing methods, were purified and the mass weights determined, with the results as shown below:

TABLE 1

| Number (M + 2)/2 | Structure |
| --- | --- |
| 1-1 931.9 | 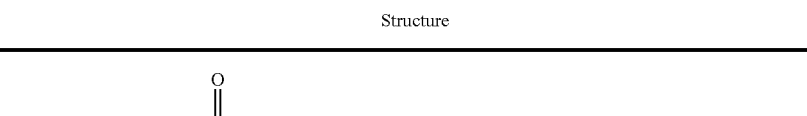 (SEQ ID NO: 3) |

TABLE 1-continued
| Number (M + 2)/2 | Structure |
|---|---|
| 1-2 932.0 | 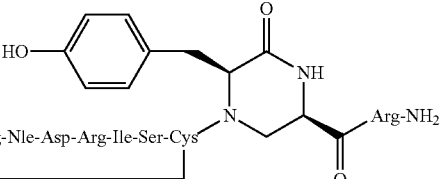<br>(SEQ ID NO: 4) |
| 1-3 938.9 | 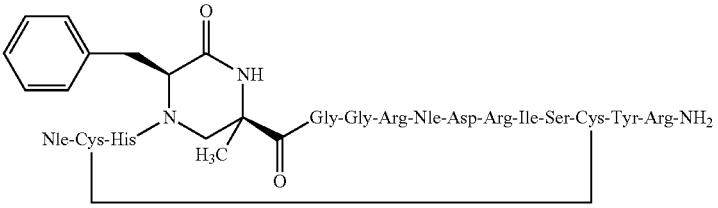<br>(SEQ ID NO: 5) |
| 1-4 932.0 | 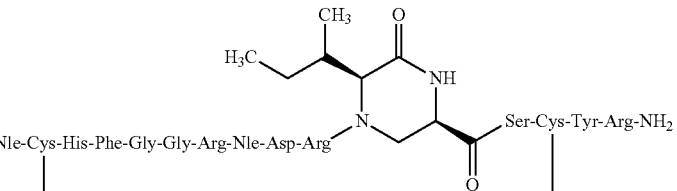<br>(SEQ ID NO: 6), (SEQ ID NO: 7) |
| 1-5 932.9 | 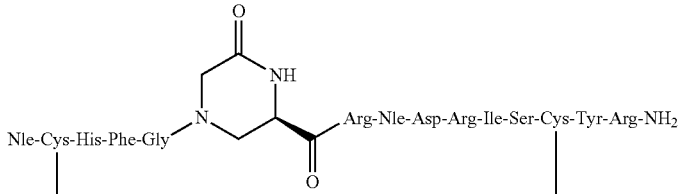<br>(SEQ ID NO: 8), (SEQ ID NO: 9) |
| 1-6 932.7 | 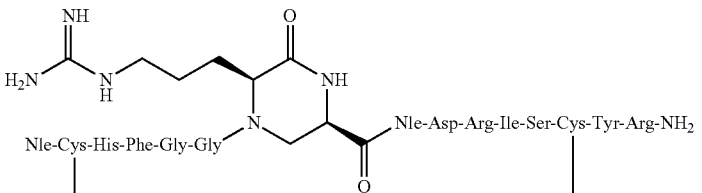<br>(SEQ ID NO: 10), (SEQ ID NO: 11) |
| 1-7 932.3 | 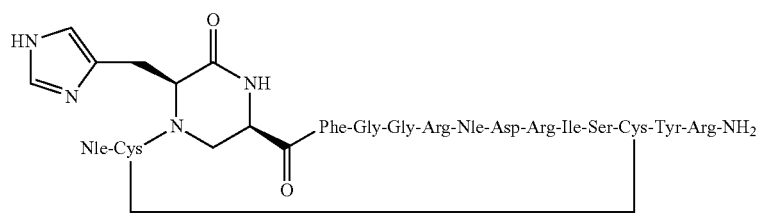<br>(SEQ ID NO: 12) |

TABLE 1-continued
| Number (M + 2)/2 | Structure |
|---|---|
| 1-8 932.0 | 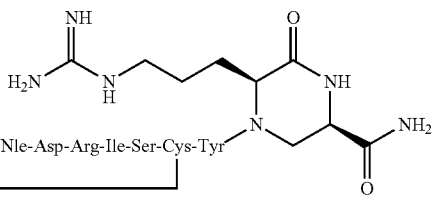 (SEQ ID NO: 13) |
| 1-9 932.2 | 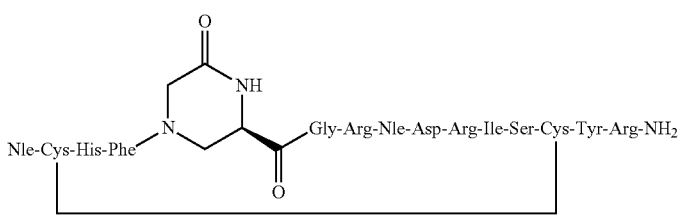 (SEQ ID NO: 14), (SEQ ID NO: 15) |
| 1-10 931.6 | 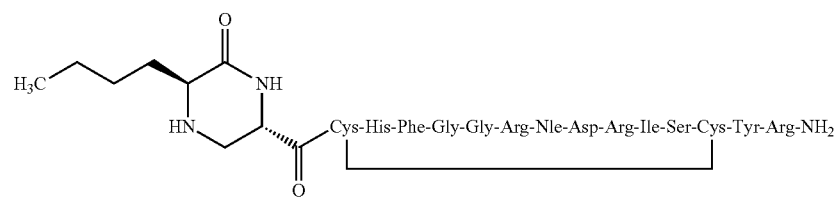 (SEQ ID NO: 3) |
| 1-11 931.6 | 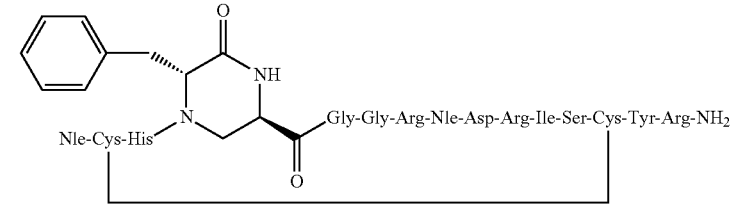 (SEQ ID NO: 5) |
| 1-12 931.6 | 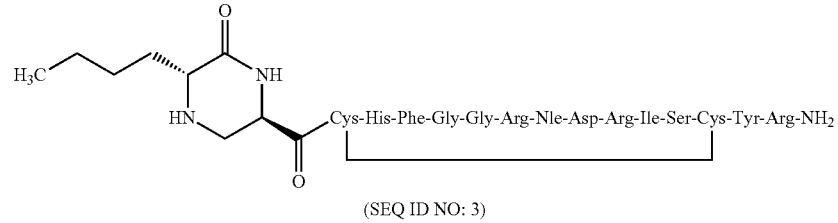 (SEQ ID NO: 3) |
| 1-13 931.3 | 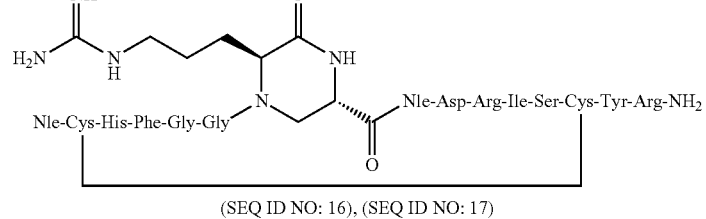 (SEQ ID NO: 16), (SEQ ID NO: 17) |

TABLE 1-continued
| Number (M + 2)/2 | Structure |
|---|---|
| 1-14 931.6 | 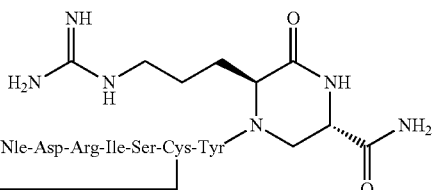<br>(SEQ ID NO: 13) |
| 1-15 966.4 | 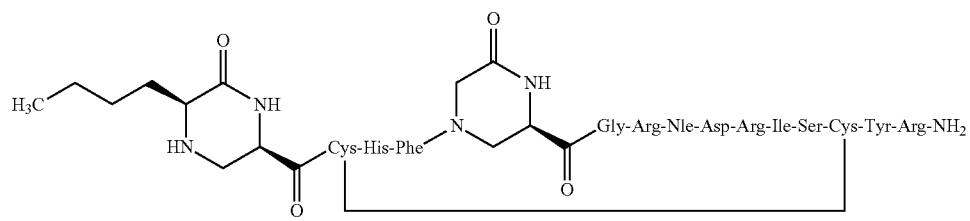<br>(SEQ ID NO: 14) |
| 1-16 966.4 | 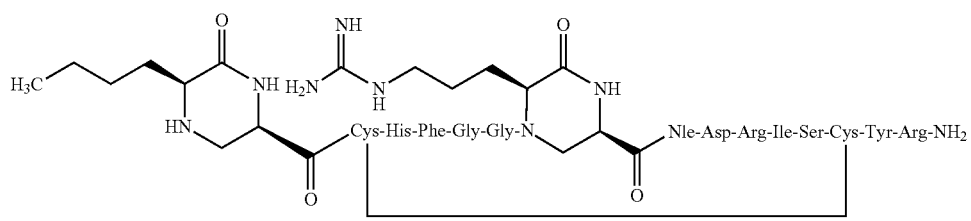<br>(SEQ ID NO: 18), (SEQ ID NO: 11) |
| 1-17 966.0 | 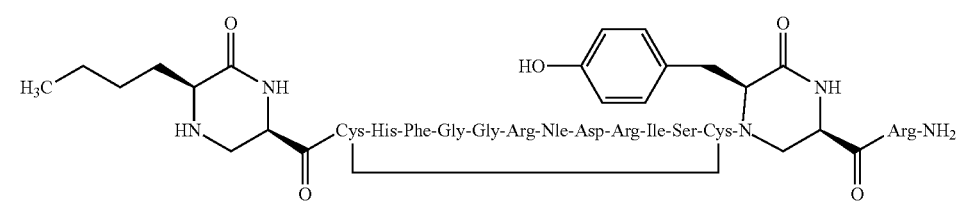<br>(SEQ ID NO: 19) |
| 1-18 966.4 | 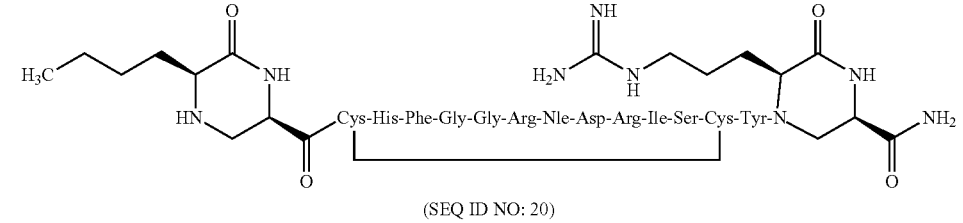<br>(SEQ ID NO: 20) |
| 1-19 965.7 | 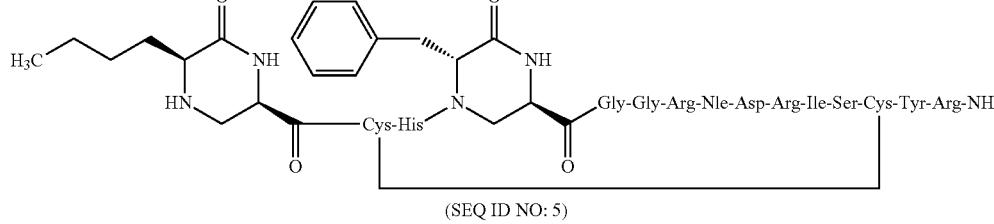<br>(SEQ ID NO: 5) |

TABLE 1-continued

| Number (M + 2)/2 | Structure |
|---|---|
| 1-20 965.9 | Nle-Cys-His—[piperazinone, benzyl]—[piperazinone]—C(O)-Gly-Gly-Arg-Nle-Asp-Arg-Ile-Ser-Cys-Tyr-N—[piperazinone, (CH₂)₃NHC(NH)NH₂]—C(O)NH₂ (SEQ ID NO: 21) |
| 1-21 965.7 | Nle-Cys-His-Phe-Gly—[piperazinone]—C(O)-Arg-Nle-Asp-Arg-Ile-Ser-Cys-Tyr-N—[piperazinone, (CH₂)₃NHC(NH)NH₂]—C(O)NH₂ (SEQ ID NO: 8), (SEQ ID NO: 22) |
| 1-22 965.6 | Nle-Cys-His-Phe-Gly-Gly—[piperazinone, (CH₂)₃NHC(NH)NH₂]—C(O)-Nle-Asp-Arg-Ile-Ser-Cys-Tyr-N—[piperazinone, (CH₂)₃NHC(NH)NH₂]—C(O)NH₂ (SEQ ID NO: 10), (SEQ ID NO: 23) |
| 1-23 1000.4 | H₃C—[piperazinone, butyl]—C(O)-Cys-His-Phe—[piperazinone]—C(O)-Gly-Arg-Nle-Asp-Arg-Ile-Ser-Cys-Tyr-N—[piperazinone, (CH₂)₃NHC(NH)NH₂]—C(O)NH₂ (SEQ ID NO: 24) |
| 1-24 938.6 | H₃C—[piperazinone, butyl]—CH₂-C(O)-Cys-His-Phe-Gly-Gly-Arg-Nle-Asp-Arg-Ile-Ser-Cys-Tyr-Arg-NH₂ (SEQ ID NO: 3) |
| 1-25 931.6 | H₃C—[piperazinone, butyl]—C(O)-Cys-His-Phe-Gly-Gly-Arg-Nle-Asp-Arg-Ile-Ser-Cys-Tyr-Arg-NH₂ (SEQ ID NO: 3) |

TABLE 1-continued

| Number (M + 2)/2 | Structure |
|---|---|
| 1-26 938.2 | Nle-Cys-His-Phe-[piperazinone(CH3)]-[piperazinone]-C(O)-Gly-Arg-Nle-Asp-Arg-Ile-Ser-Cys-Tyr-Arg-NH$_2$ (SEQ ID NO: 14), (SEQ ID NO: 15) |
| 1-27 962.2 | [benzyl-piperazinone]-CH$_2$CH$_2$-C(O)-Cys-His-Phe-Gly-Gly-Arg-Nle-Asp-Arg-Ile-Ser-Cys-Tyr-Arg-NH$_2$ (SEQ ID NO: 3) |
| 1-28 965.9 | [butyl-piperazinone]-C(O)-Cys-D-His-Phe-Gly-Gly-Arg-Nle-Asp-Arg-Ile-Ser-Cys-Tyr-N-[guanidinopropyl-piperazinone]-C(O)NH$_2$ |
| 1-29 932.8 | [butyl-piperazinone]-C(O)-Cys-Ala-Phe-Gly-Gly-Arg-Nle-Asp-Arg-Ile-Ser-Cys-Tyr-N-[guanidinopropyl-piperazinone]-C(O)NH$_2$ (SEQ ID NO: 25) |
| 1-30 927.8 | [butyl-piperazinone]-C(O)-Cys-His-Ala-Gly-Gly-Arg-Nle-Asp-Arg-Ile-Ser-Cys-Tyr-N-[guanidinopropyl-piperazinone]-C(O)NH$_2$ (SEQ ID NO: 26) |
| 1-31 972.8 | [butyl-piperazinone]-C(O)-Cys-His-Phe-Ala-Gly-Arg-Nle-Asp-Arg-Ile-Ser-Cys-Tyr-N-[guanidinopropyl-piperazinone]-C(O)NH$_2$ (SEQ ID NO: 27) |

TABLE 1-continued
| Number (M + 2)/2 | Structure |
|---|---|
| 1-32 972.9 | 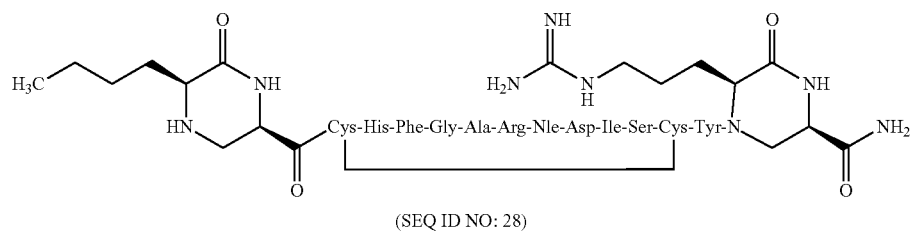<br>(SEQ ID NO: 28) |
| 1-33 923.2 | 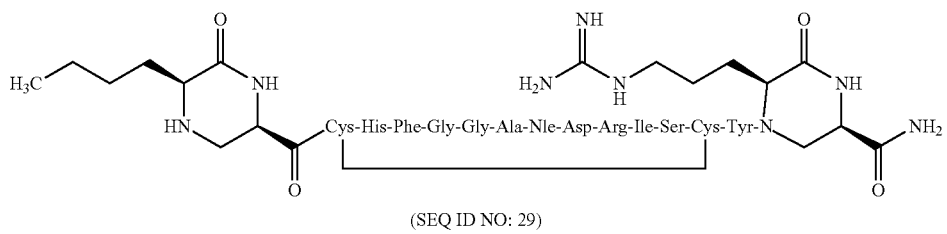<br>(SEQ ID NO: 29) |
| 1-34 944.7 | 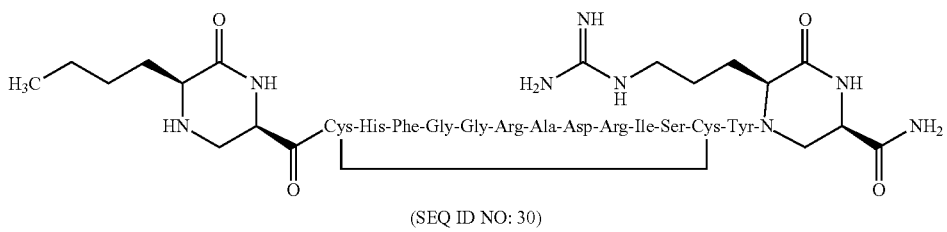<br>(SEQ ID NO: 30) |
| 1-35 943.7 | 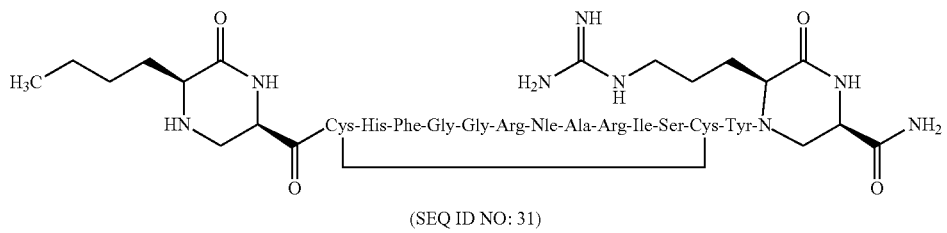<br>(SEQ ID NO: 31) |
| 1-36 923.0 | 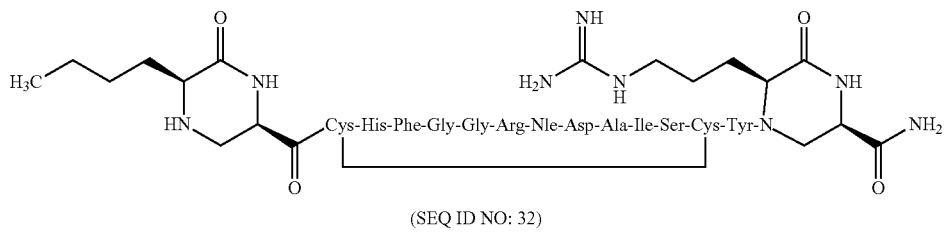<br>(SEQ ID NO: 32) |
| 1-37 944.6 | 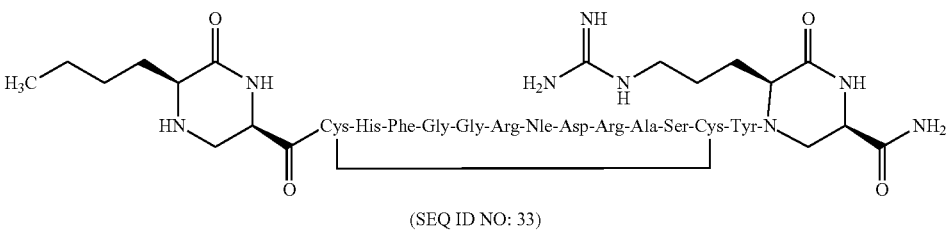<br>(SEQ ID NO: 33) |

TABLE 1-continued
| Number (M + 2)/2 | Structure |
|---|---|
| 1-38 957.7 | 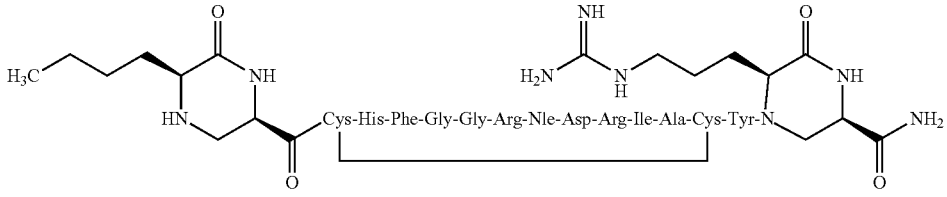<br>(SEQ ID NO: 34) |
| 1-39 965.6 | 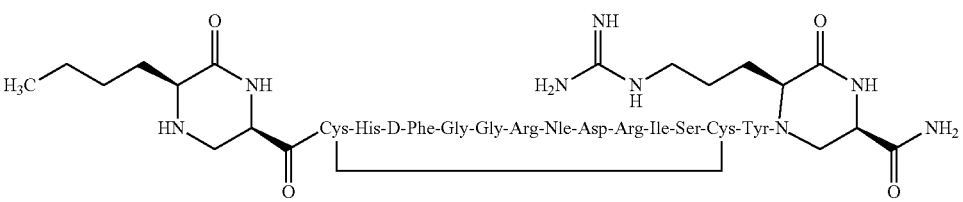 |
| 1-40 965.8 | 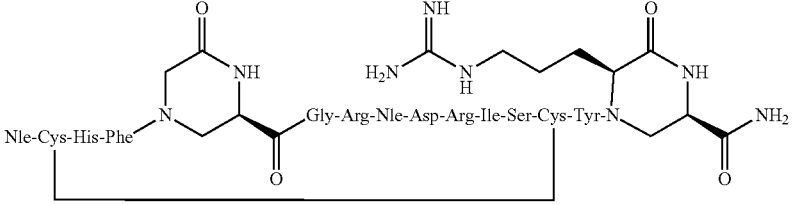<br>(SEQ ID NO: 14), (SEQ ID NO: 24) |
| 1-41 931.3 | 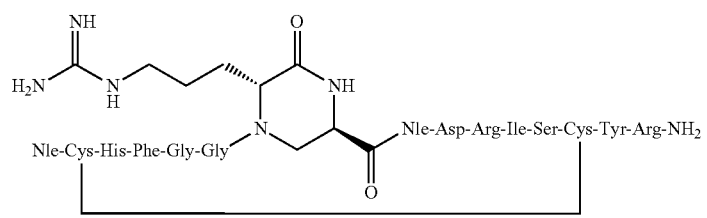<br>(SEQ ID NO: 10), (SEQ ID NO: 11) |
| 1-42 965.4 | 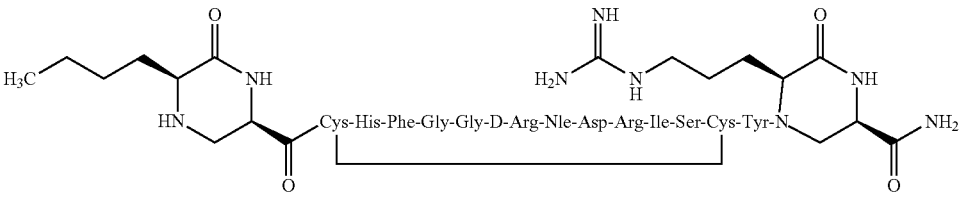 |
| 1-43 965.4 | 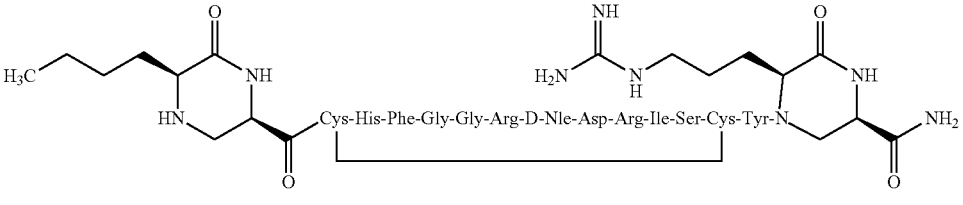 |
| 1-44 965.5 | 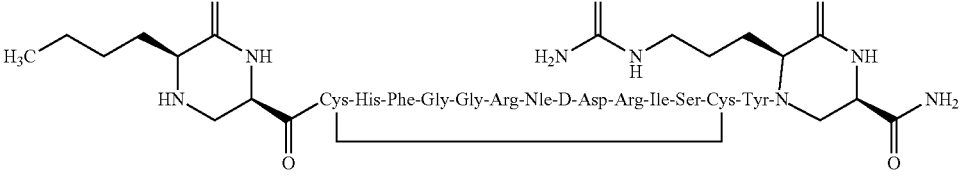 |

TABLE 1-continued
| Number (M + 2)/2 | Structure |
|---|---|
| 1-45 965.3 | 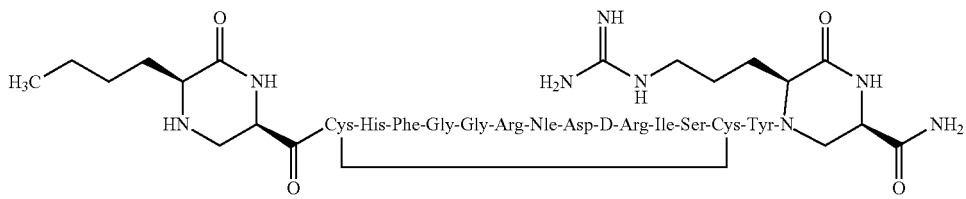 |
| 1-46 965.3 | 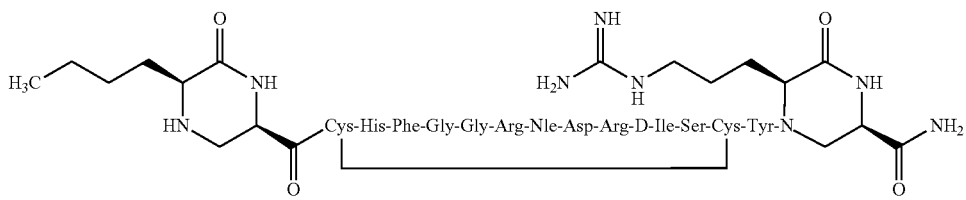 |
| 1-47 951.3 | 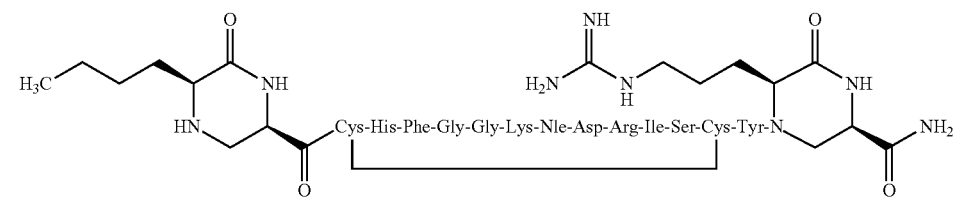  (SEQ ID NO: 35) |
| 1-48 951.2 | 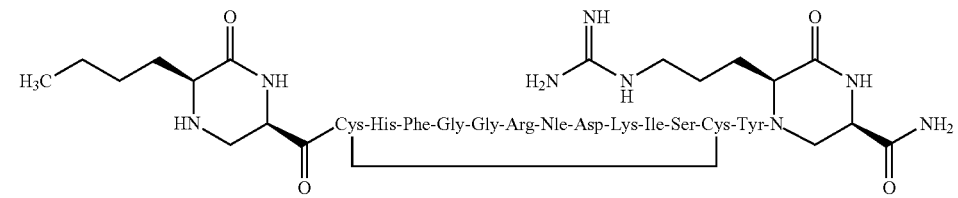  (SEQ ID NO: 36) |
| 1-49 958.2 | 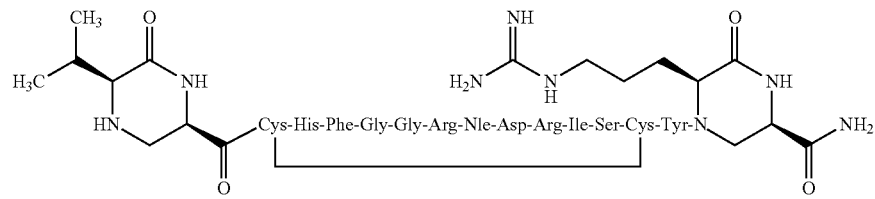  (SEQ ID NO: 13) |
| 1-50 965.2 | 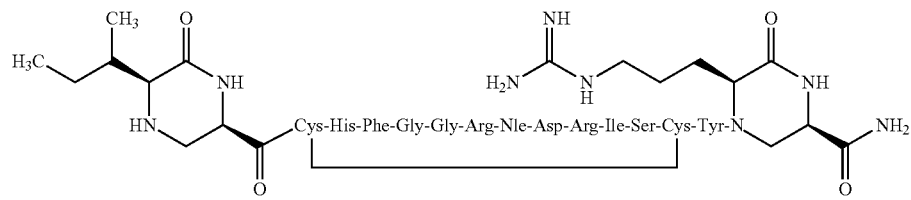  (SEQ ID NO: 13) |

TABLE 1-continued
| Number (M + 2)/2 | Structure |
|---|---|
| 1-51 965.3 | 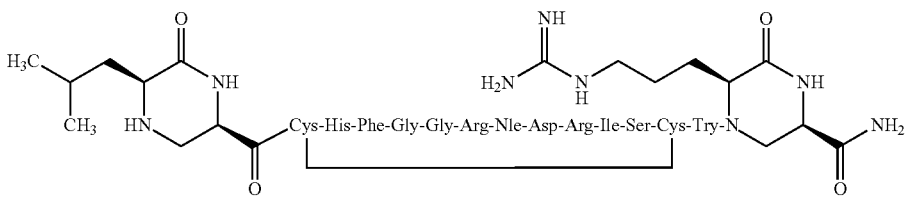<br>(SEQ ID NO: 20) |
| 1-52 919.6 | 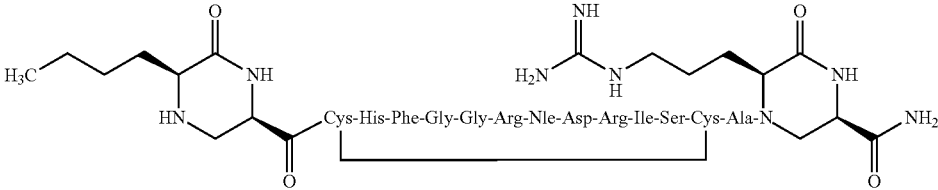<br>(SEQ ID NO: 37) |
| 1-53 965.6 | 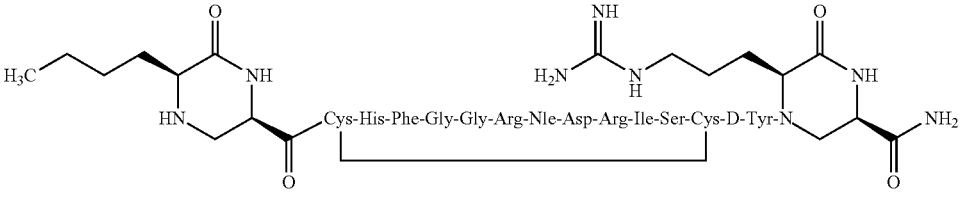 |
| 1-54 944.6 | 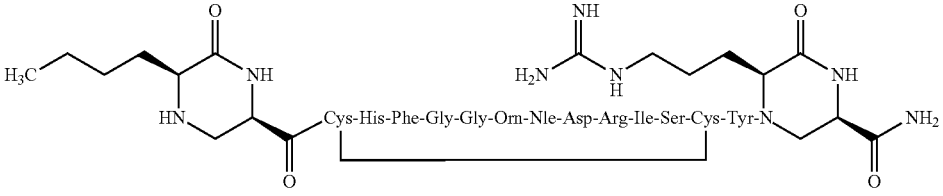<br>(SEQ ID NO: 38) |
| 1-55 944.6 | 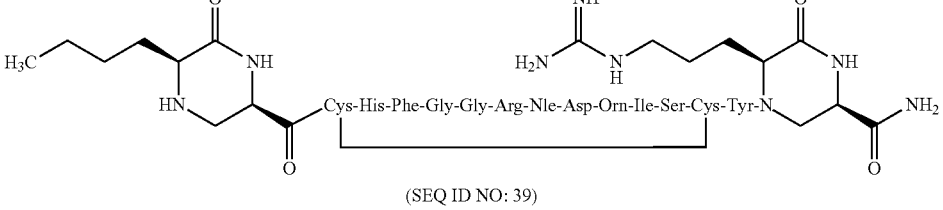<br>(SEQ ID NO: 39) |
| 1-56 930.9 | 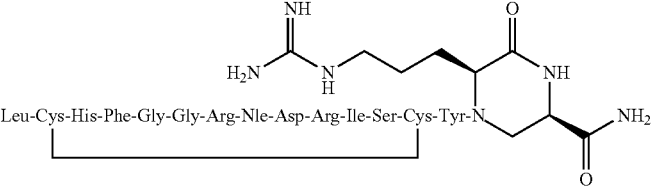<br>(SEQ ID NO: 40) |

TABLE 1-continued
| Number (M + 2)/2 | Structure |
|---|---|
| 1-57 924.0 | 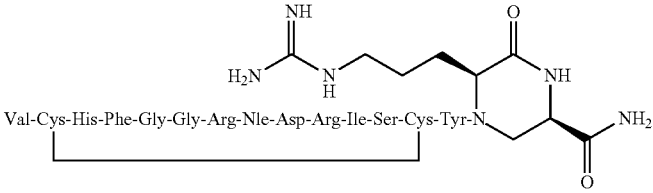 (SEQ ID NO: 41) |
| 1-58 931.0 | 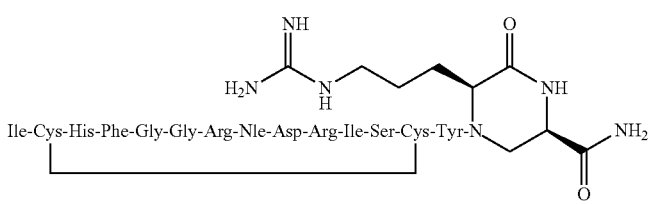 (SEQ ID NO: 42) |
| 1-59 938.1 | 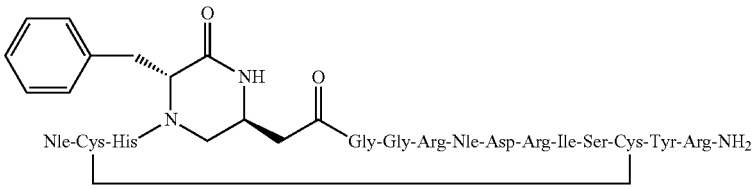 (SEQ ID NO: 5) |
| 1-60 896.0 | 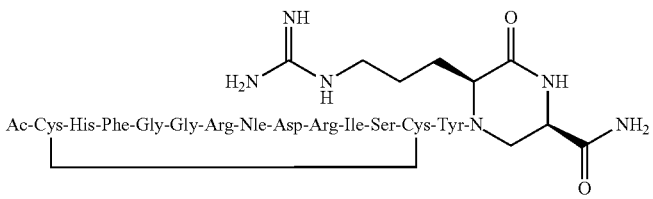 (SEQ ID NO: 20) |
| 1-61 924.1 | 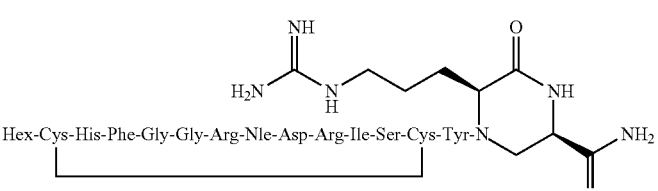 (SEQ ID NO: 20) |
| 1-62 987.7 | 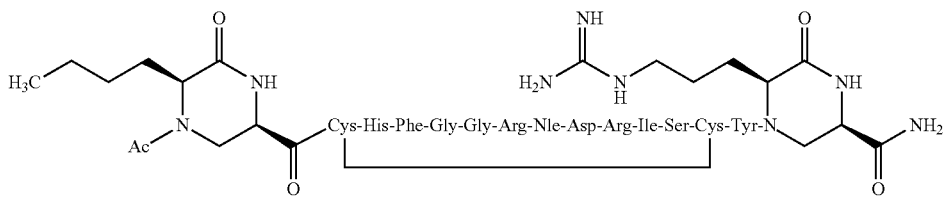 (SEQ ID NO: 13) |

TABLE 1-continued
| Number (M + 2)/2 | Structure |
|---|---|
| 1-63 931.1 | 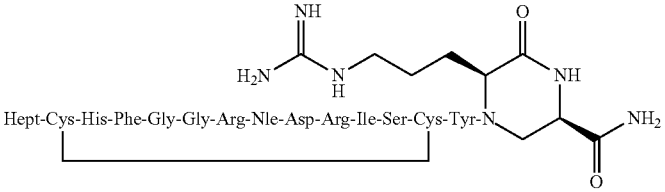 (SEQ ID NO: 20) |
| 1-64 931.1 | 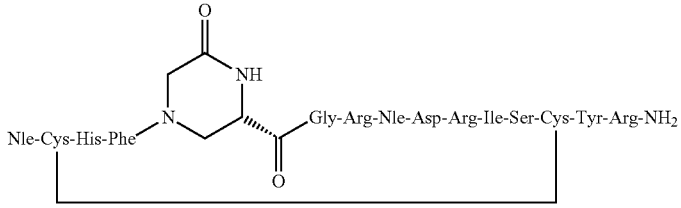 (SEQ ID NO: 14), (SEQ ID NO: 15) |
| 1-65 931.2 | 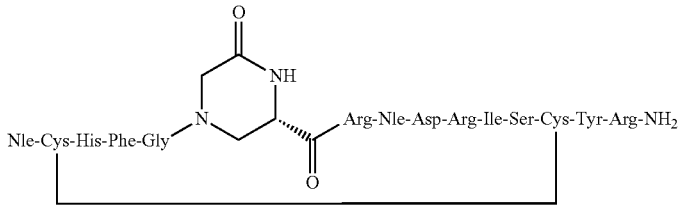 (SEQ ID NO: 8), (SEQ ID NO: 9) |
| 1-66 938.0 | 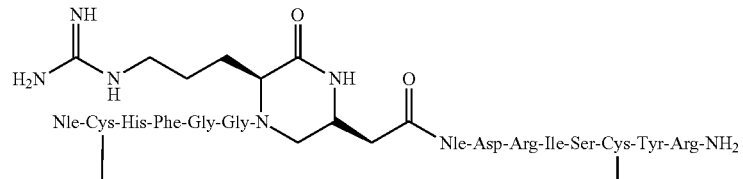 (SEQ ID NO: 10), (SEQ ID NO: 11) |
| 1-67 1000.2 | 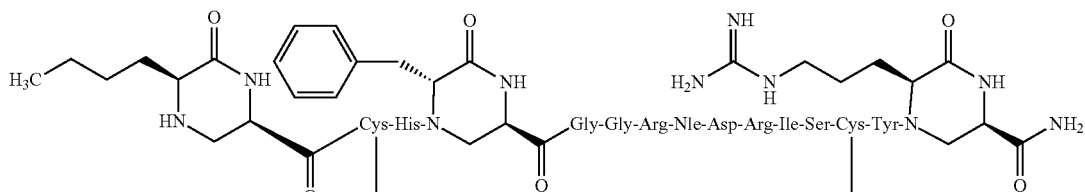 (SEQ ID NO: 20) |
| 1-68 973.1 | 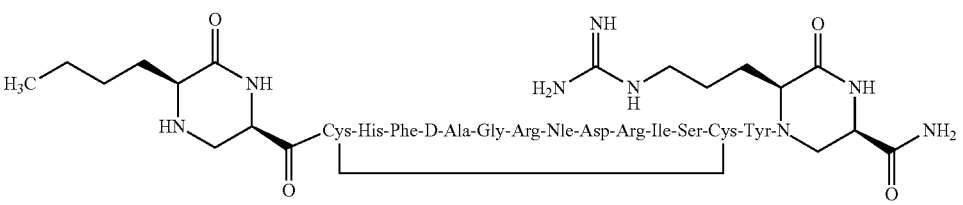 |

TABLE 1-continued
| Number (M + 2)/2 | Structure |
|---|---|
| 1-69 924.9 | 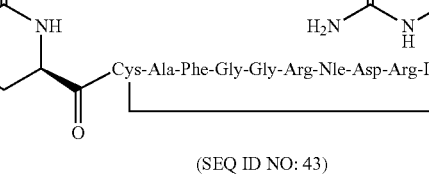<br>(SEQ ID NO: 43) |
| 1-70 853.5 | 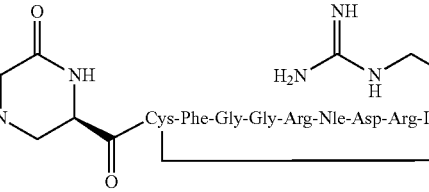<br>(SEQ ID NO: 44) |
| 1-71 931.2 | 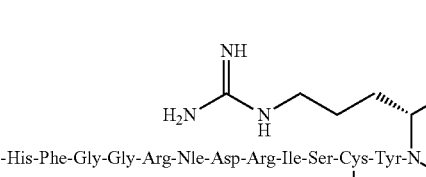<br>(SEQ ID NO: 13) |
| 1-72 874.4 | 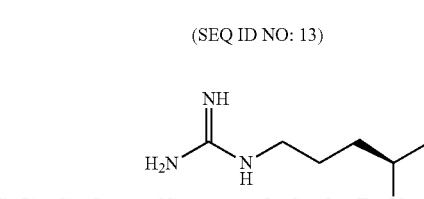<br>(SEQ ID NO: 20) |
| 1-73 944.4 | 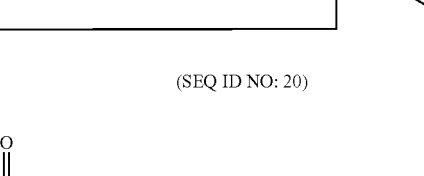<br>(SEQ ID NO: 20) |
| 1-74 952.1 | 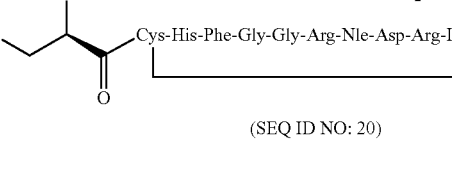<br>(SEQ ID NO: 20) |

TABLE 1-continued
| Number (M + 2)/2 | Structure |
|---|---|
| 1-75 930.9 | 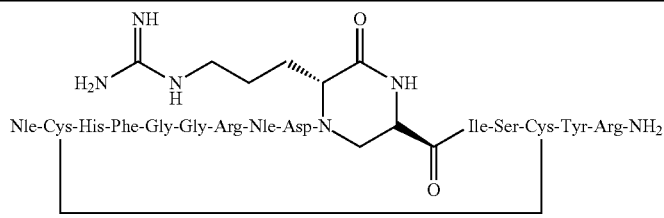 (SEQ ID NO: 45), (SEQ ID NO: 46) |
| 1-76 1007.1 | 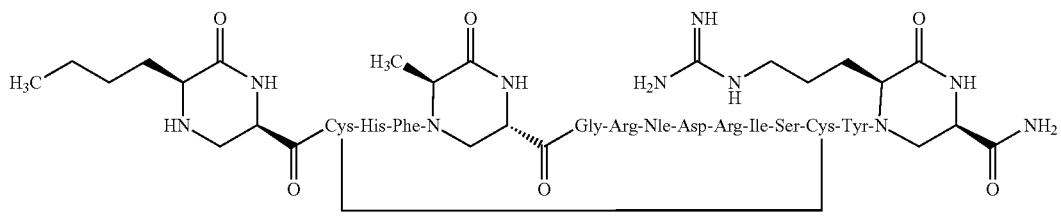 (SEQ ID NO: 24) |
| 1-77 992.4 | 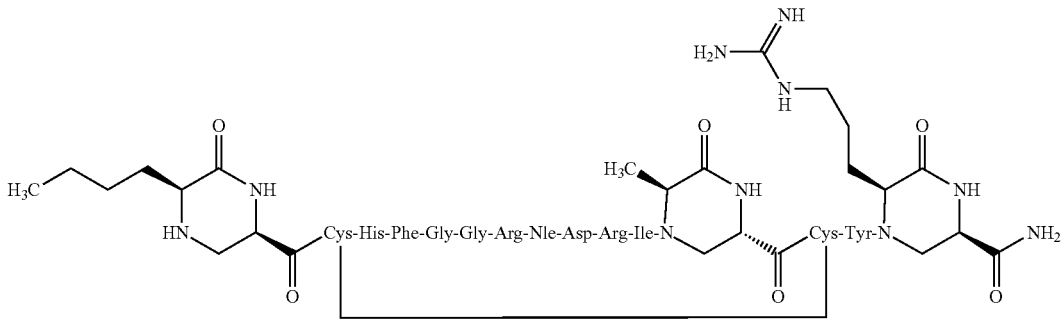 (SEQ ID NO: 47) |
| 1-78 958.7 | 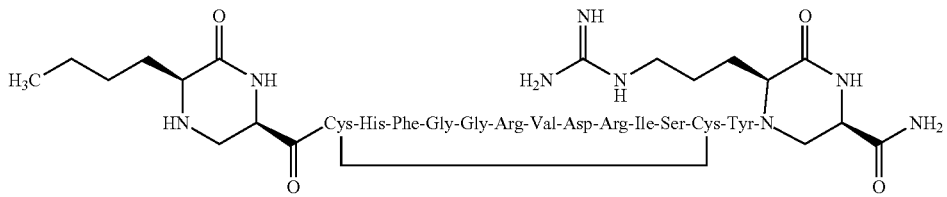 (SEQ ID NO: 48) |
| 1-79 965.6 | 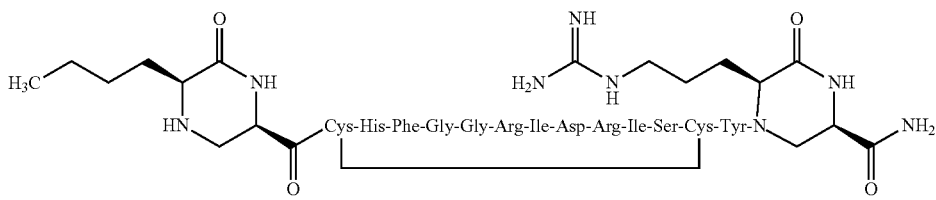 (SEQ ID NO: 49) |
| 1-80 958.8 | 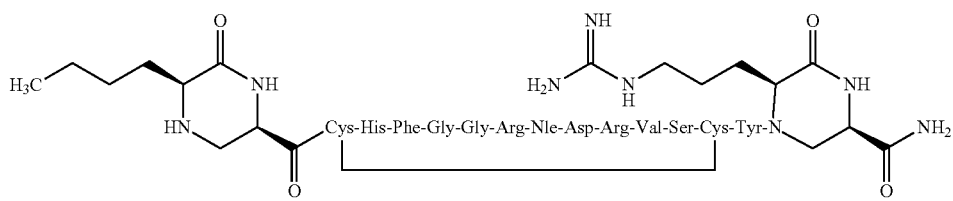 (SEQ ID NO: 50) |

TABLE 1-continued

| Number (M + 2)/2 | Structure |
|---|---|
| 1-81 964.8 | Cys-His-Phe-Gly-Gly-Arg-Nle-Asp-Arg-Leu-Ser-Cys-Tyr (SEQ ID NO: 51) |
| 1-82 948.9 | Cys-His-Leu-Gly-Gly-Arg-Nle-Asp-Arg-Ile-Ser-Cys-Tyr (SEQ ID NO: 52) |
| 1-83 972.7 | Cys-His-Phe-Gly-Gly-Arg-Nle-Asp-Arg-Ile-Ser-Cys-Tyr (SEQ ID NO: 20) |
| 1-84 965.9 | Cys-His-Phe-Gly-Gly-Arg-Leu-Asp-Arg-Ile-Ser-Cys-Tyr (SEQ ID NO: 53) |
| 1-85 993.2 | Cys-His-Phe-Gly-Gly-Arg-Nle-Asp-Arg-Ile-...-Cys-Tyr (SEQ ID NO: 47) |

TABLE 1-continued
| Number (M + 2)/2 | Structure |
|---|---|
| 1-86 1000.9 | 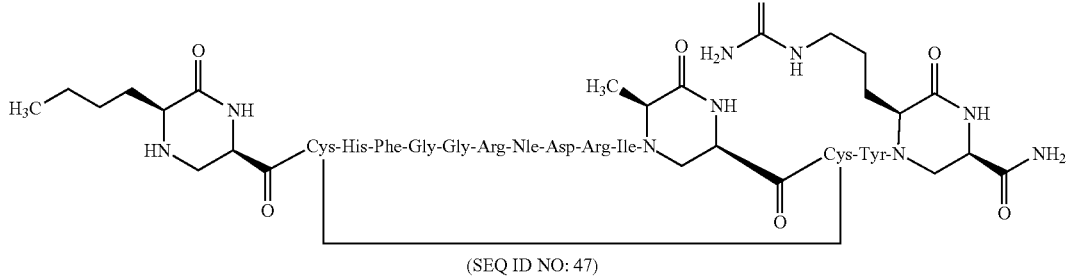 (SEQ ID NO: 47) |
| 1-87 993.7 | 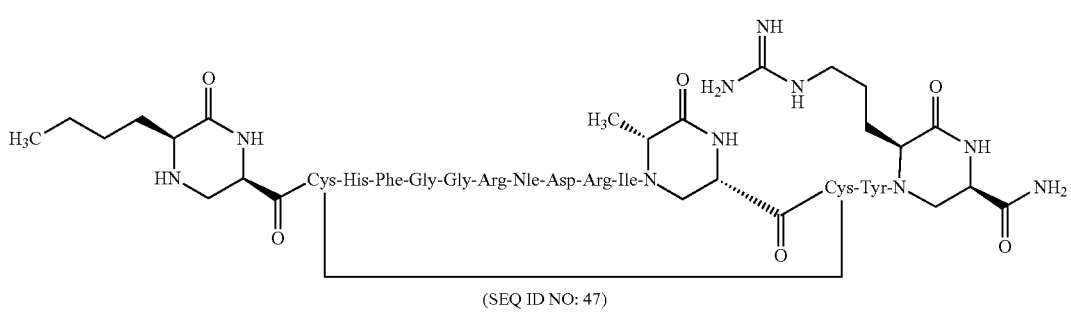 (SEQ ID NO: 47) |
| 1-88 966.7 | 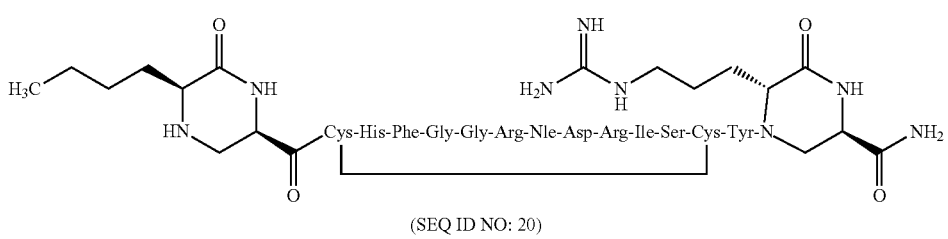 (SEQ ID NO: 20) |
| 1-89 966.9 | 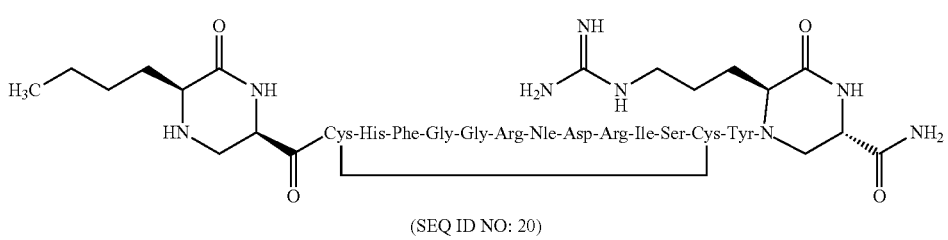 (SEQ ID NO: 20) |
| 1-90 966.6 | 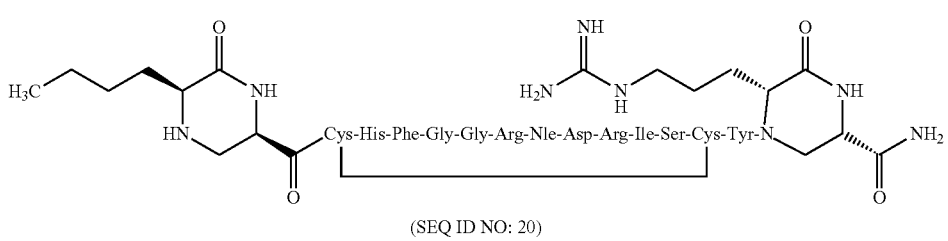 (SEQ ID NO: 20) |
| 1-91 967.0 | 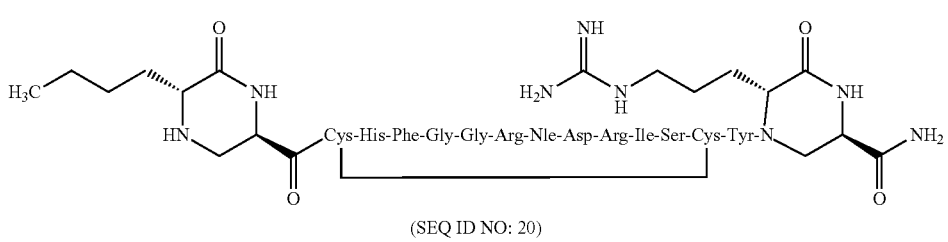 (SEQ ID NO: 20) |

TABLE 1-continued

| Number (M+2)/2 | Structure |
|---|---|
| 1-92 966.9 | Cys-His-Phe-Gly-Gly-Arg-Nle-Asp-Arg-Ile-Ser-Cys-Tyr- (SEQ ID NO: 20) |
| 1-93 966.7 | Cys-His-Phe-Gly-Gly-Arg-Nle-Asp-Arg-Ile-Ser-Cys-Tyr- (SEQ ID NO: 20) |
| 1-94 966.9 | Cys-His-Phe-Gly-Gly-Arg-Nle-Asp-Arg-Ile-Ser-Cys-Tyr- (SEQ ID NO: 20) |
| 1-95 966.7 | Cys-His-Phe-Gly-Gly-Arg-Nle-Asp-Arg-Ile-Ser-Cys-Tyr- (SEQ ID NO: 20) |
| 1-96 966.7 | Cys-His-Phe-Gly-Gly-Arg-Nle-Asp-Arg-Ile-Ser-Cys-Tyr- (SEQ ID NO: 20) |
| 1-97 966.7 | Cys-His-Phe-Gly-Gly-Arg-Nle-Asp-Arg-Ile-Ser-Cys-Tyr- (SEQ ID NO: 20) |

TABLE 1-continued
| Number (M + 2)/2 | Structure |
|---|---|
| 1-98 966.7 | 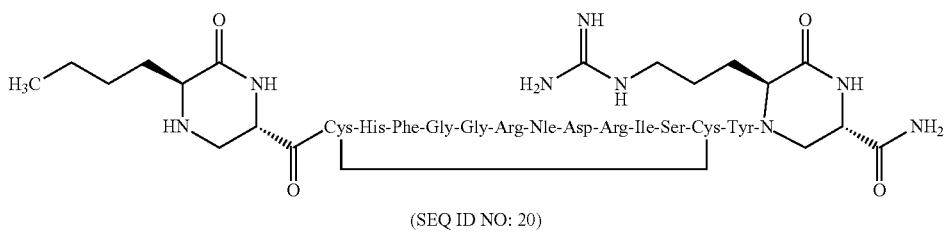<br>(SEQ ID NO: 20) |
| 1-99 966.5 | 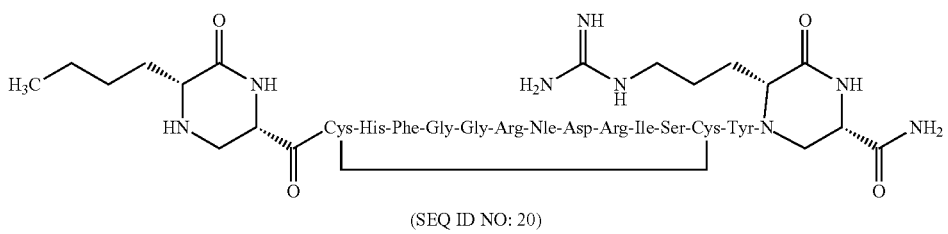<br>(SEQ ID NO: 20) |
| 1-100 881.8 | 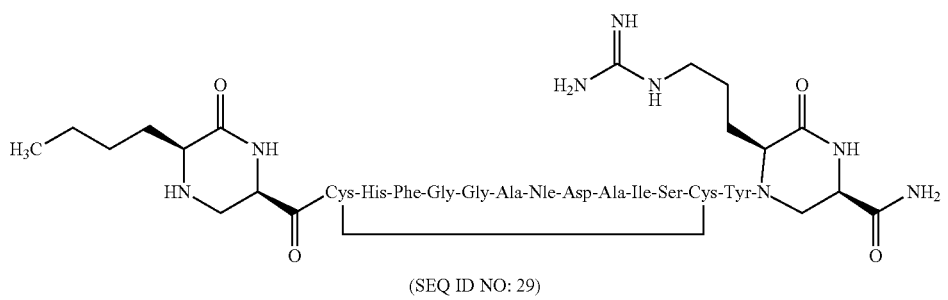<br>(SEQ ID NO: 29) |
| 1-101 922.4 | 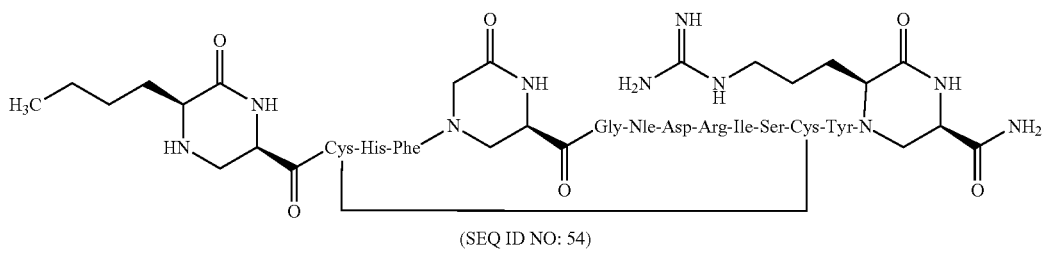<br>(SEQ ID NO: 54) |
| 1-102 938.0 | 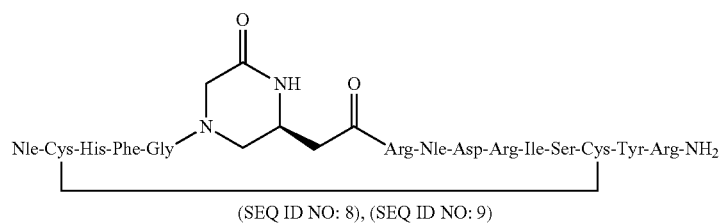<br>(SEQ ID NO: 8), (SEQ ID NO: 9) |
| 1-103 937.8 | 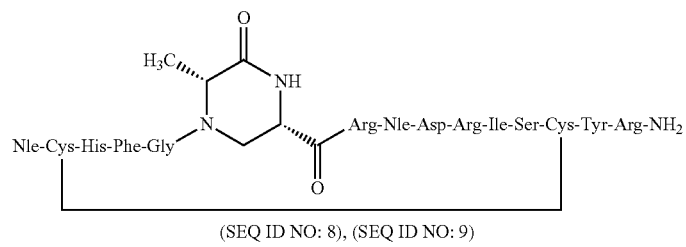<br>(SEQ ID NO: 8), (SEQ ID NO: 9) |

TABLE 1-continued
| Number (M + 2)/2 | Structure |
|---|---|
| 1-104 931.1 | 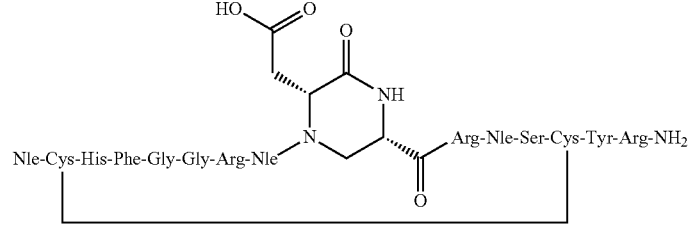<br>(SEQ ID NO: 55), (SEQ ID NO: 56) |
| 1-105 931.2 | 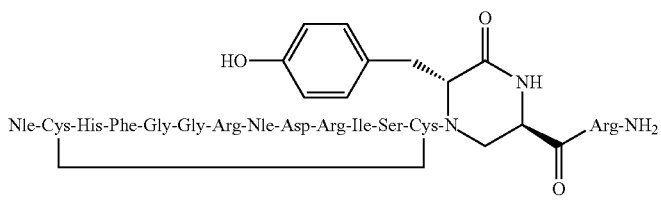<br>(SEQ ID NO: 4) |
| 1-106 930.9 | 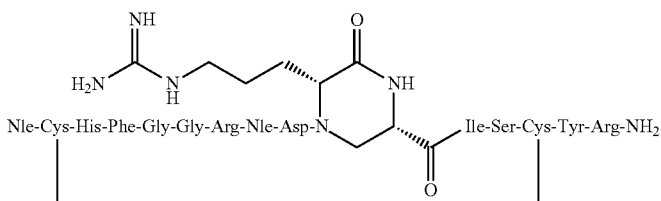<br>(SEQ ID NO: 45), (SEQ ID NO: 46) |
| 1-107 938.5 | 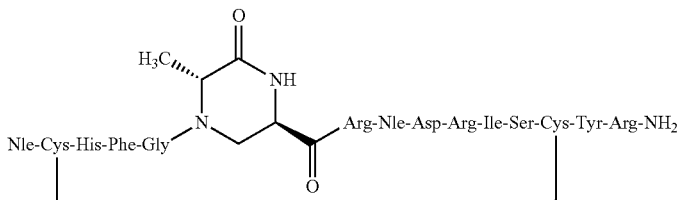<br>(SEQ ID NO: 8), (SEQ ID NO: 9) |
| 1-108 931.0 | 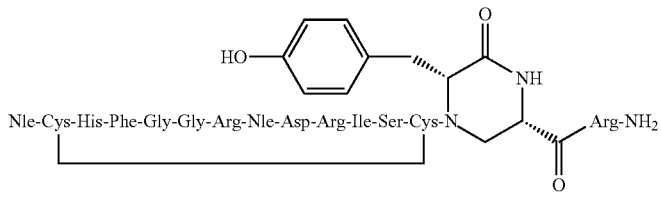<br>(SEQ ID NO: 4) |
| 1-109 945.2 | 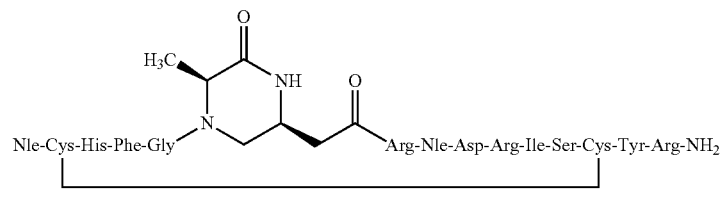<br>(SEQ ID NO: 8), (SEQ ID NO: 9) |

TABLE 1-continued
| Number (M + 2)/2 | Structure |
|---|---|
| 1-110 938.1 | 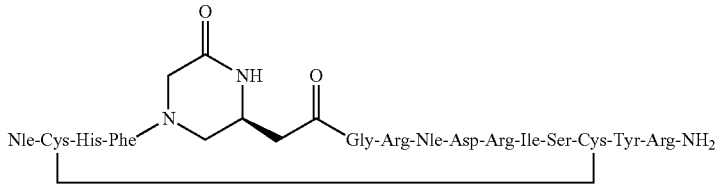<br>(SEQ ID NO: 14), (SEQ ID NO: 15) |
| 1-111 931.5 | 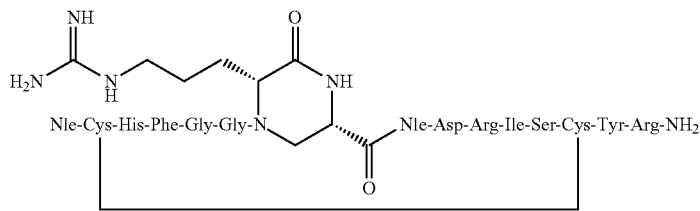<br>(SEQ ID NO: 16), (SEQ ID NO: 17) |
| 1-112 1929.6 (M + 1) | 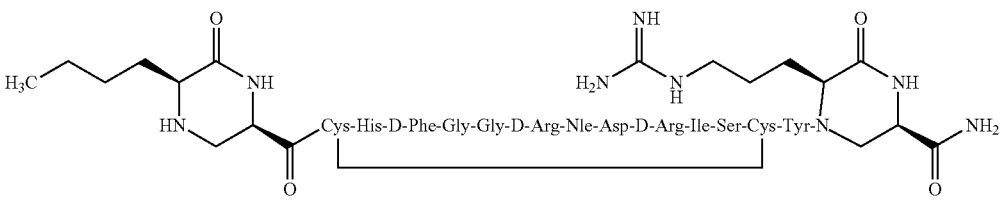 |
| 1-113 965.2 | 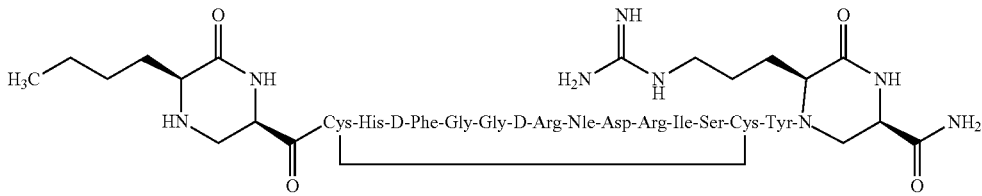 |
| 1-114 965.3 | 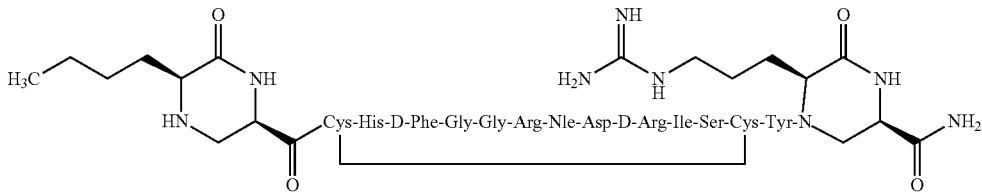 |
| 1-115 1822.3 (M + 1) | 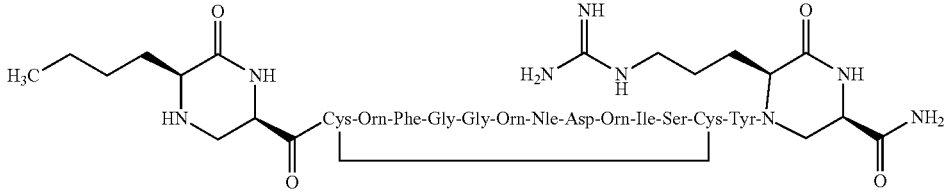<br>(SEQ ID NO: 57) |
| 1-116 1849.3 (M + 1) | 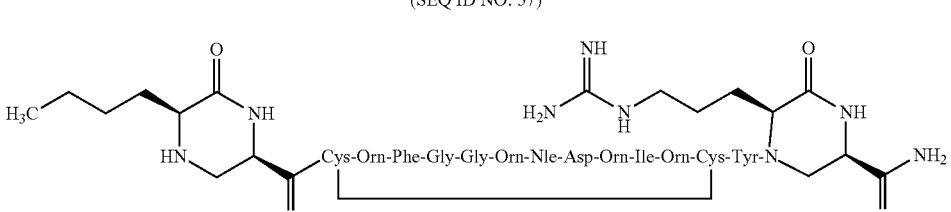<br>(SEQ ID NO: 58) |

TABLE 1-continued

| Number (M + 2)/2 | Structure |
|---|---|
| 1-117 978.7 | Cys-His-Phe-Gly-Gly-Arg-Nle-Asp-Arg-Ile-Orn-Cys-Tyr (SEQ ID NO: 59) |
| 1-118 965.0 | Cys-His-Phe-Gly-Gly-D-Arg-Nle-Asp-D-Arg-Ile-Ser-Cys-Tyr |
| 1-119 937.0 | Cys-His-Phe-Gly-Gly-Lys-Nle-Asp-Lys-Ile-Ser-Cys-Tyr (SEQ ID NO: 60) |
| 1-120 960.5 | Cys-Lys-Phe-Gly-Gly-Arg-Nle-Asp-Arg-Ile-Ser-Cys-Tyr (SEQ ID NO: 61) |
| 1-121 967.0 | Cys-Orn-Phe-Gly-Gly-Arg-Nle-Asp-Arg-Ile-Orn-Cys-Tyr (SEQ ID NO: 62) |
| 1-122 981.0 | Cys-Lys-Phe-Gly-Gly-Arg-Nle-Asp-Arg-Ile-Lys-Cys-Tyr (SEQ ID NO: 63) |

TABLE 1-continued

| Number (M+2)/2 | Structure |
|---|---|
| 1-123 953.4 | Cys-Orn-Phe-Gly-Gly-Arg-Nle-Asp-Arg-Ile-Ser-Cys-Tyr (SEQ ID NO: 64) |
| 1-124 922.8 | Cys-His-Phe-Gly-Gly-Orn-Nle-Asp-Orn-Ile-Ser-Cys-Tyr (SEQ ID NO: 65) |
| 1-125 965.2 | D-Cys-His-Phe-Gly-Gly-Arg-Nle-Asp-Arg-Ile-Ser-Cys-Tyr |
| 1-126 967.3 | Cys-His-Phe-Gly-Gly-Arg-Nle-Asp-Arg-Ile-Ser-D-Cys-Tyr |
| 1-127 967.3 | D-Cys-His-Phe-Gly-Gly-Arg-Nle-Asp-Arg-Ile-Ser-D-Cys-Tyr |
| 1-128 1030.3 | H$_2$N-Hept- Cys-His-Phe-Gly-Gly-Arg-Nle-Asp-Arg-Ile-Ser-Cys-Tyr (SEQ ID NO: 20) |

TABLE 1-continued
| Number (M + 2)/2 | Structure |
|---|---|
| 1-129 995.7 | 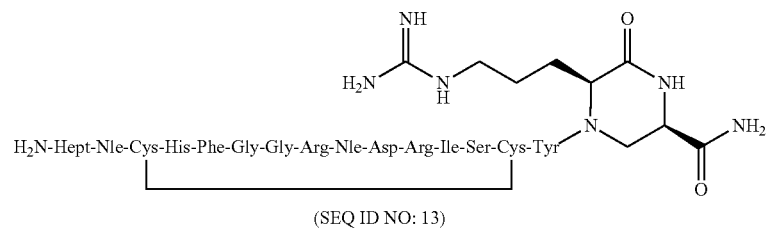 (SEQ ID NO: 13) |
| 1-130 939.1 | 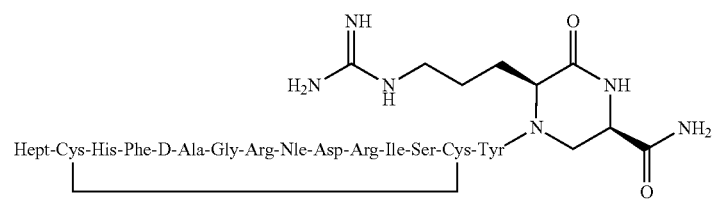 |
| 1-131 932.0 | 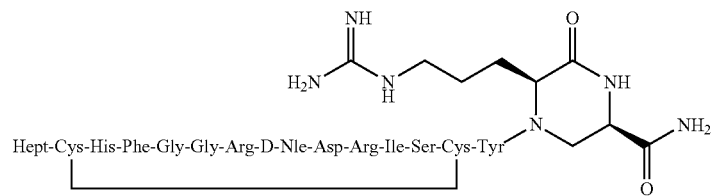 |
| 1-132 938.7 | 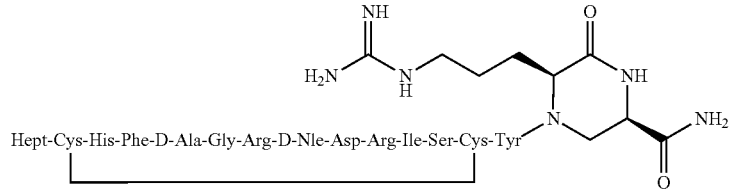 |
| 1-133 974.0 | 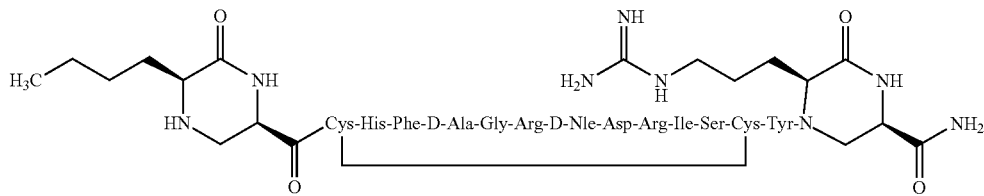 |
| 1-134 949 | 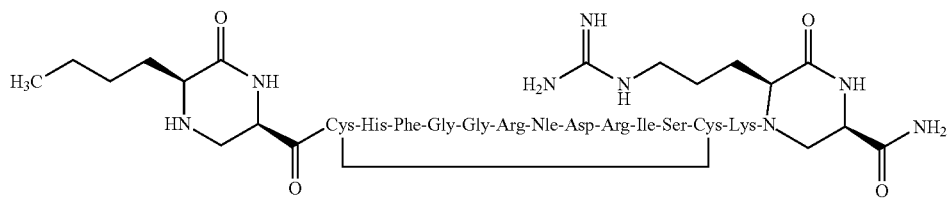 (SEQ ID NO: 66) |
| 1-135 966.3 | 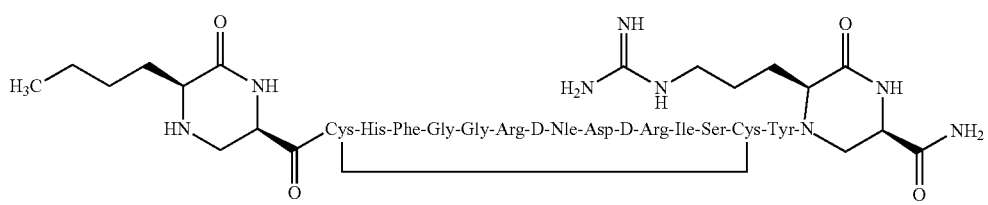 |

TABLE 1-continued
| Number (M + 2)/2 | Structure |
|---|---|
| 1-136 1022.6 | 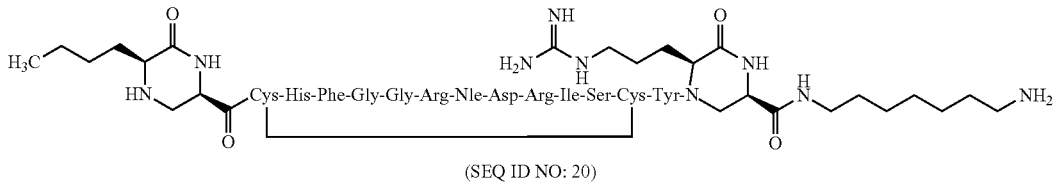<br>(SEQ ID NO: 20) |
| 1-137 1015.5 | 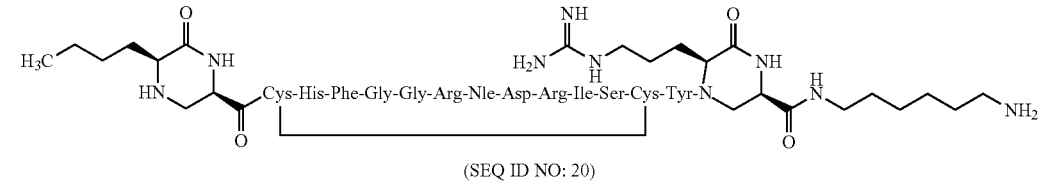<br>(SEQ ID NO: 20) |
| 1-138 980.7 | 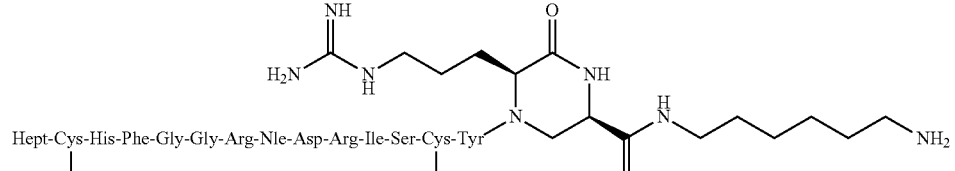<br>(SEQ ID NO: 67) |
| 1-139 930.8 | 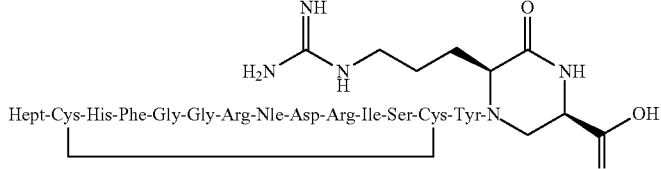<br>(SEQ ID NO: 20) |
| 1-140 923.8 | 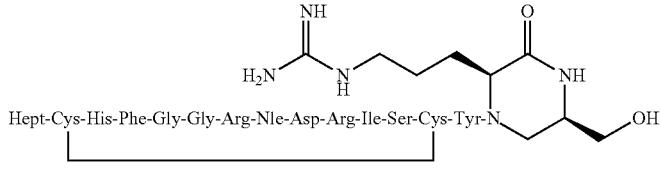<br>(SEQ ID NO: 20) |
| 1-141 902.9 | 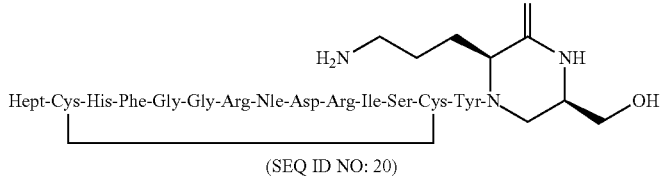<br>(SEQ ID NO: 20) |
| 1-142 988.1 | 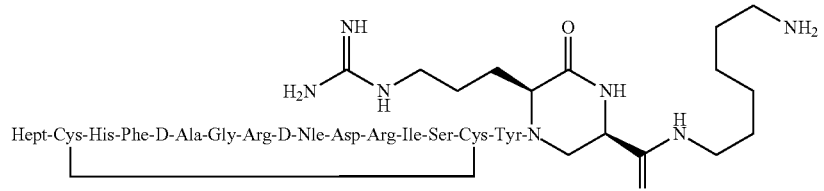 |

TABLE 1-continued
| Number (M + 2)/2 | Structure |
|---|---|
| 1-143 1023.4 | 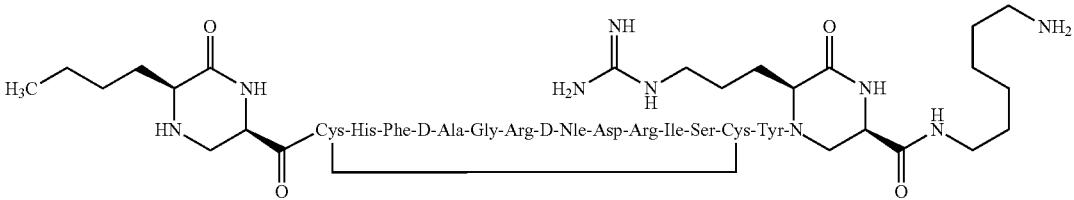 |
| 1-144 1033.6 | 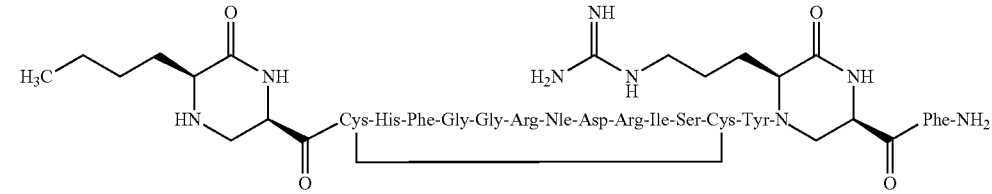<br>(SEQ ID NO: 20) |
| 1-145 1001.5 | 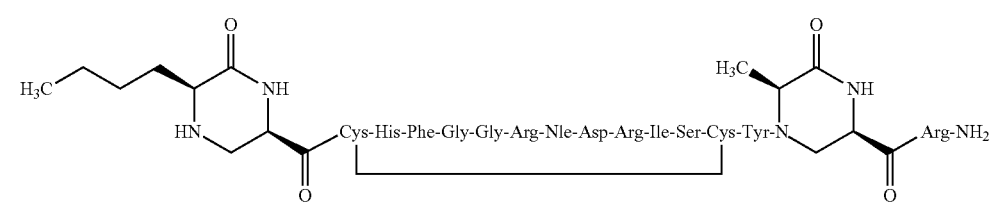<br>(SEQ ID NO: 20) |
| 1-146 888.9 | 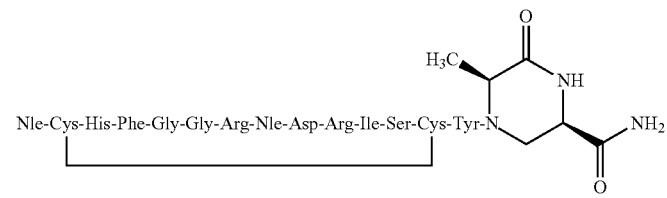<br>(SEQ ID NO: 13) |
| 1-147 1001.6 | 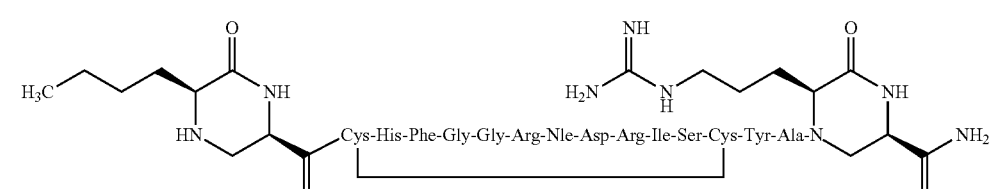<br>(SEQ ID NO: 68) |
| 1-148 910.5 | 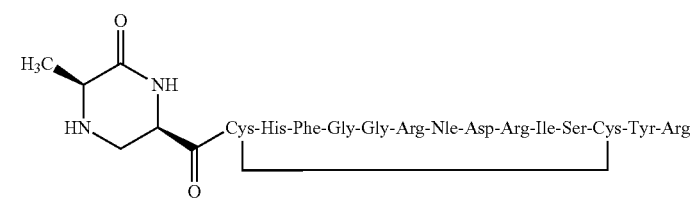<br>(SEQ ID NO: 69) |

TABLE 1-continued

| Number (M + 2)/2 | Structure |
|---|---|
| 1-149 967.1 | [Butyl-piperazinone]-Cys-His-Phe-Gly-Gly-Arg-Nle-Asp-Arg-Ile-Ser-Cys-Tyr-Ala-Arg-NH$_2$ (SEQ ID NO: 70) |
| 1-150 966.0 | [Butyl-piperazinone]-Cys-His-Phe-Gly-Gly-Arg-D-Leu-Asp-Arg-Ile-Ser-Cys-Tyr-N-[guanidinopropyl-piperazinone-carboxamide] |
| 1-151 973.1 | [Butyl-piperazinone]-Cys-His-Phe-D-Ala-Gly-Arg-Nle-Asp-D-Arg-Ile-Ser-Cys-Tyr-N-[guanidinopropyl-piperazinone-carboxamide] |
| 1-152 973.1 | [Butyl-piperazinone]-Cys-His-Phe-Gly-D-Ala-Arg-Nle-Asp-Arg-Ile-Ser-Cys-Tyr-N-[guanidinopropyl-piperazinone-carboxamide] |
| 1-153 923.5 | Hept-Cys-His-Phe-Gly-Gly-Arg-Nle-Asp-Arg-Ile-Ser-Cys-Phe-N-[guanidinopropyl-piperazinone-carboxamide] (SEQ ID NO: 71) |
| 1-154 938.1 | Hept-Cys-His-Phe-D-Ala-Gly-Arg-D-Nle-Asp-Arg-Ile-Ser-Cys-D-Tyr-N-[guanidinopropyl-piperazinone-carboxamide] |
| 1-155 938.8 | Hept-Cys-His-Phe-D-Ala-Gly-Arg-D-Nle-Asp-Arg-Ile-Ser-Cys-D-Tyr-N-[guanidinopropyl-piperazinone-carboxamide] |

TABLE 1-continued
| Number (M + 2)/2 | Structure |
|---|---|
| 1-156 930.9 | 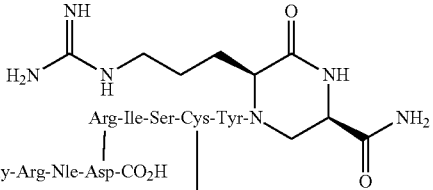 (SEQ ID NO: 72) |
| 1-157 931.2 | 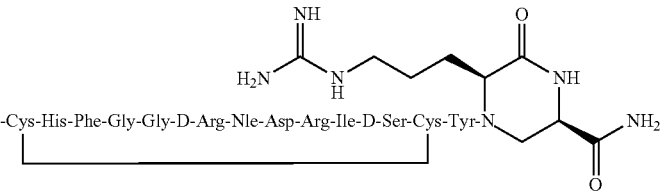 |
| 1-158 931.3 | 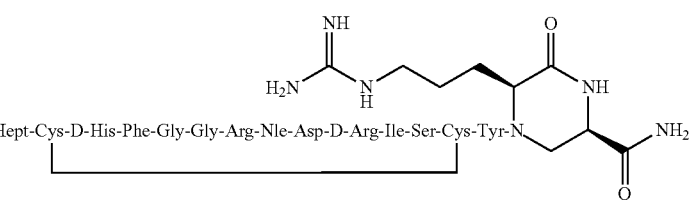 |
| 1-159 931.3 | 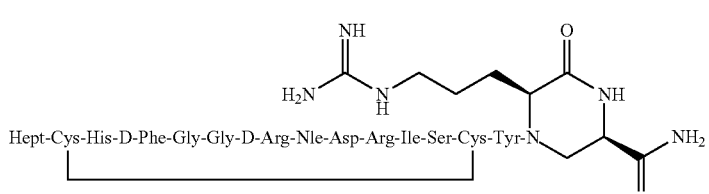 |
| 1-160 931.3 | 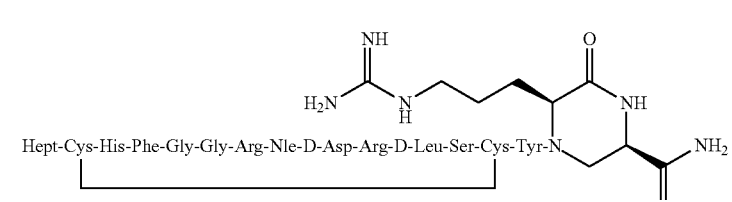 |
| 1-161 931.1 | 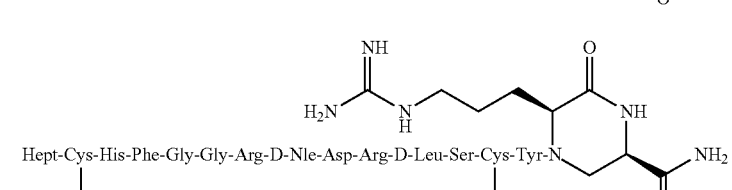 |
| 1-162 931.3 | 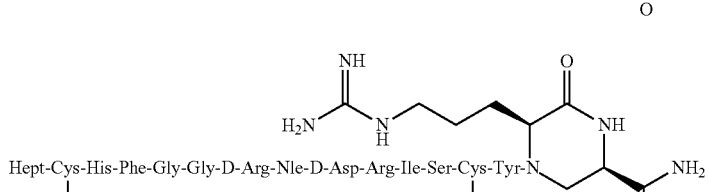 |

TABLE 1-continued

| Number (M + 2)/2 | Structure |
|---|---|
| 1-163 930.5 | Hept-Cys-D-His-Phe-Gly-Gly-D-Arg-Nle-Asp-Arg-Ile-Cys-Tyr-[piperazinone-CONH₂] (with Arg side chain) |
| 1-164 938.3 | Hept-Cys-His-Phe-D-Ala-Gly-Arg-Nle-Asp-Arg-Ile-Ser-Cys-D-Tyr-[piperazinone-CONH₂] |
| 1-165 930.8 | Hept-Cys-His-Phe-Gly-Gly-D-Arg-Nle-Asp-Arg-Ile-Ser-Cys-D-Tyr-[piperazinone-CONH₂] |
| 1-166 945.1 | Hept-Cys-His-Phe-Aib-Gly-Arg-Nle-Asp-Arg-Ile-Ser-Cys-D-Tyr-[piperazinone-CONH₂] |
| 1-167 930.9 | Hept-Cys-His-Phe-Gly-Gly-Arg-Nle-Asp-D-Arg-Ile-Ser-Cys-D-Tyr-[piperazinone-CONH₂] |
| 1-168 931.1 | Hept-Cys-His-Phe-Gly-Gly-Arg-Nle-Asp-Arg-D-Ile-Ser-Cys-D-Tyr-[piperazinone-CONH₂] |
| 1-169 938.0 | Hept-Cys-His-Phe-D-Ala-Gly-Arg-D-Nle-Asp-Arg-Ile-Ser-Cys-Tyr-[piperazinone-CONH₂] |

TABLE 1-continued

| Number (M + 2)/2 | Structure |
|---|---|
| 1-170 931.1 | Hept-Cys-His-Phe-Gly-Gly-Arg-D-Nle-Asp-Arg-Ile-Ser-Cys-D-Tyr-[piperazinone-Arg/CONH₂] |
| 1-171 930.4 | Hept-Cys-His-Phe-Gly-Gly-D-Arg-Nle-Asp-Arg-D-Leu-Ser-Cys-Tyr-[piperazinone-Arg/CONH₂] |
| 1-172 930.5 | Hept-Cys-D-His-Phe-Gly-Gly-Arg-Nle-Asp-Arg-D-Leu-Ser-Cys-Tyr-[piperazinone-Arg/CONH₂] |
| 1-173 937.7 | Hept-Cys-His-Phe-D-Ala-Gly-Arg-Nle-Asp-Arg-D-Leu-Ser-Cys-Tyr-[piperazinone-Arg/CONH₂] |
| 1-174 937.2 | Hept-Cys-D-His-Phe-D-Ala-Gly-Arg-Nle-Asp-Arg-Ile-Ser-Cys-Tyr-[piperazinone-Arg/CONH₂] |
| 1-175 930.4 | Hept-Cys-His-D-Phe-Gly-Gly-Arg-Nle-Asp-Arg-D-Leu-Ser-Cys-Tyr-[piperazinone-Arg/CONH₂] |
| 1-176 916.5 | Hept-Cys-His-Phe-Gly-Gly-Arg-Nle-Asp-Arg-Aib-Ser-Cys-Tyr-[piperazinone-Arg/CONH₂] |

(SEQ ID NO: 73)

TABLE 1-continued
| Number (M + 2)/2 | Structure |
|---|---|
| 1-177 916.4 | 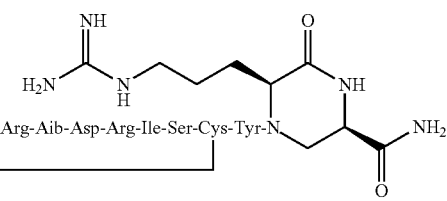 (SEQ ID NO: 74) |
| 1-178 944.6 | 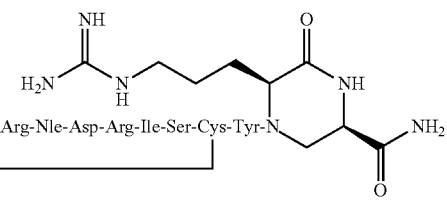 (SEQ ID NO: 75) |
| 1-179 937.1 | 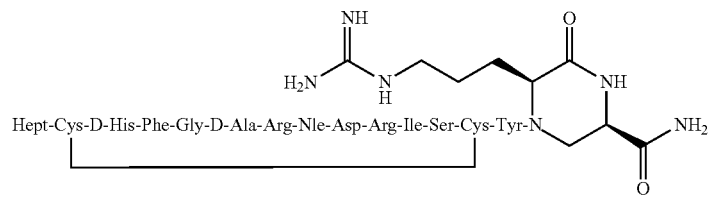 |
| 1-180 944.6 | 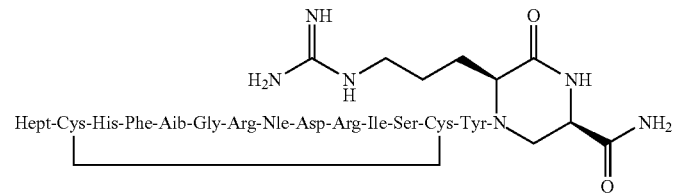 (SEQ ID NO: 76) |
| 1-181 930.4 | 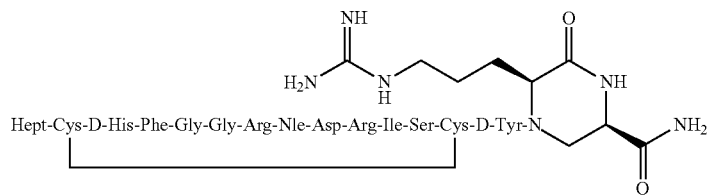 |
| 1-182 930.3 | 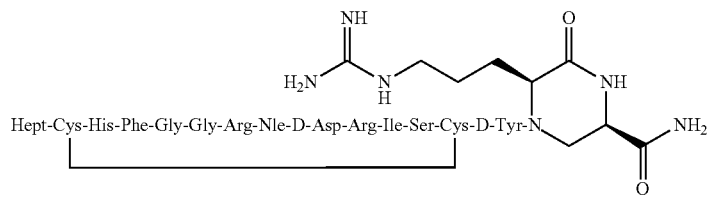 |
| 1-183 930.3 | 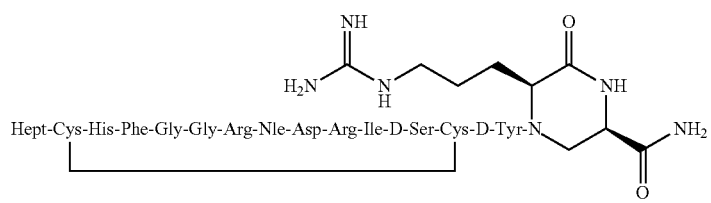 |

150

TABLE 1-continued

| Number (M + 2)/2 | Structure |
|---|---|
| 1-184 930.9 | 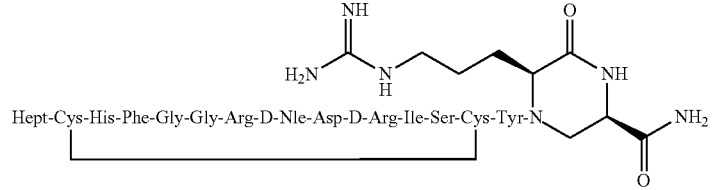 Hept-Cys-His-Phe-Gly-Gly-Arg-D-Nle-Asp-D-Arg-Ile-Ser-Cys-Tyr- |
| 1-185 930.4 | 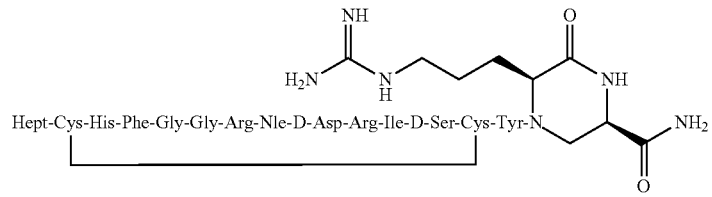 Hept-Cys-His-Phe-Gly-Gly-Arg-Nle-D-Asp-Arg-Ile-D-Ser-Cys-Tyr- |
| 1-186 930.4 | 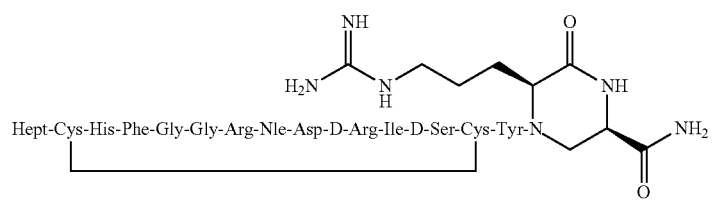 Hept-Cys-His-Phe-Gly-Gly-Arg-Nle-Asp-D-Arg-Ile-D-Ser-Cys-Tyr- |
| 1-187 937.7 | 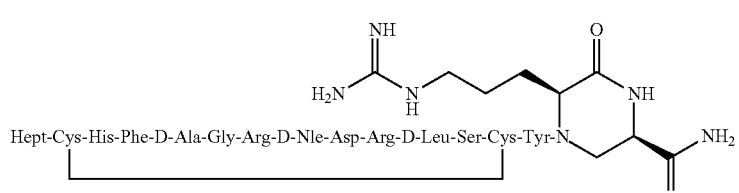 Hept-Cys-His-Phe-D-Ala-Gly-Arg-D-Nle-Asp-Arg-D-Leu-Ser-Cys-Tyr- |
| 1-188 938.8 | 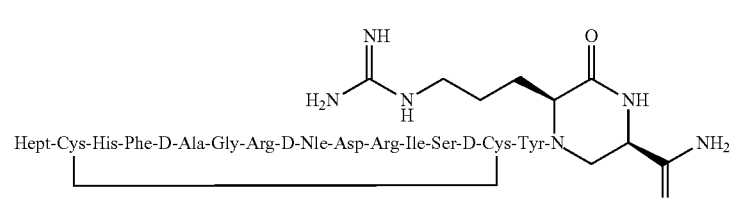 Hept-Cys-His-Phe-D-Ala-Gly-Arg-D-Nle-Asp-Arg-Ile-Ser-D-Cys-Tyr- |
| 1-189 937.3 | 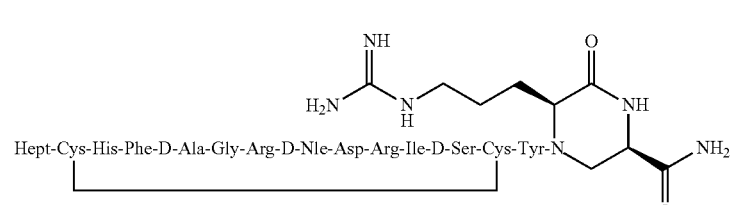 Hept-Cys-His-Phe-D-Ala-Gly-Arg-D-Nle-Asp-Arg-Ile-D-Ser-Cys-Tyr- |
| 1-190 937.6 | 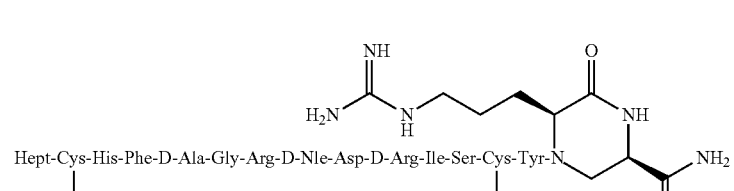 Hept-Cys-His-Phe-D-Ala-Gly-Arg-D-Nle-Asp-D-Arg-Ile-Ser-Cys-Tyr- |

TABLE 1-continued

| Number (M + 2)/2 | Structure |
|---|---|
| 1-191 938.5 | 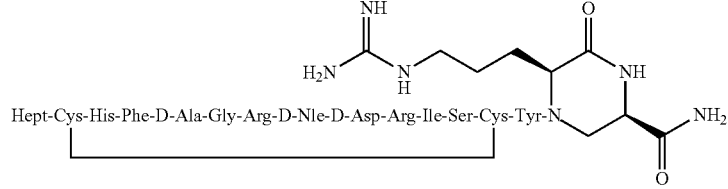 Hept-Cys-His-Phe-D-Ala-Gly-Arg-D-Nle-D-Asp-Arg-Ile-Ser-Cys-Tyr- |
| 1-192 938.4 | 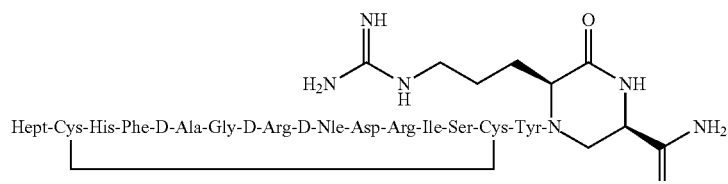 Hept-Cys-His-Phe-D-Ala-Gly-D-Arg-D-Nle-Asp-Arg-Ile-Ser-Cys-Tyr- |
| 1-193 938.9 | 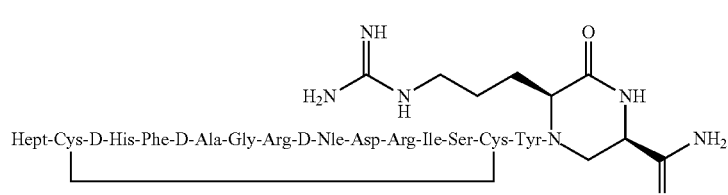 Hept-Cys-D-His-Phe-D-Ala-Gly-Arg-D-Nle-Asp-Arg-Ile-Ser-Cys-Tyr- |
| 1-194 938.3 | 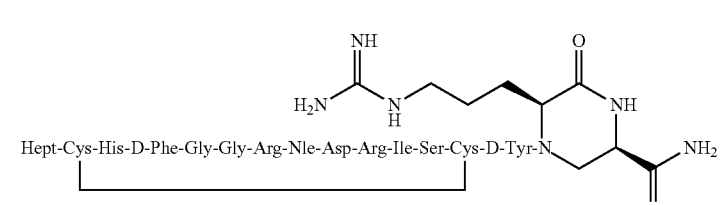 Hept-Cys-His-D-Phe-Gly-Gly-Arg-Nle-Asp-Arg-Ile-Ser-Cys-D-Tyr- |
| 1-195 931.5 | 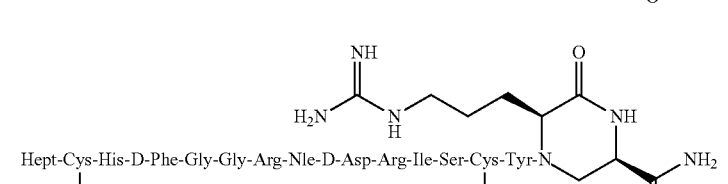 Hept-Cys-His-D-Phe-Gly-Gly-Arg-Nle-D-Asp-Arg-Ile-Ser-Cys-Tyr- |
| 1-196 931.4 | 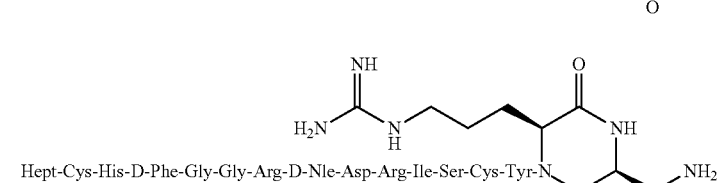 Hept-Cys-His-D-Phe-Gly-Gly-Arg-D-Nle-Asp-Arg-Ile-Ser-Cys-Tyr- |
| 1-197 938.7 | 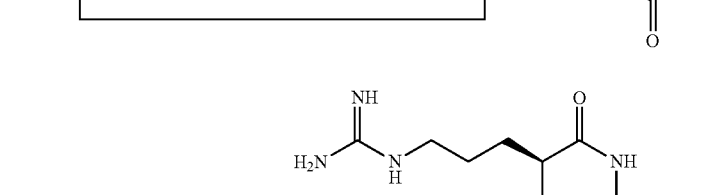 Hept-Cys-His-Phe-D-Ala-Gly-Arg-Nle-Asp-Arg-Ile-D-Ser-Cys-Tyr- |

TABLE 1-continued

| Number (M + 2)/2 | Structure |
|---|---|
| 1-198 931.4 | Hept-Cys-His-Phe-Gly-Gly-Arg-D-Nle-Asp-Arg-Ile-D-Ser-Cys-Tyr-[piperazinone-Arg side chain]-NH₂ |
| 1-199 938.3 | Hept-Cys-His-D-Phe-Gly-D-Ala-Arg-Nle-Asp-Arg-Ile-Ser-Cys-Tyr-[piperazinone-Arg side chain]-NH₂ |
| 1-200 931.3 | Hept-Cys-D-His-Phe-Gly-Gly-Arg-Nle-Asp-Arg-Ile-D-Ser-Cys-Tyr-[piperazinone-Arg side chain]-NH₂ |
| 1-201 931.6 | Hept-Cys-His-D-Phe-Gly-Gly-Arg-Nle-Asp-Arg-Ile-D-Ser-Cys-Tyr-[piperazinone-Arg side chain]-NH₂ |
| 1-202 938.5 | Hept-Cys-His-Phe-D-Ala-Gly-D-Arg-Nle-Asp-Arg-Ile-Ser-Cys-Tyr-[piperazinone-Arg side chain]-NH₂ |
| 1-203 938.2 | Hept-Cys-His-Phe-D-Ala-Gly-Arg-Nle-D-Asp-Arg-Ile-Ser-Cys-Tyr-[piperazinone-Arg side chain]-NH₂ |
| 1-204 938.4 | Hept-Cys-His-Phe-D-Ala-Gly-Arg-Nle-Asp-D-Arg-Ile-Ser-Cys-Tyr-[piperazinone-Arg side chain]-NH₂ |

TABLE 1-continued

| Number (M + 2)/2 | Structure |
|---|---|
| 1-205 937.9 | Hept-D-Cys-His-Phe-Gly-D-Ala-Arg-Nle-Asp-Arg-Ile-Ser-Cys-Tyr- 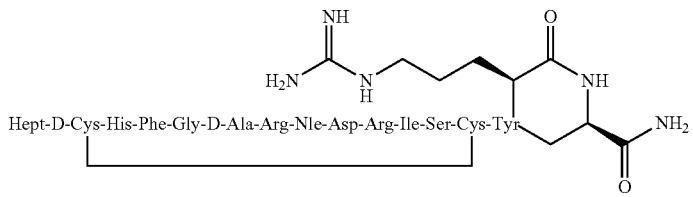 |
| 1-206 930.7 | Hept-D-Cys-His-D-Phe-Gly-Gly-Arg-Nle-Asp-Arg-Ile-Ser-Cys-Tyr- 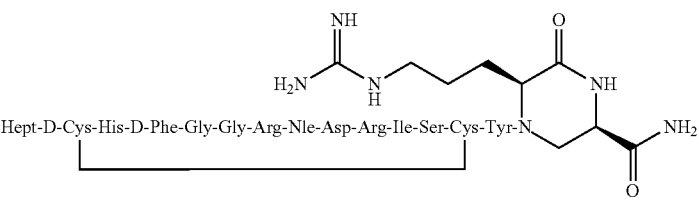 |
| 1-207 930.7 | Hept-D-Cys-D-His-Phe-Gly-Gly-Arg-Nle-Asp-Arg-Ile-Ser-Cys-Tyr- 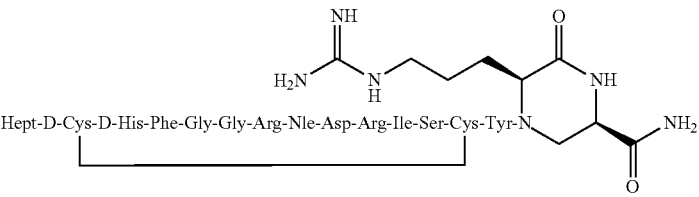 |
| 1-208 937.7 | Hept-Cys-His-Phe-D-Ala-Gly-Arg-Nle-Asp-Arg-Ile-Ser-D-Cys-Tyr- 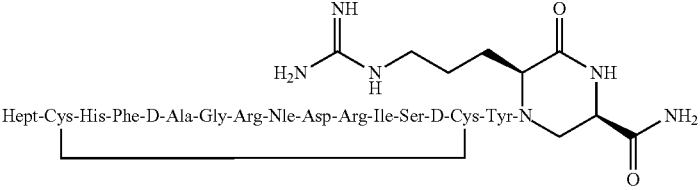 |
| 1-209 930.8 | Hept-Cys-His-Phe-Gly-Gly-Arg-Nle-Asp-Arg-D-Leu-Ser-D-Cys-Tyr- 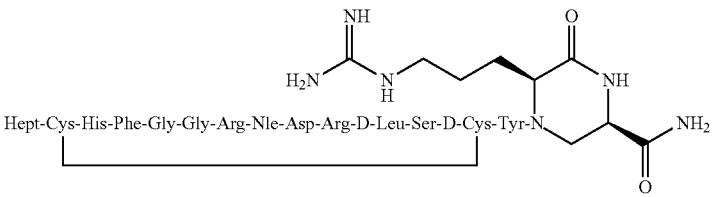 |
| 1-210 930.5 | Hept-Cys-His-Phe-Gly-Gly-Arg-Nle-Asp-D-Arg-Ile-Ser-D-Cys-Tyr- 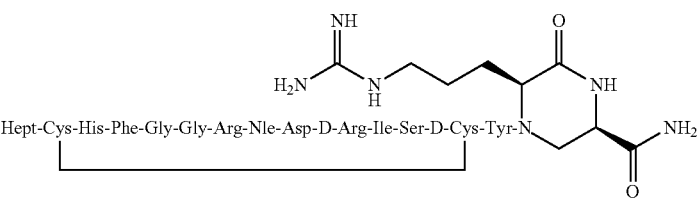 |
| 1-211 930.5 | Hept-Cys-His-Phe-Gly-Gly-Arg-D-Nle-Asp-Arg-Ile-Ser-D-Cys-Tyr- 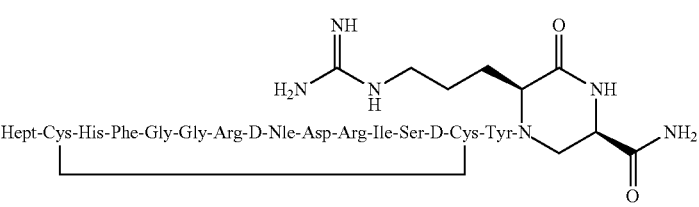 |

TABLE 1-continued

| Number (M + 2)/2 | Structure |
|---|---|
| 1-212 930.8 | 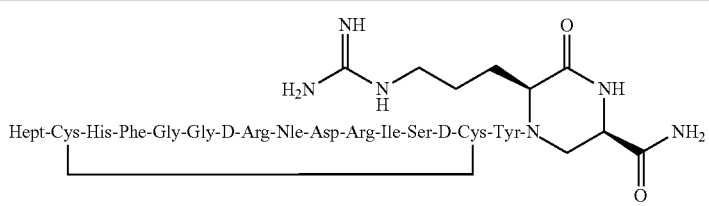Hept-Cys-His-Phe-Gly-Gly-D-Arg-Nle-Asp-Arg-Ile-Ser-D-Cys-Tyr- |
| 1-213 931.3 | 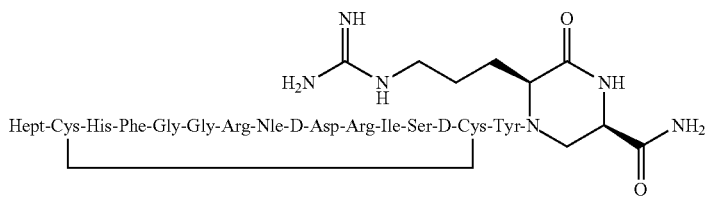Hept-Cys-His-Phe-Gly-Gly-Arg-Nle-D-Asp-Arg-Ile-Ser-D-Cys-Tyr- |
| 1-214 944.9 | 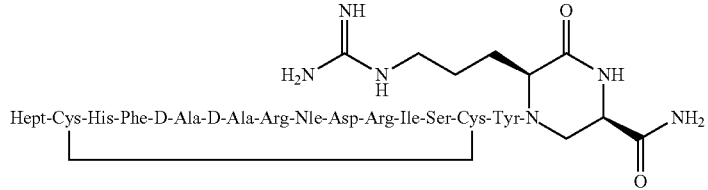Hept-Cys-His-Phe-D-Ala-D-Ala-Arg-Nle-Asp-Arg-Ile-Ser-Cys-Tyr- |
| 1-215 937.9 | 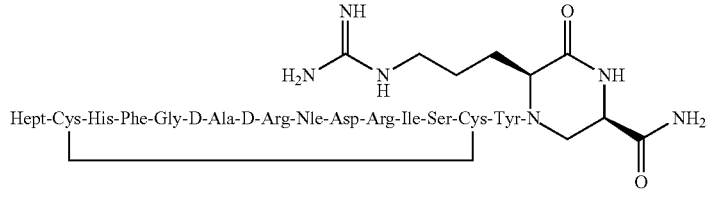Hept-Cys-His-Phe-Gly-D-Ala-D-Arg-Nle-Asp-Arg-Ile-Ser-Cys-Tyr- |
| 1-216 930.6 | 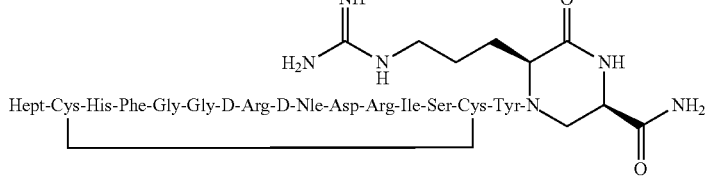Hept-Cys-His-Phe-Gly-Gly-D-Arg-D-Nle-Asp-Arg-Ile-Ser-Cys-Tyr- |
| 1-217 930.7 | 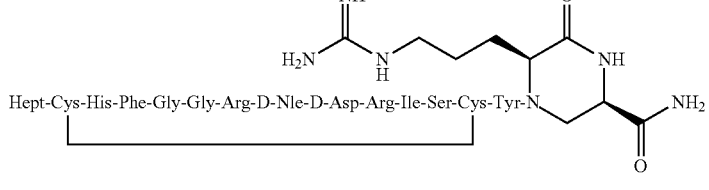Hept-Cys-His-Phe-Gly-Gly-Arg-D-Nle-D-Asp-Arg-Ile-Ser-Cys-Tyr- |
| 1-218 930.8 | 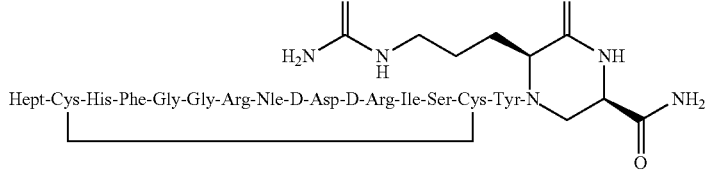Hept-Cys-His-Phe-Gly-Gly-Arg-Nle-D-Asp-D-Arg-Ile-Ser-Cys-Tyr- |

TABLE 1-continued

| Number (M + 2)/2 | Structure |
|---|---|
| 1-219 930.8 | 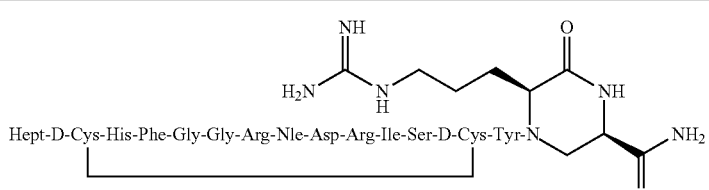 Hept-D-Cys-His-Phe-Gly-Gly-Arg-Nle-Asp-Arg-Ile-Ser-D-Cys-Tyr- |
| 1-220 930.9 | 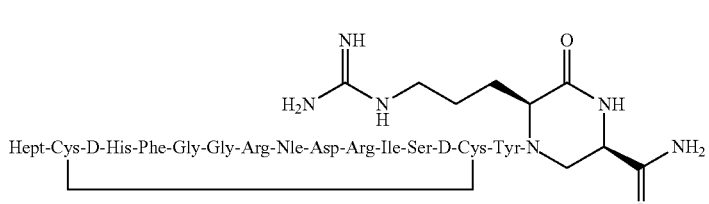 Hept-Cys-D-His-Phe-Gly-Gly-Arg-Nle-Asp-Arg-Ile-Ser-D-Cys-Tyr- |
| 1-221 931.6 | 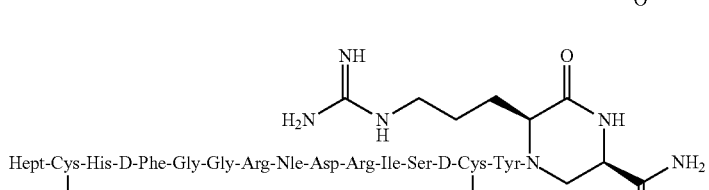 Hept-Cys-His-D-Phe-Gly-Gly-Arg-Nle-Asp-Arg-Ile-Ser-D-Cys-Tyr- |
| 1-222 937.8 | 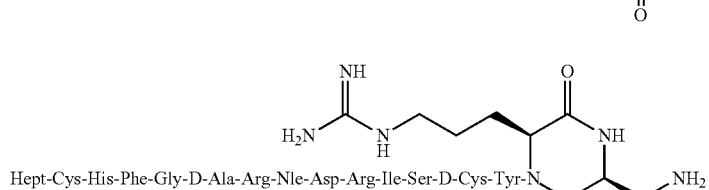 Hept-Cys-His-Phe-Gly-D-Ala-Arg-Nle-Asp-Arg-Ile-Ser-D-Cys-Tyr- |
| 1-223 931.1 | 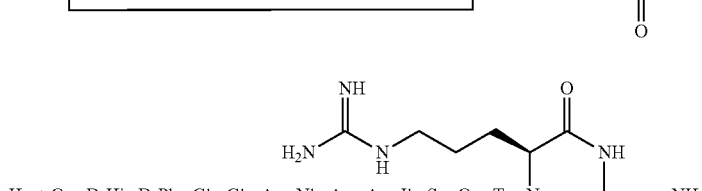 Hept-Cys-D-His-D-Phe-Gly-Gly-Arg-Nle-Asp-Arg-Ile-Ser-Cys-Tyr- |
| 1-224 938.2 | 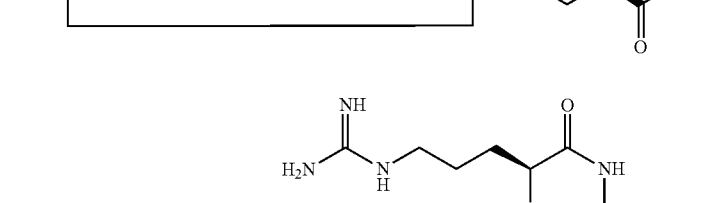 Hept-D-Cys-His-Phe-D-Ala-Gly-Arg-Nle-Asp-Arg-Ile-Ser-Cys-Tyr- |
| 1-225 937.8 | 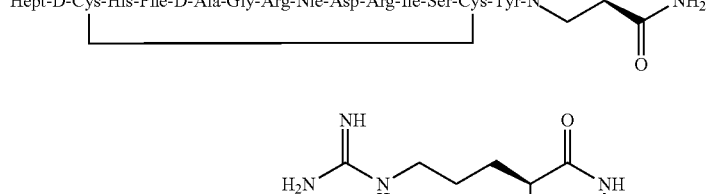 Hept-Cys-His-D-Phe-D-Ala-Gly-Arg-Nle-Asp-Arg-Ile-Ser-Cys-Tyr- |

TABLE 1-continued

| Number (M+2)/2 | Structure |
|---|---|
| 1-226 945.4 | 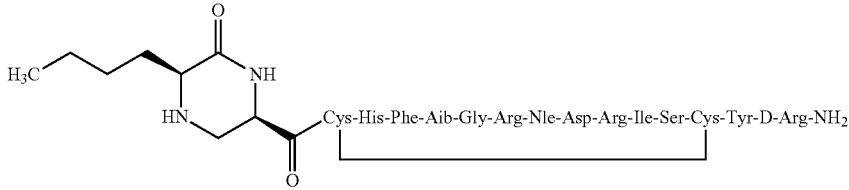 Cys-His-Phe-Aib-Gly-Arg-Nle-Asp-Arg-Ile-Ser-Cys-Tyr-D-Arg-NH$_2$ |
| 1-227 938.5 | 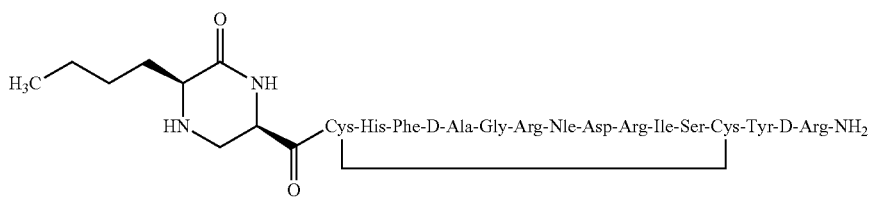 Cys-His-Phe-D-Ala-Gly-Arg-Nle-Asp-Arg-Ile-Ser-Cys-Tyr-D-Arg-NH$_2$ |
| 1-228 930.5 | 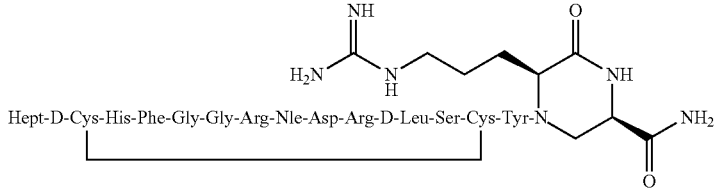 Hept-D-Cys-His-Phe-Gly-Gly-Arg-Nle-Asp-Arg-D-Leu-Ser-Cys-Tyr-N |
| 1-229 930.4 | 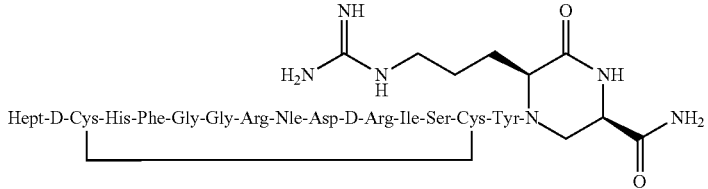 Hept-D-Cys-His-Phe-Gly-Gly-Arg-Nle-Asp-D-Arg-Ile-Ser-Cys-Tyr-N |
| 1-230 930.5 | 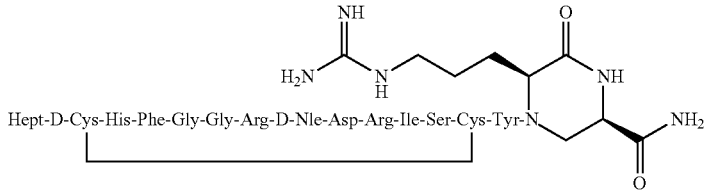 Hept-D-Cys-His-Phe-Gly-Gly-Arg-D-Nle-Asp-Arg-Ile-Ser-Cys-Tyr-N |
| 1-231 930.9 | 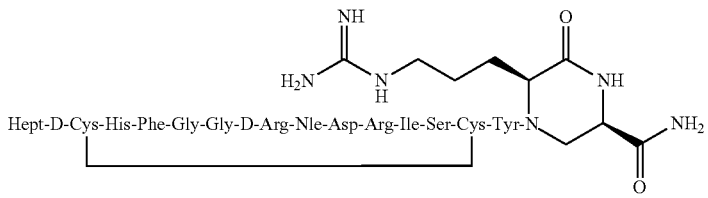 Hept-D-Cys-His-Phe-Gly-Gly-D-Arg-Nle-Asp-Arg-Ile-Ser-Cys-Tyr-N |
| 1-232 938.8 | 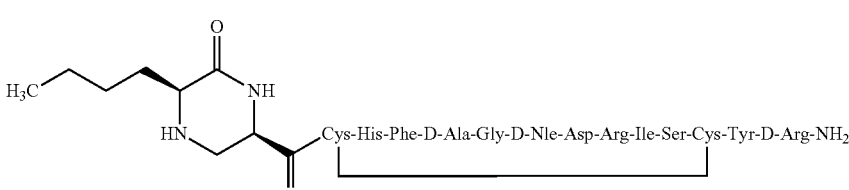 Cys-His-Phe-D-Ala-Gly-D-Nle-Asp-Arg-Ile-Ser-Cys-Tyr-D-Arg-NH$_2$ |

TABLE 1-continued
| Number (M + 2)/2 | Structure |
|---|---|
| 1-233 930.8 | 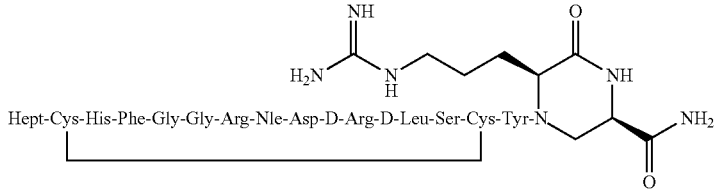 |
| 1-234 1030.8 | 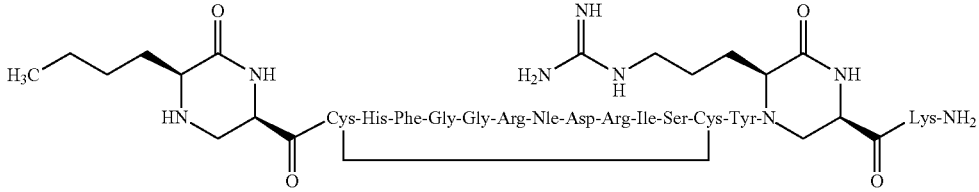(SEQ ID NO: 20) |
| 1-235 1023.3 | 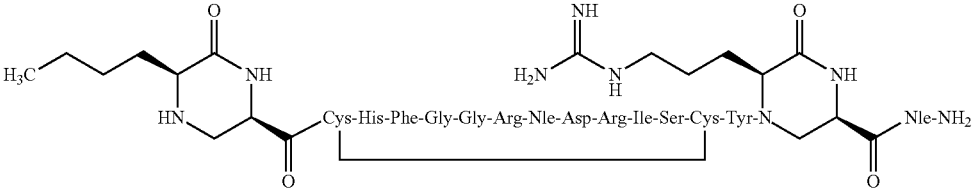(SEQ ID NO: 20) |
| 1-236 1031.2 | 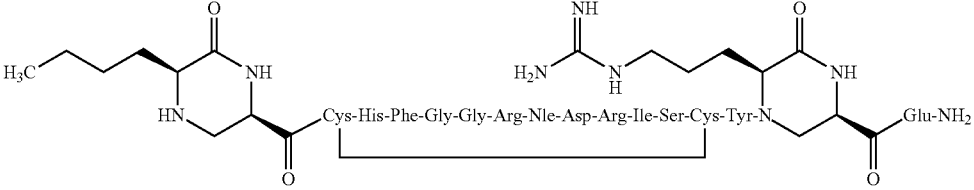(SEQ ID NO: 20) |
| 1-237 938.1 | 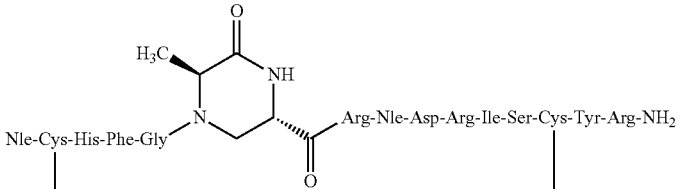(SEQ ID NO: 8), (SEQ ID NO: 9) |
| 1-238 971.8 | 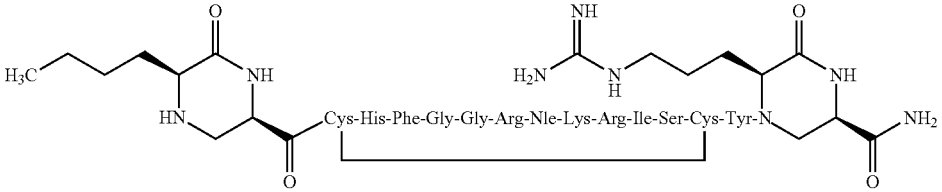(SEQ ID NO: 77) |

TABLE 1-continued

| Number (M + 2)/2 | Structure |
|---|---|
| 1-239 955.4 | 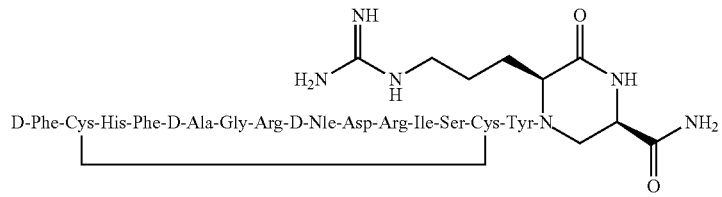 D-Phe-Cys-His-Phe-D-Ala-Gly-Arg-D-Nle-Asp-Arg-Ile-Ser-Cys-Tyr-N... |
| 1-240 917.4 | 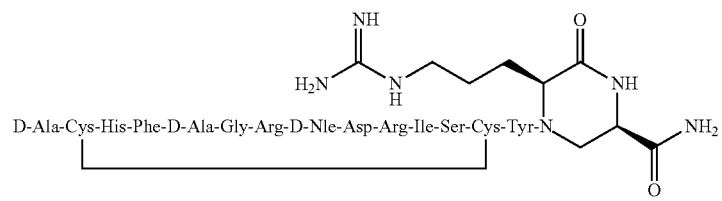 D-Ala-Cys-His-Phe-D-Ala-Gly-Arg-D-Nle-Asp-Arg-Ile-Ser-Cys-Tyr-N... |
| 1-241 937.8 | 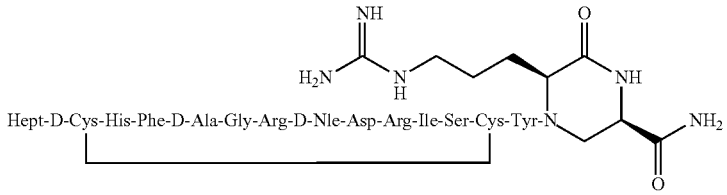 Hept-D-Cys-His-Phe-D-Ala-Gly-Arg-D-Nle-Asp-Arg-Ile-Ser-Cys-Tyr-N... |
| 1-242 938.5 | 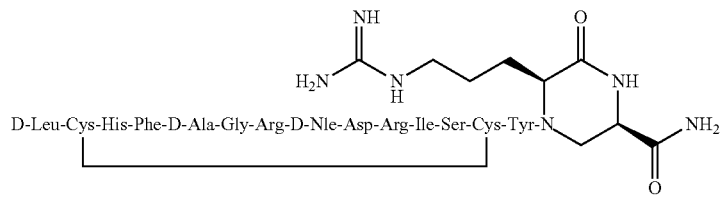 D-Leu-Cys-His-Phe-D-Ala-Gly-Arg-D-Nle-Asp-Arg-Ile-Ser-Cys-Tyr-N... |
| 1-243 930.8 | 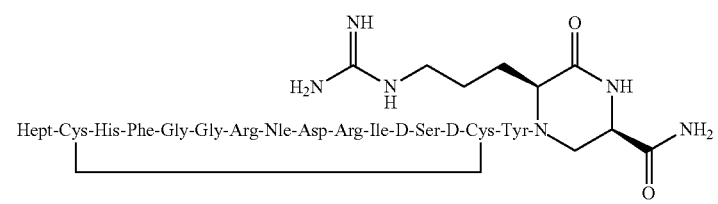 Hept-Cys-His-Phe-Gly-Gly-Arg-Nle-Asp-Arg-Ile-D-Ser-Cys-Tyr-N... |
| 1-244 930.8 | 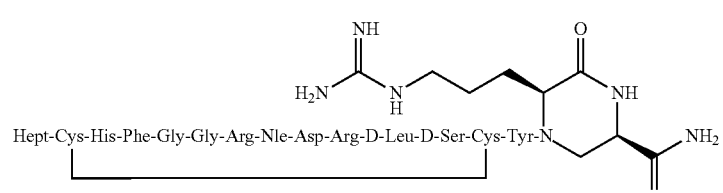 Hept-Cys-His-Phe-Gly-Gly-Arg-Nle-Asp-Arg-D-Leu-D-Ser-Cys-Tyr-N... |
| 1-245 963.3 | 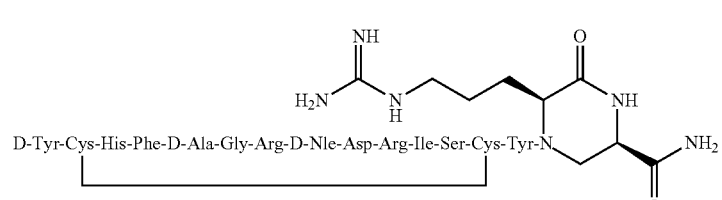 D-Tyr-Cys-His-Phe-D-Ala-Gly-Arg-D-Nle-Asp-Arg-Ile-Ser-Cys-Tyr-N... |

TABLE 1-continued

| Number (M + 2)/2 | Structure |
|---|---|
| 1-246 944.8 | Hept-Cys-His-Phe-D-Ala-D-Ala-Arg-D-Nle-Asp-Arg-Ile-Ser-Cys-Tyr-[piperazinone-Arg sidechain]-NH₂ |
| 1-247 959.9 | D-Arg-Cys-His-Phe-D-Ala-Gly-Arg-D-Nle-Asp-Arg-Ile-Ser-Cys-Tyr-[piperazinone-Arg sidechain]-NH₂ |
| 1-248 964.3 | [Nle-piperazinone]-Cys-His-Phe-Gly-Gly-Arg-Nle-Orn-Arg-Ile-Ser-Cys-Tyr-[piperazinone-Arg sidechain]-NH₂ (SEQ ID NO: 78) |

Example 2

The following constructs of Table 2 are synthesized, using amino acid surrogates of one or more of the foregoing methods, are purified and the mass weights determined:

TABLE 2

| Number | Structure |
|---|---|
| 2-1 | [Nle-piperazinone]-Cys-His-Phe-Gly-Gly-Arg-Nle-Asp-Arg-Ile-Ser-Cys-Tyr-[piperazinone-Arg sidechain]-N(CH₂CH₂CH₂CH₃)₂ (SEQ ID NO: 20) |
| 2-2 | [Nle-piperazinone]-Cys-His-Phe-Gly-Gly-Arg-Nle-Asp-Arg-Ile-Ser-Cys-Tyr-[piperazinone-Arg sidechain]-CH₂-NH-C(O)-CH₂CH₂CH₃ (SEQ ID NO: 20) |

TABLE 2-continued

| Number | Structure |
|---|---|
| 2-3 | (chemical structure) Cys-His-Phe-Gly-Gly-Arg-Nle-Asp-Arg-Ile-Ser-Cys-Tyr (SEQ ID NO: 20) |
| 2-4 | (chemical structure) Cys-His-Phe-Gly-Gly-Arg-Nle-Asp-Arg-Ile-Ser-Cys-Tyr (SEQ ID NO: 20) |
| 2-5 | (chemical structure) Cys-His-Phe-Gly-Gly-Arg-Nle-Asp-Arg-Ile-Ser-Cys-Tyr (SEQ ID NO: 20) |
| 2-6 | (chemical structure) Cys-His-Phe-Gly-Gly-Arg-Nle-Asp-Arg-Ile-Ser-Cys-Tyr (SEQ ID NO: 20) |
| 2-7 | (chemical structure) Cys-His-Phe-Gly-Gly-Arg-N...Asp-Arg-Ile-Ser-Cys-Tyr (SEQ ID NO: 79) |
| 2-8 | (chemical structure) Cys-D-His-Phe-Gly-Gly-Arg-Nle-Asp-D-Arg-Ile-Ser-Cys-Tyr |

TABLE 2-continued

| Number | Structure |
|---|---|
| 2-9 | 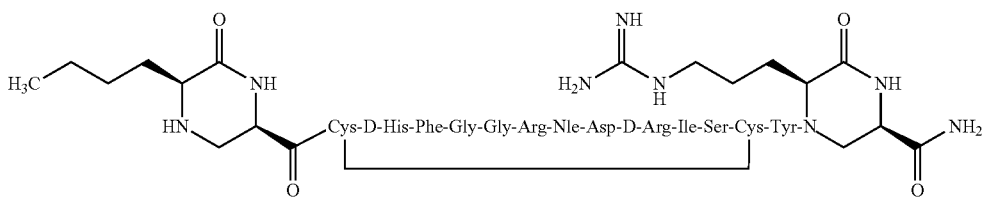 Cys-D-His-Phe-Gly-Gly-Arg-Nle-Asp-D-Arg-Ile-Ser-Cys-Tyr |
| 2-10 | 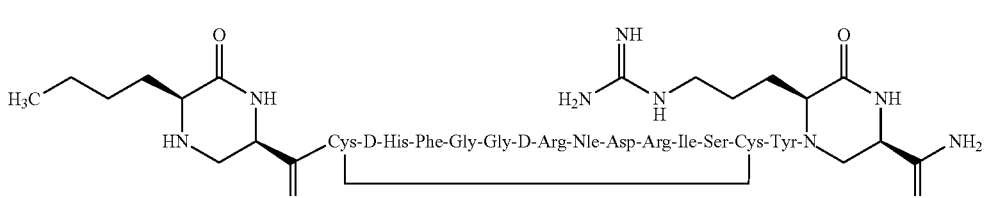 Cys-D-His-Phe-Gly-Gly-D-Arg-Nle-Asp-Arg-Ile-Ser-Cys-Tyr |
| 2-11 | 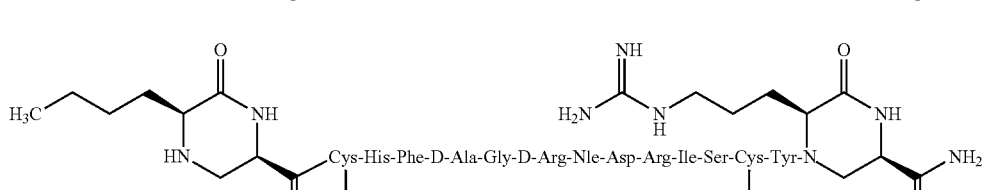 Cys-His-Phe-D-Ala-Gly-D-Arg-Nle-Asp-Arg-Ile-Ser-Cys-Tyr |
| 2-12 | 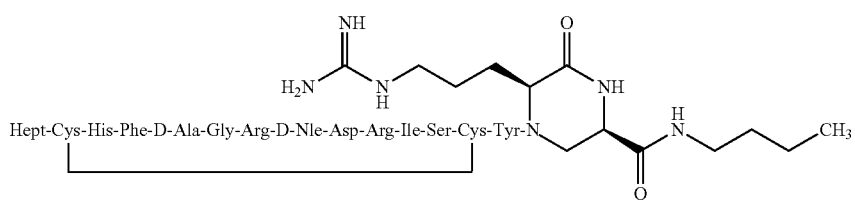 Hept-Cys-His-Phe-D-Ala-Gly-Arg-D-Nle-Asp-Arg-Ile-Ser-Cys-Tyr |
| 2-13 | 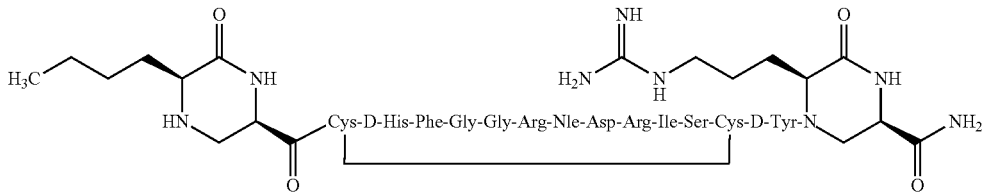 Cys-D-His-Phe-Gly-Gly-Arg-Nle-Asp-Arg-Ile-Ser-Cys-D-Tyr |
| 2-14 | 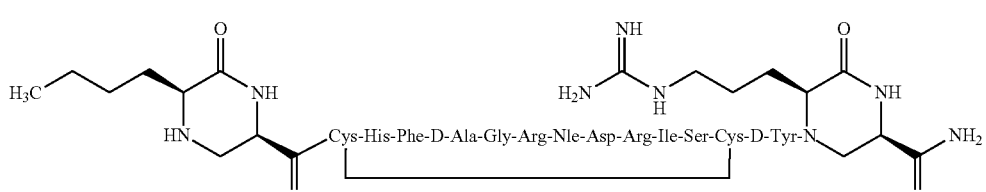 Cys-His-Phe-D-Ala-Gly-Arg-Nle-Asp-Arg-Ile-Ser-Cys-D-Tyr |
| 2-15 | 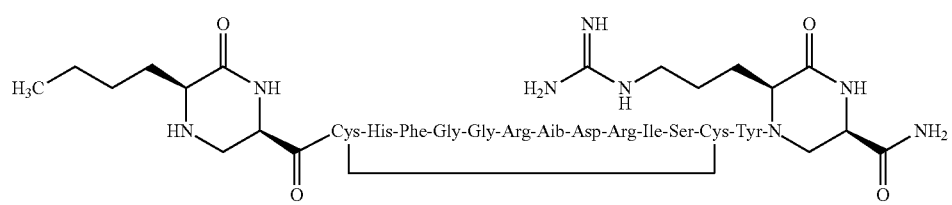 Cys-His-Phe-Gly-Gly-Arg-Aib-Asp-Arg-Ile-Ser-Cys-Tyr |

(SEQ ID NO: 80)

TABLE 2-continued

| Number | Structure |
|---|---|
| 2-16 | Cys-His-Phe-Aib-Gly-Arg-Nle-Asp-Arg-Ile-Ser-Cys-Tyr- (with N-terminal butyl-diketopiperazine and C-terminal arginyl-diketopiperazine-carboxamide) (SEQ ID NO: 81) |
| 2-17 | Cys-His-Phe-Gly-Aib-Arg-Nle-Asp-Arg-Ile-Ser-Cys-Tyr- (with N-terminal butyl-diketopiperazine and C-terminal arginyl-diketopiperazine-carboxamide) (SEQ ID NO: 82) |
| 2-18 | Hept-Cys-His-Phe-Gly-D-Ala-Arg-Nle-Asp-Arg-Ile-Ser-Cys-Tyr- (with C-terminal arginyl-diketopiperazine-carboxamide) |
| 2-19 | Hept-Cys-His-Phe-Gly-Gly-Arg-Nle-Asp-Arg-Ile-Ser-Cys-Tyr- (with C-terminal arginyl-methyl-piperazinone) (SEQ ID NO: 20) |
| 2-20 | Hept-Cys-His-Phe-Gly-Gly-Arg-Nle-Asp-Arg-Ile-Ser-Cys-Tyr- (with C-terminal arginyl-piperazinone-acetamide) (SEQ ID NO: 20) |
| 2-21 | Hept-Cys-His-Phe-Gly-Gly-Arg-Nle-Asp-Arg-Ile-Ser-Cys-Tyr- (with C-terminal arginyl-piperazinone-acetamide) (SEQ ID NO: 20) |
| 2-22 | Hept-Cys-His-Phe-Gly-Gly-Arg-Nle-Asp-Arg-Ile-Ser-Cys-Tyr- (with C-terminal arginyl-acetyl-methylpiperazine) (SEQ ID NO: 20) |

TABLE 2-continued

| Number | Structure |
|---|---|
| 2-23 | Hept-Cys-His-Phe-Gly-Gly-Arg-Nle-Asp-Arg-Ile-Ser-Cys-Tyr-N[piperazinone with guanidinopropyl substituent] (SEQ ID NO: 20) |
| 2-24 | Hept-Cys-His-Phe-Gly-Gly-Arg-Nle-Asp-Arg-Ile-Ser-Cys-Tyr-N[piperidine with guanidinopropyl and methyl substituents, N-acylated with 6-aminohexanoyl] (SEQ ID NO: 20) |
| 2-25 | Hept-Cys-His-Phe-Gly-Gly-Arg-Nle-Asp-Arg-Ile-Ser-Cys-Tyr-N[piperazinone with guanidinopropyl, methyl, and carboxamide substituents] (SEQ ID NO: 20) |
| 2-26 | [butyl-piperazinone]-Cys-His-Phe-D-Ala-Gly-D-Arg-Nle-Asp-Arg-Ile-Ser-Cys-Tyr-N[piperazinone with guanidinopropyl and carboxamide]-NH$_2$ |
| 2-27 | [butyl-piperazinone]-Cys-His-Phe-Gly-Gly-Arg-Nle-Asp-Arg-Ile-Ser-Cys-Tyr-N[piperazinone with guanidinopropyl]-C(O)-NH-(CH$_2$)$_7$-NH-C(O)-CH(NH$_2$)-(CH$_2$)$_4$-NH$_2$ (SEQ ID NO: 20) |

Example 3

Construct 1-1 (SEQ ID NO:3), with the following structure, was tested as described above.

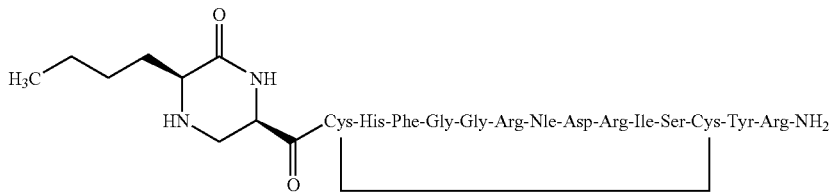

In receptor binding studies this construct had an average Ki of 0.3 nM in an assay system in which hANP had a Ki of 0.05 nM and mini-ANP had a Ki of 0.6 nM. Construct 1-1 had an EC$_{50}$ of 2 nM in an assay system in which hANP had an EC$_{50}$ of 0.6 nM and mini-ANP had an EC$_{50}$ of 3.3 nM.

Example 4

Construct 1-9 (SEQ ID NO:14), (SEQ ID NO:15), with the following structure, was tested as described above.

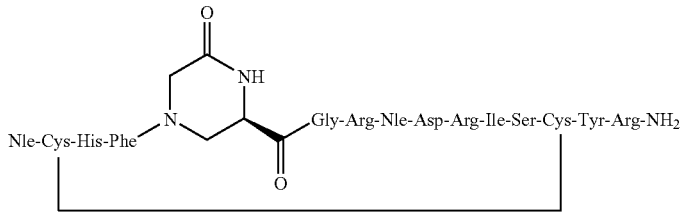

In receptor binding studies this construct had an average Ki of 0.9 nM in an assay system in which hANP had a Ki of 0.05 nM and mini-ANP had a Ki of 0.6 nM. Construct 1-9 had an $EC_{50}$ of 3.5 nM in an assay system in which hANP had an $EC_{50}$ of 0.6 nM and mini-ANP had an $EC_{50}$ of 3.3 nM.

Example 5

Construct 1-8 (SEQ ID NO:13), with the following structure, was tested as described above.

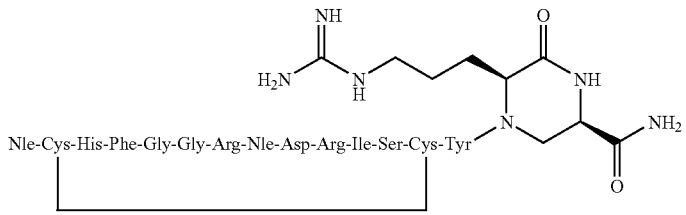

In receptor binding studies this construct had an average Ki of 0.2 nM in an assay system in which hANP had a Ki of 0.05 nM and mini-ANP had a Ki of 0.6 nM. Construct 1-8 had an $EC_{50}$ of 2 nM in an assay system in which the construct of FIG. 1 had an $EC_{50}$ of 0.6 nM and mini-ANP had an $EC_{50}$ of 3.3 nM.

Example 6

Construct 1-18 (SEQ ID NO:20), with the following structure, was tested as described above.

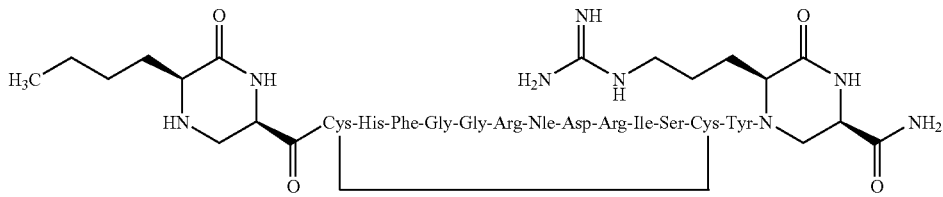

In receptor binding studies this construct had an average Ki of 0.027 nM in an assay system in which hANP had a Ki of 0.05 nM and mini-ANP had a Ki of 0.6 nM. Construct 1-18 had an $EC_{50}$ of 0.2 nM in an assay system in which hANP had an $EC_{50}$ of 0.6 nM and mini-ANP had an $EC_{50}$ of 3.3 nM.

Figure 2:
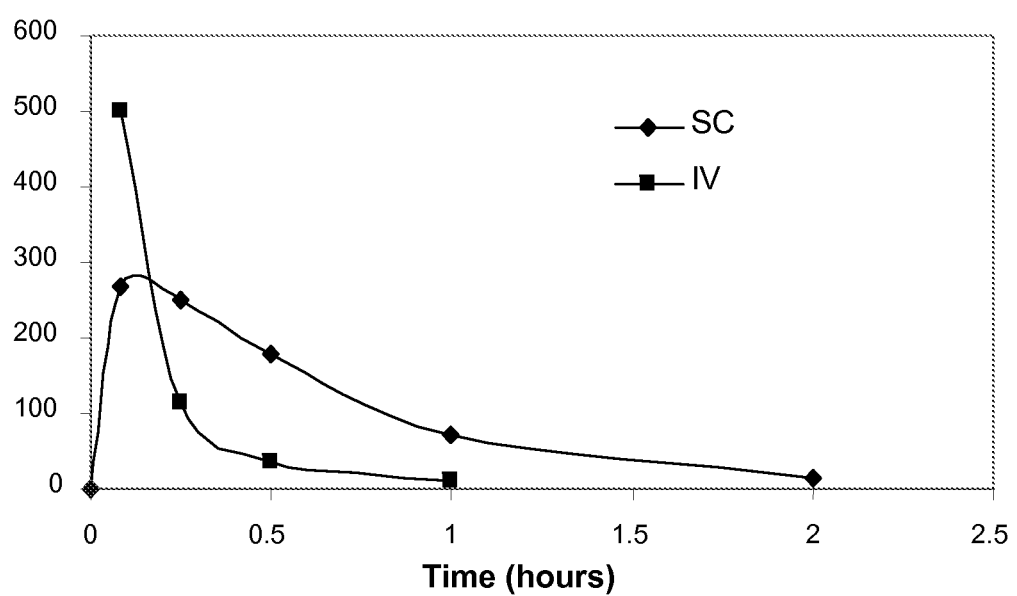
FIG. 2 is a graph of the concentration of construct 1-18 in rats over time when administered by subcutaneous means at 5 mg/kg and by intravenous means at 2 mg/kg.

Construct 1-18 was stable in both rat and human plasma, with $T_{1/2}$ of ~2 hours at 37° C. When administered IV, the in vivo $T_{1/2}$ in rats was ~20 minutes. Approximately 25 to 50% of the injected dose was bioavailable in rats when administered by a subcutaneous route. FIG. 2 depicts the concentration of construct 1-18 in ng/mL over time in rats, with the curve for "SC" indicating subcutaneous administration at a dose of 5 mg/kg, and the curve for "IV" indicating intravenous administration at a dose of 2 mg/kg.

Example 7

Blood pressure transducers were implanted in rats as described under the heading "Animal Models—Blood Pressure Transducer Implantation." Studies were conducted as described under the heading "Blood Pressure Monitoring." Studies included determination of changes in systolic blood pressure compared to saline following administration of constructs of the invention. In one study, rats were administered construct 1-63 (SEQ ID NO:20) by an IV route at 0.03 mg/kg body weight (n=4), 0.1 mg/kg (n=7) or 0.3 mg/kg (n=8). The blood pressure was monitored at 5 minutes prior to IV administration and at 5, 10 and 15 minutes after administration, and thereafter at 15 minute intervals until 135 minutes post administration. At all time points for all doses the measured systolic blood pressure was lower than saline control, with the decrease in blood pressure ranging from a minimum of about 5% to a maximum of about 19%, generally in a dose dependent manner, and with the greatest response seen at 10 to 45 minutes after administration.

In a second study, rats were administered construct 1-63 (SEQ ID NO:20) by a subcutaneous route at 0.3 mg/kg body weight (n=8), 1.0 mg/kg (n=7) or 3.0 mg/kg (n=7). The blood pressure was monitored at 15 and 5 minutes prior to SC administration and at 5, 10 and 15 minutes after administration, and thereafter at 15 minute intervals until 210 minutes post administration. At all time points for all doses the measured systolic blood pressure was lower than saline control. At 0.3 mg/kg SC, the decrease in systolic pressure was in the range of 2% at time points after 2 hours post administration, which was within the error range. However, at all other time points for 0.3 mg/kg SC, and at all time points for 1.0 and 3.0 mg/kg, the decrease was statistically different and lower than the saline control. At 3.0 mg/kg a maximum decrease of approximately 20% to 23% in systolic pressure was seen at 45 to 120 minutes post administration, with a maximum decrease in the same time period at 1.0 mg/kg of 17% to 19%.

In a third study, rats were administered construct 1-18 (SEQ ID NO:20) by an IV route at 0.3 mg/kg of body weight (n=8). The blood pressure was monitored at 5 minutes prior to IV administration and at 5, 10 and 15 minutes after administration, and thereafter at 15 minute intervals until 135 minutes post administration. At all time points for all doses the measured systolic blood pressure was lower than saline control, with the decrease in blood pressure ranging from a minimum of about 5% to a maximum of about 13%, with the greatest response seen at 15 minutes after administration.

In a fourth study, rats were administered construct 1-18 (SEQ ID NO:20) by a subcutaneous route at 0.1 mg/kg body weight (n=4), 0.3 mg/kg (n=7) or 1.0 mg/kg (n=8). The blood pressure was monitored at 15 and 5 minutes prior to SC administration and at 5, 10 and 15 minutes after administration, and thereafter at 15 minute intervals until 225 minutes post administration. At all time points for all doses the measured systolic blood pressure was lower than saline control. At 0.1 mg/kg SC, the decrease in systolic pressure was not statistically relevant after about two and one-half hours. However, at all other time points for 0.1 mg/kg SC, and at all time points less than about two and one-half hours for 0.3 and at all time points for 1.0 mg/kg, the decrease was statistically different and lower than the saline control. At 1.0 mg/kg a maximum decrease of approximately 9% to 13% in systolic pressure was seen at 45 to 120 minutes post administration.

Example 8

Figure 3:
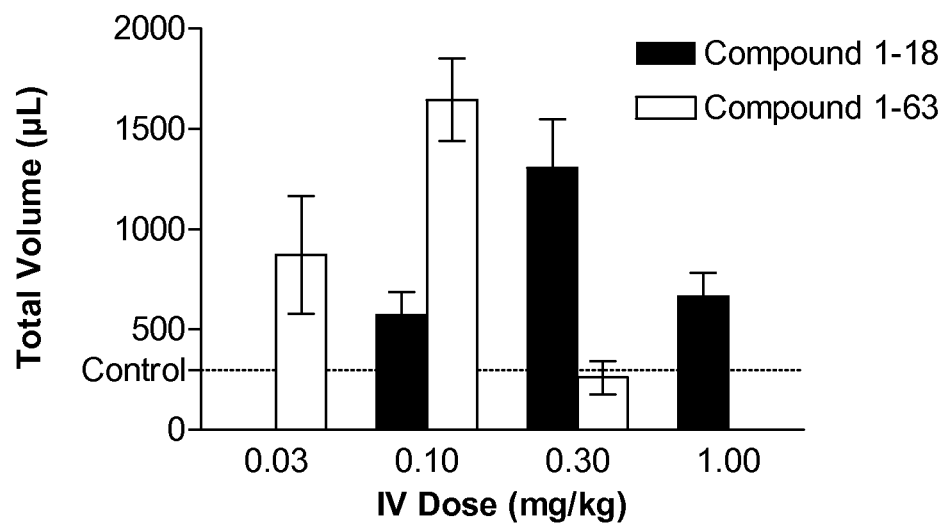
FIG. 3 is a graph of total urine output over thirty minutes in a group of four rats when administered constructs 1-18 and 1-63 by IV routes; and, FIG. 4 is a graph of total urine output over forty-five minutes in a group of four rats when administered construct 1-18 in different doses by SC routes.

Total urine output in rats was measured as described under the heading "Diuresis and Natriuresis." Groups of four animals were administered constructs 1-18 (SEQ ID NO:20) and 1-63 (SEQ ID NO:44) by IV routes, with animals receiving 0.03 mg/kg of body weight, 0.1 mg/kg and 0.3 mg/kg of construct 1-18, and 0.1 mg/kg of body weight, 0.3 mg/kg and 1.0 mg/kg of construct 1-63 (SEQ ID NO:44). Total urine output over 30 minutes postdose was measured, with results as shown in FIG. 3.

Figure 4:
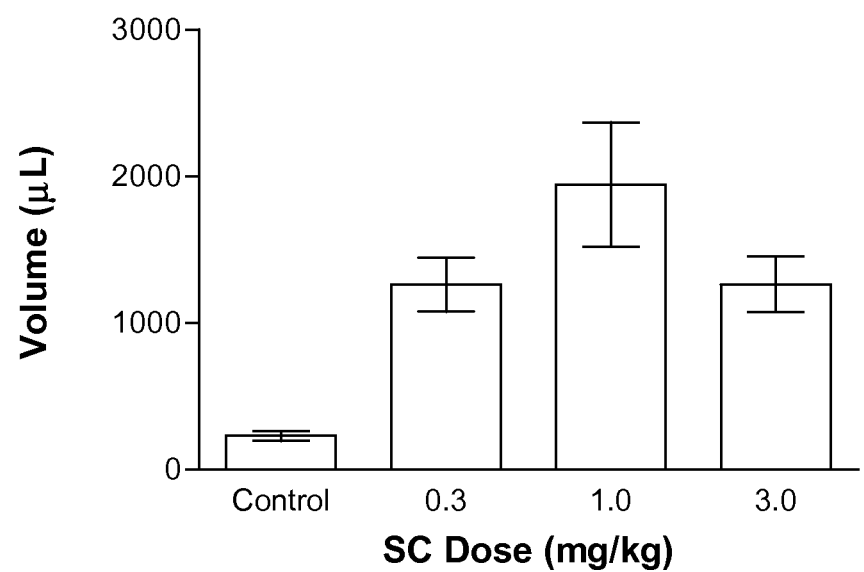

In a separate study, total urine about was similarly measured in a group of four animals receiving doses of 0.3, 1.0 and 3.0 mg/kg of body weight of construct 1-63 (SEQ ID NO:44) by a SC route, with saline used as a control. Total urine output over 45 minutes postdose was measured. Results are as shown in FIG. 4.

Example 9

The pharmacokinetics of selected constructs of the invention were studied in male Sprague-Dawley rats following intravenous (IV) or subcutaneous (SC) administration. Pharmacokinetic parameters of selected constructs in rats were determined and summarized in Tables 3 and 4.

Constructs of the invention as indicated in Tables 4 and 5 were prepared as the TFA salt and dissolved in saline at 1 mL/kg for both IV and SC dosing routes. The IV dose was administered via a femoral artery cannula at target doses of 0.3 and 2 mg/kg. The SC dose was administered at target doses of 1 and 5 mg/kg. Animals were not fasted overnight before dosing. Blood was collected into containers containing dipotassium EDTA at predetermined intervals from a previously implanted cannula in the jugular vein. Plasma was obtained by centrifugation of the blood and stored at −70° C. until analysis.

Data analysis utilized a LC-MS/MS system including a Leap Technologies HTS-PAL autosampler equipped with a 100 μL injection loop, two Shimadzu Pumps and a Sciex API 4000 mass spectrometer. Chromatographic separation of the analytes was achieved on a Luna $C_{18}$ column (4.6×100 mm; 3μ) eluted at 1 mL/min with a step-wise procedure. Solvent A (water containing 0.1% formic acid v/v) and solvent B (acetonitrile containing 0.1% formic acid v/v) were used as the mobile phases. Initially, the column was equilibrated with 5% B and, 2 minutes after sample injection, B was increased to 60% over a period of 0.5 minutes and held at this concentration for 1.1 minutes. The composition of B was increased to 80% in 1.4 minutes and maintained for 0.3 minutes. The composition of B was returned to 5% in 0.2 minutes. The total run time was 6 minutes. Mass spectrometric detection of the analytes was accomplished using the Turbo Ionspray interface operated in the positive ion mode. Analyte response was measured by multiple reaction monitoring (MRM) of the transitions of the protonated precursor ions to the selected product ions.

Aliquots of plasma (100 μL) were mixed with the internal standard (IS) and subjected to solid phase extraction using $C_8$ cartridges in a 96 well format. After preconditioning of the $C_8$ cartridges with 1 mL of methanol and 1 mL of 2% ammonium hydroxide in water, plasma samples were loaded onto the cartridges. Following washing the cartridges with 2% ammonium hydroxide in 40% methanol, constructs were eluted from the cartridges with 1 mL of 2% acetic acid in 60% methanol. The eluents were transferred to a clean plate, evaporated under a stream of $N_2$ and the residues were resuspended in 100 μL of 20 mM ammonium acetate and acetonitrile (6:4, v:v) prior to LC-MS/MS analysis. Calibration standards (2-1000 ng/mL) were prepared in the same manner by adding construct at various concentrations and its respective IS to 100 μL of untreated rat plasma. Similarly, quality control samples were prepared by adding construct and IS to 100 μL of control plasma at 3 different concentrations (3.5, 75 and 750 ng/mL) of construct.

Data were acquired and processed by Sciex Analyst 1.4.1 software. Peak area ratios of construct to IS were plotted as a function of the nominal concentrations of construct. Linear regression using a weighting factor of 1/x was used to calculate the concentration of construct in plasma samples. The lower limit of quantification (LLOQ) for this assay typically was 2 or 5 ng/mL.

Pharmacokinetic parameters were calculated by established non-compartmental method (Win-Nonlin version 2.1; Consulting Inc., Palo Alto, Calif.). The area under the plasma concentration versus time curve (AUC) was determined using linear trapezoidal interpolation in the ascending slope and logarithmic trapezoidal interpolation in the descending slope. The portion of the AUC from the last measurable concentration to infinity was estimated from the equation $C_t/k_{el}$, where $C_t$ represents the last measurable concentration and $k_{el}$ is the elimination rate constant. The latter was determined from the concentration versus time curve by linear regression at the terminal phase of the semi-logarithmic plot.

TABLE 3

Summary of Pharmacokinetic Parameters of Constructs in SD Rats Following IV Administration

| Construct | Dose (mg/kg) | AUC (nM · hr) | Vdss (L/kg) | Cl (mL/min/kg) | $T_{1/2}$ (hr) |
|---|---|---|---|---|---|
| 1-18 (SEQ ID NO: 20) | 2 | 263 | 0.7 | 72 | 0.2 |
| 1-18 (SEQ ID NO: 20) | 0.3 | 61 | 0.4 | 43 | 0.2 |
| 1-63 (SEQ ID NO: 20) | 2 | 67 | 4.6 | 290 | 0.3 |
| 1-63 (SEQ ID NO: 20) | 0.3 | 33 | 5.8 | 546 | 0.3 |
| 1-55 (SEQ ID NO: 39) | 2 | 828 | 0.3 | 21 | 0.3 |
| 1-55 (SEQ ID NO: 39) | 0.3 | 116 | 0.2 | 15 | 0.2 |
| 1-54 (SEQ ID NO: 38) | 2 | 277 | 1.0 | 66 | 0.2 |
| 1-35 (SEQ ID NO: 31) | 2 | 10 | 57 | 1857 | 0.4 |
| 1-39 | 2 | 142 | 2.8 | 134 | 0.3 |
| 1-42 | 2 | 369 | 0.7 | 50 | 0.3 |
| 1-45 | 2 | 850 | 0.3 | 23 | 0.3 |
| 1-28 | 2 | 351 | 1.1 | 51 | 0.4 |
| 1-69 (SEQ ID NO: 43) | 2 | 113 | 0.8 | 168 | 0.1 |
| 1-100 (SEQ ID NO: 29) | 2 | 42 | 0.8 | 456 | 0.1 |
| 1-68 | 2 | 478 | 0.5 | 40 | 0.3 |
| 1-43 | 2 | 1247 | 0.6 | 14 | 0.7 |
| 1-44 | 2 | 1539 | 0.4 | 15 | 0.5 |
| 1-51 (SEQ ID NO: 20) | 2 | 190 | 1.0 | 94 | 0.2 |

TABLE 4

Pharmacokinetics of Constructs in SD Rats Following SC Administration PK Parameters in SD Rats

| Construct | Dose (mg/kg) | AUC (nM · hr) | Tmax (hr) | Cmax (nM) | $T_{1/2}$ (hr) |
|---|---|---|---|---|---|
| 1-18 (SEQ ID NO: 20) | 5 | 255 | 0.2 | 131 | 1.6 |
| 1-18 (SEQ ID NO: 20) | 1 | 40 | 0.1 | 85 | 0.2 |
| 1-55 (SEQ ID NO: 39) | 5 | 232 | 0.3 | 250 | 0.5 |
| 1-63 (SEQ ID NO: 20) | 1 | 7 | 0.1 | 26 | 0.2 |

Example 10

A formulation of 1-132 was made for pharmaceutical use. 1-132 was used in the acetate salt form. The formulation was dispensed into a 1 mL vial which was stoppered and sealed, with each vial containing:

0.1 mg of 1-132 acetate, based on peptide weight net of acetate
1.181 mg succinic acid, NF
47.0 mannitol, USP
1N NaOH, USP, as needed to adjust pH
1N HCl, USP, as needed to adjust pH
Water for injection, to 1 mL volume The pH of the final product was adjusted to pH 4.00±0.05 with 1N NAOH or 1N HCl, as required. The resulting solution was filtered through a sterile 0.22 micron filter prior to vialing, and was stored at 5° C. until used.

An alternative formulation of 1-132 was made for pharmaceutical use, similar to the formulation above, but additionally including between about 0.02 mg and 0.06 mg of disodium pamoate, such that the resulting solution was a pamoate suspension.

Example 11

The following constructs were synthesized, using amino acid surrogates of one or more of the foregoing methods, purified and conjugated with PEG-5K-OSu and the mass weights determined, with the results as shown in Table 5 below:

TABLE 5

| Construct (M + 1) | Structure |
|---|---|
| 5-1 6391-8332 | 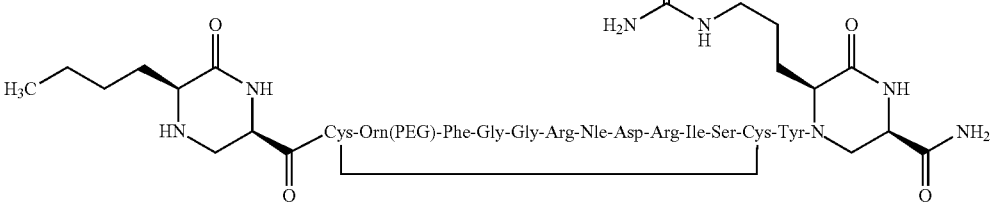 (SEQ ID NO: 83) |
| 5-2 6338-8412 | 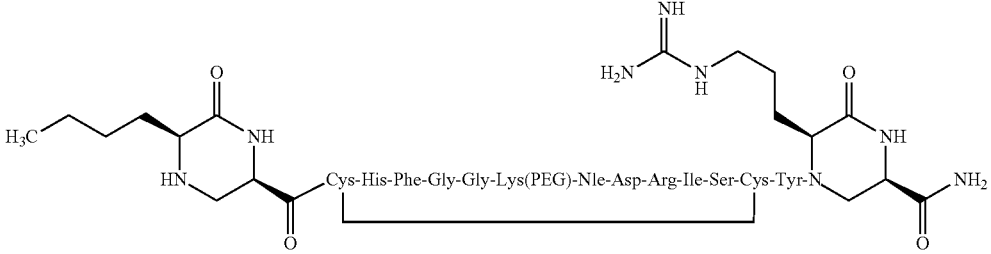 (SEQ ID NO: 84) |

TABLE 5-continued
| Construct (M + 1) | Structure |
|---|---|
| 5-3<br>6427-8159 | 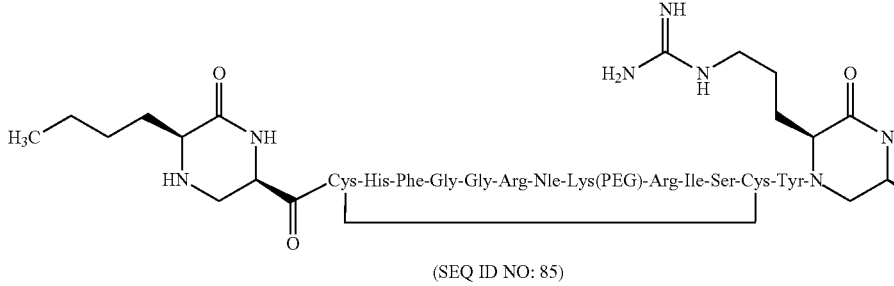<br>(SEQ ID NO: 85) |
| 5-4<br>6406-8219 | 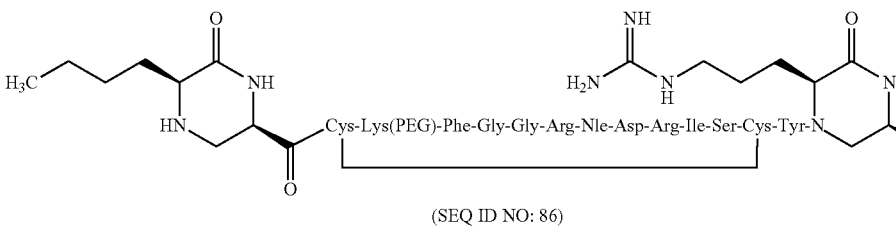<br>(SEQ ID NO: 86) |
| 5-5<br>11959-13514 | 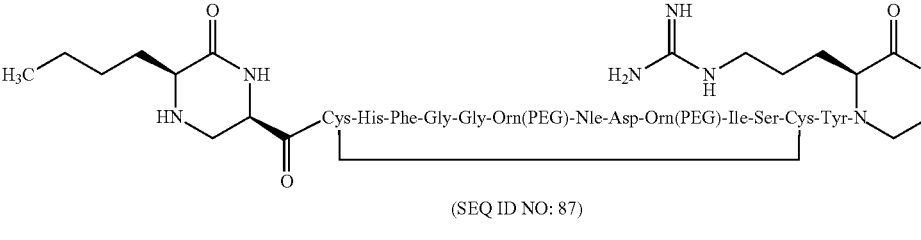<br>(SEQ ID NO: 87) |
| 5-6<br>6602-8279 | 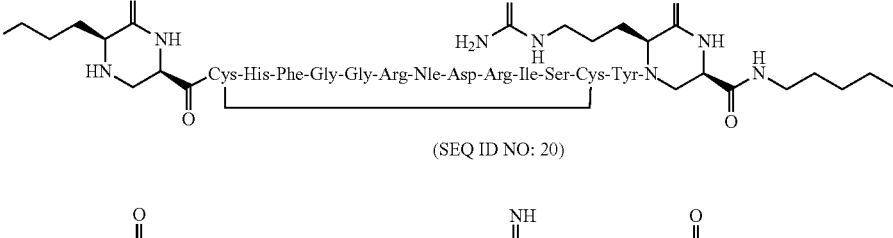<br>(SEQ ID NO: 20) |
| 5-7<br>6506-8580 | 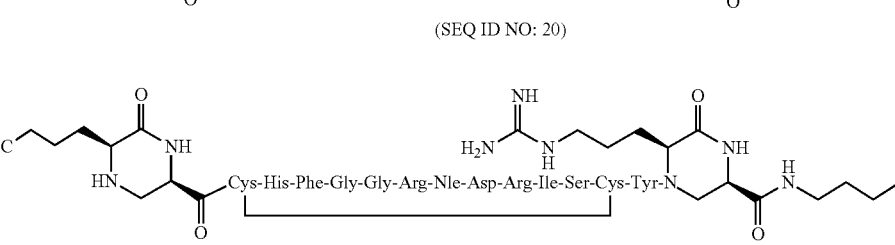<br>(SEQ ID NO: 20) |
| 5-8<br>6319-8387 | 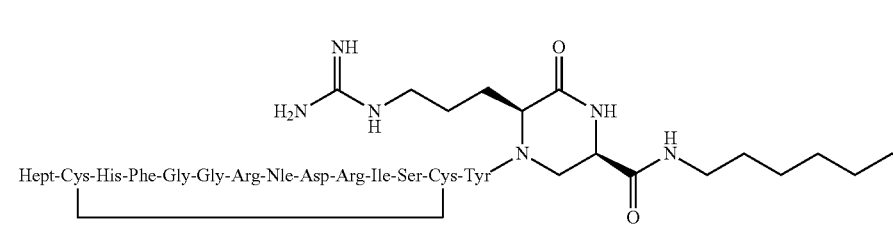<br>(SEQ ID NO: 20) |

TABLE 5-continued

| Construct (M + 1) | Structure |
|---|---|
| 5-9 6660-8505 | (SEQ ID NO: 20) |
| 5-10 6444-8174 | (SEQ ID NO: 47) |
| 5-11 6383-8103 | (SEQ ID NO: 88), (SEQ ID NO: 89) |
| 5-12 6479-8289 | (SEQ ID NO: 90) |
| 5-13 6564-8869 | (SEQ ID NO: 91) |

Example 12

The following constructs of Table 6 are synthesized, using amino acid surrogates of one or more of the foregoing methods, purified and conjugated with PEG-5K-OSu or another reactive PEG, and the mass weights determined:

TABLE 6
| Construct | Structure |
|---|---|
| 6-1 | 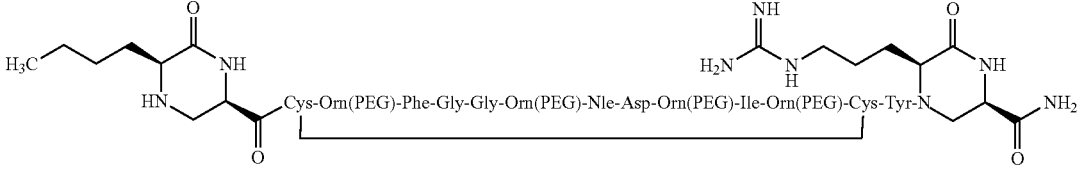<br>(SEQ ID NO: 91) |
| 6-2 | 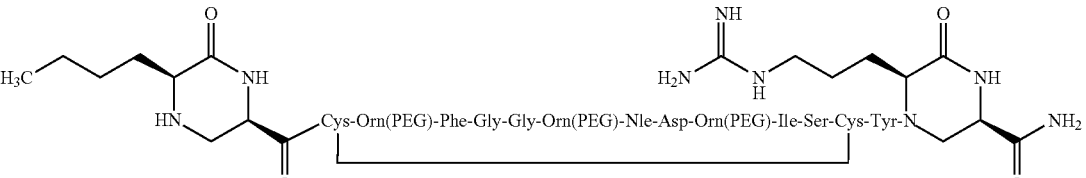<br>(SEQ ID NO: 92) |
| 6-3 | 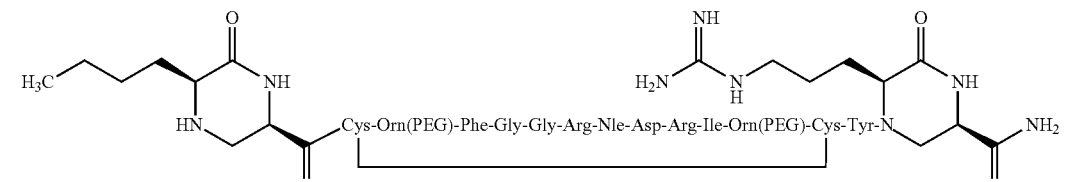<br>(SEQ ID NO: 93) |
| 6-4 | 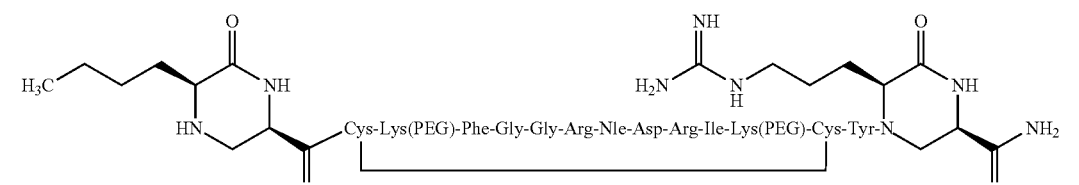<br>(SEQ ID NO: 94) |
| 6-5 | 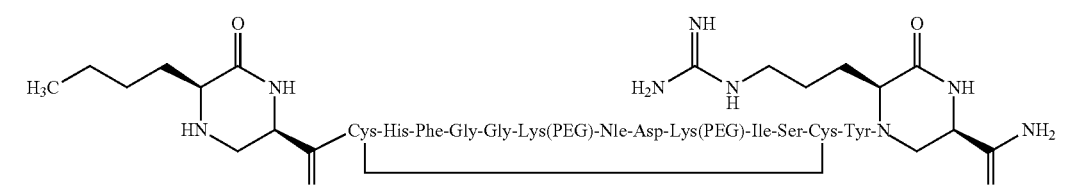<br>(SEQ ID NO: 95) |
| 6-6 | 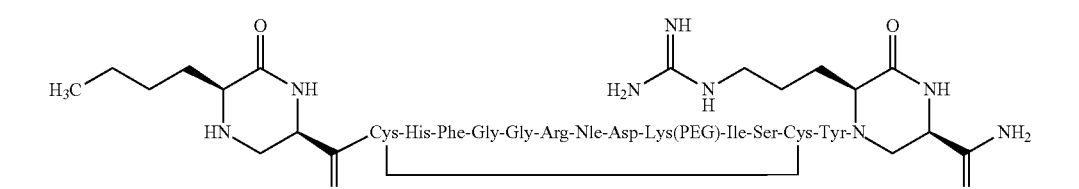<br>(SEQ ID NO: 96) |

TABLE 6-continued

| Construct | Structure |
|---|---|
| 6-7 | Cys-Lys(PEG)-Phe-Gly-Gly-Arg-Nle-Asp-Lys(PEG)-Ile-Ser-Cys-Tyr (SEQ ID NO: 97) |
| 6-8 | Cys-Orn(PEG)-Phe-Gly-Gly-Arg-Nle-Asp-Orn(PEG)-Ile-Ser-Cys-Tyr (SEQ ID NO: 98) |
| 6-9 | Cys-Lys(PEG)-Phe-Gly-Gly-Lys(PEG)-Nle-Asp-Arg-Ile-Ser-Cys-Tyr (SEQ ID NO: 99) |
| 6-10 | Cys-Orn(PEG)-Phe-Gly-Gly-Orn(PEG)-Nle-Asp-Arg-Ile-Ser-Cys-Tyr (SEQ ID NO: 100) |
| 6-11 | Cys-His-Phe-Gly-Gly-Arg-Nle-Asp-Arg-Ile-Lys(PEG)-Cys-Tyr (SEQ ID NO: 101) |
| 6-12 | Cys-His-Phe-Gly-Gly-Arg-Nle-Asp-Arg-Ile-Ser-Cys-Tyr (SEQ ID NO: 20) |

Example 13

Construct 5-1 (SEQ ID NO:83), with the following structure, was tested as described above.

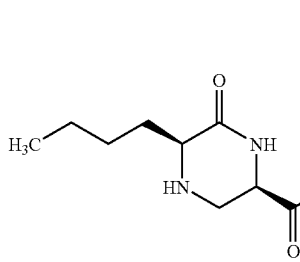

In receptor binding studies this construct had an average Ki of 70 nM in an assay system in which hANP had a Ki of 0.05 nM and mini-ANP had a Ki of 0.6 nM.

Example 14

Construct 5-9 (SEQ ID NO:20), with the following structure, was tested as described above.

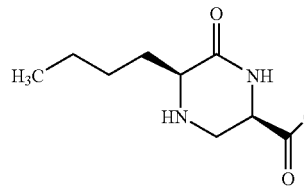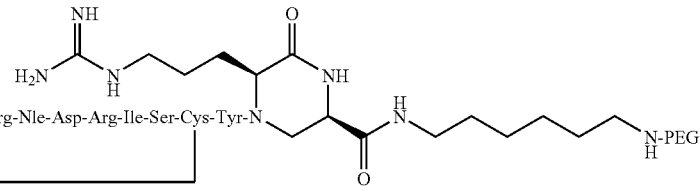

In receptor binding studies this construct had an average Ki of approximately 2 nM in an assay system in which hANP had a Ki of 0.05 nM and mini-ANP had a Ki of 0.6 nM. Construct 5-9 had an $EC_{50}$ of approximately 9.5 nM in an assay system in which hANP had an $EC_{50}$ of 0.6 nM and mini-ANP had an $EC_{50}$ of 3.3 nM.

Example 15

Any of constructs of the invention, including without limitation constructs 1-1 to 1-248, 2-1 to 2-21, 5-1 to 5-18 and 6-1 to 6-12, is formulated for time-release injection. Any of the constructs is formulated with a PEG, such as poly(ethylene glycol) 3350, and optionally one or more additional excipients and preservatives, including but not limited to excipients such as salts, polysorbate 80, sodium hydroxide or hydrochloric acid to adjust pH, and the like. Alternatively, any of the constructs is formulated with a poly(ortho ester), including an auto-catalyzed poly(ortho ester) with any of a variable percentage of lactic acid in the polymeric backbone, and optionally one or more additional excipients. Poly(D,L-lactide-co-glycolide) polymer (PLGA polymer) may be employed, preferably a PLGA polymer with a hydrophilic end group.

Example 16

A patient with congestive heart failure, such as acutely decomponensated congestive heart failure with dyspnea at rest or with minimal activity, is administered a formulation including one or more of any of constructs 1-1 to 1-248, 2-1 to 2-21, 5-1 to 5-18 and 6-1 to 6-12, including a formulation such as by any method of Example 10, by means of subcutaneous injection.

Example 17

A patient with chronic congestive heart failure is administered a time release injectable formulation of Example 15 by means of an injection, such as a deep intramuscular injection, for example, in the gluteal or deltoid muscle.

Example 18

Applicants have also discovered an inverse correlation between the extent of resistance to digestion by neutral endopeptidase of a construct according to the invention and its pharmacokinetic clearance (CL), as shown in Table 7 below. Neutral endopeptidase ("NEP") is an endogenous enzyme that inactivates and clears all three human natriuretic peptides. NEP is present within renal tubular cells and vascular cells. NEP is highly homologous between mammalian species. The percent identity of NEP between Rat and Mouse is 98.5%, between Human and Mouse is 93.6%, and between Human and Rat is 93.7%.

NEP resistance of various constructs of the invention was evaluated using the following experimental procedure. All constructs were diluted in 0.1 M Tris-HCL buffer (pH 7.4) to 100 μM. 40 μL of diluted constructs were added to each tube and all tubes were kept on ice. 40 μL of diluted NEP, either human recombinant NEP (R&D Systems, Minneapolis, Minn., catalogue #1182-ZN) at 8 ng/μL or mouse NEP (R&D Systems, catalog #1126-ZN) at 2.5 ng/μL, was added to each tube. The tubes were mixed gently and spun. All tubes were then incubated at 37° C. for 0, 0.5, 1, 1.5 and 2 hours. At the end of the incubation time, the reaction was stopped by adding 5 μL of 10% TFA. Constructs were linearized using TCEP (Tris[2-carboxyethyl]phosphine. The extent to which NEP was active against the constructs was then analyzed by HPLC and/or LC/MS. Data analysis included determining the percent of remaining starting material, i.e., undigested peptide construct, and the percent and sequence of each proteolytic fragment.

TABLE 7

| Compound ID | IV Dosing, PK Cl (mL/min/kg) | cGMP AUC (nM·hr) | cGMP AUCnom (nM·hr) | cGMP Cmax (nM) | hNEP % of Starting Material 1 h | hNEP % of Starting Material 2 h |
|---|---|---|---|---|---|---|
| 1-18 (SEQ ID NO: 20) | 55 | 102 | 119 | 172 | 91 | 82 |
| 1-43 | 14 | 238 | 119 | 242 | 97 | 92 |
| 1-44 | 15 | 18 | 9 | 35 | 93 | 86 |
| 1-53 | 40 | 66 | 33 | 105 | 87 | 78 |
| 1-54 (SEQ ID NO: 38) | 66 | 128 | 64 | 220 | 85 | 82 |
| 1-55 (SEQ ID NO: 39) | 21 | 116 | 144 | 170 | 83 | 70 |
| 1-63 (SEQ ID NO: 20) | 203 | 89 | 189 | 197 | 67 | 44 |
| 1-100 (SEQ ID NO: 29) | 456 | 8 | 4 | 30 | 6 | 0 |
| 1-118 | 10 | 11 | 6 | 27 | 96 | 92 |
| 1-130 | 92 | 276 | 138 | 524 | 75 | 56 |
| 1-131 | 21 | 161 | 81 | 422 | 87 | 70 |
| 1-133 | 12 | 169 | 563 | 171 | 96 | 93 |

Accordingly, one embodiment of the invention provides a construct according to any of the formulas of the invention that demonstrates at least 80% of starting material remaining after 1 hour under the hNEP resistance assay conditions described. A related embodiment of the invention provides a construct according to any of the formulas of the invention that demonstrates at least 90% of starting material remaining after 1 hour under the hNEP resistance assay conditions described. A further related embodiment of the invention provides a construct according to any of the formulas of the invention that demonstrates at least 95% of starting material remaining after 1 hour under the hNEP resistance assay conditions described. In a variation of any of these embodiments, the construct also demonstrates at least 80% of starting material remaining after 2 hours under the assay conditions. In a related variation, the construct also demonstrates at least 90% of starting material remaining after 2 hours under the assay conditions.

Another embodiment of the invention provides a construct according to any of the formulas of the invention that demonstrates no more than 90% of starting material remaining after 1 hour under the hNEP resistance assay conditions described. A related embodiment of the invention provides a construct according to any of the formulas of the invention that demonstrates no more than 80% of starting material remaining after 1 hour under the hNEP resistance assay conditions described. In a variation of either embodiment, the construct also demonstrates no more than 90% of starting material remaining after 2 hours under the assay conditions. In a related variation, the construct also demonstrates no more than 80% of starting material remaining after 2 hours under the assay conditions.

Thus, constructs of the invention may be selected for pharmokinetic properties based on the extent of NEP resistance they demonstrate.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated by reference.

What is claimed is:

1. A peptide construct with an N-terminus and a C-terminus comprising from eleven to thirteen amino acid residues with an amino acid surrogate at the C-terminus position of the following formula:

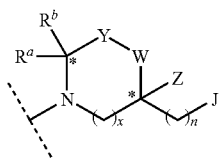

wherein
Y is CH$_2$ or C=O;
W is CH$_2$, NH or NR′′′;
Z is H or CH$_3$;
J is —H, —OH, —C(=O)—OH, —C(=O)—NH$_2$, or a C-terminus capping group;
one of R$^a$ and R$^b$ is H and the other of R$^a$ and R$^b$ is —(CH$_2$)$_y$—R′′;
R′′ is:
  —NH$_2$,
  —NH—C(=NH)—NH$_2$,
  —NH—(CH$_2$)$_y$—NH$_2$,
  —NH—C(=O)—NH$_2$,
  —C(=O)—NH$_2$,
  —C(=O)—NH—CH$_3$,
  —C(=O)—NH—(CH$_2$)$_y$—NH$_2$,
  —NH—C(=NH)—NH-Me,
  —NH—C(=NH)—NH-Et,
  —NH—C(=NH)—NH-Pr,
  —NH—C(=NH)—NH-Pr-i,
  —NH—C(=O)—CH$_3$,
  —NH—C(=O)—CH$_2$—CH$_3$,
  —NH—C(=O)—CH—(CH$_3$)$_2$,
  —NH—C(=O)—O—CH$_3$,
  —NH—C(=O)—O—CH$_2$—CH$_3$,
  —NH—C(=O)—O—C—(CH$_3$)$_3$,
  —NH—C(=O)—NH—CH$_3$,
  —NH—C(=N—C(=O)—O—C—(CH$_3$)$_3$)—NH—C(=O)—O—C—(CH$_3$)$_3$,
  —N(C(=O)—O—C—(CH$_3$)$_3$)—C(=NH)—NH—C(=O)—O—C—(CH$_3$)$_3$,

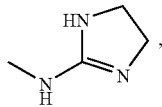, 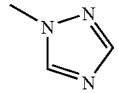, 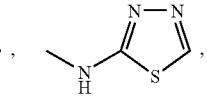,

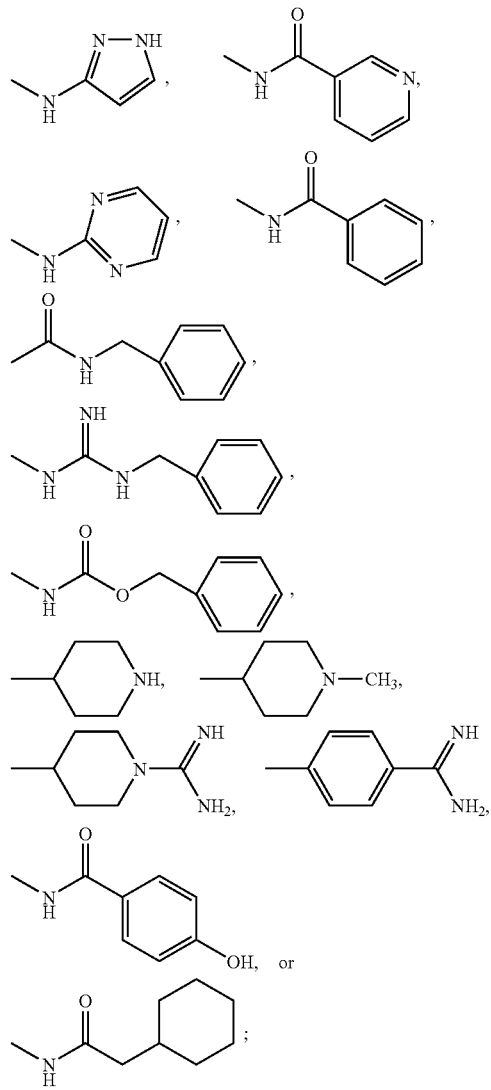

R′′′ is an acyl, a C$_1$ to C$_{17}$ linear or branched alkyl chain, a C$_2$ to C$_{19}$ linear or branched alkyl acyl chain, a C$_1$ to C$_{17}$ linear or branched omega amino aliphatic, or a C$_1$ to C$_{17}$ linear or branched omega amino aliphatic acyl;

x is 1 or 2;
y is 1 to 5;
n is 0, 1 or 2; and
the carbon atoms marked with an asterisk can have any stereochemical configuration;
with the amino acid surrogate at the C-terminus position being covalently bonded to the immediately adjacent amino acid residue, and the peptide cyclized by a bond between the side chains of two amino acid residues;

the eleven to thirteen amino acid residues comprise the sequence Aaa³-Aaa⁴-Aaa⁵-Aaa⁶-Aaa⁷-Aaa⁸-Aaa⁹-Aaa¹⁰-Aaa¹¹-Aaa¹² where Aaa³ is an L- or D-isomer of an α-amino acid selected from the group consisting of: His, Ala, Ser, Thr, Lys, HLys, Orn, Cys, HCys, Dap, or Dab, or an α,α-disubstituted amino acid derived from His, Ala, Ser, Thr, Lys, HLys, Orn, Cys, HCys, Dap, or Dab, or Aaa³ is an amino acid surrogate of the structure:

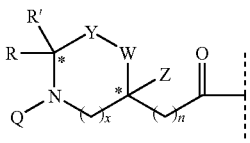

where R and R' are independently H or an amino acid side chain moiety of His, Ala, Ser, Thr, Lys, HLys, Orn, Cys, HCys, Dap, or Dab; x is 1 or 2; Y is $CH_2$ or C=O; W is $CH_2$, NH or NR'''; Z is H or $CH_3$; R''' is an acyl, a $C_1$ to $C_{17}$ linear or branched alkyl chain, a $C_2$ to $C_{19}$ linear or branched alkyl acyl chain, a $C_1$ to $C_{17}$ linear or branched omega amino aliphatic, or a $C_1$ to $C_{17}$ linear or branched omega amino aliphatic acyl; and n is 0, 1 or 2;

Aaa⁴ is an L- or D-isomer of an α-amino acid selected from the group consisting of: substituted or unsubstituted Phe, HPhe or Pgl, or Tyr, Leu, Ile, Val, Ala, Nle, Nva or Tle, or an α,α-disubstituted amino acid derived from substituted or unsubstituted Phe, HPhe or Pgl, or Tyr, Leu, Ile, Val, Ala, Nle, Nva or Tle, or Aaa⁴ is an amino acid surrogate as for Aaa³ where R and R' are independently H or an amino acid side chain moiety of substituted or unsubstituted Phe, HPhe or Pgl, or Tyr, Leu, Ile, Val, Ala, Nle, Nva or Tle;

Aaa⁵ is Gly, Sar, Aib, L- or D-isomer of Ala, or Aaa⁵ is an amino acid surrogate as for Aaa³ where R and R' are independently H or —$CH_3$;

Aaa⁶ is Gly, Sar, Aib, an L- or D-isomer of Ala, or Aaa⁶ is an amino acid surrogate as for Aaa³ where R and R' are independently H or —$CH_3$;

Aaa⁷ is an L- or D-isomer of an α-amino acid selected from the group consisting of: Arg, His, Ala, Ser, HSer, Thr, Lys, HLys, Orn, Cys, HCys, Cit, Abu, Dap, or Dab, or an α,α-disubstituted amino acid derived from Arg, His, Ala, Ser, Ser, Thy, Lys, HLys, Orn, Cys, HCys, Cit, Abu, Dap, or Dab, or Aaa⁷ is an amino acid surrogate as for Aaa³ where R and R' are independently H or an amino acid side chain moiety of Arg, His, Ala, Ser, HSer, Thr, Lys, HLys, Orn, Cys, HCys, Abu, Dap, or Dab;

Aaa⁸ is Gly, an L- or D-isomer of an α-amino acid selected from the group consisting of: from Nle, Ile, Leu, Val, Phe, Ala, Nva, Met(O), Met($O_2$), or Tle, or an α,α-disubstituted amino acid derived from Nle, Ile, Leu, Val, Phe, Ala, Nva, Met(O), Met($O_2$), or Aaa⁸ is an amino acid surrogate as for Aaa³ where R and R' are independently H or an amino acid side chain moiety of Nle, Ile, Leu, Val, Phe, Ala, Nva, Met(O), Met($O_2$), or Tle;

Aaa⁹ is an L- or D-isomer of an α-amino acid selected from the group consisting of: Asp, Glu, His, Ala, Set, Thr, Lys, HLys, Cys, HCys, Met(O), Met($O_2$), Orn, Dap, or Dab, or an α,α-disubstituted amino acid derived from Asp, Glu, His, Ala, Ser, Thr, Lys, HLys, Cys, HCys, Met(O), Met($O_2$), Orn, Dap, or Dab, or Aaa⁹ is an amino acid surrogate as for Aaa³ where R and R' are independently H or an amino acid side chain moiety of Asp, Glu, His, Ala, Ser, Thr, Lys, HLys, Cys, HCys, Met(O), Met($O_2$), Orn, Dap, or Dab;

Aaa¹⁰ is an L- or D-isomer of an α-amino acid selected from the group consisting of: Arg, His, Ala, Ser, Thr, Lys, HLys, Cys, HCys, Cit, Met(O), Orn, Dap, or Dab, or an α,α-disubstituted amino acid derived from Arg, His, Ala, Ser, Thr, Lys, HLys, Cys, HCys, Met(O), Orn, Dap, or Dab, or Aaa¹⁰ is an amino acid surrogate as for Aaa³ where R and R' are independently H or an amino acid side chain moiety of Arg, His, Ala, Ser, Thr, Lys, HLys, Cys, HCys, Cit, Met(O), Orn, Dap, or Dab;

Aaa¹¹ is Gly or a D- or L-isomer of an α-amino acid selected from the group consisting of: from Nle, Ile, Leu, Val, Phe, Ala, Nva, Cys, HCys, Abu or Tle, or an α,α-disubstituted amino acid derived from Nle, Ile, Leu, Val, Phe, Ala, Nva, Cys, HCys, Abu or Tle, or Aaa¹¹ is an amino acid surrogate as for Aaa³ where R and R' are independently H or an amino acid side chain moiety of Nle, Ile, Leu, Val, Phe, Ala, Nva, Cys, HCys, Abu or Tle;

Aaa¹² is Gly, an L- or D-isomer of an α-amino acid selected from the group consisting of: from Ser, Nle, Ile, Leu, Val, Phe, Ala, Nva, Arg, Lys, Orn, Cys, HCys, Abu or Tle, or an α,α-disubstituted amino acid derived from Ser, Nle, Ile, Leu, Val, Phe, Ala, Nva, Arg, Lys, Orn, Cys, HCys, Abu or Tle, or Aaa¹² is an amino acid surrogate as for Aaa³ where R and R' are independently H or an amino acid side chain moiety of Ser, Nle, Ile, Leu, Val, Phe, Ala, Nva, Arg, Lys, Orn, Cys, HCys, Abu or Tle; and the amino acid residue immediately adjacent to and covalently bonded to the amino acid surrogate at the C-terminus position is an L- or D-isomer of an α-amino acid selected from the group consisting of: substituted or unsubstituted Phe, HPhe or Pgl, or Tyr, Leu, Ile: Val, Ala, Lys, Orn, Nle, Nva or Tle, or an α,α-disubstituted amino acid derived from substituted or unsubstituted Phe, HPhe or Pgl, or Tyr, Leu, Ile, Val, Ala, Lys, Orn, Nle, Nva or Tle, or is an amino acid surrogate of the structure of formula II as for Aaa³ where R and R' are independently H or an amino acid side chain moiety of substituted or unsubstituted Phe, HPhe or Pgl, or Tyr, Leu, Ile, Val, Ala, Lys, Orn, Nle, Nva or Tle.

2. The peptide construct of claim 1, wherein the C-terminus capping group is:

—$(CH_2)_m$—OH,
—C(=O)—$(CH_2)_m$—N($v_1$)($v_2$),
—C(=O)—O—$(CH_2)_m$—$CH_3$,
—O—$(CH_2)_m$—$CH_3$,
—O—$(CH_2)_m$—N($v_1$)($v_2$),
—O—$(CH_2)_m$—OH,
—C(=O)—NH—$(CH_2)_m$—S($v_1$),
—C(=O)—NH—$(CH_2)_m$—$CH_3$,
—C(=O)—NH—$(CH_2)_m$—N($v_1$)($v_2$),
—C(=O)—N—(($CH_2)_m$—N($v_1$)($v_2$))$_2$,

—C(=O)—NH—CH(—C(=O)—OH)—(CH$_2$)$_m$—N(v$_1$)(v$_2$),

—C(=O)—NH—(CH$_2$)$_m$—NH—C(=O)—CH(N(v$_1$)(v$_2$))((CH$_2$)$_m$—N(v$_1$)(v$_2$)), or

—C(=O)—NH—CH(—C(=O)—N(v$_1$)(v$_2$))—(CH$_2$)$_m$—N(v$_1$)(v$_2$), including all (R) or (S) configurations of the foregoing;
v$_1$ and v$_2$ are each independently H or a C$_1$ to C$_{17}$ linear or branched alkyl chain; and
m is in each instance independently 0 to 17.

3. The peptide construct of claim 1, comprising at least one further amino acid surrogate at any position other than the C-terminus position.

4. The peptide construct of claim 3, wherein the at least one further amino acid surrogate is at the N-terminus position of the construct and is of The formula:

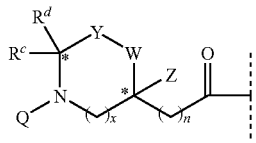

wherein
R$^c$ and R$^d$ are each independently H or a natural or unnatural amino acid side chain moiety;
Q is an amine capping group of the formula:
—(CH$_2$)$_m$—N(v$_3$)(v$_4$),
—(CH$_2$)$_m$—CH$_3$,
—(CH$_2$)$_m$—O(v$_3$),
—(CH$_2$)$_m$—C(=O)—(v$_3$),
—(CH$_2$)$_m$—C(=O)—O—(v$_3$),
—(CH$_2$)$_m$—S(v$_3$),
—C(=O)—(CH$_2$)$_m$—CH$_3$,
—C(=O)—(CH$_2$)$_m$—N(v$_3$)(v$_4$),
—C(=O)—(CH$_2$)$_m$—C(=O)—(v$_3$),
—C(=O)—(CH$_2$)$_m$—O(v$_3$), or
—C(=O)—(CH$_2$)$_m$—S(v$_3$);
v$_3$ and v$_4$ are each independently H, a C$_1$ to C$_{17}$ linear or branched alkyl chain or a C$_2$ to C$_{19}$ linear or branched alkyl acyl chain, on the proviso that if one of v$_3$ or v$_4$ is an alkyl acyl chain, then the other of v$_3$ or v$_4$ is H; and
m is 0 to 17.

5. The peptide construct of claim 1, further comprising an N-terminus acyl comprising a C$_2$ to C$_{18}$ linear alkyl, a C$_3$ to C$_{17}$ branched alkyl, a C$_2$ to C$_{18}$ linear alkenyl or alkynyl or a C$_3$ to C$_{18}$ branched alkenyl or alkynyl.

6. The peptide construct of claim 5 wherein the N-terminus acyl is —C(=O)—(CH$_2$)$_p$—CH$_3$ where p is 1 to 18.

7. The peptide construct of claim 6 of the formula:

(SEQ ID NO: 20)

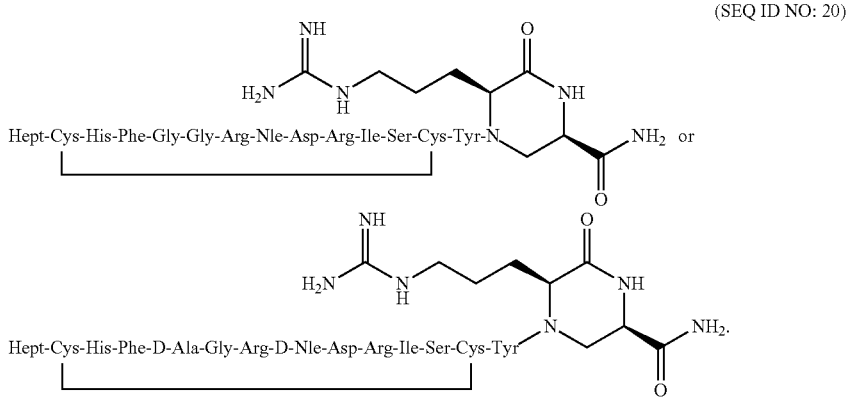

8. The peptide construct of claim 1, wherein at least two of the amino acid residues are joined by a non-peptide bond.

9. The peptide construct of claim 8, wherein the at least one non-peptide bond is —CH$_2$—NH—, —CH$_2$—S—, —CH$_2$—O—, or —C(=O)—CH$_2$—, an isostere of any of the foregoing, or —CH$_2$—CH$_2$— or —CH=CH—.

10. The peptide construct of claim 1, wherein the cyclic peptide construct binds to a natriuretic peptide receptor selected from the group consisting of a receptor for ANP, BNP, CNP, sCP, DNP, TNP-a, TNP-b or TNP-c.

11. The peptide construct of claim 10, wherein the cyclic peptide construct exhibits, upon administration to a mammal, one or more advantages relative to the corresponding amino acid sequence not comprising an amino acid surrogate, the advantages selected from the group consisting of increased resistance to enzymatic degradation, increased circulation half life, increased bioavailability, increased efficacy, and prolonged duration of effect.

12. The peptide construct of claim 1, wherein for the amino acid surrogate at the C-terminus position Y is C=O, W is NH, Z is H, x is 1 and n is 0.

13. The peptide construct of claim 1, further comprising at least one prosthetic group covalently bonded to a reactive group in a side chain or terminal group of at least one of the amino acid residues or to a carboxyl group, amine group or reactive group in a C-terminus capping group of the amino acid surrogate.

14. The peptide construct of claim 13, wherein the prosthetic group comprises at least one polymeric sequence comprising repeat units including carbon and hydrogen atoms.

15. The peptide construct of claim 14, wherein the polymeric sequence is poly(alkylene oxide), poly(vinyl pyrrolidone), poly(vinyl alcohol), polyoxazoline or poly(acryloylmorpholine).

16. The peptide construct of claim 15, wherein the poly(alkylene oxide) is poly(ethylene glycol) (PEG).

17. The peptide construct of claim 16, wherein the prosthetic group comprising PEG is derivatized with a linking group.

18. A pharmaceutical composition, comprising the peptide construct of claim 1 or a pharmaceutically acceptable salt of the peptide construct of claim 1 and a pharmaceutically acceptable carrier.

19. A pharmaceutical composition, comprising the peptide construct of claim 7 or a pharmaceutically acceptable salt of the peptide construct of claim 7 and a pharmaceutically acceptable carrier.

* * * * *

UNITED STATES PATENT AND TRADEMARK OFFICE
CERTIFICATE OF CORRECTION

PATENT NO. : 8,580,747 B2
APPLICATION NO. : 12/622055
DATED : November 12, 2013
INVENTOR(S) : Shubh D. Sharma et al.

Page 1 of 1

It is certified that error appears in the above-identified patent and that said Letters Patent is hereby corrected as shown below:

In the Claims

Claim 1, Column 251, line 43, after "AIB," insert --an--.
Claim 1, Column 251, line 53, replace "Thy," with --Thr,--.
Claim 1, Column 252, line 3, replace "Set," with --Ser,--.
Claim 1, Column 252, line 47, replace "Ile:" with --Ile;--.
Claim 4, Column 253, line 36, replace "The" with --the--.

Signed and Sealed this
Eighth Day of July, 2014

Michelle K. Lee
*Deputy Director of the United States Patent and Trademark Office*